(12) United States Patent
Hahn et al.

(10) Patent No.: US 12,317,748 B2
(45) Date of Patent: May 27, 2025

(54) ORGANIC ELECTRONIC ELEMENT COMPRISING COMPOUND FOR ORGANIC ELECTRONIC ELEMENT AND AN ELECTRONIC DEVICE THEREOF

(71) Applicant: DUK SAN NEOLUX CO., LTD., Cheonan-si (KR)

(72) Inventors: Seung Hoon Hahn, Cheonan-si (KR); Junggeun Lee, Cheonan-si (KR); Ki Hwan Yoon, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 0 days.

(21) Appl. No.: 18/677,122

(22) Filed: May 29, 2024

(65) Prior Publication Data
US 2024/0341182 A1   Oct. 10, 2024

Related U.S. Application Data

(63) Continuation-in-part of application No. 18/180,625, filed on Mar. 8, 2023, which is a continuation-in-part
(Continued)

(30) Foreign Application Priority Data

Oct. 26, 2020 (KR) .................. 10-2020-0139441

(51) Int. Cl.
*H10K 85/60* (2023.01)
*C07D 251/24* (2006.01)
(Continued)

(52) U.S. Cl.
CPC ....... *H10K 85/6574* (2023.02); *C07D 251/24* (2013.01); *C09K 11/06* (2013.01); *H10K 85/626* (2023.02); *H10K 85/631* (2023.02); *H10K 85/653* (2023.02); *H10K 85/654* (2023.02); *H10K 85/6572* (2023.02); *H10K 85/6576* (2023.02); *C07B 2200/05* (2013.01); *C09K 2211/1018* (2013.01); *H10K 50/11* (2023.02);
(Continued)

(58) Field of Classification Search
CPC .......................... C07D 251/24; H10K 85/6574
See application file for complete search history.

(56) References Cited

U.S. PATENT DOCUMENTS

2014/0367654 A1   12/2014   Kim et al.
2015/0303379 A1   10/2015   Lee et al.
(Continued)

FOREIGN PATENT DOCUMENTS

KR   10-2009-0079134 A   7/2009
KR   10-2016-0111780 A   9/2016
(Continued)

OTHER PUBLICATIONS

SciFinder Search, 4 pages, Apr. 7, 2021.
STN Search, 351 pages, Apr. 7, 2021.

*Primary Examiner* — Vu A Nguyen
(74) *Attorney, Agent, or Firm* — Vorys, Sater, Seymour and Pease LLP; Mih Suhn Koh

(57) ABSTRACT

Provided are a compound that can improve the luminous efficiency, stability, and lifespan of an organic electronic element, an organic electronic element employing the compound, and an electronic device thereof.

17 Claims, 8 Drawing Sheets

Related U.S. Application Data of application No. 17/212,886, filed on Mar. 25, 2021, now Pat. No. 11,678,577, which is a continuation of application No. 17/096,790, filed on Nov. 12, 2020, now Pat. No. 11,063,226.

(51) Int. Cl.

| | |
|---|---|
| *C09K 11/06* | (2006.01) |
| *H10K 50/11* | (2023.01) |
| *H10K 50/15* | (2023.01) |
| *H10K 50/16* | (2023.01) |
| *H10K 50/18* | (2023.01) |
| *H10K 101/00* | (2023.01) |
| *H10K 101/10* | (2023.01) |

(52) U.S. Cl.
CPC ............. *H10K 50/15* (2023.02); *H10K 50/16* (2023.02); *H10K 50/18* (2023.02); *H10K 2101/10* (2023.02); *H10K 2101/90* (2023.02)

(56) References Cited

U.S. PATENT DOCUMENTS

| | | |
|---|---|---|
| 2016/0133674 A1 | 5/2016 | Lee et al. |
| 2018/0072695 A1 | 3/2018 | Byun et al. |
| 2018/0123048 A1 | 5/2018 | So et al. |
| 2018/0151806 A2 | 5/2018 | Park et al. |
| 2018/0261774 A1 | 9/2018 | Park et al. |

FOREIGN PATENT DOCUMENTS

| | | | | |
|---|---|---|---|---|
| WO | 2017/171420 A1 | | 10/2017 | |
| WO | 2019/124902 A1 | | 6/2019 | |
| WO | 2020/045981 A1 | | 3/2020 | |
| WO | WO-2020171531 A1 | * | 8/2020 | ........... C07D 405/14 |
| WO | WO-2021182834 A1 | * | 9/2021 | ........... C07D 405/04 |
| WO | WO-2021182893 A1 | * | 9/2021 | ........... C07C 211/54 |
| WO | WO-2021230714 A1 | * | 11/2021 | |
| WO | WO-2021230715 A1 | * | 11/2021 | |
| WO | WO-2022240267 A1 | * | 11/2022 | |
| WO | WO-2023287228 A1 | * | 1/2023 | ............. H10K 50/11 |

\* cited by examiner

FIG. 13
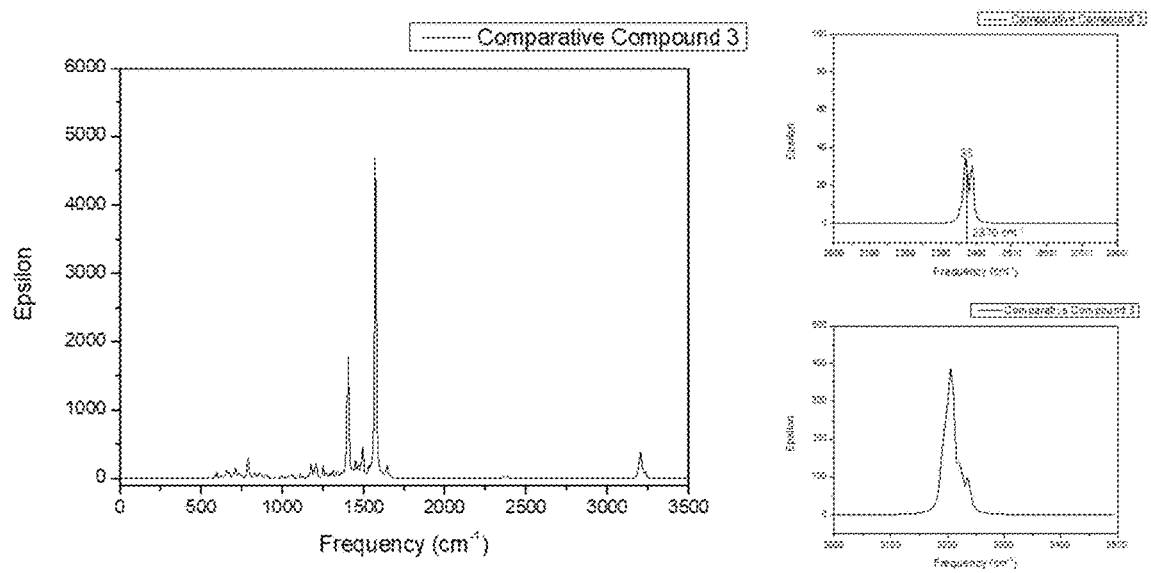
[FIG. 14]
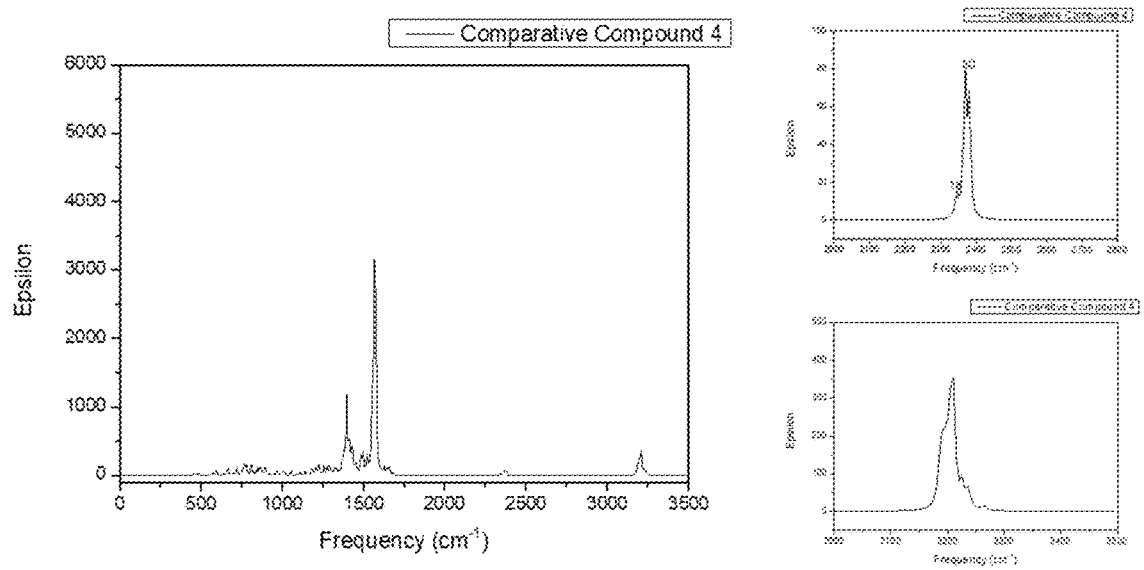

ORGANIC ELECTRONIC ELEMENT COMPRISING COMPOUND FOR ORGANIC ELECTRONIC ELEMENT AND AN ELECTRONIC DEVICE THEREOF

BACKGROUND

Technical Field

The present invention relates to organic electronic elements using compounds for organic electronic elements, and an electronic device thereof.

Background Art

In general, organic light emitting phenomenon refers to a phenomenon that converts electric energy into light energy by using an organic material. An organic electronic element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electronic element may be classified into a light emitting material and a charge transport material, such as a hole injection material, a hole transport material, an electron transport material, an electron injection material and the like depending on its function. And the light emitting material can be classified into a high molecular weight type and a low molecular weight type according to the molecular weight, and it can be classified into a fluorescent material derived from a singlet excited state of an electron and a phosphorescent material derived from a triplet excited state of an electron depending on the light emission mechanism. Also, the light emitting material may be divided into blue, green, and red light emitting materials and yellow and orange light emitting materials necessary for realizing a better natural color according to the emission color.

However, when only one material is used as a light emitting material, due to intermolecular interaction, the maximum emission wavelength shifts to a longer wavelength, and there are problems in that the color purity is lowered or the device efficiency is reduced due to the emission attenuation effect, therefore in order to increase color purity and increase luminous efficiency through energy transfer, a host/dopant system may be used as a light emitting material. The principle is that when a small amount of a dopant having a smaller energy band gap than that of the host forming the emitting layer is mixed in the emitting layer, excitons generated in the emitting layer are transported to the dopant to emit light with high efficiency. Here, since the wavelength of the host moves to the wavelength band of the dopant, light having a desired wavelength can be obtained according to the type of dopant used.

Currently, the portable display market is a large-area display, and the size thereof is increasing, and thus, more power consumption than the power consumption required for the existing portable display is required. Therefore, power consumption has become a very important factor for a portable display having a limited power supply such as a battery, and the problem of efficiency and lifespan must also be solved.

Efficiency, lifespan and driving voltage are related to each other, and when the efficiency is increased, the driving voltage is relatively decreased, and as the driving voltage is decreased, crystallization of organic materials due to Joule heating generated during driving decreases, and consequently, the lifespan tends to increase. However, the efficiency cannot be maximized simply by improving the organic material layer. This is because, when the energy level and T1 value between each organic material layer, and the intrinsic properties (mobility, interfacial properties, etc.) of materials are optimally combined, long lifespan and high efficiency can be achieved at the same time.

Therefore, while delaying the penetration and diffusion of metal oxide from the anode electrode (ITO) into the organic layer, which is one of the causes of shortening the lifespan of the organic electronic element, it should have stable characteristics against Joule heating generated during device driving, and OLED devices are mainly formed by a deposition method, and it is necessary to develop a material that can withstand a long time during deposition, that is, a material with strong heat resistance.

That is, in order to fully exhibit the excellent characteristics of an organic electronic element, it should be preceded that the material constituting the organic material layer in the device, such as a hole injection material, a hole transport material, a light emitting material, an electron transport material, an electron injection material, etc., is supported by a stable and efficient material. But the development of a stable and efficient organic material layer material for an organic electronic element has not yet been sufficiently made. Therefore, the development of new materials is continuously required, and in particular, the development of a host material for the emitting layer is urgently needed.

BRIEF DESCRIPTION OF THE INVENTION

Summary

The purpose of the present invention is to provide a composition comprising a compound that can lower the driving voltage of the element and improve the luminous efficiency, color purity, stability, and lifespan of the element, an organic electronic element, and an electronic device thereof.

Technical Solution

The present invention provides a composition for an organic electronic element comprising a mixture of a compound represented by Formula 1 and a compound represented by Formula 2 or Formula 5

Formula 1

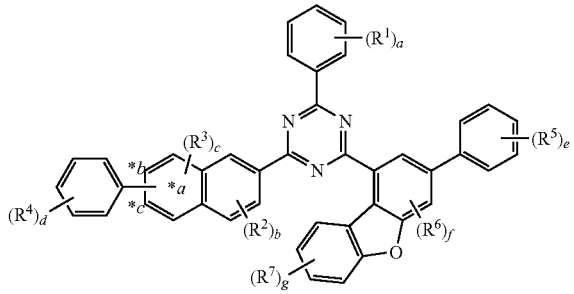

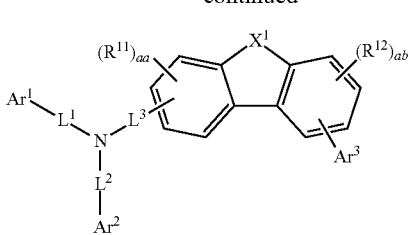

Formula 2

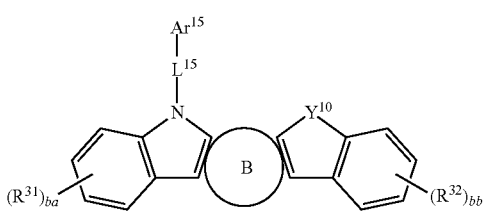

Formula 5

In another aspect, the present invention provides an organic electronic element comprising the composition for an organic electronic element, and an electronic device thereof.

Effects of the Invention

By using the compound according to the present invention, high luminous efficiency, low driving voltage and high heat resistance of the element can be achieved, and color purity and lifespan of the element can be greatly improved.

BRIEF DESCRIPTION OF THE DRAWINGS

FIG. 4 to FIG. 16 show IR spectrum measurement data of the compounds of the present invention and comparative compounds according to an embodiment of the present invention.

DESCRIPTION OF THE NUMERALS

Figure 1:
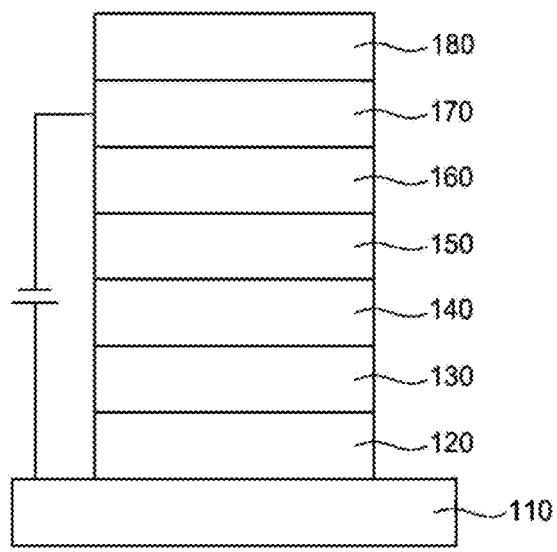
FIG. 1 to FIG. 3 are each an exemplary view of an organic electroluminescent device according to the present invention.

| | |
|---|---|
| 100, 200, 300: organic electronic element | 110: the first electrode |
| 120: hole injection layer | 130: hole transport layer |
| 140: emitting layer | 150: electron transport layer |
| 160: electron injection layer | 170: second electrode |
| 180: light efficiency enhancing Layer | 210: buffer layer |
| 220: emitting auxiliary layer | 320: first hole injection layer |
| 330: first hole transport layer | 340: first emitting layer |
| 350: first electron transport layer | 360: first charge generation layer |
| 361: second charge generation layer | 420: second hole injection layer |
| 430: second hole transport layer | 440: second emitting layer |
| 450: second electron transport layer | CGL: charge generation layer |
| STI: first stack | ST2: second stack |

DETAILED DESCRIPTION OF THE INVENTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected ", " coupled" or "connected" between each component.

As used in the specification and the accompanying claims, unless otherwise stated, the following is the meaning of the term as follows.

Unless otherwise stated, the term "halo" or "halogen", as used herein, includes fluorine, bromine, chlorine, or iodine.

Unless otherwise stated, the term "alkyl" or "alkyl group", as used herein, has a single bond of 1 to 60 carbon atoms, 1 to 30 carbon atoms, 1 to 25 carbon atoms, 1 to 18 carbon atoms, or 1 to 12 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "alkenyl" or "alkynyl", as used herein, has double or triple bonds of 2 to 60 carbon atoms, 2 to 30 carbon atoms, 2 to 25 carbon atoms, 2 to 18 carbon atoms, 2 to 12 carbon atoms, but is not limited thereto, and includes a linear or a branched chain group.

Unless otherwise stated, the term "cycloalkyl", as used herein, means alkyl forming a ring having 3 to 60 carbon atoms, 3 to 30 carbon atoms, 3 to 25 carbon atoms, 3 to 18 carbon atoms, 3 to 12 carbon atoms, but is not limited thereto.

Unless otherwise stated, the term "alkoxyl group", "alkoxy group" or "alkyloxy group", as used herein, means an alkyl group bonded to oxygen radical, but is not limited thereto, and has 1 to 60 carbon atoms, 1 to 30 carbon atoms, 1 to 25 carbon atoms, 1 to 18 carbon atoms, or 1 to 12 carbon atoms.

Unless otherwise stated, the term "aryloxyl group" or "aryloxy group", as used herein, means an aryl group bonded to oxygen radical, but is not limited thereto, and has 6 to 60 carbon atoms, 6 to 30 carbon atoms, 6 to 25 carbon atoms, 6 to 18 carbon atoms, or 6 to 12 carbon atoms.

Unless otherwise specified, the terms "aryl group" and "arylene group" used in the present invention have 6 to 60 carbon atoms, 6 to 30 carbon atoms, 6 to 25 carbon atoms, 6 to 18 carbon atoms, or 6 to 12 carbon atoms, respectively, but are not limited thereto. In the present invention, an aryl group or arylene group refers to an aromatic group of a single ring or multiple rings, and includes an aromatic ring formed by combining adjacent substituents or participating in a reaction. For example, the aryl group may be a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalkenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heterocyclic group", as used herein, contains one or more heteroatoms, but is not limited thereto, has 2 to 60 carbon atoms, 2 to 30 carbon atoms, 2 to 25 carbon atoms, 2 to 18 carbon atoms, 2 to 12 carbon atoms, and includes any one of a single ring or multiple ring, and may include heteroaliphadic ring and heteroaromatic ring. Also, the heterocyclic group may also be formed in conjunction with an adjacent group.

Unless otherwise stated, the term "heteroatom", as used herein, represents at least one of N, O, S, P, or Si.

Also, "heterocyclic group" refers to a single ring containing heteroatoms, a ring aggregate, multiple fused ring systems, spiro compounds, etc. Additionally, compounds containing heteroatom groups such as $SO_2$, $P=O$, etc., such as the compounds below, instead of carbon forming a ring, may also be included in the heterocyclic group. For example, "heterocyclic group" includes the following compound.

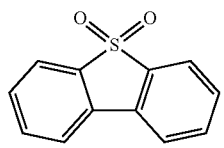 [SMILES: O=S1(=O)c2ccccc2-c2ccccc21]

The term "aliphatic ring group" used in the present invention refers to cyclic hydrocarbons excluding aromatic hydrocarbons, and includes single rings, ring aggregates, fused multiple ring systems, spiro compounds, etc., and means a ring having 3 to 60 carbon atoms, 3 to 30 carbon atoms, 3 to 25 carbon atoms, 3 to 18 carbon atoms, 3 to 12 carbon atoms, but is not limited thereto. For example, even when benzene, an aromatic ring, and cyclohexane, a non-aromatic ring, are fused, it is an aliphatic ring.

Unless otherwise stated, the term "fluorenyl group", "fluorenylene group" or "fluorentriyl group" as used herein, means a monovalent, divalent or trivalent functional group, in which R, R' and R" are all hydrogen in the following structures, and the term "substituted fluorenyl group", "substituted fluorenylene group" or "substituted fluorentriyl group" means that at least one of the substituents R, R' and R" is a substituent other than hydrogen, and include those in which R and R' are bonded to each other to form a spiro compound together with the carbon to which they are bonded. In this specification, fluorenyl group, fluorenylene group, and fluorenetriyl group may all be referred to as fluorene groups, regardless of valence.

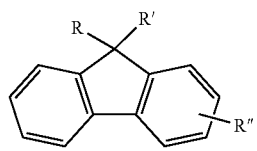

The term "spiro compound", as used herein, has a 'spiro union', and a spiro union means a connection in which 2 rings share only one atom. Wherein atoms shared in the 2 rings are called 'spiro atoms', and these compounds are called 'monospiro-', 'di-spiro-' and 'tri-spiro-', respectively, depending on the number of spiro atoms in a compound.

Unless otherwise stated, the term "aliphatic", as used herein, means an aliphatic hydrocarbon having 1 to 60 carbon atoms, 1 to 30 carbon atoms, 1 to 25 carbon atoms, 1 to 18 carbon atoms, or 1 to 12 carbon atoms, and the term "aliphatic ring", as used herein, means an aliphatic hydrocarbon ring having 3 to 60 carbon atoms, 3 to 30 carbon atoms, 3 to 25 carbon atoms, 3 to 18 carbon atoms or 3 to 12 carbon atoms.

Unless otherwise stated, the term "ring", as used herein, means an aliphatic ring having 3 to 60 carbon atoms, 3 to 30 carbon atoms, 3 to 25 carbon atoms, 3 to 18 carbon atoms or 3 to 12 carbon atoms; or an aromatic ring having 6 to 60 carbon atoms, 6 to 30 carbon atoms, 6 to 25 carbon atoms, 6 to 18 carbon atoms, or 6 to 12 carbon atoms; or a hetero ring having 2 to 60 carbon atoms, 2 to 30 carbon atoms, 2 to 25 carbon atoms, 2 to 18 carbon atoms, 2 to 12 carbon atoms, or a fused ring formed by the combination thereof, and includes a saturated or unsaturated ring.

Other hetero compounds or hetero radicals other than the above-mentioned hetero compounds include, but are not limited thereto, one or more heteroatoms.

Also, unless expressly stated, as used herein, "substituted" in the term "substituted or unsubstituted" means substituted with one or more substituents selected from the group consisting of deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group, but is not limited to these substituents.

In this specification, the 'group name' corresponding to the aryl group, arylene group, heterocyclic group, etc., as examples of each symbol and its substituent, may be written as the 'name of the group reflecting the valence', but is written as the 'parent compound name'. For example, in the case of 'phenanthrene', a type of aryl group, the name of the group may be written by distinguishing the valence, such as the monovalent 'group' is 'phenanthryl' and the divalent group is 'phenanthrylene', but may be written as 'phenanthrene', which is the name of the parent compound, regardless of the valence. Similarly, in the case of pyrimidine, it can be written as 'pyrimidine' regardless of the valence, or it can be written as the 'name of the group' of the valence, such as pyrimidineyl group in the case of monovalent group, pyrimidineylene in the case of divalent group, etc.

Additionally, in this specification, when describing compound names or substituent names, numbers or alphabets indicating positions may be omitted. For example, pyrido[4,3-d]pyrimidine to pyridopyrimidine, benzofuro[2,3-d]pyrimidine to benzofuropyrimidine, 9,9-dimethyl-9H-fluorene can be described as dimethylfluorene, etc. Therefore, both benzo[g]quinoxaline and benzo[f]quinoxaline can be described as benzoquinoxaline.

Also, unless there is an explicit explanation, the formula used in the present invention is the same as the definition of the substituent by the exponent definition of the following formula.

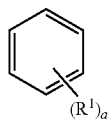

$(R^1)_a$

Here, when a is an integer of 0, the substituent $R^1$ is absent, when a is an integer of 1, the sole substituent $R^1$ is linked to any one of the carbon constituting the benzene ring, when a is an integer of 2 or 3, each is combined as follows, where $R^1$ may be the same or different from each other, when a is an integer of 4 to 6, it is bonded to the carbon of the benzene ring in a similar manner, while the indication of the hydrogen bonded to the carbon forming the benzene ring is omitted.

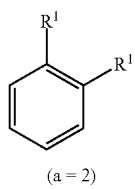

(a = 2)

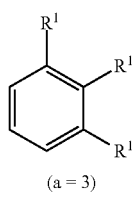

(a = 3)

Unless otherwise expressly stated, the terms "ortho", "meta", and "para" used in the present invention refer to the substitution positions of all substituents, and the ortho position refers to a compound in which the position of the substituent is immediately adjacent, for example, when benzene is used, it means 1 or 2 position, and the meta position is the next substitution position of the neighbor substitution position, when benzene as an example stands for 1 or 3 position, and the para position is the next substitution position of the meta position, which means 1 and 4 position when benzene is taken as an example. A more detailed example of the substitution position is as follows, and it can be confirmed that the ortho-, and meta-position are substituted by non-linear type and para-positions are substituted by linear type.

Example of Ortho-Position

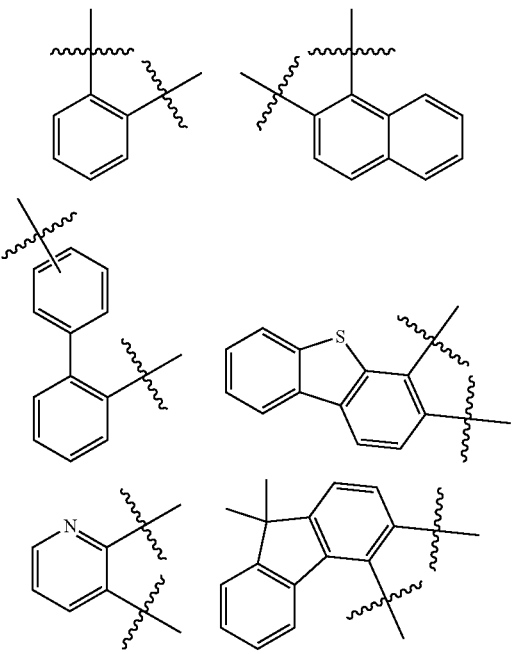

Example of Meta-Position

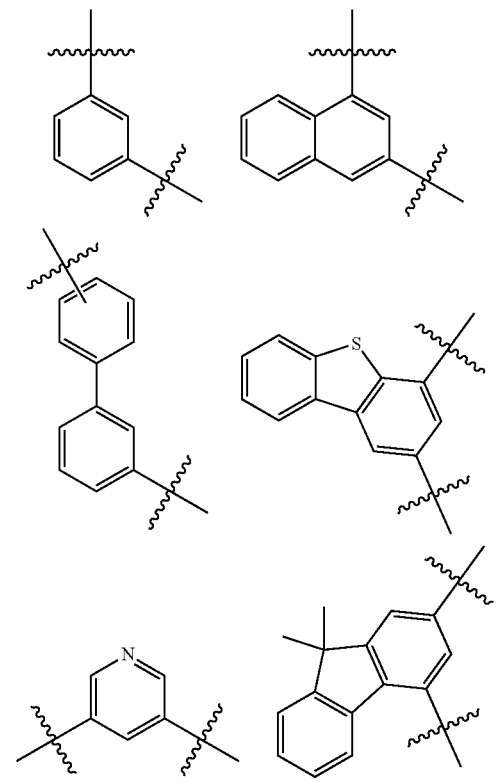

Example of Para-Position

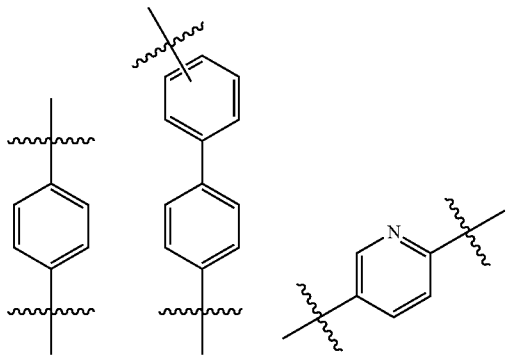

As used herein, the term "composition" is intended to be interpreted broadly, comprising compounds as well as solutions, dispersions, liquids and solid mixtures (mixture, admixture). The composition of the present invention may comprise the compound of the present invention alone, or the compounds are comprised in a combination of 2 or more different types, or the compounds may be comprised in combinations of 2 or more types with other compounds. In other words, the composition may comprise a compound corresponding to Formula 1 alone, a mixture of 2 or more compounds of Formula 1, or a mixture of a compound of Formula 1 and a compound that does not correspond to the present invention. Wherein, the compound that does not correspond to the present invention may be a single compound, and may be 2 or more types of compounds. Here, when the compound is comprised in a combination of 2 or more types of other compounds, the other compounds may be already known compounds of each organic material layer, or may be compounds to be developed in the future. Here, the compound contained in the organic material layer may consist of only the same type of compound, but may also be a mixture of 2 or more types of different compounds represented by Formula 1.

Hereinafter, a composition for an organic electronic element according to an aspect of the present invention, and an organic electronic element comprising the same will be described.

The present invention provides a composition for an organic electronic element comprising a mixture of a compound represented by Formula 1 and a compound represented by Formula 2 or Formula 5.

Formula 1

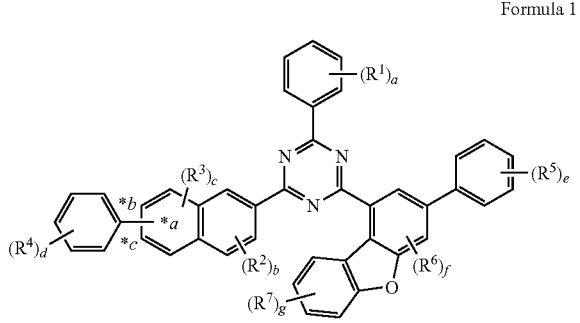

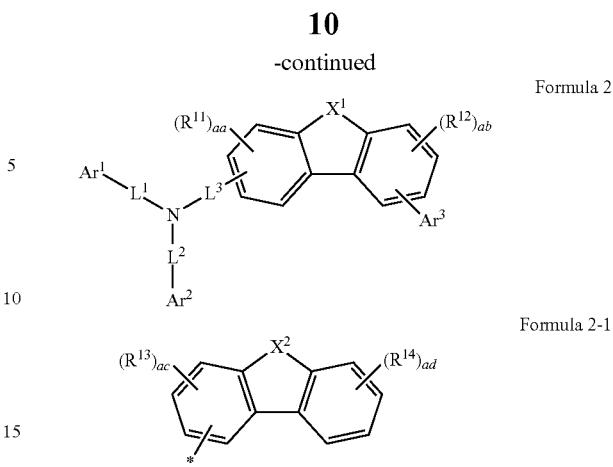

Wherein:
$R^1$, $R^2$, $R^3$, $R^4$, $R^5$, $R^6$ and $R^7$ are each the same or different, and each independently hydrogen; or deuterium;

$R^{11}$, $R^{12}$, $R^{13}$ and $R^{14}$ are each independently same or different, and each independently selected from the group consisting of a hydrogen; deuterium; $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and a $C_3$-$C_{60}$ aliphatic ring; or can form a ring by combining adjacent groups, When $R^{11}$, $R^{12}$, $R^{13}$ and $R^{14}$ are an aryl group, it is preferably an $C_6$-$C_{30}$ aryl group, more preferably an $C_6$-$C_{25}$ aryl group, $C_6$-$C_{18}$ aryl group, or $C_6$-$C_{12}$ aryl group, for example, it may be phenyl, biphenyl, terphenyl, naphthalene, phenanthrene, chryshene and the like.

When $R^{11}$, $R^{12}$, $R^{13}$ and $R^{14}$ are a heterocyclic group, it is preferably a $C_2$-$C_{30}$ heterocyclic group, more preferably a $C_2$-$C_{25}$ heterocyclic group, $C_2$-$C_{18}$ heterocyclic group, or $C_2$-$C_{12}$ heterocyclic group, for example, it may be pyrazine, thiophene, pyridine, pyrimidine, quinoline, pyrimidoindole, 5-phenyl-5H-pyrimido[5,4-b]indole, quinazoline, quinoxaline, benzoquinazoline, carbazole, dibenzoquinazoline, benzofuran, benzothiophene, dibenzofuran, dibenzothiophene, benzothienopyrimidine, benzofuropyrimidine, phenothiazine, phenylphenothiazine, naphthobenzofuran, naphthobenzothiophene, etc.

When $R^{11}$, $R^{12}$, $R^{13}$ and $R^{14}$ are a fused ring group, it is preferably a fused ring group of a $C_3$-$C_{30}$ aliphatic ring and an $C_6$-$C_{30}$ aromatic ring, more preferably a fused ring group of an $C_3$-$C_{25}$ aliphatic ring and an $C_6$-$C_{25}$ aromatic ring.

When $R^{11}$, $R^{12}$, $R^{13}$ and $R^{14}$ are an alkyl group, it is preferably a $C_1$-$C_{30}$ alkyl group, more preferably a $C_1$-$C_{25}$ alkyl group, a $C_1$-$C_{18}$ alkyl group, or a $C_1$-$C_{12}$ alkyl group. For example, it may be a methyl group, ethyl group, propyl group, isopropyl group, butyl group, t-butyl group, pentyl group, etc.

When $R^{11}$, $R^{12}$, $R^{13}$ and $R^{14}$ are an alkoxyl group, it is preferably a $C_1$-$C_{25}$ alkoxyl group, a $C_1$-$C_{18}$ alkoxyl group or a $C_1$-$C_{12}$ alkoxyl group.

When $R^{11}$, $R^{12}$, $R^{13}$ and $R^{14}$ are an aryloxy group, it is preferably a $C_6$-$C_{25}$ aryloxy group, a $C_6$-$C_{18}$ aryloxy group or a $C_6$-$C_{12}$ aryloxy group.

When $R^{11}$, $R^{12}$, $R^{13}$ and $R^{14}$ are an aliphatic ring group, preferably a $C_3$-$C_{30}$ aliphatic ring group, more preferably a $C_3$-$C_{25}$ aliphatic ring group, $C_3$-$C_{18}$ aliphatic ring group or $C_3$-$C_{12}$ aliphatic ring group, and may specifically be cyclobutane, cyclopentane, cyclohexane, bicycloheptane, adamantyl, etc.

$Ar^1$ and $Ar^2$ are each independently selected from the group consisting of an $C_6$-$C_{60}$ aryl group; a fluorenyl group; a $C_2$-$C_{60}$ heterocyclic group including at least one heteroatom of O, N, S, Si or P; a $C_1$-$C_{50}$ alkyl group; and a $C_3$-$C_{60}$ aliphatic ring;

When $Ar^1$ and $Ar^2$ are an aryl group, it is preferably an $C_6$-$C_{30}$ aryl group, more preferably an $C_6$-$C_{25}$ aryl group, $C_6$-$C_{18}$ aryl group, or $C_6$-$C_{12}$ aryl group, for example, it may be phenyl, biphenyl, terphenyl, naphthalene, phenanthrene, chryshene and the like.

When $Ar^1$ and $Ar^2$ are a heterocyclic group, it is preferably a $C_2$-$C_{30}$ heterocyclic group, more preferably a $C_2$-$C_{25}$ heterocyclic group, $C_2$-$C_{18}$ heterocyclic group, or $C_2$-$C_{12}$ heterocyclic group, for example, it may be pyrazine, thiophene, pyridine, pyrimidine, quinoline, pyrimidoindole, 5-phenyl-5H-pyrimido[5,4-b]indole, quinazoline, quinoxaline, benzoquinazoline, carbazole, dibenzoquinazoline, benzofuran, benzothiophene, dibenzofuran, dibenzothiophene, benzothienopyrimidine, benzofuropyrimidine, phenothiazine, phenylphenothiazine, naphthobenzofuran, naphthobenzothiophene, etc.

When $Ar^1$ and $Ar^2$ are an alkyl group, it is preferably a $C_1$-$C_{30}$ alkyl group, more preferably a $C_1$-$C_{25}$ alkyl group, a $C_1$-$C_{18}$ alkyl group, or a $C_1$-$C_{12}$ alkyl group. For example, it may be a methyl group, ethyl group, propyl group, isopropyl group, butyl group, t-butyl group, pentyl group, etc.

When $Ar^1$ and $Ar^2$ are an aliphatic ring group, preferably a $C_3$-$C_{30}$ aliphatic ring group, more preferably a $C_3$-$C_{25}$ aliphatic ring group, $C_3$-$C_{18}$ aliphatic ring group or $C_5$-$C_{12}$ aliphatic ring group, and may specifically be cyclobutane, cyclopentane, cyclohexane, bicycloheptane, adamantyl, etc.

$Ar^3$ is a substituent represented by Formula 2-1, $L^1$, $L^2$ and $L^3$ are each selected from the group consisting of single bond; an arylene group; a fluorenylene group; a $C_2$-$C_{60}$ heterocyclic group including at least one heteroatom of O, N, S, Si or P;

When $L^1$, $L^2$ and $L^3$ are an arylene group, it is preferably an $C_6$-$C_{30}$ arylene group, more preferably an $C_6$-$C_{25}$ arylene group, $C_6$-$C_{18}$ arylene group, or $C_6$-$C_{12}$ arylene group, for example, it may be phenylene, biphenylene, naphthylene, terphenylene, anthracenylene and the like.

When $L^1$, $L^2$ and $L^3$ are a heterocyclic group, it is preferably a $C_2$-$C_{30}$ heterocyclic group, more preferably a $C_2$-$C_{25}$ heterocyclic group, $C_2$-$C_{18}$ heterocyclic group, or $C_2$-$C_{12}$ heterocyclic group, for example, it may be pyrazine, thiophene, pyridine, pyrimidine, quinoline, pyrimidoindole, 5-phenyl-5H-pyrimido[5,4-b]indole, quinazoline, quinoxaline, benzoquinazoline, carbazole, dibenzoquinazoline, benzofuran, benzothiophene, dibenzofuran, dibenzothiophene, benzothienopyrimidine, benzofuropyrimidine, phenothiazine, phenylphenothiazine, naphthobenzofuran, naphthobenzothiophene, etc.

$X^1$ is O or S, $X^2$ is O, S or CR'R",

R' and R" are selected from the group consisting of a $C_6$-$C_{60}$ aryl group; a fluorenyl group; a $C_2$-$C_{60}$ heterocyclic group including at least one hetero atom of O, N, S, Si or P; a fused ring group of a $C_5$-$C_{60}$ aliphatic ring and a $C_6$-$C_{60}$ aromatic ring; and a $C_1$-$C_{50}$ alkyl group;

When R' and R" are an aryl group, it is preferably an $C_6$-$C_{30}$ aryl group, more preferably an $C_6$-$C_{25}$ aryl group, $C_6$-$C_{18}$ aryl group, or $C_6$-$C_{12}$ aryl group, for example, it may be phenyl, biphenyl, terphenyl, naphthalene, phenanthrene, chryshene and the like.

When R' and R" are a heterocyclic group, it is preferably a $C_2$-$C_{30}$ heterocyclic group, more preferably a $C_2$-$C_{25}$ heterocyclic group, $C_2$-$C_{18}$ heterocyclic group, or $C_2$-$C_{12}$ heterocyclic group, for example, it may be pyrazine, thiophene, pyridine, pyrimidine, quinoline, pyrimidoindole, 5-phenyl-5H-pyrimido[5,4-b]indole, quinazoline, quinoxaline, benzoquinazoline, carbazole, dibenzoquinazoline, benzofuran, benzothiophene, dibenzofuran, dibenzothiophene, benzothienopyrimidine, benzofuropyrimidine, phenothiazine, phenylphenothiazine, naphthobenzofuran, naphthobenzothiophene, etc.

When R' and R" are a fused ring group, it is preferably a fused ring group of a $C_3$-$C_{30}$ aliphatic ring and an $C_6$-$C_{30}$ aromatic ring, more preferably a fused ring group of an $C_3$-$C_{25}$ aliphatic ring and an $C_6$-$C_{25}$ aromatic ring.

When R' and R" are an alkyl group, it is preferably a $C_1$-$C_{30}$ alkyl group, more preferably a $C_1$-$C_{25}$ alkyl group, a $C_1$-$C_{18}$ alkyl group, or a $C_1$-$C_{12}$ alkyl group. For example, it may be a methyl group, ethyl group, propyl group, isopropyl group, butyl group, t-butyl group, pentyl group, etc.

a, d and e are independently integers from 0 to 5, b, c, aa, ab and ac are independently integers from 0 to 3, f is an integer from 0 to 2, and g and ad are independently an integer from 0 to 4, a is bonded to *b or *c,

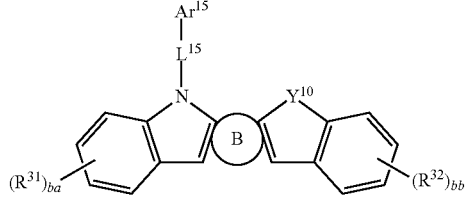

Formula 5

Wherein:

$L^{15}$ is each selected from the group consisting of single bond; an $C_6$-$C_{60}$ arylene group; a fluorenylene group; a $C_2$-$C_{60}$ heterocyclic group including at least one heteroatom of O, N, S, Si or P; and a fused ring group of a $C_3$-$C_{60}$ aliphatic ring and an $C_6$-$C_{60}$ aromatic ring;

When $L^{15}$ is an arylene group, it is preferably an $C_6$-$C_{30}$ arylene group, more preferably an $C_6$-$C_{25}$ arylene group, $C_6$-$C_{18}$ arylene group, or $C_6$-$C_{12}$ arylene group, for example, it may be phenylene, biphenylene, naphthylene, terphenylene, anthracenylene and the like.

When $L^{15}$ is a heterocyclic group, it is preferably a $C_2$-$C_{30}$ heterocyclic group, more preferably a $C_2$-$C_{25}$ heterocyclic group, $C_2$-$C_{18}$ heterocyclic group, or $C_2$-$C_{12}$ heterocyclic group, for example, it may be pyrazine, thiophene, pyridine, pyrimidine, quinoline, pyrimidoindole, 5-phenyl-5H-pyrimido[5,4-b]indole, quinazoline, quinoxaline, benzoquinazoline, carbazole, dibenzoquinazoline, benzofuran, benzothiophene, dibenzofuran, dibenzothiophene, benzothienopyrimidine, benzofuropyrimidine, phenothiazine, phenylphenothiazine, naphthobenzofuran, naphthobenzothiophene, etc.

When $L^{15}$ is a fused ring group, it is preferably a fused ring group of a $C_3$-$C_{30}$ aliphatic ring and an $C_6$-$C_{30}$ aromatic ring, more preferably a fused ring group of an $C_3$-$C_{25}$ aliphatic ring and an $C_6$-$C_{25}$ aromatic ring.

$Ar^{15}$ is each independently selected from the group consisting of an $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; and -L'-N($R^a$)($R^b$);

When $Ar^{15}$ is an aryl group, it is preferably an $C_6$-$C_{30}$ aryl group, more preferably an $C_6$-$C_{25}$ aryl group, $C_6$-$C_{18}$ aryl group, or $C_6$-$C_{12}$ aryl group, for example, it may be phenyl, biphenyl, terphenyl, naphthalene, phenanthrene, chryshene and the like.

When $Ar^{15}$ is a heterocyclic group, it is preferably a $C_2$-$C_{30}$ heterocyclic group, more preferably a $C_2$-$C_{25}$ heterocyclic group, $C_2$-$C_{18}$ heterocyclic group, or $C_2$-$C_{12}$ heterocyclic group, for example, it may be pyrazine, thiophene, pyridine, pyrimidine, quinoline, pyrimidoindole, 5-phenyl-5H-pyrimido[5,4-b]indole, quinazoline, quinoxaline, benzoquinazoline, carbazole, dibenzoquinazoline, benzofuran, benzothiophene, dibenzofuran, dibenzothiophene, benzothienopyrimidine, benzofuropyrimidine, phenothiazine, phenylphenothiazine, naphthobenzofuran, naphthobenzothiophene, etc.

When $Ar^{15}$ is a fused ring group, it is preferably a fused ring group of a $C_3$-$C_{30}$ aliphatic ring and an $C_6$-$C_{30}$ aromatic ring, more preferably a fused ring group of an $C_3$-$C_{25}$ aliphatic ring and an $C_6$-$C_{25}$ aromatic ring.

$Y^{10}$ is O, S, C($R^{51}$)($R^{52}$) or N$R^{53}$,

Ring B is an $C_6$~$C_{20}$ aryl group, $R^{31}$ and $R^{32}$ are each the same or different, and each independently selected from the group consisting of hydrogen; deuterium; halogen; cyano group; a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group; or an adjacent plurality of $R^{31}$ or plurality of $R^{32}$ may be bonded to each other to form a ring, When $R^{31}$ and $R^{32}$ are an aryl group, it is preferably an $C_6$-$C_{30}$ aryl group, more preferably an $C_6$-$C_{25}$ aryl group, $C_6$-$C_{18}$ aryl group, or $C_6$-$C_{12}$ aryl group, for example, it may be phenyl, biphenyl, terphenyl, naphthalene, phenanthrene, chryshene and the like.

When $R^{31}$ and $R^{32}$ are a heterocyclic group, it is preferably a $C_2$-$C_{30}$ heterocyclic group, more preferably a $C_2$-$C_{25}$ heterocyclic group, $C_2$-$C_{18}$ heterocyclic group, or $C_2$-$C_{12}$ heterocyclic group, for example, it may be pyrazine, thiophene, pyridine, pyrimidine, quinoline, pyrimidoindole, 5-phenyl-5H-pyrimido[5,4-b]indole, quinazoline, quinoxaline, benzoquinazoline, carbazole, dibenzoquinazoline, benzofuran, benzothiophene, dibenzofuran, dibenzothiophene, benzothienopyrimidine, benzofuropyrimidine, phenothiazine, phenylphenothiazine, naphthobenzofuran, naphthobenzothiophene, etc.

When $R^{31}$ and $R^{32}$ are a fused ring group, it is preferably a fused ring group of a $C_3$-$C_{30}$ aliphatic ring and an $C_6$-$C_{30}$ aromatic ring, more preferably a fused ring group of an $C_5$-$C_{25}$ aliphatic ring and an $C_6$-$C_{25}$ aromatic ring.

When $R^{31}$ and $R^{32}$ are an alkyl group, it is preferably a $C_1$-$C_{30}$ alkyl group, more preferably a $C_1$-$C_{25}$ alkyl group, a $C_1$-$C_{18}$ alkyl group, or a $C_1$-$C_{12}$ alkyl group. For example, it may be a methyl group, ethyl group, propyl group, isopropyl group, butyl group, t-butyl group, pentyl group, etc.

When $R^{31}$ and $R^{32}$ are an alkoxyl group, it is preferably a $C_1$-$C_{25}$ alkoxyl group, a $C_1$-$C_{18}$ alkoxyl group or a $C_1$-$C_{12}$ alkoxyl group.

When $R^{31}$ and $R^{32}$ are an aryloxy group, it is preferably a $C_6$-$C_{25}$ aryloxy group, a $C_6$-$C_{18}$ aryloxy group or a $C_6$-$C_{12}$ aryloxy group.

ba and bb are each an integer from 0 to 4,

L' is each selected from the group consisting of single bond; an $C_6$-$C_{60}$ arylene group; a fluorenylene group; a $C_2$-$C_{60}$ heterocyclic group including at least one heteroatom of O, N, S, Si or P; and a $C_3$-$C_{60}$ aliphatic ring;

When L' is an arylene group, it is preferably an $C_6$-$C_{30}$ arylene group, more preferably an $C_6$-$C_{25}$ arylene group, $C_6$-$C_{18}$ arylene group, or $C_6$-$C_{12}$ arylene group, for example, it may be phenylene, biphenylene, naphthylene, terphenylene, anthracenylene and the like.

When L' is a heterocyclic group, it is preferably a $C_2$-$C_{30}$ heterocyclic group, more preferably a $C_2$-$C_{25}$ heterocyclic group, $C_2$-$C_{18}$ heterocyclic group, or $C_2$-$C_{12}$ heterocyclic group, for example, it may be pyrazine, thiophene, pyridine, pyrimidine, quinoline, pyrimidoindole, 5-phenyl-5H-pyrimido[5,4-b]indole, quinazoline, quinoxaline, benzoquinazoline, carbazole, dibenzoquinazoline, benzofuran, benzothiophene, dibenzofuran, dibenzothiophene, benzothienopyrimidine, benzofuropyrimidine, phenothiazine, phenylphenothiazine, naphthobenzofuran, naphthobenzothiophene, etc.

When L' is an aliphatic ring group, preferably a $C_3$-$C_{30}$ aliphatic ring group, more preferably a $C_3$-$C_{25}$ aliphatic ring group, $C_3$-$C_{18}$ aliphatic ring group or $C_5$-$C_{12}$ aliphatic ring group, and may specifically be cyclobutane, cyclopentane, cyclohexane, bicycloheptane, adamantyl, etc.

$R^{51}$, $R^{52}$, $R^{53}$, $R^a$ and $R^b$ are each independently selected from the group consisting of a $C_6$-$C_{60}$ aryl group; a fluorenyl group; a $C_2$-$C_{60}$ heterocyclic group including at least one hetero atom of O, N, S, Si or P; a fused ring group of a $C_5$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and a $C_5$-$C_{60}$ aliphatic ring; or $R^{51}$ and $R^{52}$ can be bonded to each other to form a spiro ring, When $R^{51}$, $R^{52}$, $R^{53}$, $R^a$ and $R^b$ are an aryl group, it is preferably an $C_6$-$C_{30}$ aryl group, more preferably an $C_6$-$C_{25}$ aryl group, $C_6$-$C_{18}$ aryl group, or $C_6$-$C_{12}$ aryl group, for example, it may be phenyl, biphenyl, terphenyl, naphthalene, phenanthrene, chryshene and the like.

When $R^{51}$, $R^{52}$, $R^{53}$, $R^a$ and $R^b$ are a heterocyclic group, it is preferably a $C_2$-$C_{30}$ heterocyclic group, more preferably a $C_2$-$C_{25}$ heterocyclic group, $C_2$-$C_{18}$ heterocyclic group, or $C_2$-$C_{12}$ heterocyclic group, for example, it may be pyrazine, thiophene, pyridine, pyrimidine, quinoline, pyrimidoindole, 5-phenyl-5H-pyrimido[5,4-b]indole, quinazoline, quinoxaline, benzoquinazoline, carbazole, dibenzoquinazoline, benzofuran, benzothiophene, dibenzofuran, dibenzothiophene, benzothienopyrimidine, benzofuropyrimidine, phenothiazine, phenylphenothiazine, naphthobenzofuran, naphthobenzothiophene, etc.

When $R^{51}$, $R^{52}$, $R^{53}$, $R^a$ and $R^b$ are a fused ring group, it is preferably a fused ring group of a $C_3$-$C_{30}$ aliphatic ring and an $C_6$-$C_{30}$ aromatic ring, more preferably a fused ring group of an $C_5$-$C_{25}$ aliphatic ring and an $C_6$-$C_{25}$ aromatic ring.

When $R^{51}$, $R^{52}$, $R^{53}$, $R^a$ and $R^b$ are an alkyl group, it is preferably a $C_1$-$C_{30}$ alkyl group, more preferably a $C_1$-$C_{25}$ alkyl group, a $C_1$-$C_{18}$ alkyl group, or a $C_1$-$C_{12}$ alkyl group. For example, it may be a methyl group, ethyl group, propyl group, isopropyl group, butyl group, t-butyl group, pentyl group, etc.

When $R^{51}$, $R^{52}$, $R^{53}$, $R^a$ and $R^b$ are an alkoxyl group, it is preferably a $C_1$-$C_{25}$ alkoxyl group, a $C_1$-$C_{18}$ alkoxyl group or a $C_1$-$C_{12}$ alkoxyl group.

When $R^{51}$, $R^{52}$, $R^{53}$, $R^a$ and $R^b$ are an aryloxy group, it is preferably a $C_6$-$C_{25}$ aryloxy group, a $C_6$-$C_{18}$ aryloxy group or a $C_6$-$C_{12}$ aryloxy group.

refers to position to be bonded, wherein the aryl group, arylene group, heterocyclic group, fluorenyl group, fluorenylene group, fused ring group, aliphatic ring group, alkyl group, alkenyl group, alkynyl group, alkoxy group and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; a $C_3$-$C_{20}$ aliphatic ring; $C_7$-$C_{20}$ arylalkyl group; $C_8$-$C_{20}$ arylalkenyl group; $C_7$-$C_{20}$ alkylaryl group; and -L'-N($R^a$)($R^b$); also the hydrogen of these substituents may be further substituted with one or more deuteriums, and the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

Preferably, the composition for an organic electronic element may be used as a host for an emitting layer.

Also, Formula 1 is represented by the following formula 1-1 or formula 1-2:

Formula 1-1

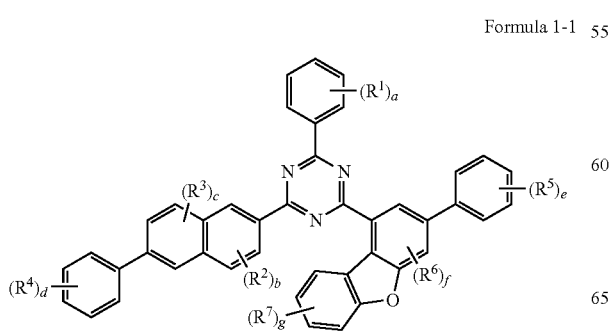

Formula 1-2

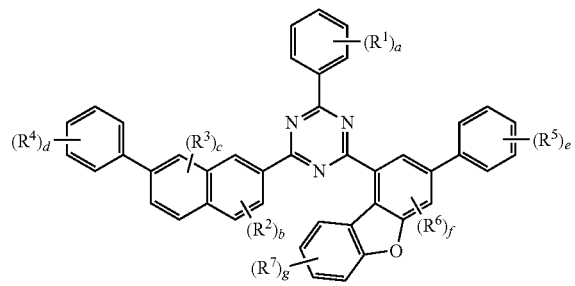

Wherein: $R^1$, $R^2$, $R^3$, $R^4$, $R^5$, $R^6$, $R^7$, a, b, c, d, e, f and g are the same as defined in Formula 1.

Additionally, any one of $R^1$, $R^2$, $R^3$, $R^4$, $R^5$, $R^6$ and $R^7$ is deuterium. Preferably, at least one of $R^4$ and $R^5$ may be deuterium.

Also, Formula 2 is represented by any one of the following formulas 2-A to 2-D.

Formula 2-A

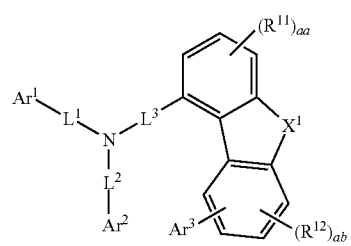

Formula 2-B

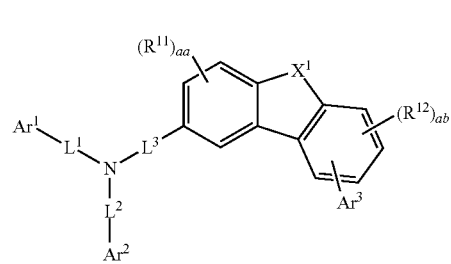

Formula 2-C

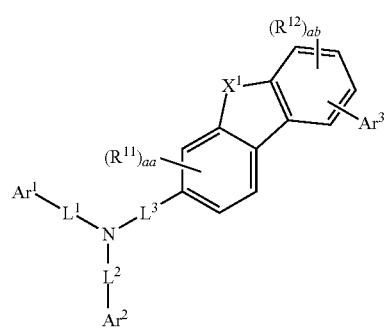

Formula 2-D
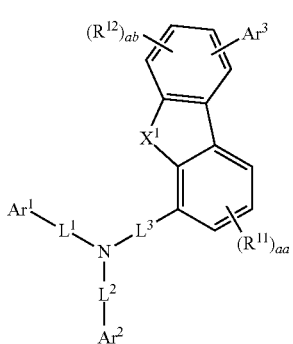
Wherein, $X^1$, $Ar^1$, $Ar^2$, $Ar^3$, $L^1$, $L^2$, $L^3$, $R^{11}$, $R^{12}$, aa and ab are the same as defined in Formula 2.
Formula 2 may preferably be selected from the group consisting of the following formulas 2-A-1 to 2-A-4, formulas 2-B-1 to 2-B-4, formulas 2-C-1 to 2-C-4, and formulas 2-D-1 to 2-D-4.
Formula 2-A-1
Formula 2-A-2
Formula 2-A-3
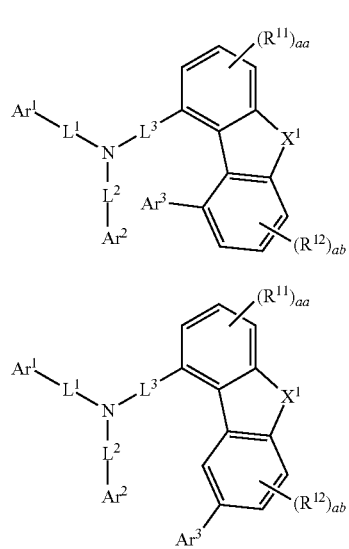
Formula 2-A-4
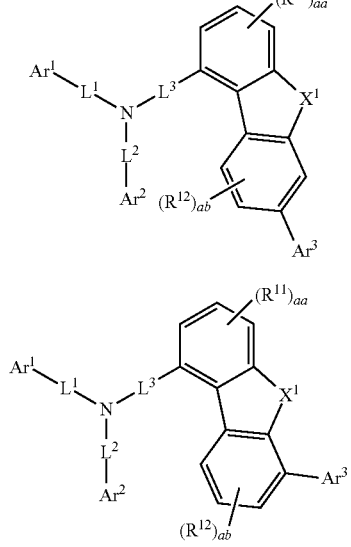
Formula 2-B-1
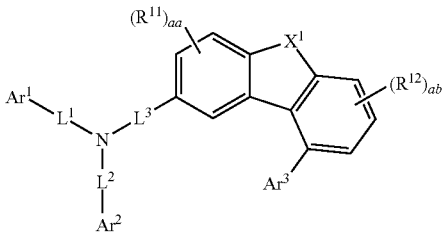
Formula 2-B-2
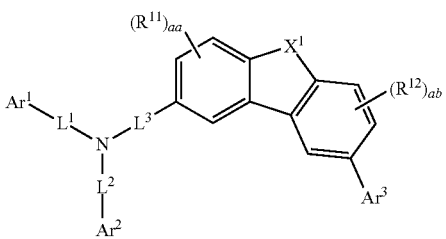
Formula 2-B-3
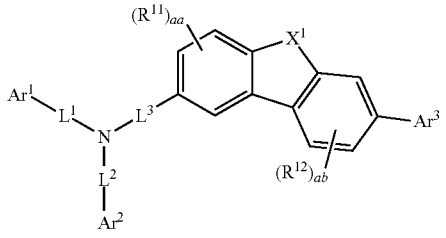
Formula 2-B-4
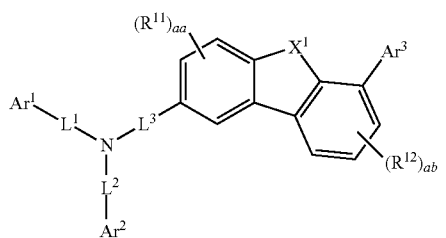
Formula 2-C-1
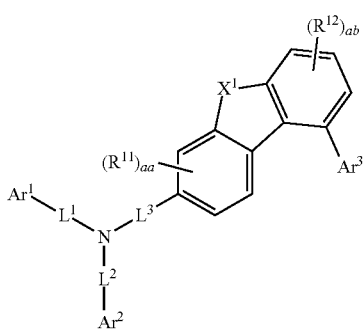

-continued
Formula 2-C-2
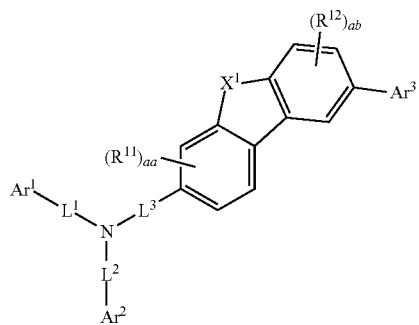
Formula 2-C-3
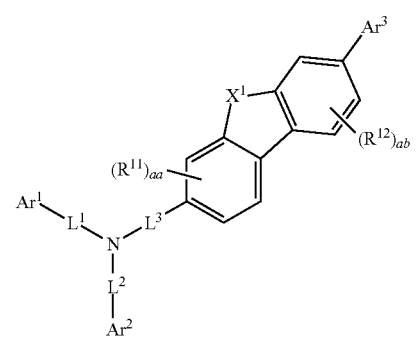
Formula 2-C-4
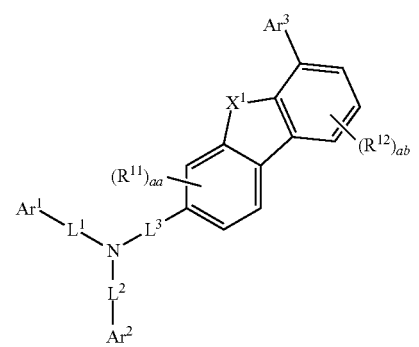
Formula 2-D-1
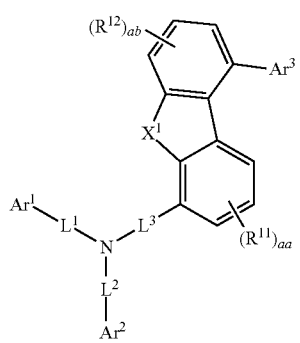
-continued
Formula 2-D-2
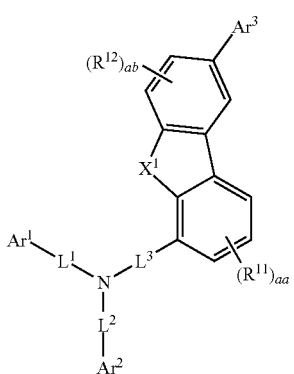
Formula 2-D-3
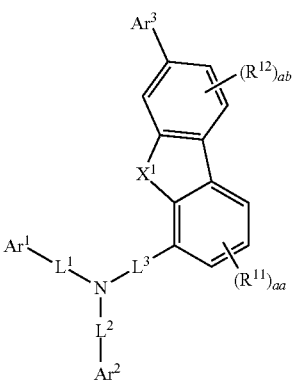
Formula 2-D-4
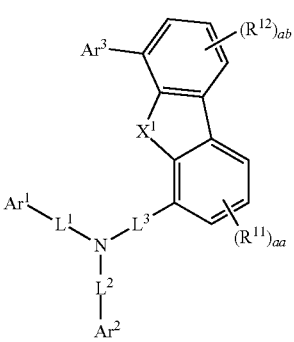
Wherein, $X^1$, $Ar^1$, $Ar^2$, $Ar^3$, $L^1$, $L^2$, $L^3$, $R^{11}$, $R^{12}$, aa and ab are the same as defined in Formula 2.
Formula 2-1 is represented by any one of the formulas 2-1-A to 2-1-D.
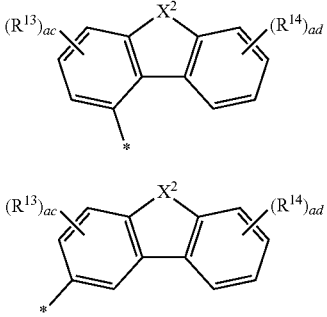
Formula 2-1-A
Formula 2-1-B

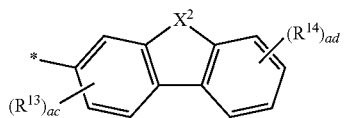
Formula 2-1-C
Formula 2-1-D
Wherein, $X^2$, $R^{13}$, $R^{14}$, ac, ad and * are the same as defined in Formula 2-1.
Specifically, the compound represented by Formula 1 may be any one of the following compounds P-1 to P-40, but is not limited thereto.
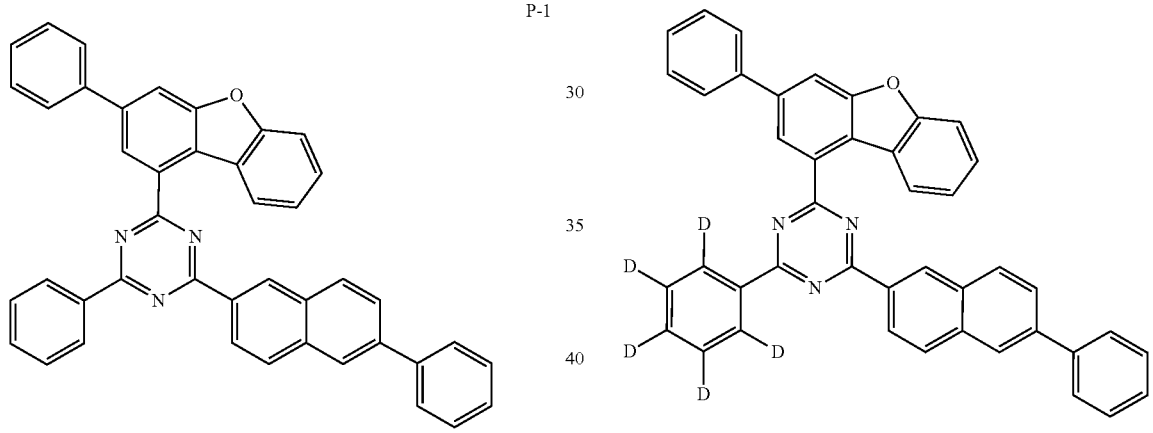
P-1
P-2
P-3
P-4
P-5
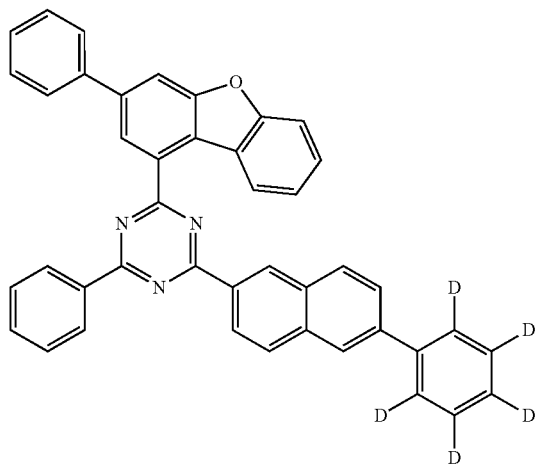
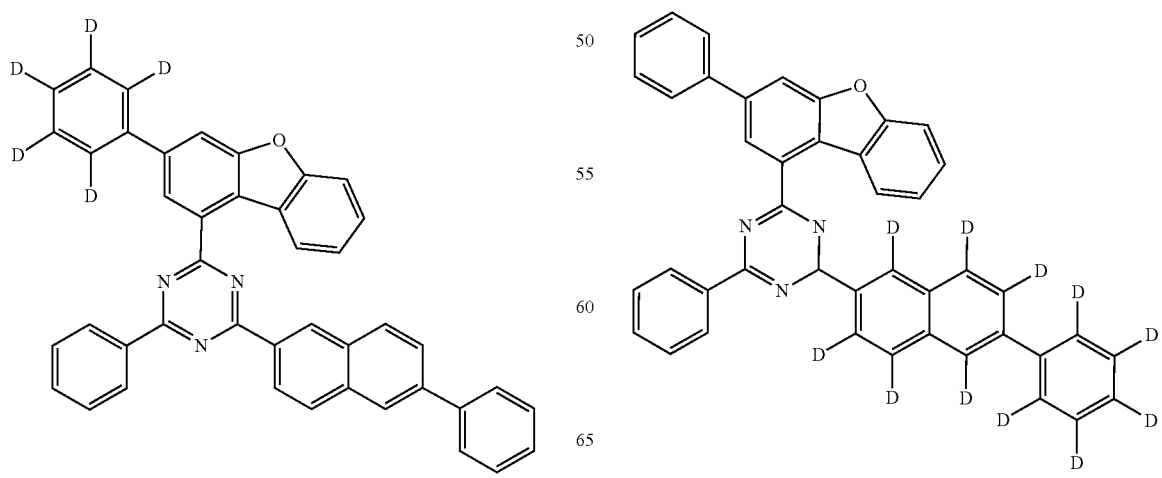

P-6
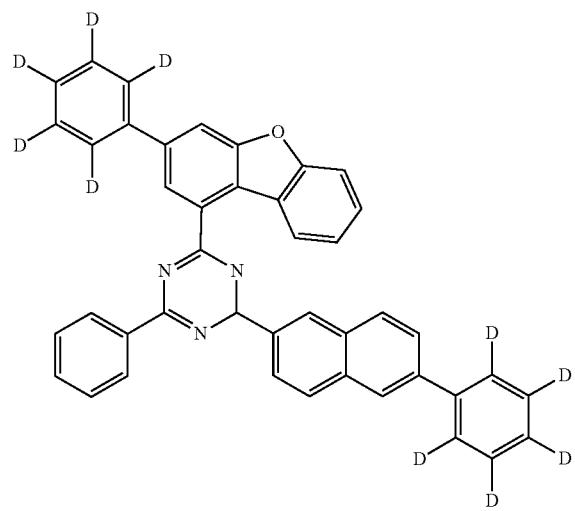
P-7
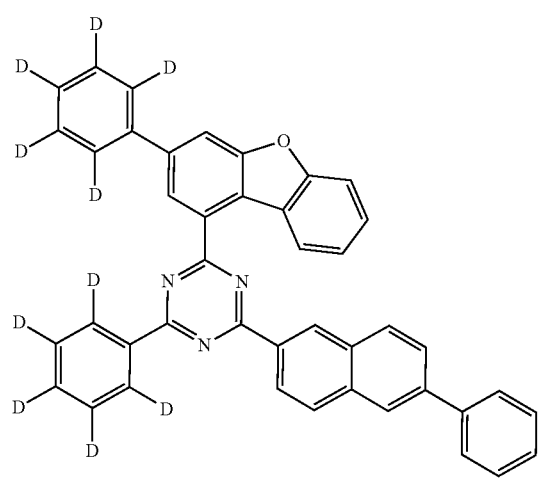
P-8
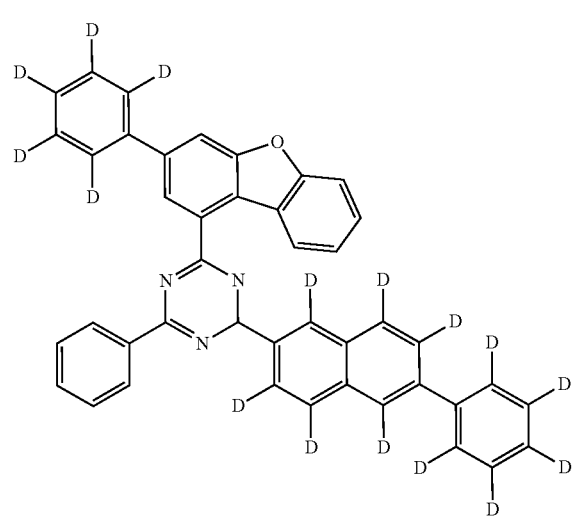
P-9
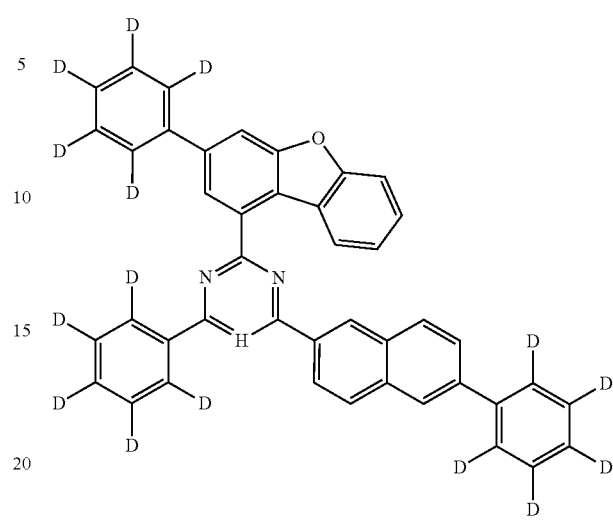
P-10
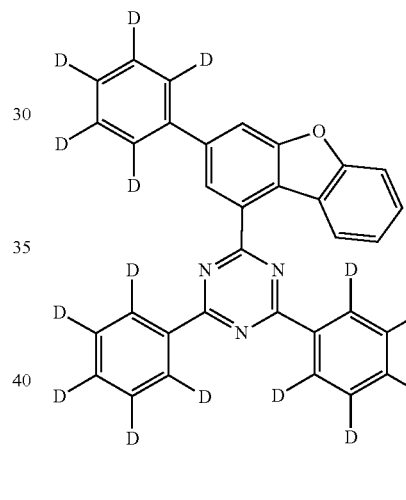
P-11
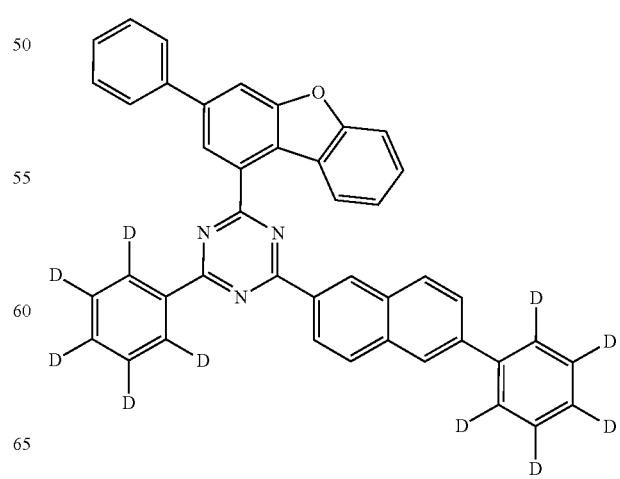

P-12
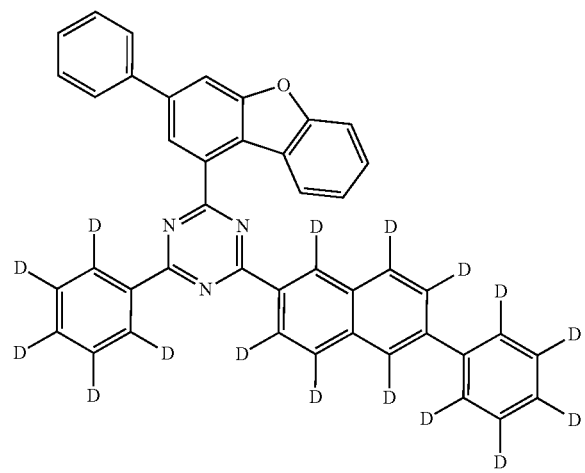
P-13
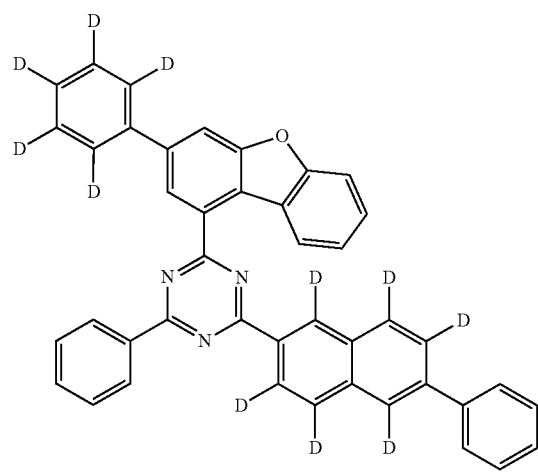
P-14
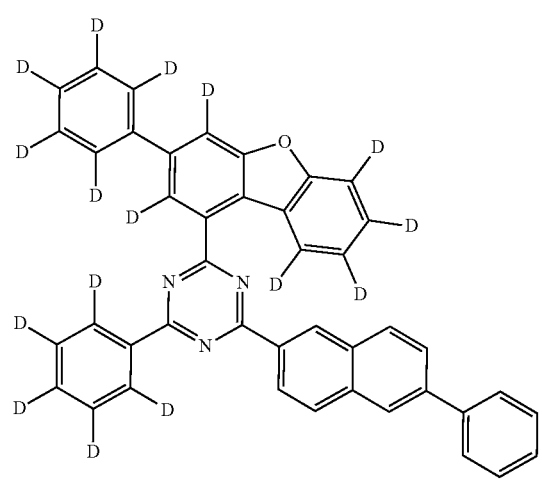
P-15
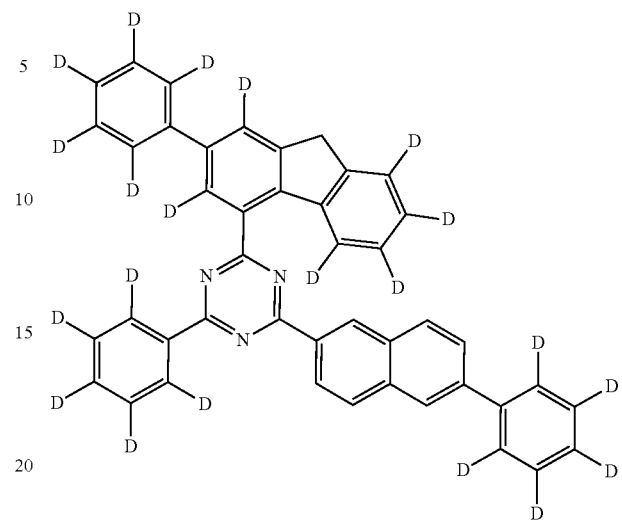
P-16
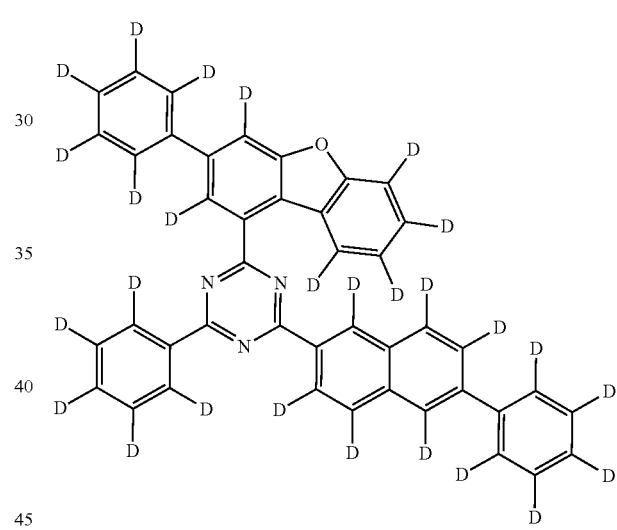
P-17
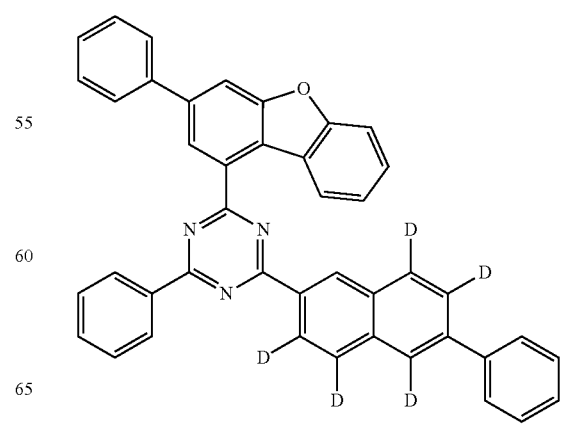

P-18
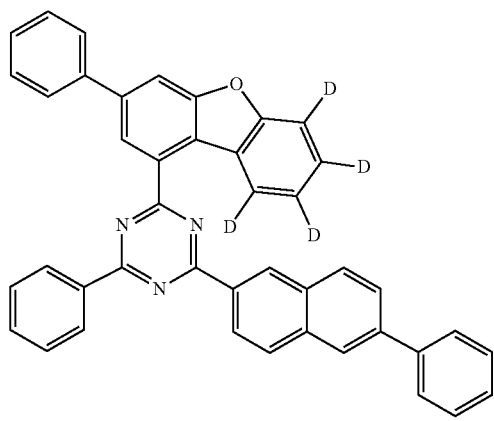
P-19
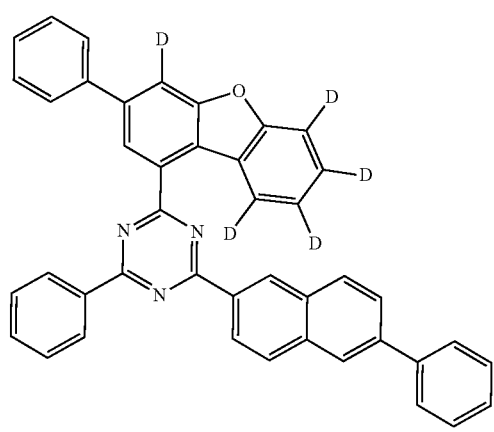
P-20
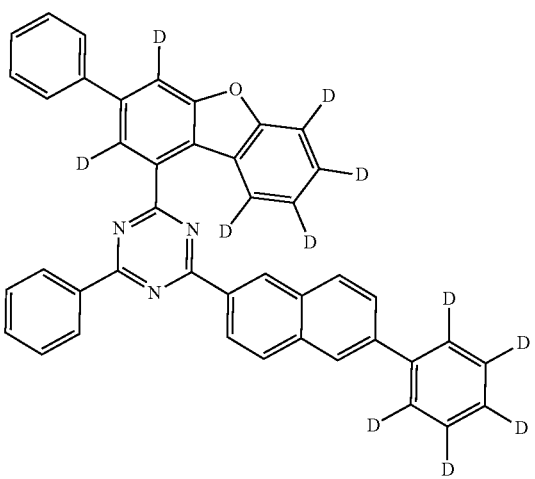
P-21
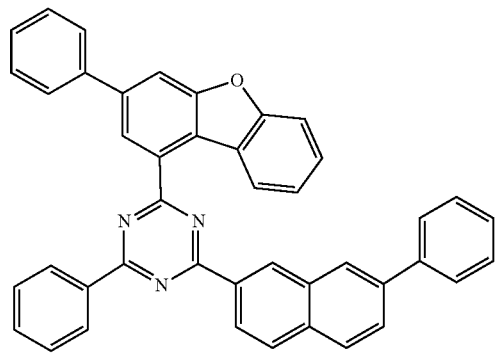
P-22
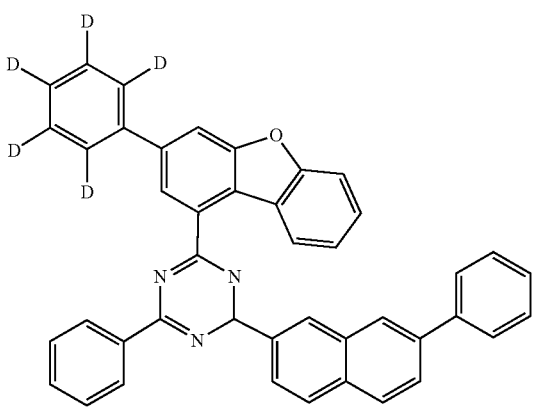
P-23
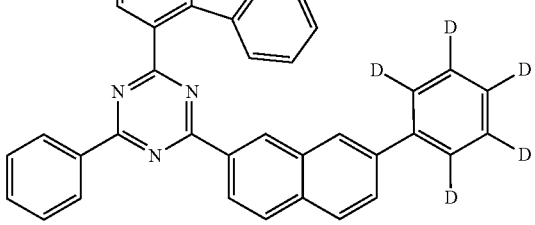
P-24
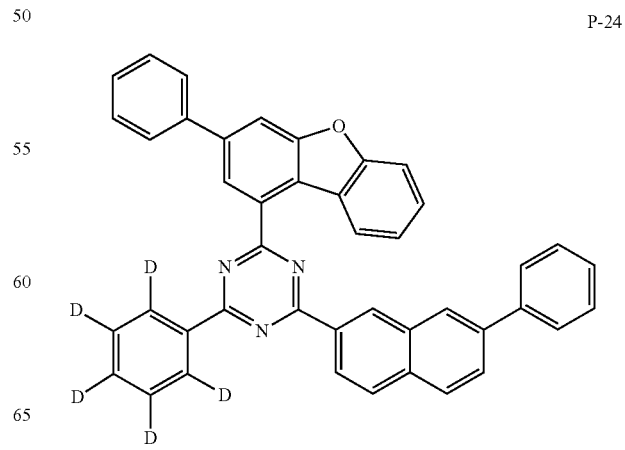

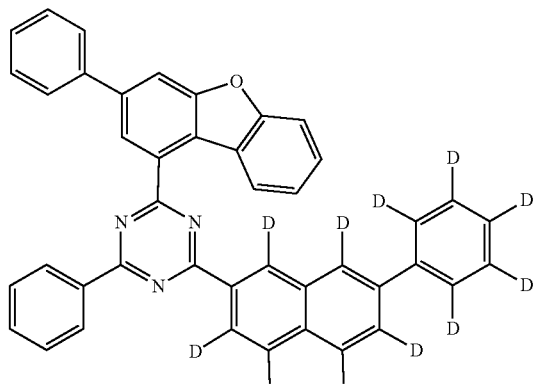
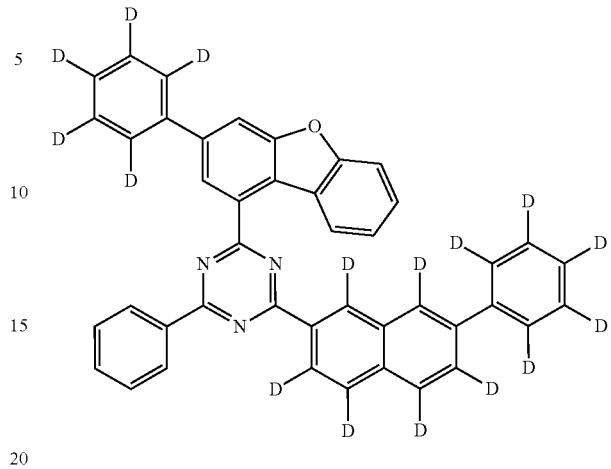

P-31
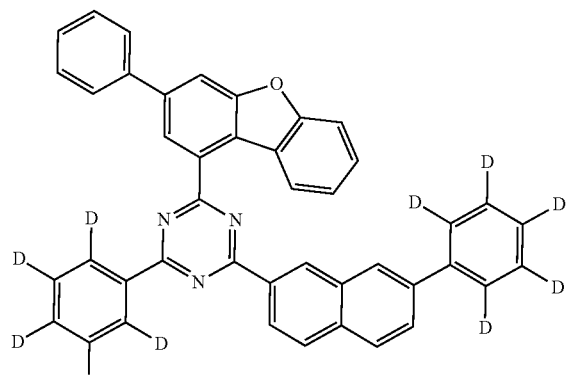
P-34
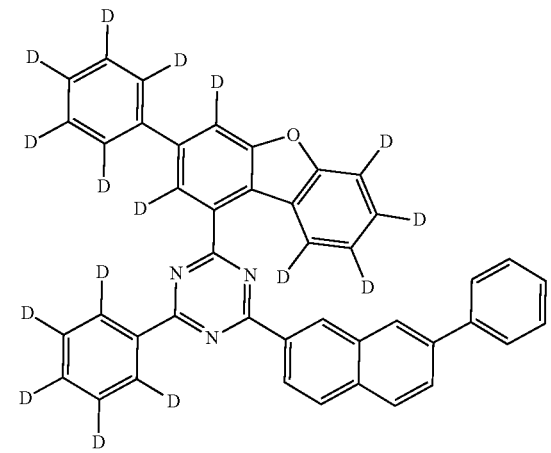
P-32
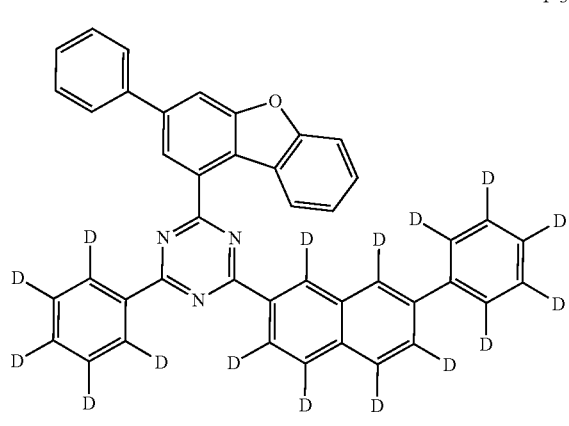
P-35
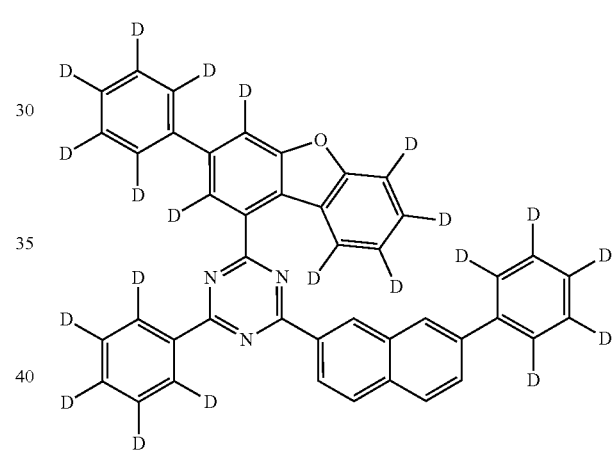
P-33
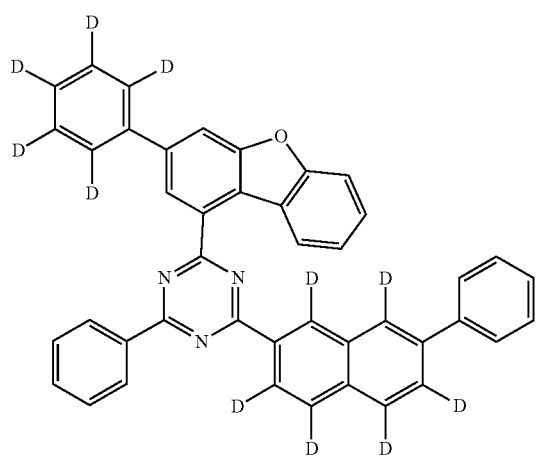
P-36
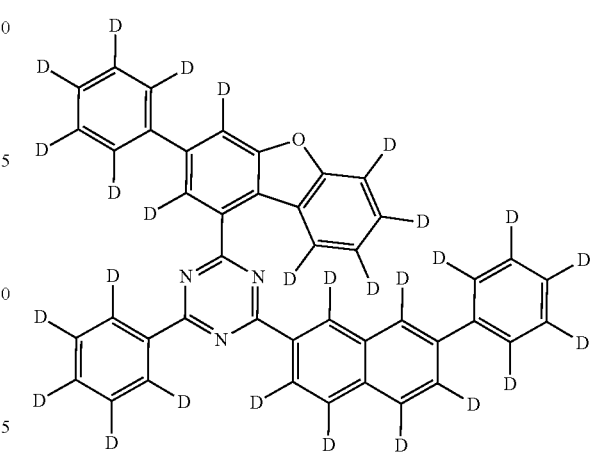

P-37
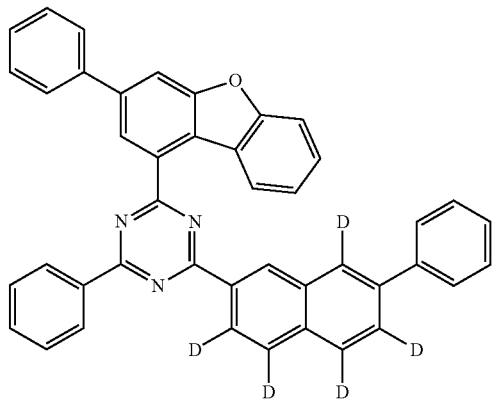
P-38
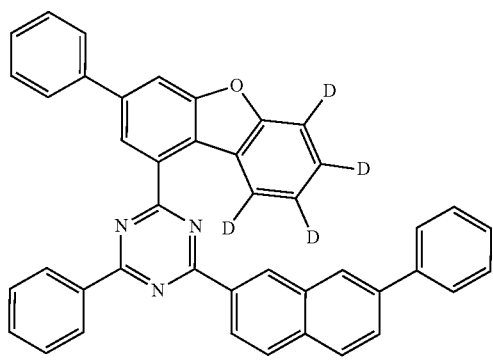
P-39
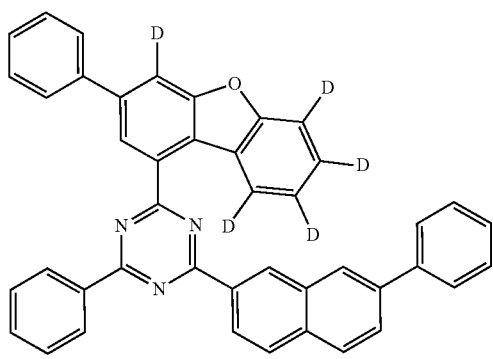
P-40
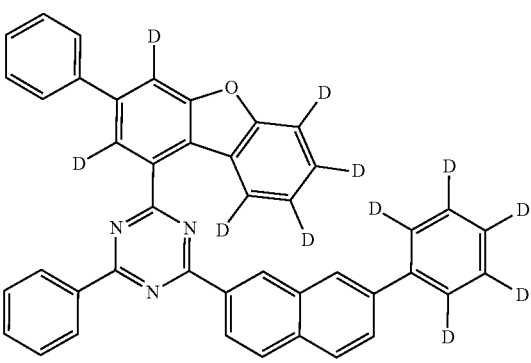
Formula 5 may be represented by any one of the following Formulas 5-1 to 5-6.
<Formula 5-1>
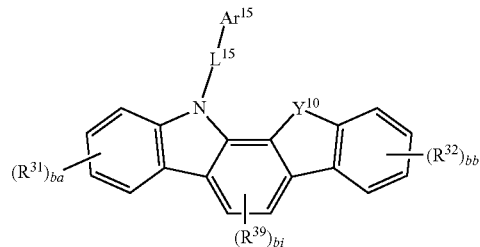
<Formula 5-2>
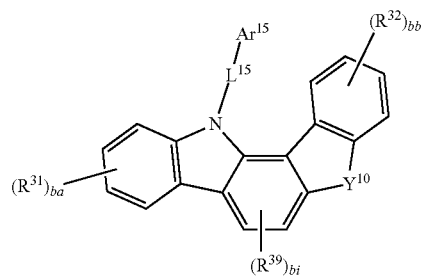
<Formula 5-3>
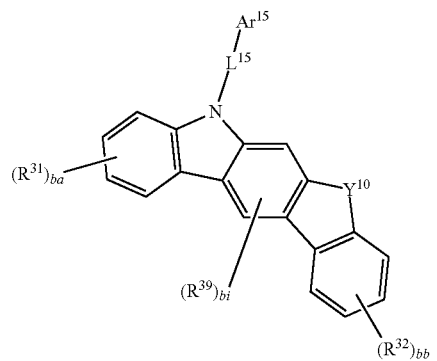
<Formula 5-4>
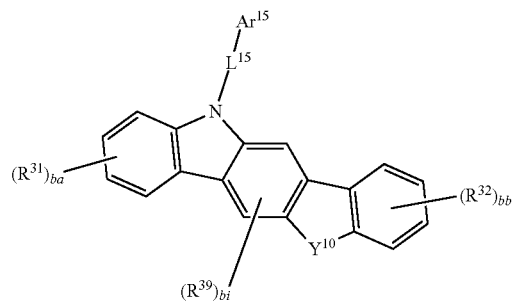

<Formula 5-5>

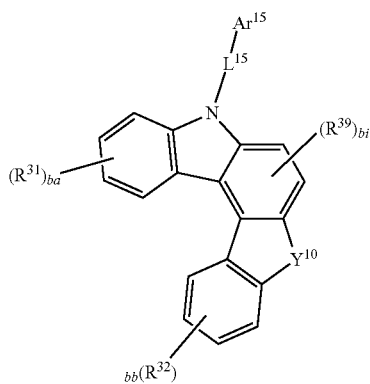

<Formula 5-6>

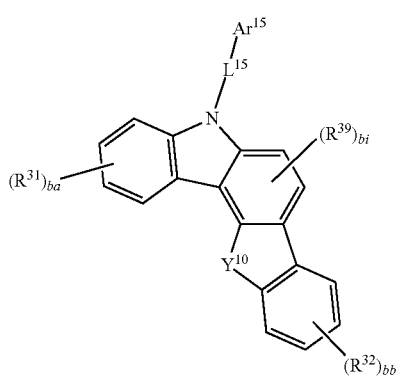

Wherein:
$Y^{10}, Ar^{15}, L^{15}, R^{31}, R^{32}$, ba and bb are the same as defined in Formula 5,
$R^{39}$ is the same as the definition of $R^{31}$, or a plurality of adjacent $R^{39}$s can be bonded to each other to form a ring,
bi is an integer from 0 to 2.

Formula 5 may be represented by any one of the following Formulas 5-7 to 5-9.

<Formula 5-7>

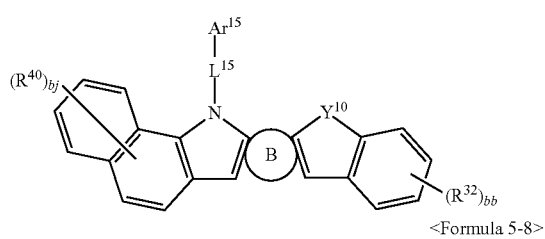

<Formula 5-8>

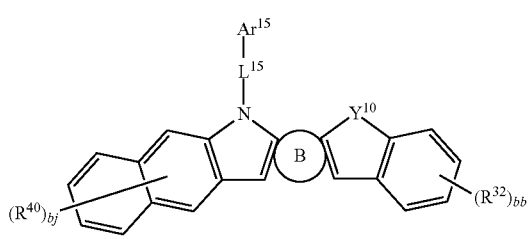

<Formula 5-9>

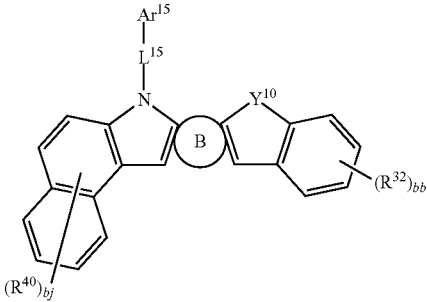

Wherein:
$Y^{10}$, Ring B, $Ar^{15}, L^{15}, R^{32}$ and bb are the same as defined in Formula 5,
$R^{40}$ is the same as the definition of $R^{31}$, or a plurality of adjacent $R^{40}$s can be bonded to each other to form a ring,
bj is an integer from 0 to 6.

Formula 5 may be represented by any one of the following Formulas 5-10 to 5-12.

<Formula 5-10>

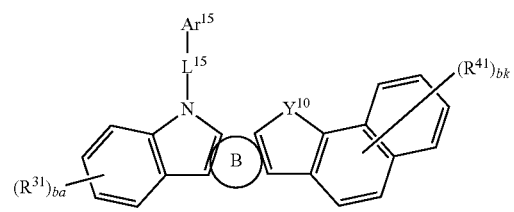

<Formula 5-11>

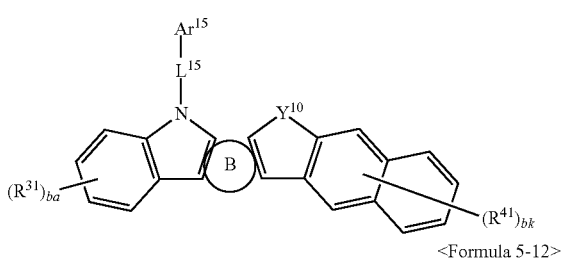

<Formula 5-12>

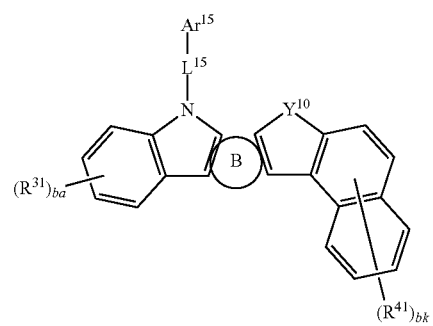

Wherein:
$Y^{10}$, Ring B, $Ar^{15}, L^{16}, R^{31}$ and ba are the same as defined in Formula 5,
$R^{41}$ is the same as the definition of $R^{31}$, or a plurality of adjacent $R^{41}$s can be bonded to each other to form a ring,
bk is an integer from 0 to 6.

Formula 5 may be represented by any one of the following Formulas 5-13 to 5-18.

<Formula 5-13>

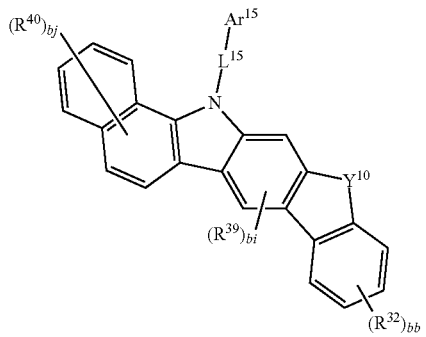

<Formula 5-14>

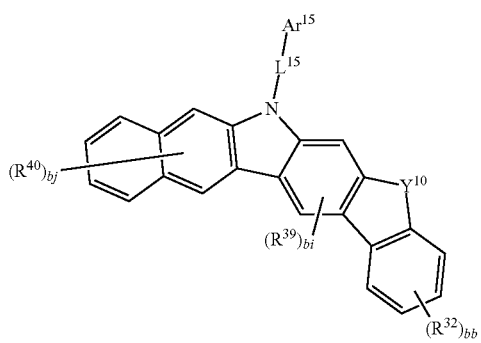

<Formula 5-15>

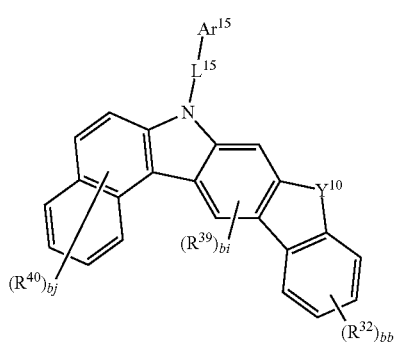

<Formula 5-16>

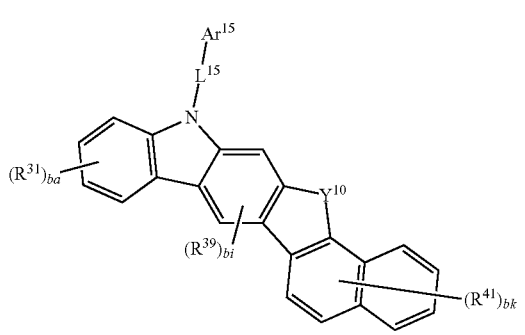

<Formula 5-17>

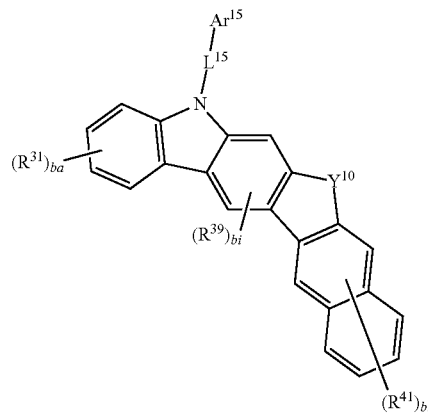

<Formula 5-18>

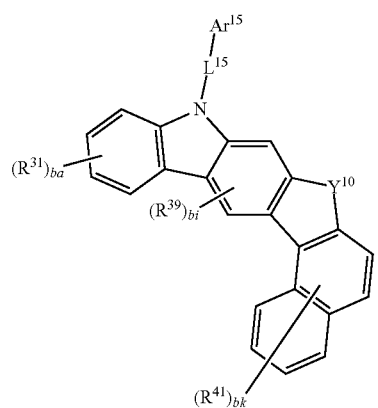

Wherein:

$Y^{10}$, $Ar^{15}$, $L^{15}$, $R^{31}$, $R^{32}$, ba and bb are the same as defined in Formula 5, $R^{39}$, $R^{40}$ and $R^{41}$ are the same as the definition of $R^{31}$, or a plurality of adjacent $R^{39}$s or a plurality of adjacent $R^{40}$s or a plurality of adjacent $R^{41}$s can be bonded to each other to form a ring, bi is an integer from 0 to 2, bj and bk are each an integer from 0 to 6.

Formula 5 may be represented by Formula 5-19.

<Formula 5-19>

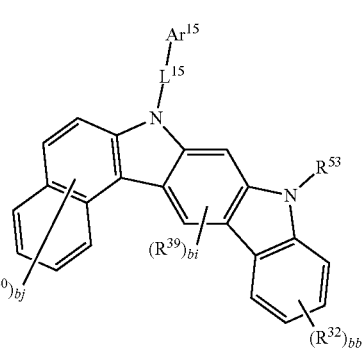

Wherein:

$Ar^{15}$, $L^{15}$, $R^{32}$, $R^{53}$ and bb are the same as defined in Formula 5, $R^{39}$ and $R^{40}$ are the same as the definition of $R^{31}$, or a plurality of adjacent $R^{39}$s or a plurality of adjacent $R^{40}$s can be bonded to each other to form a ring, bi is an integer from 0 to 2, bj is an integer from 0 to 6.

Specifically, the compound represented by Formula 2 may be a compound represented by any one of the following compounds H-1 to H-132, but is not limited thereto.

H-1
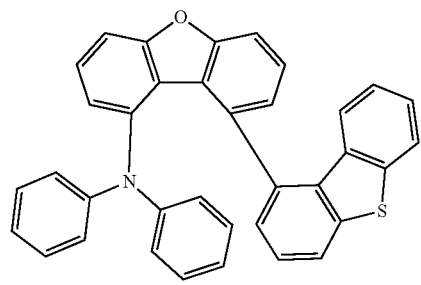

H-2
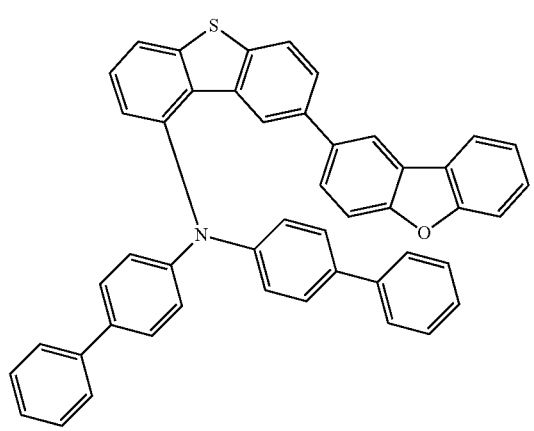

H-3
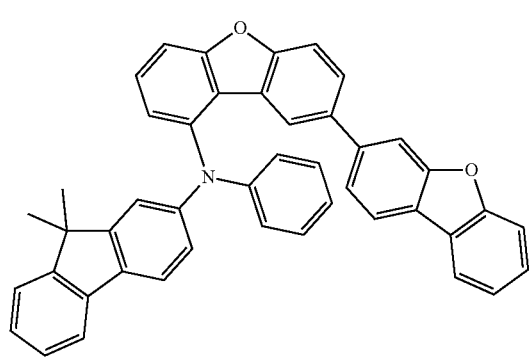

H-4
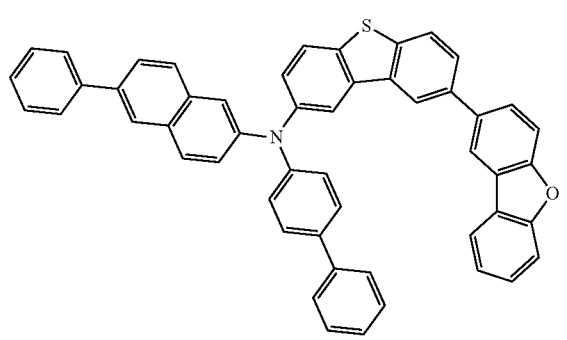

H-5
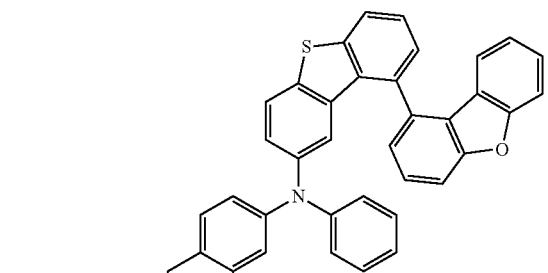

H-6
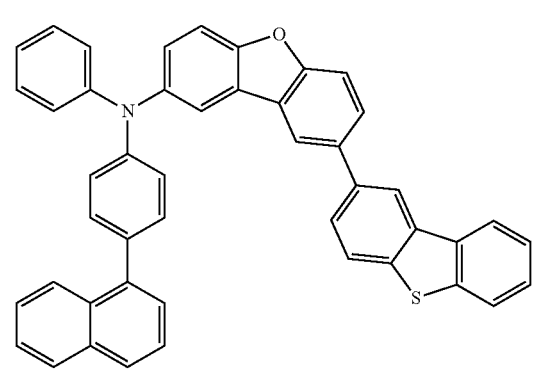

H-7
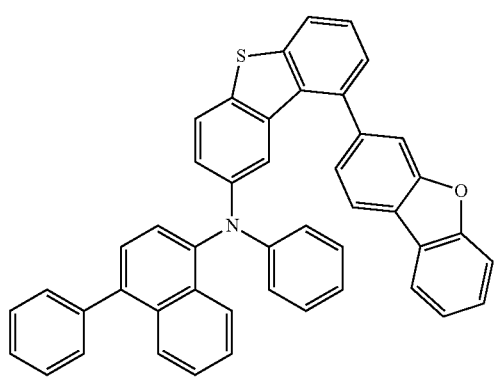

H-8
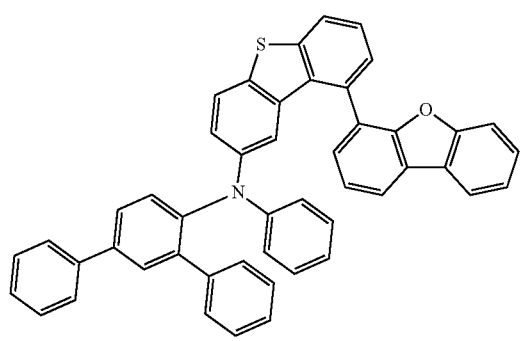

H-9
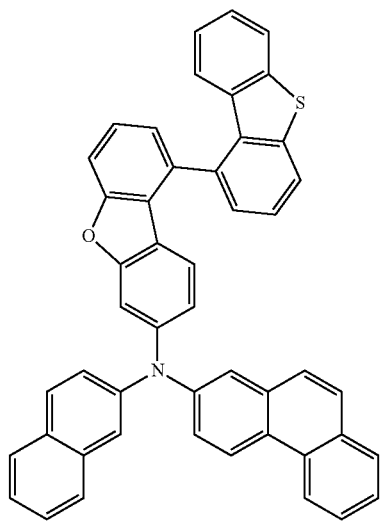
H-10
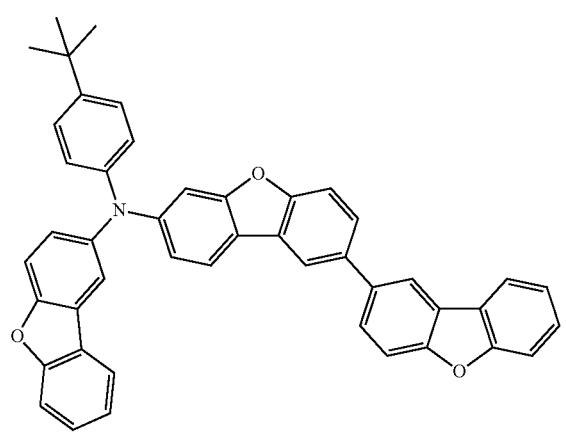
H-11
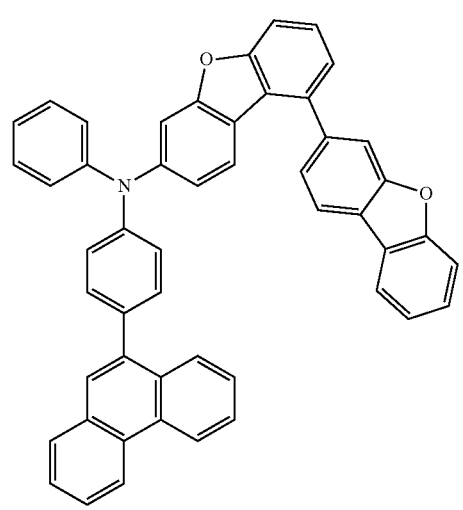
H-12
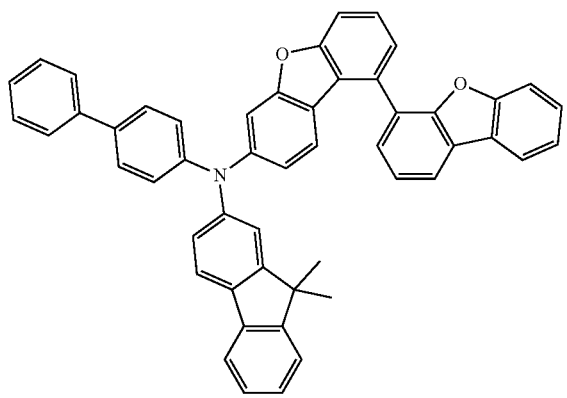
H-13
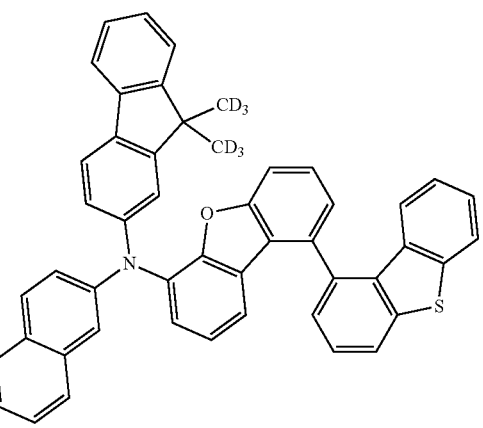
H-14
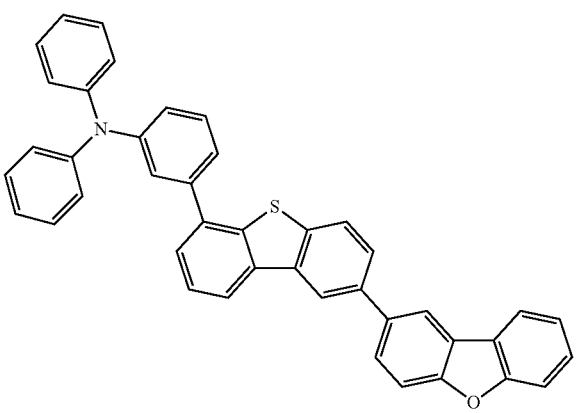

H-15
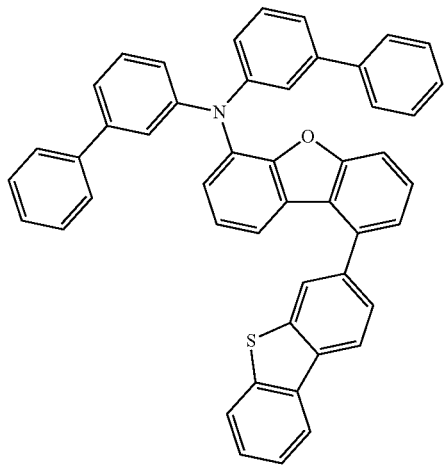
H-18
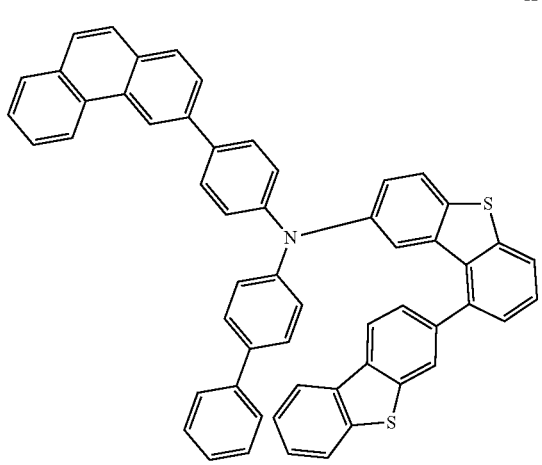
H-16
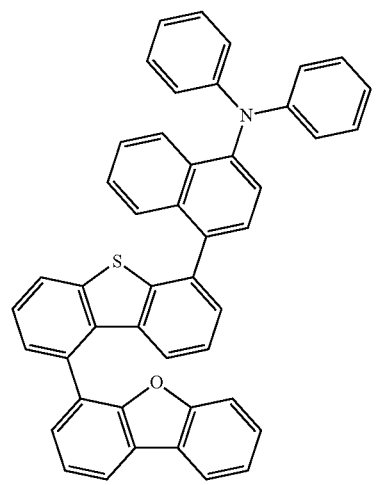
H-19
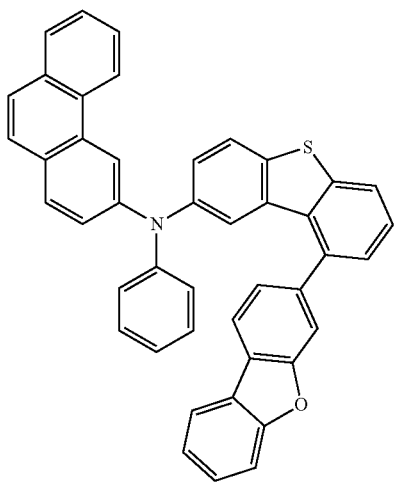
H-17
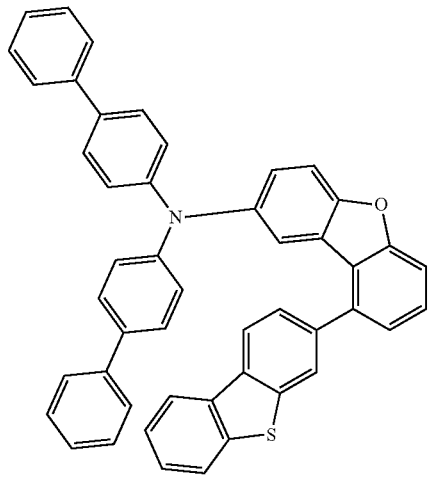
H-20
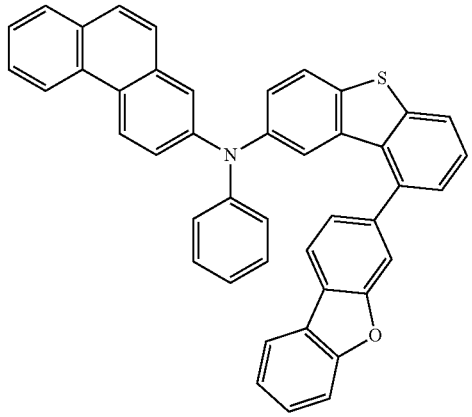

-continued
H-21
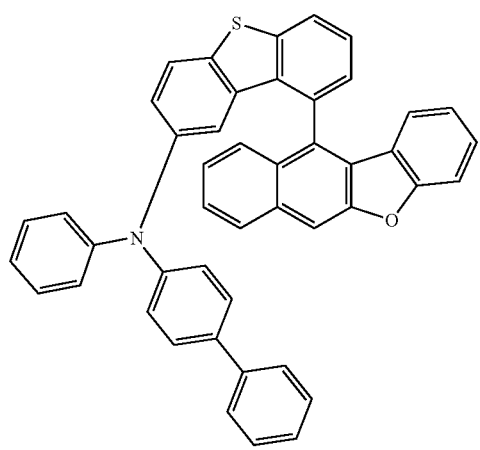
H-22
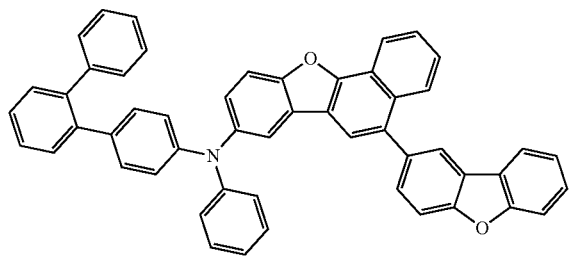
H-23
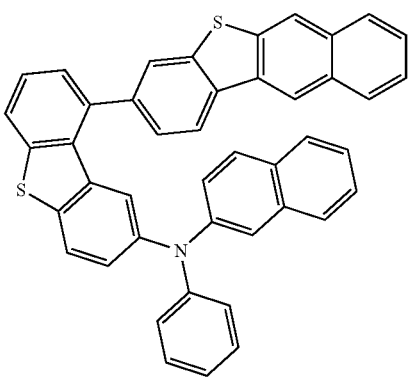
H-24
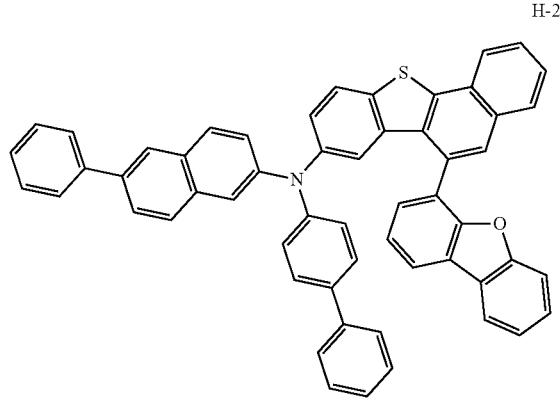
H-25
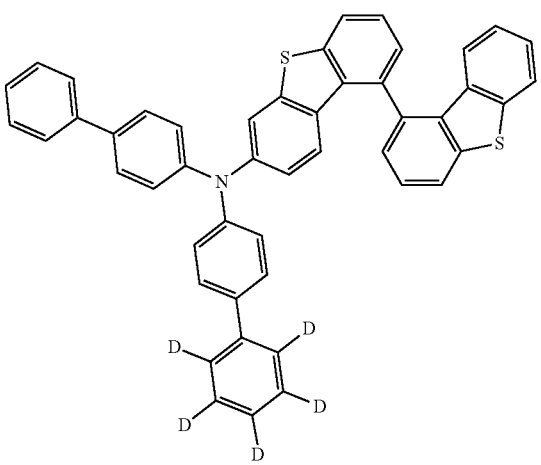
H-26
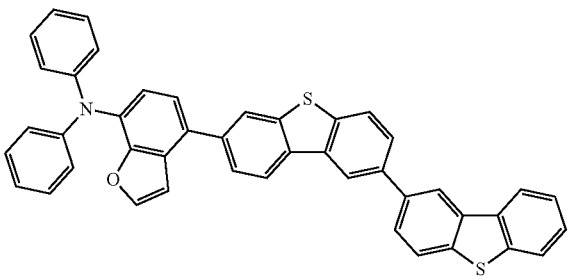
H-27
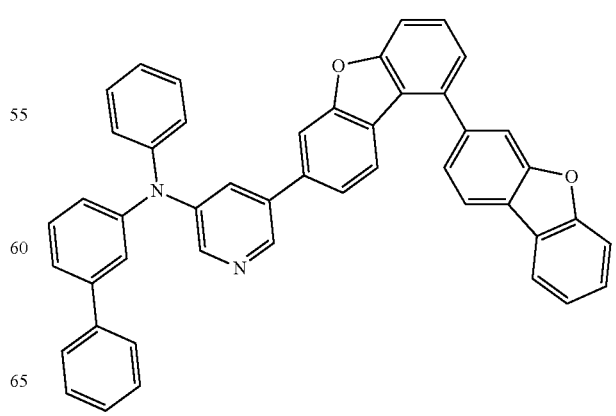

H-28
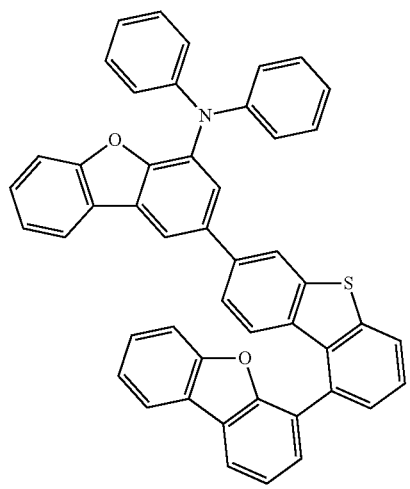
H-29
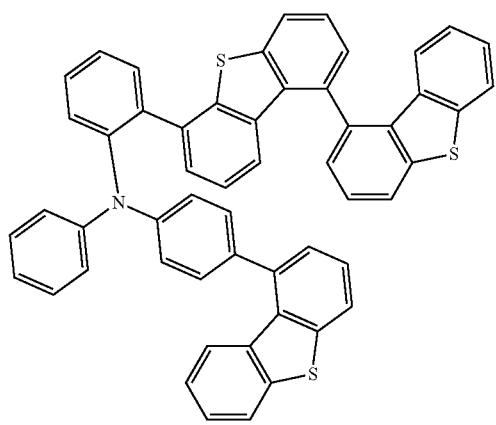
H-30
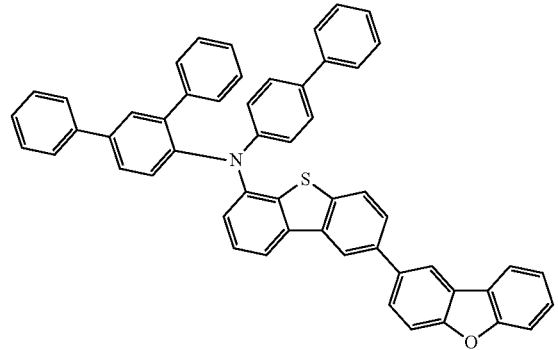
H-31
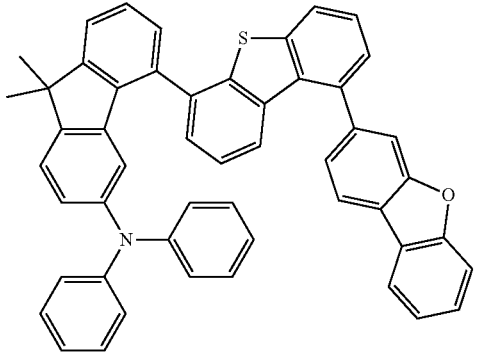
H-32
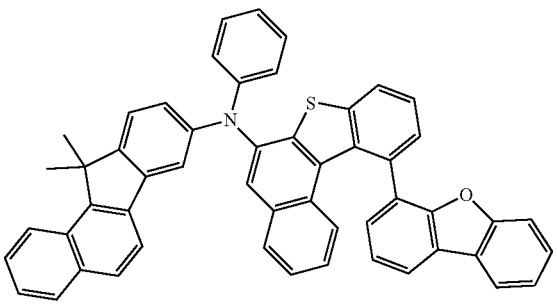
H-33
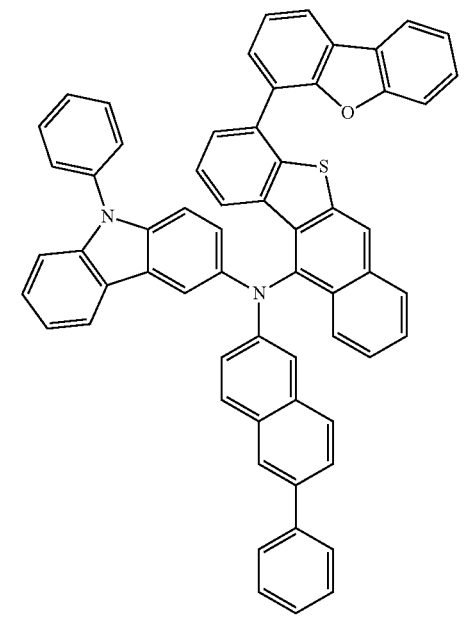
H-34
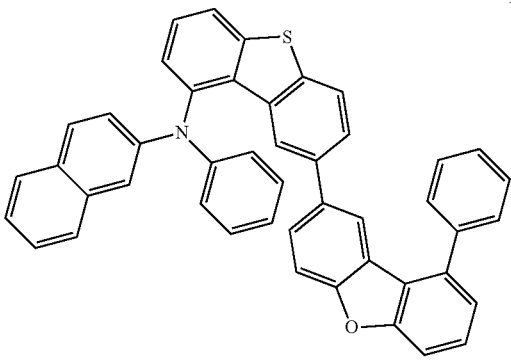

H-35
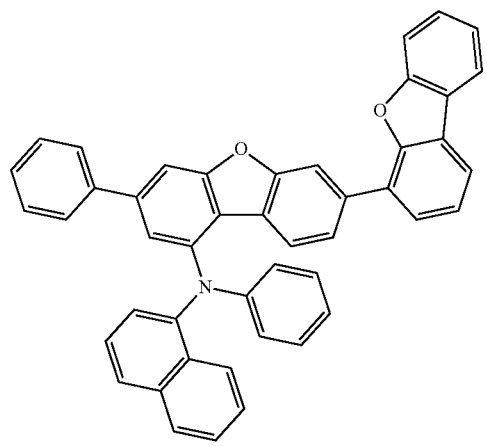
H-36
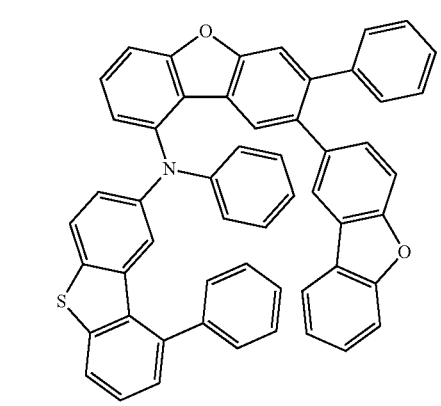
H-37
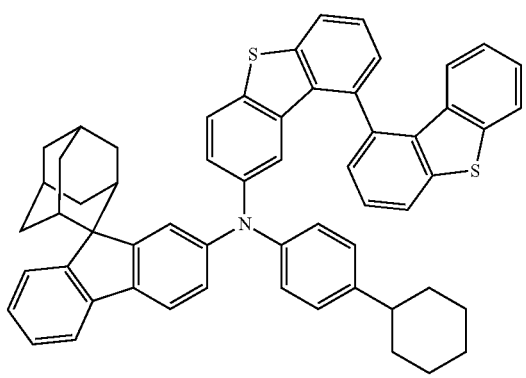
H-38
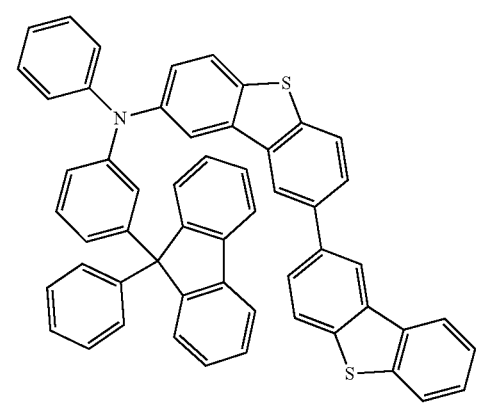
H-39
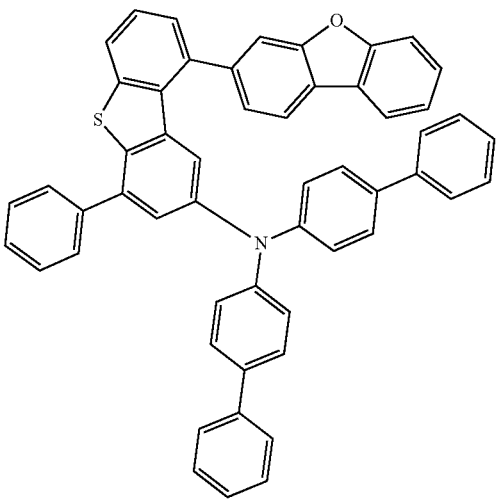
H-40
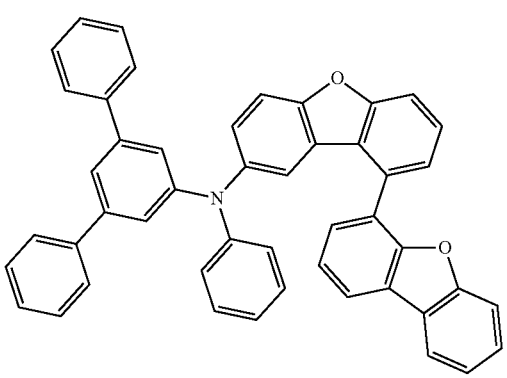
H-41
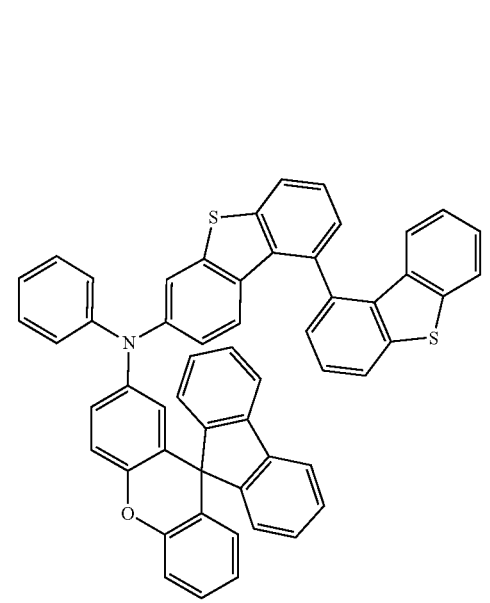

H-42
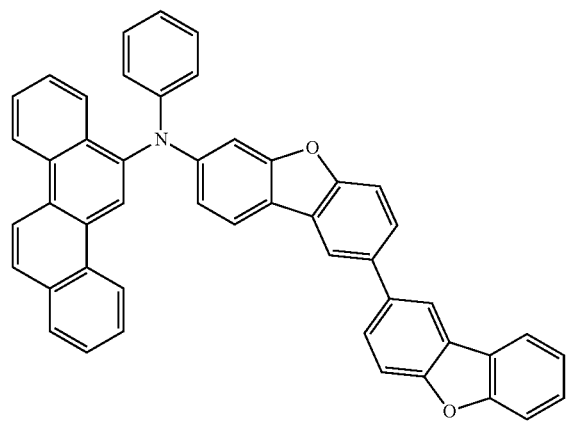
H-45
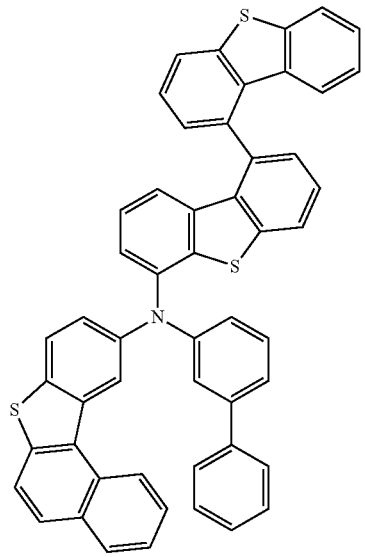
H-43
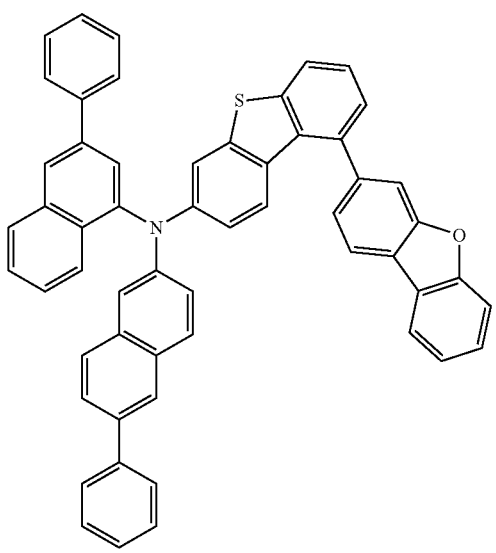
H-46
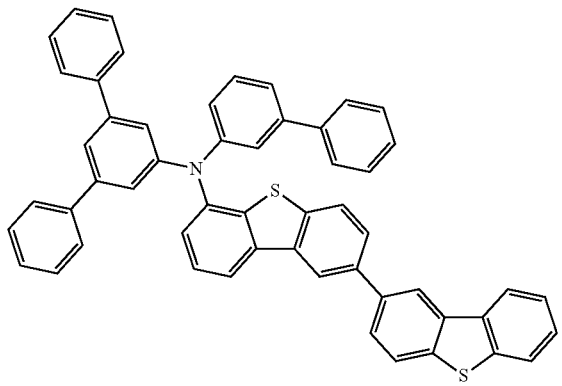
H-44
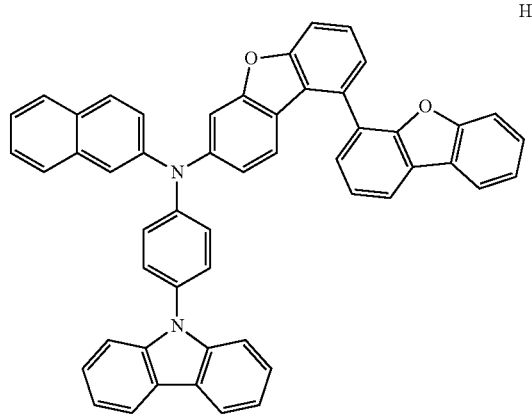
H-47
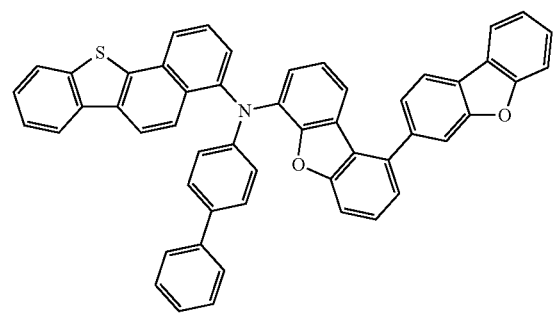

H-48
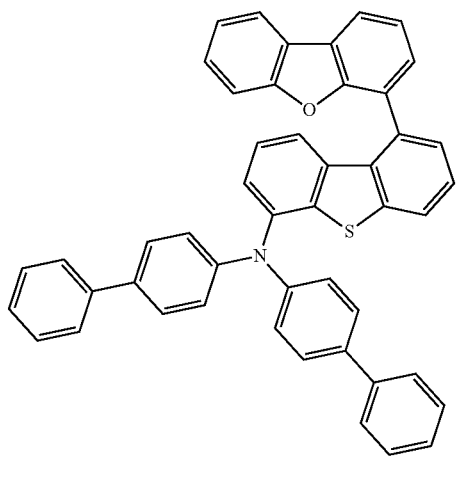
H-49
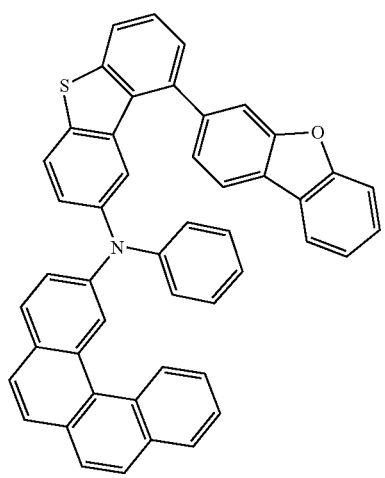
H-50
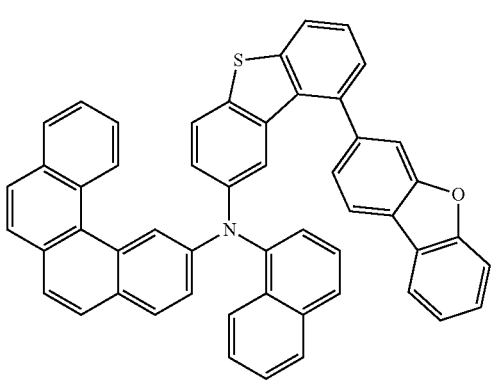
H-51
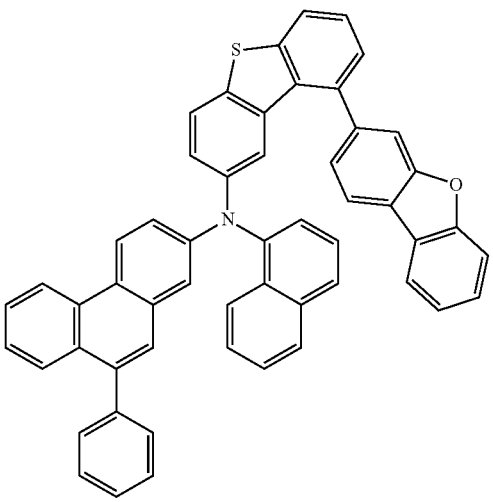
H-52
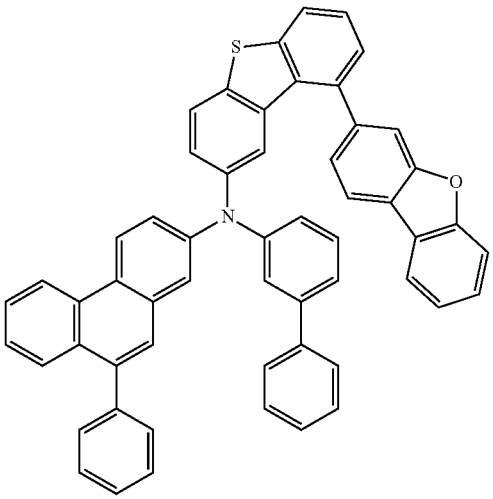
H-53
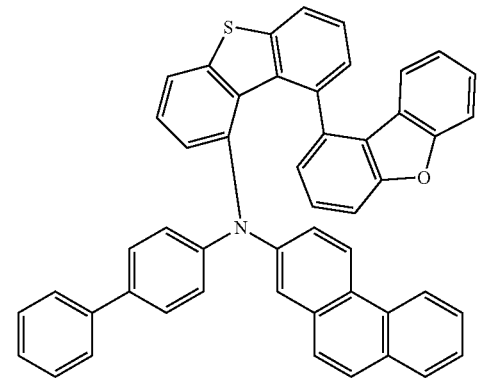

H-54
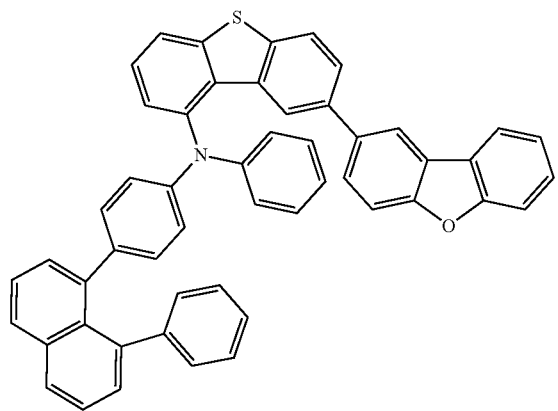
H-57
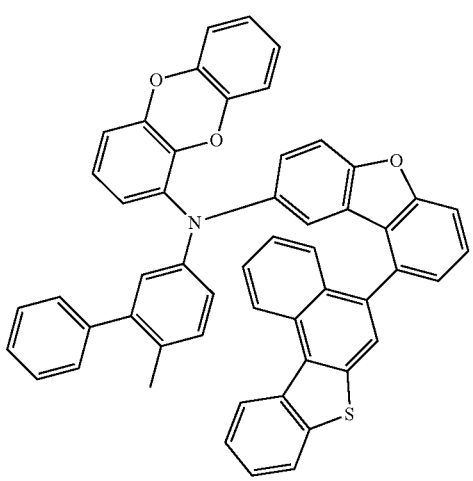
H-55
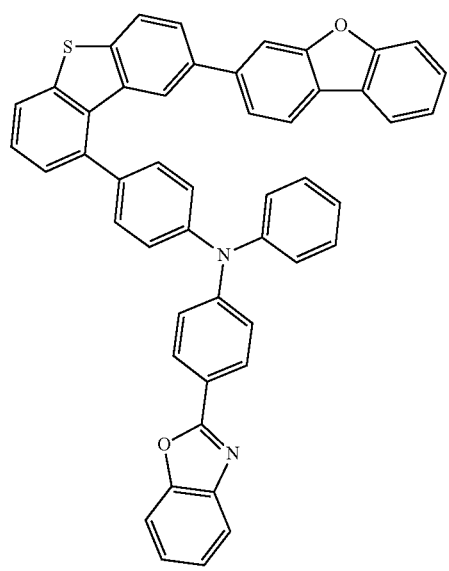
H-58
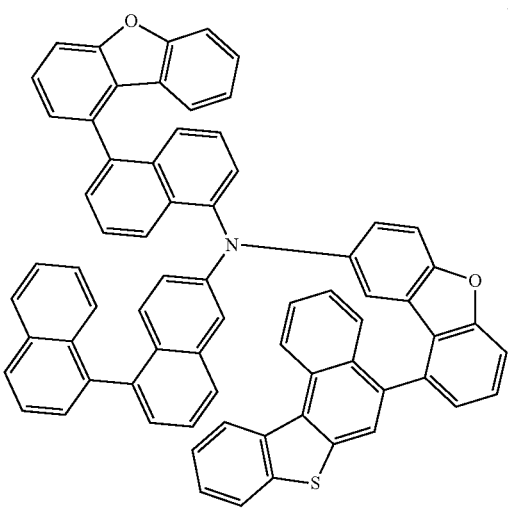
H-56
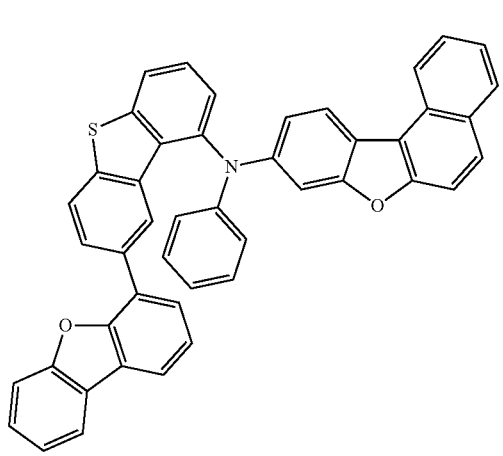
H-59
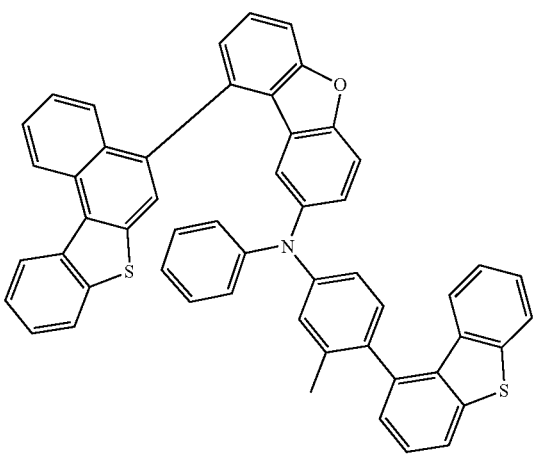

-continued
H-60
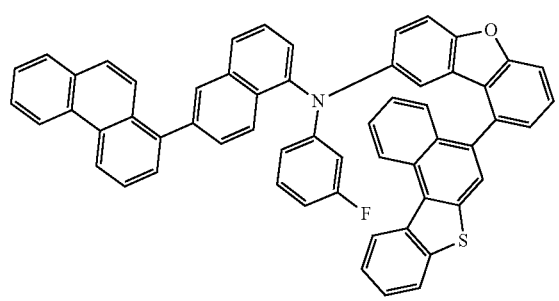
H-61
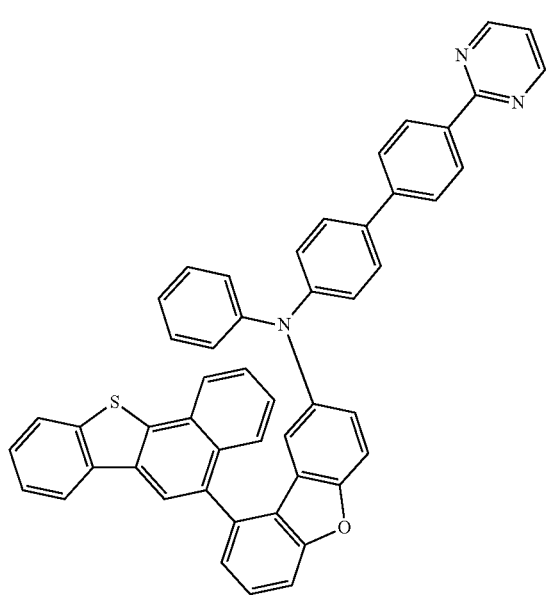
H-62
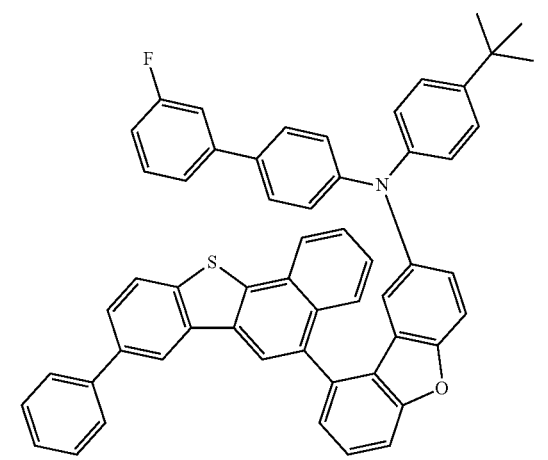
-continued
H-63
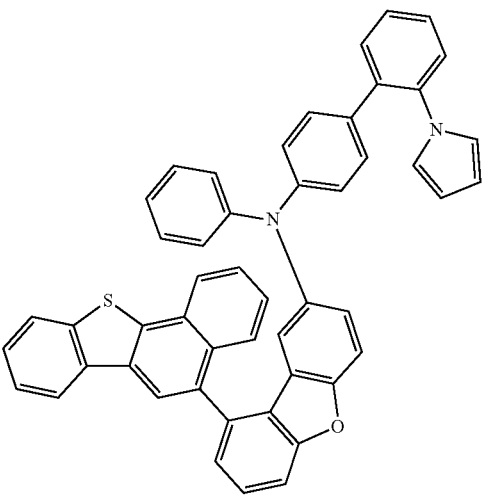
H-64
H-65
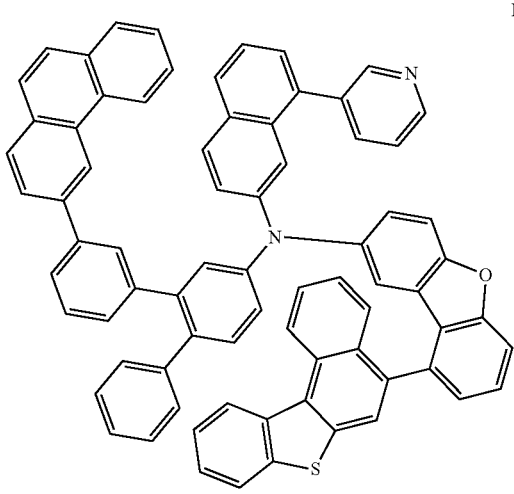

H-66
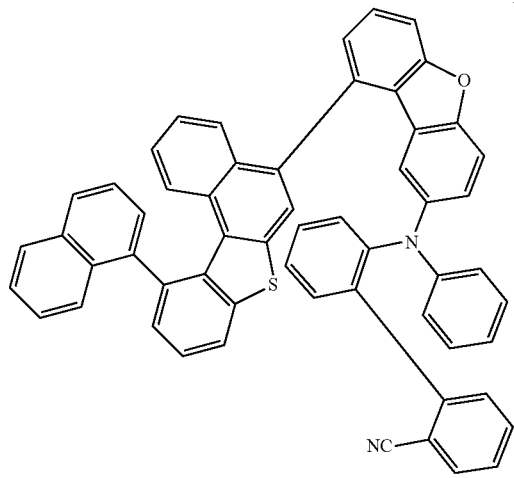
H-69
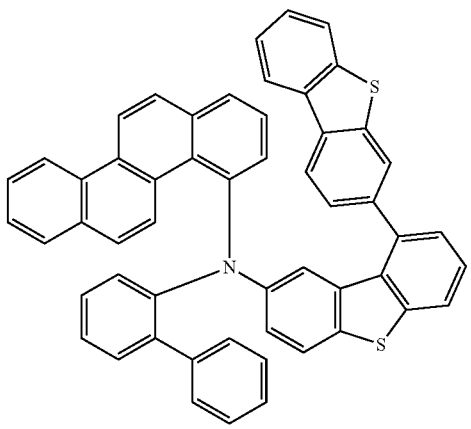
H-67
H-70
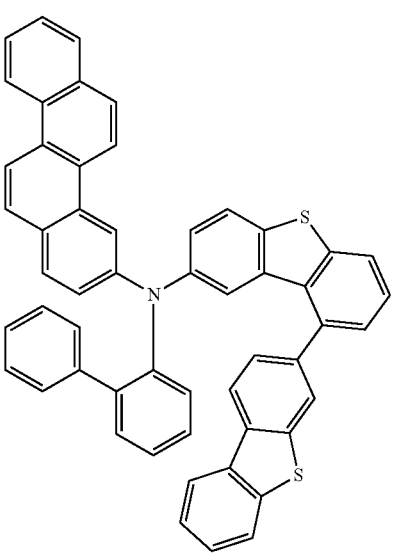
H-68
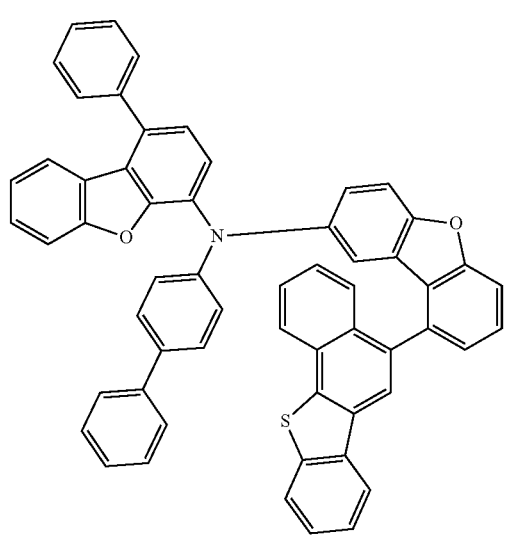
H-71
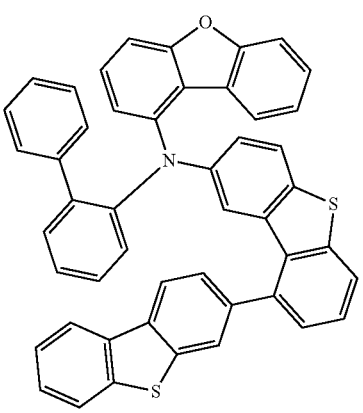

H-72
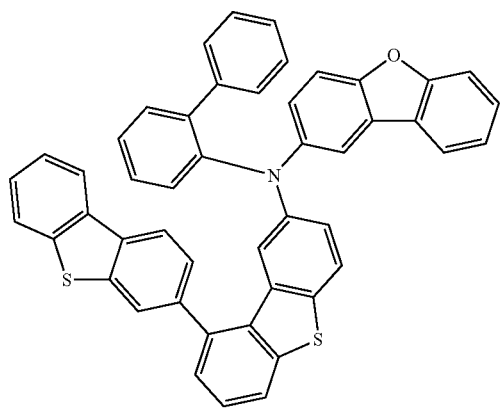
H-73
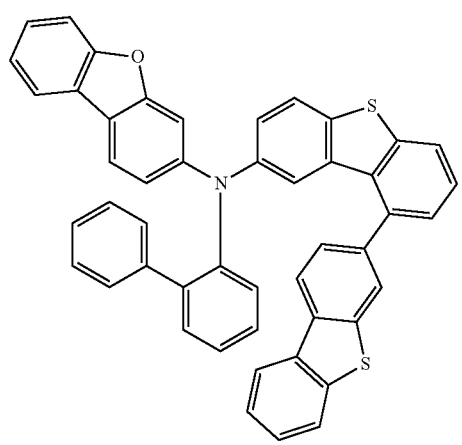
H-74
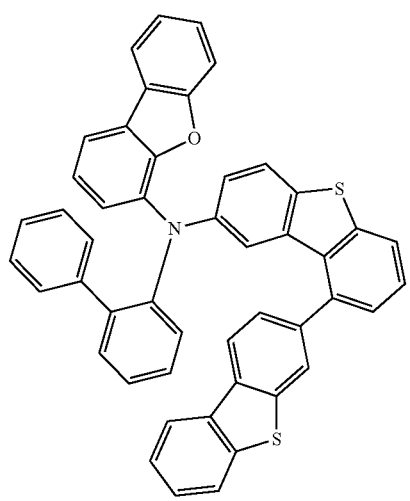
H-75
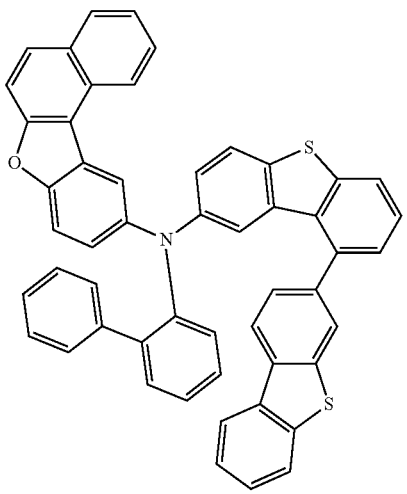
H-76
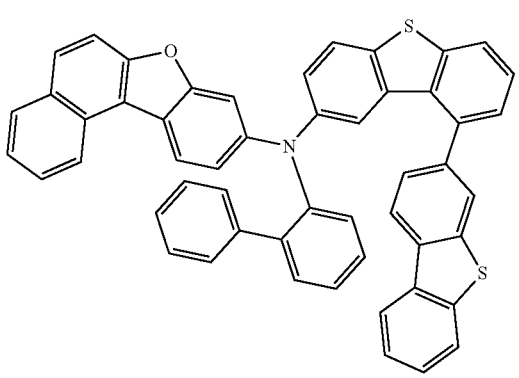
H-77
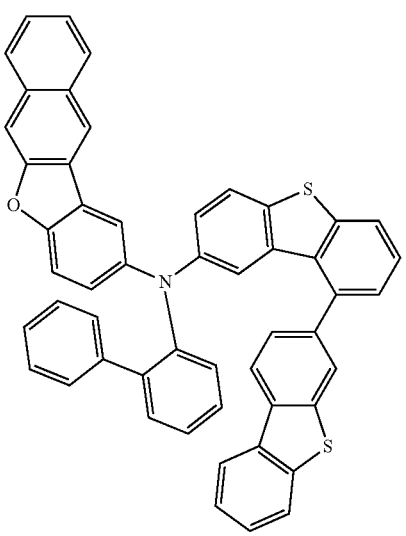

-continued
H-78
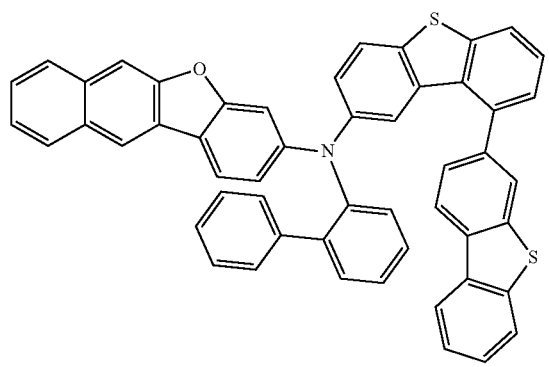
H-79
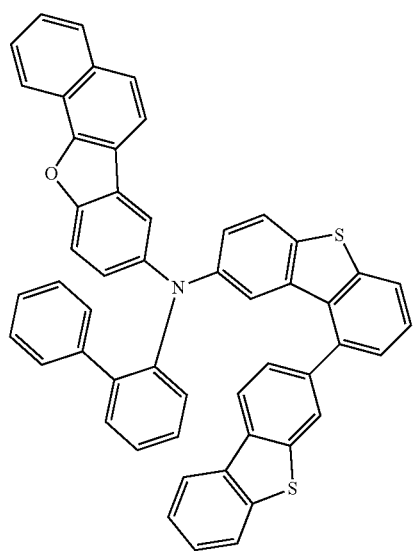
H-80
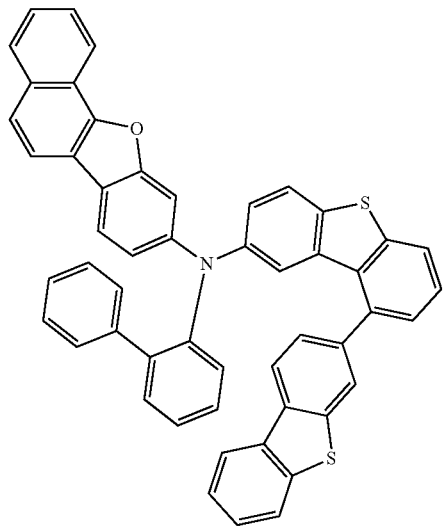
-continued
H-81
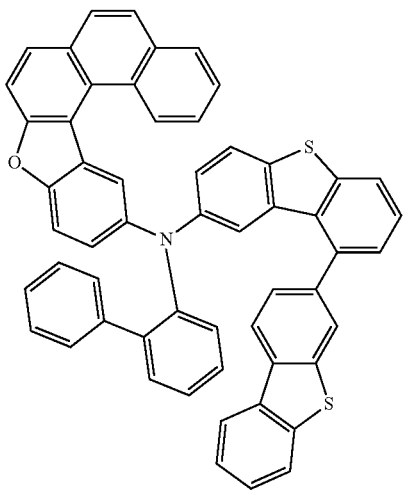
H-82
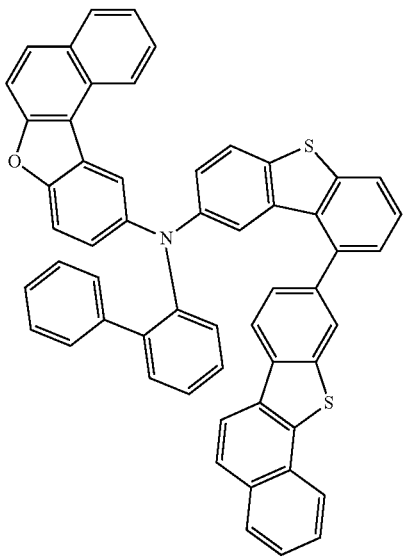
H-83
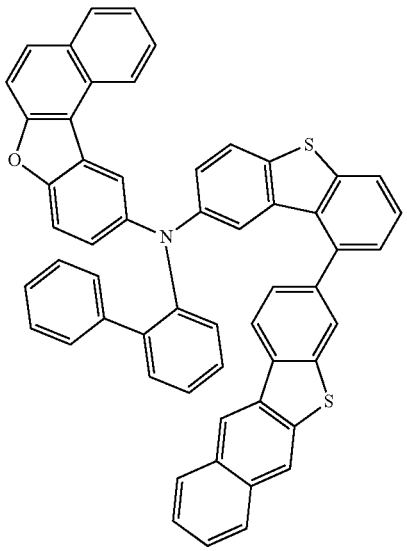

H-84
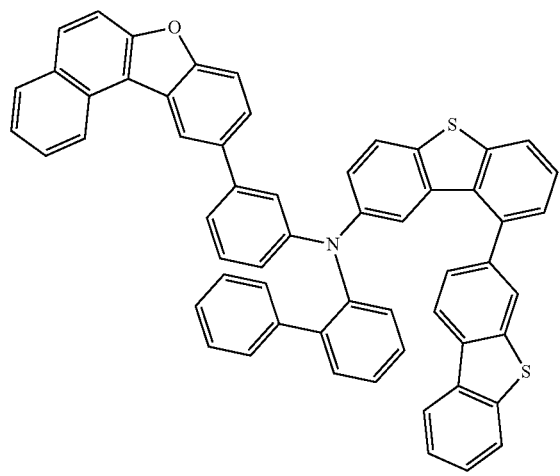
H-87
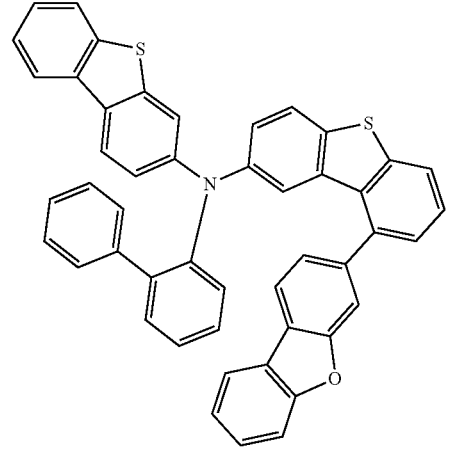
H-85
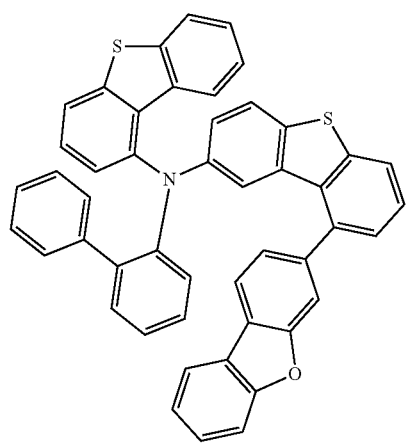
H-88
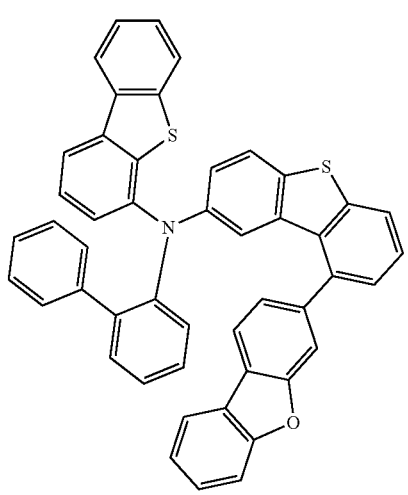
H-86
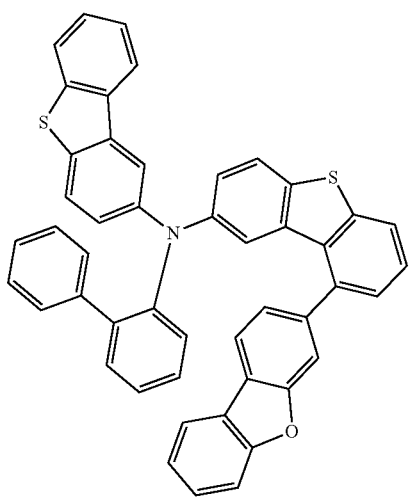
H-89
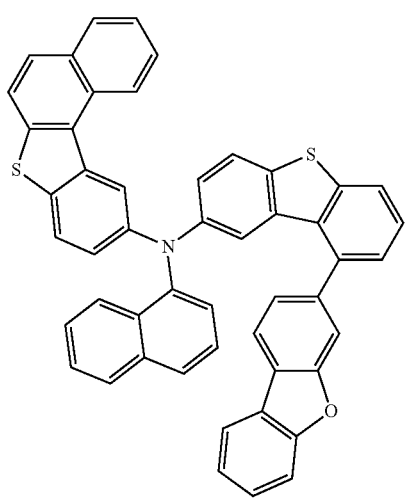

H-90
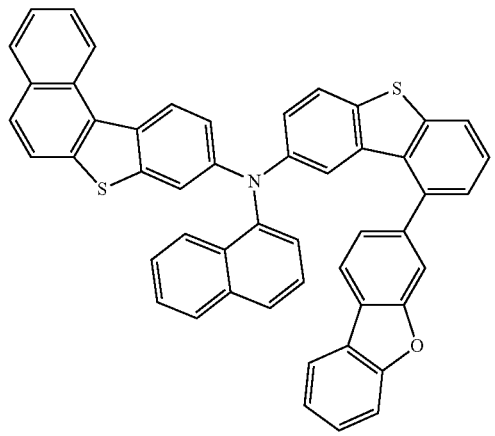
H-91
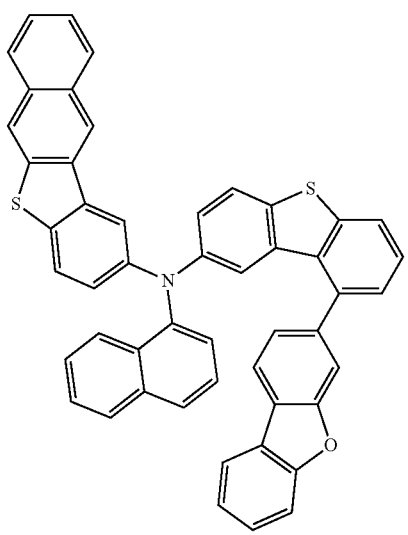
H-92
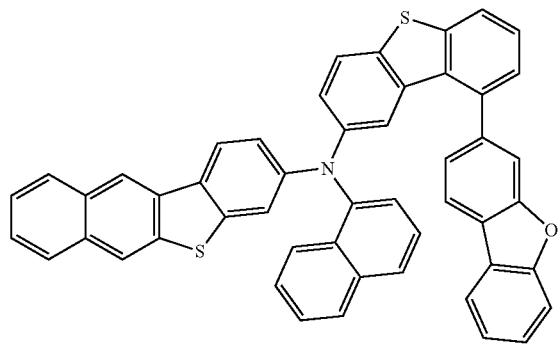
H-93
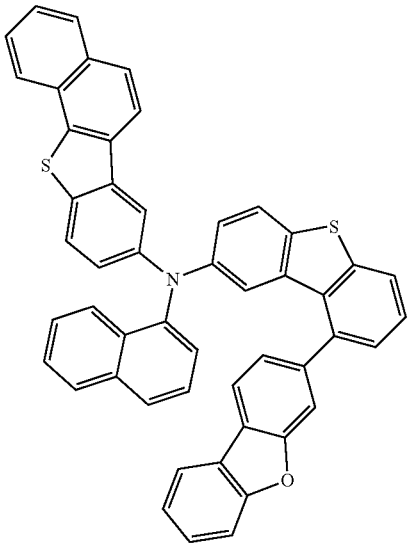
H-94
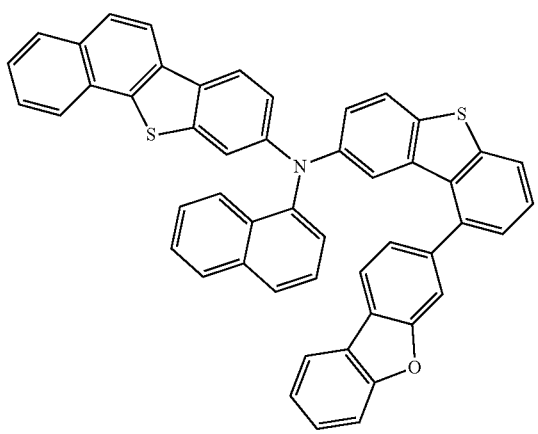
H-95
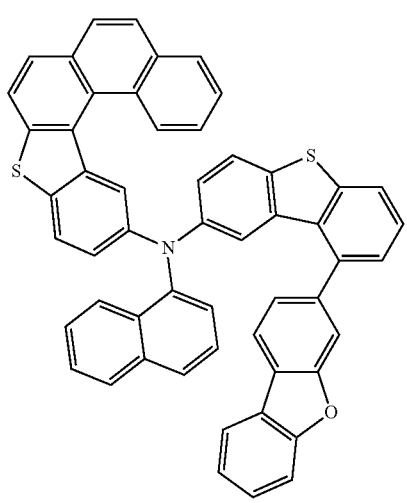

H-96
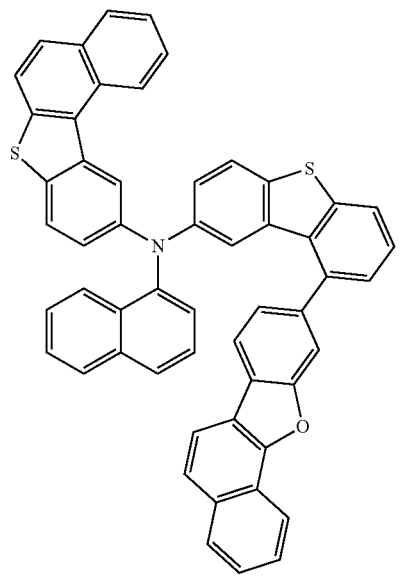
H-97
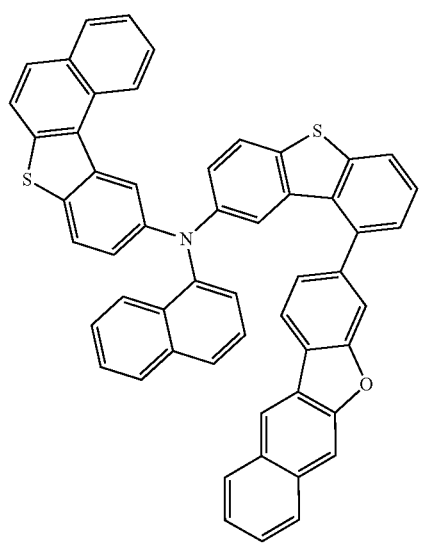
H-98
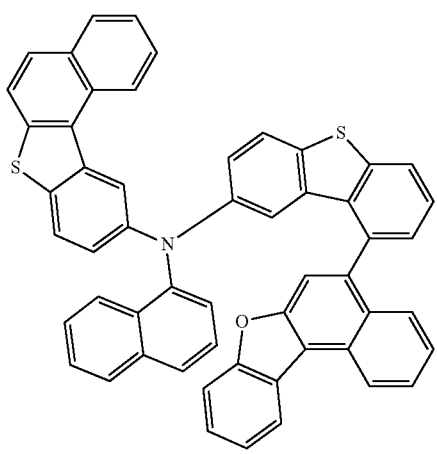
H-99
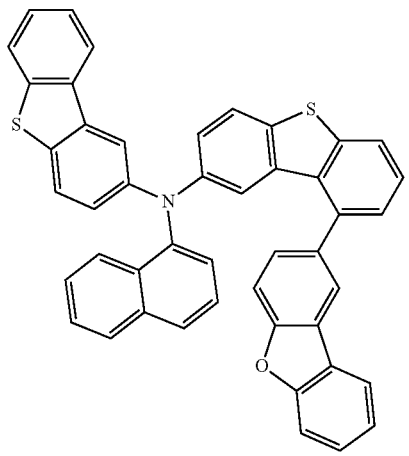
H-100
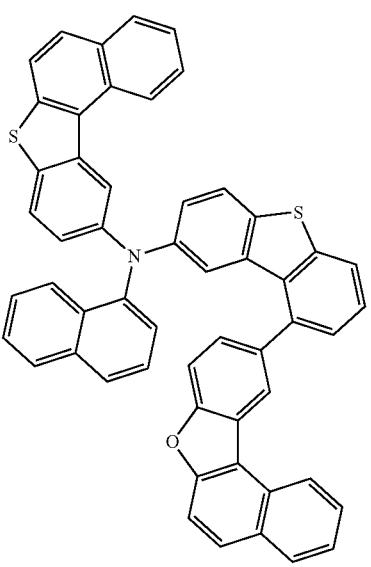
H-101
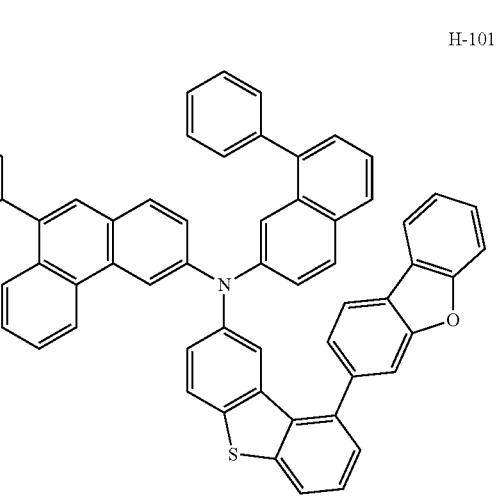

H-102
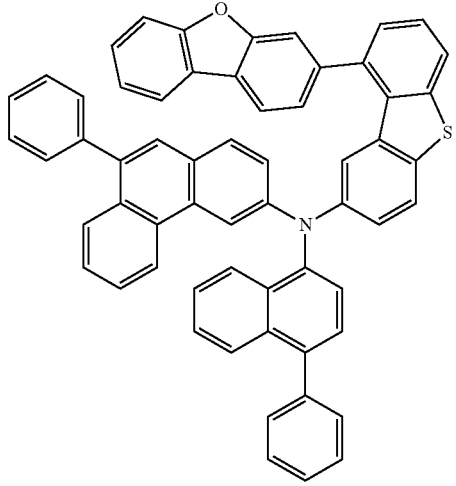
H-103
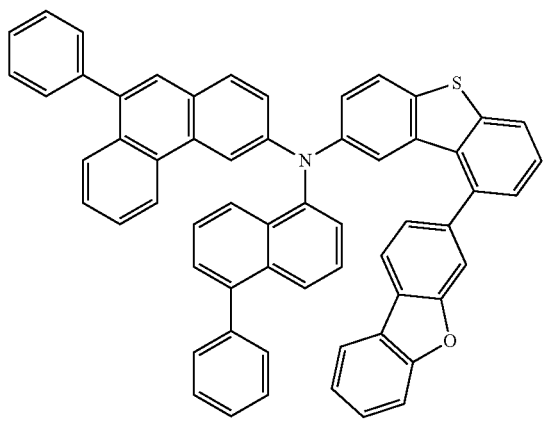
H-104
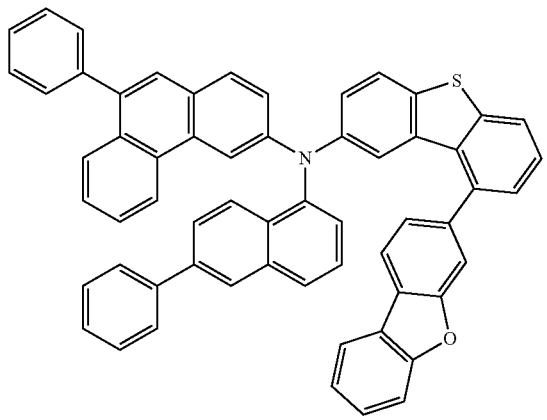
H-105
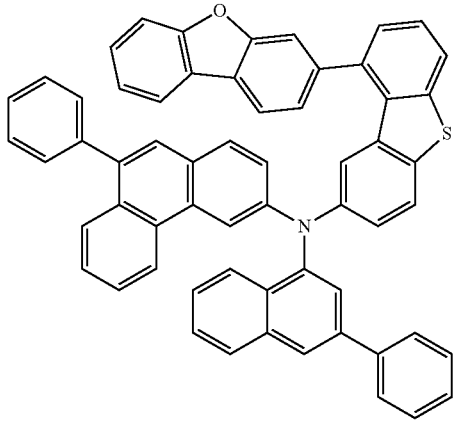
H-106
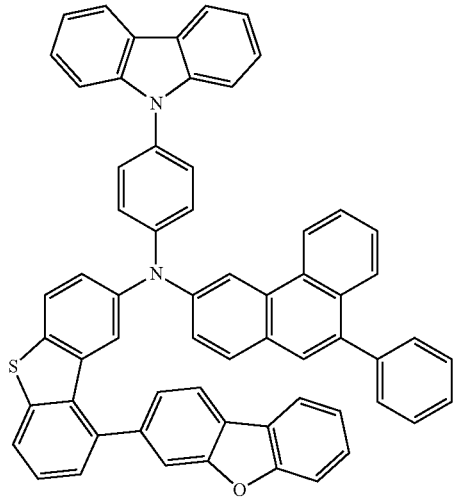
H-107
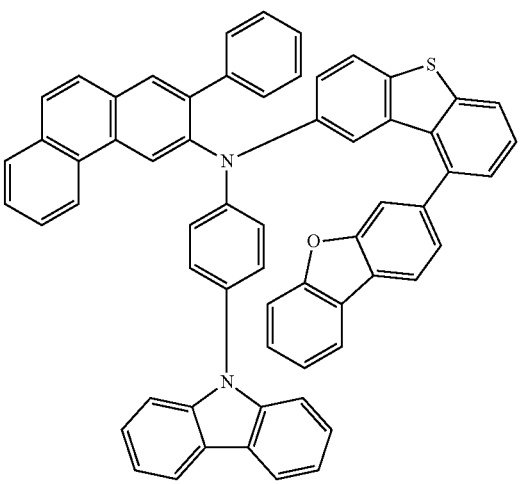

H-108
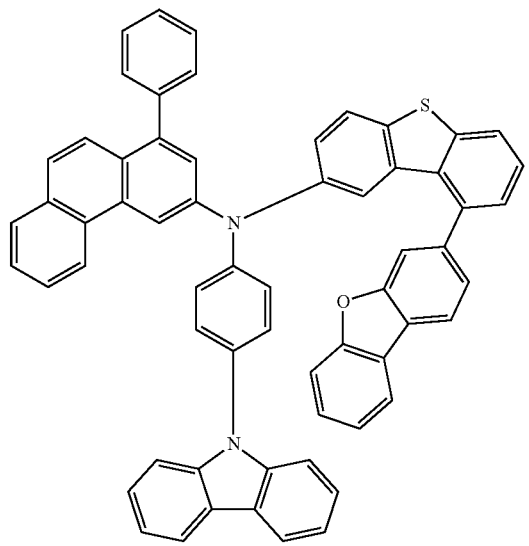
H-109
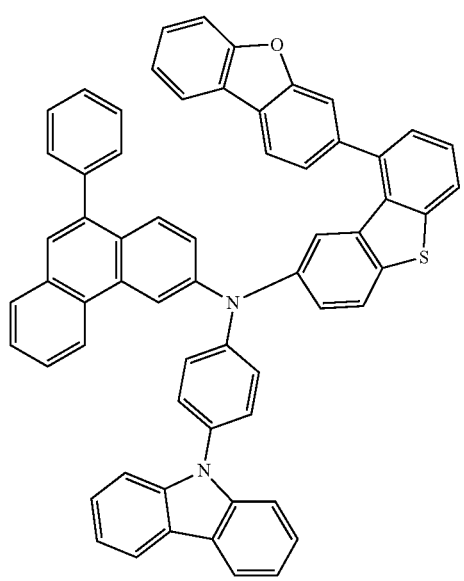
H-110
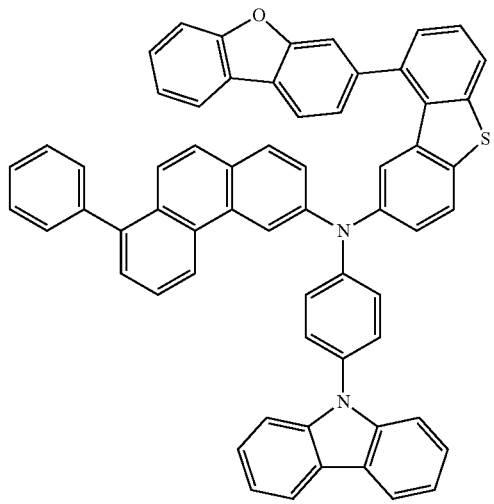
H-111
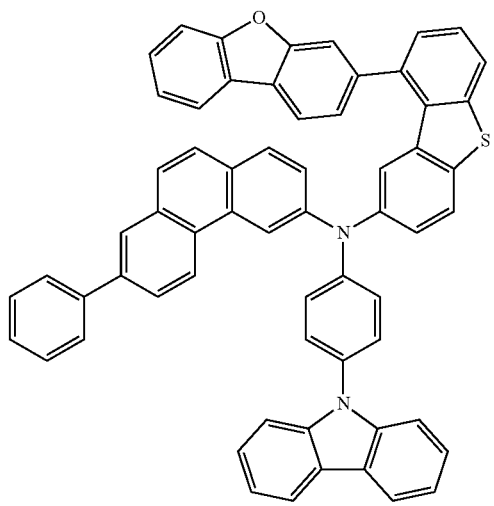
H-112
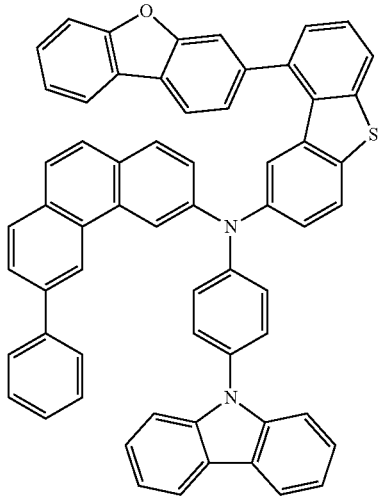

H-113
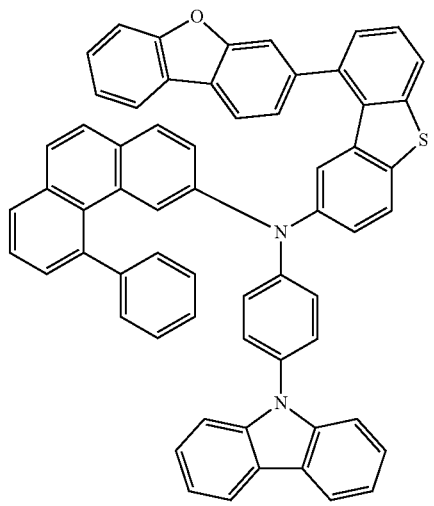
H-114
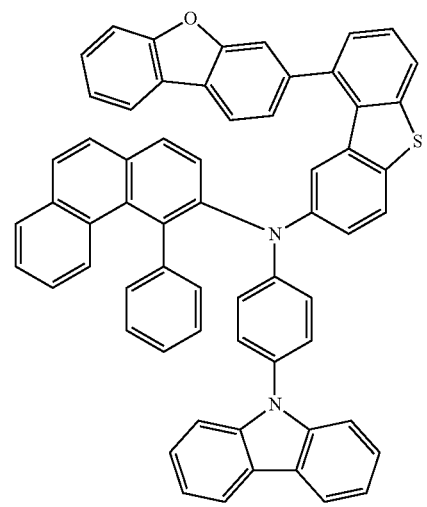
H-115
H-116
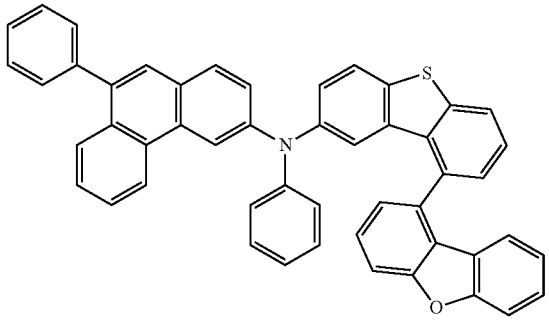
H-117
H-118
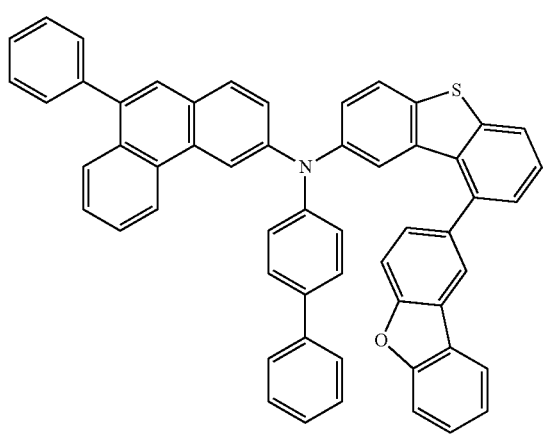

H-119
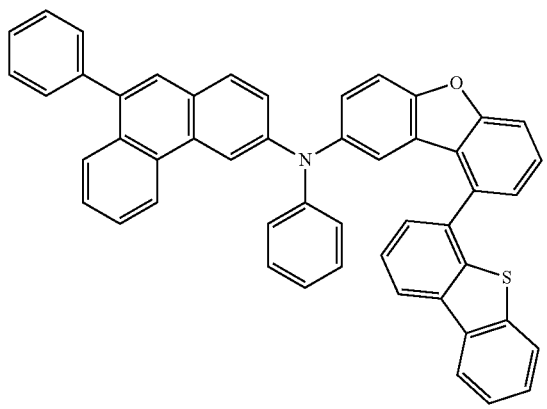
H-120
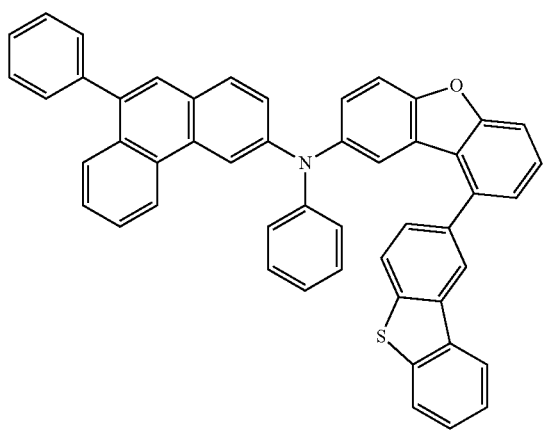
H-121
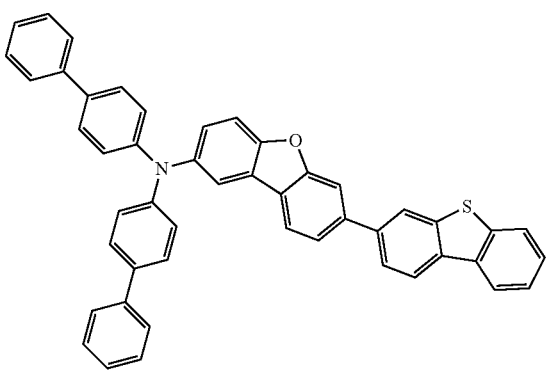
H-122
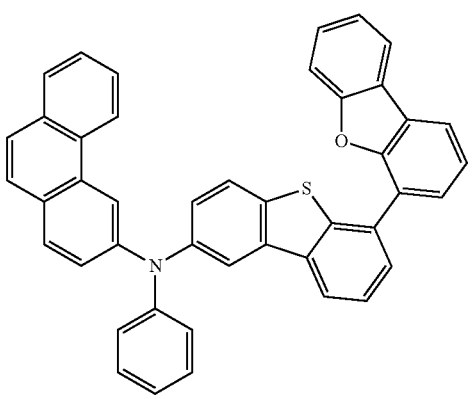
H-123
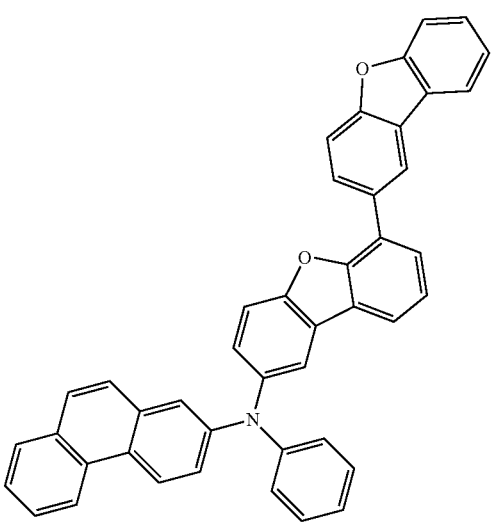
H-124

H-125
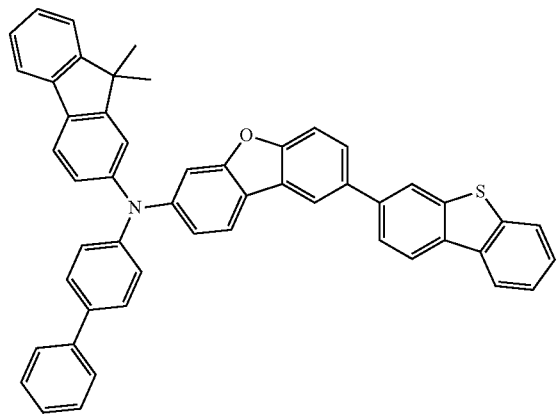
H-126
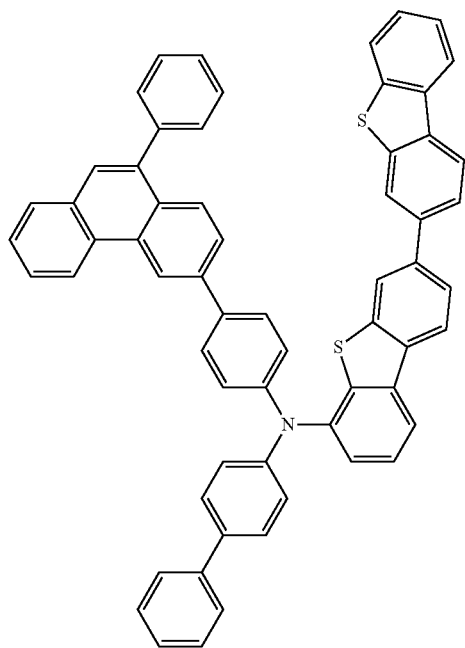
H-127
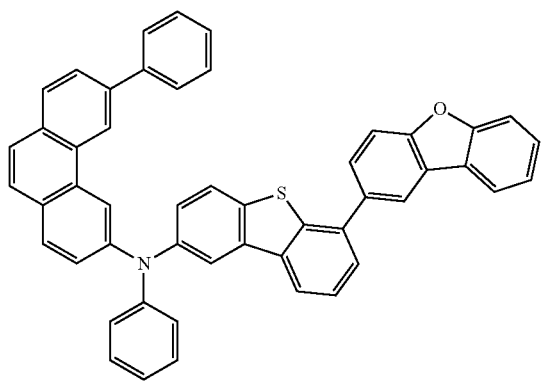
H-128
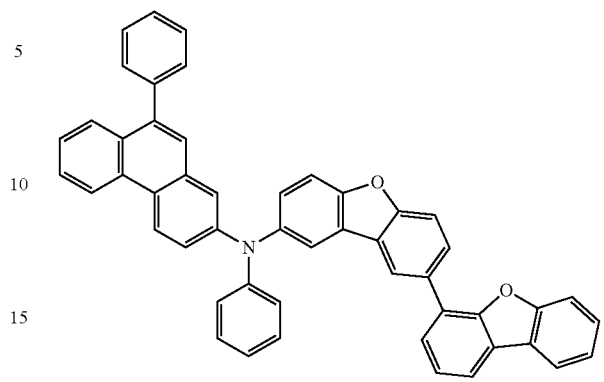
H-129
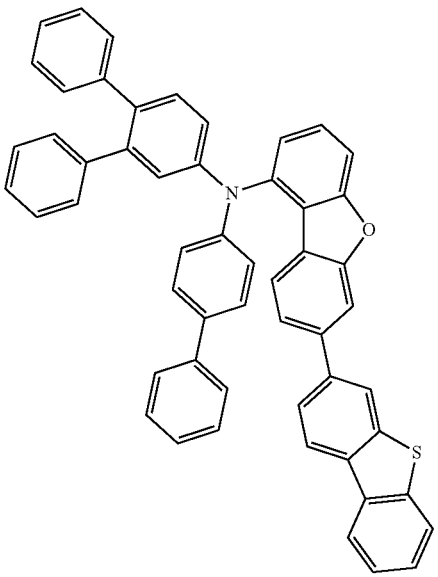
H-130
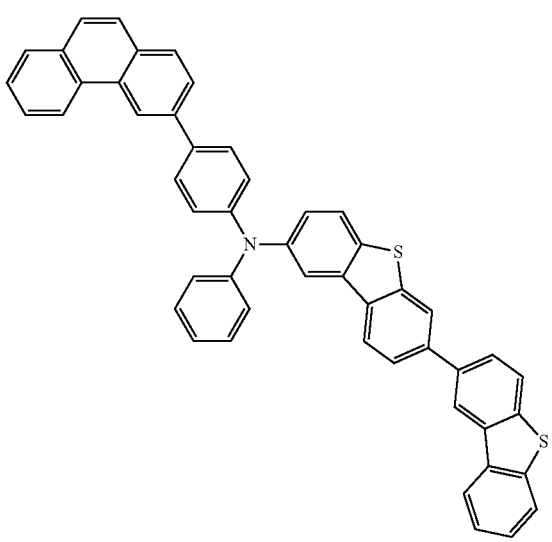

H-131
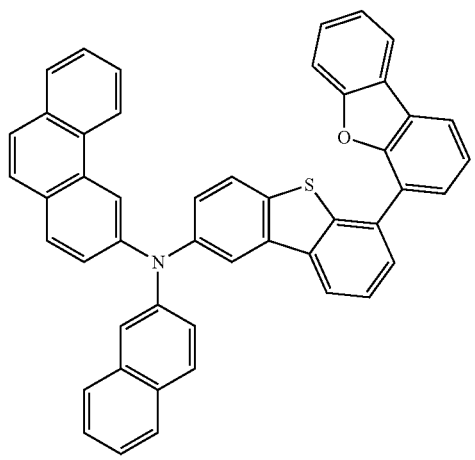
H-132
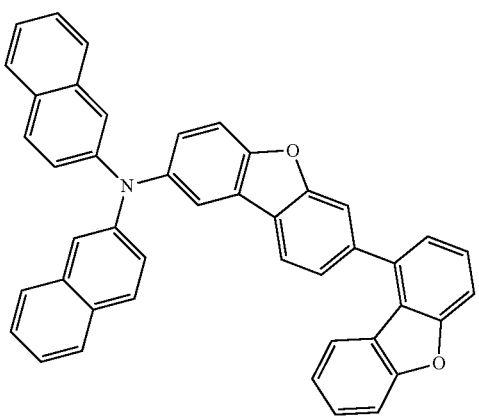
Specifically, the compound represented by Formula 5 may be a compound represented by any one of the following compounds S-1 to S-116, but is not limited thereto.
S-1
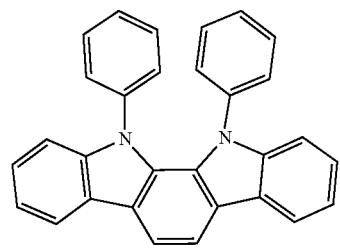
S-2
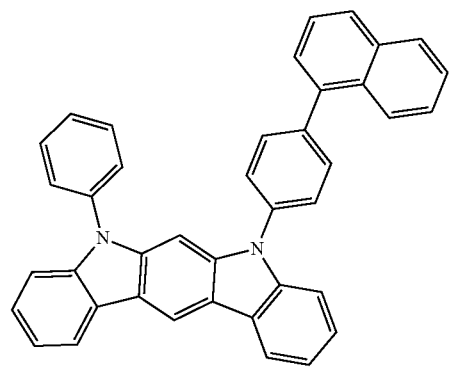
S-3
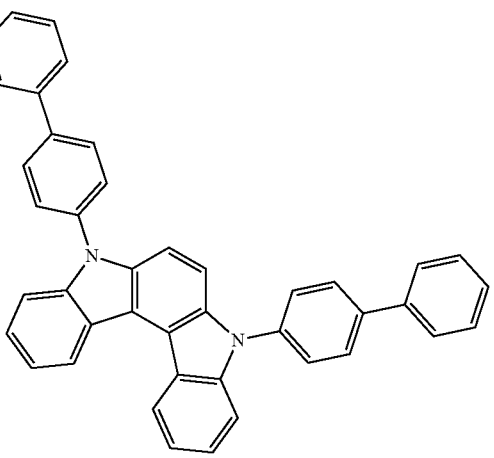
S-4
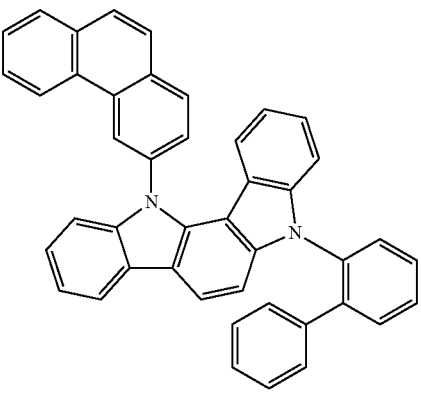
S-5
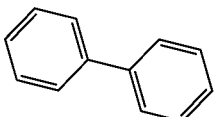

S-6
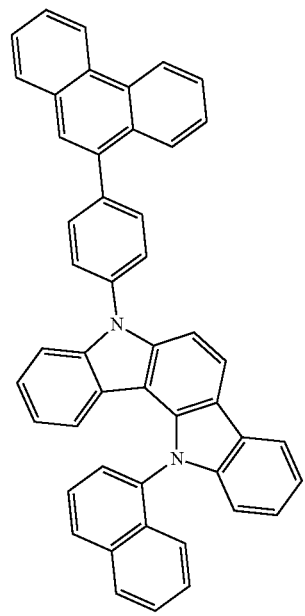
S-7
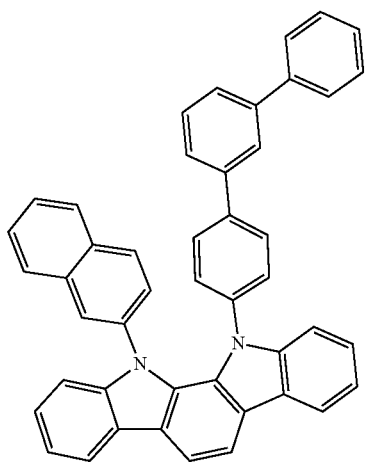
S-8
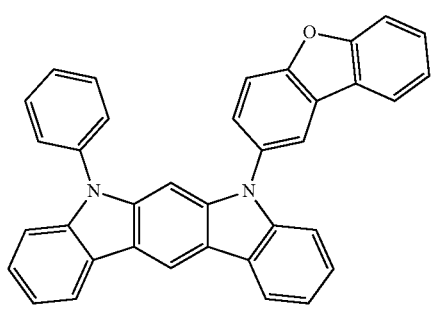
S-9
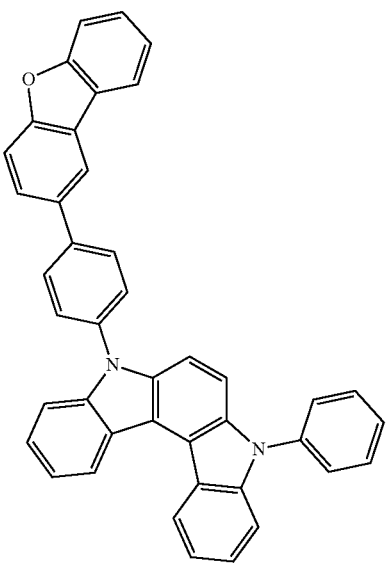
S-10
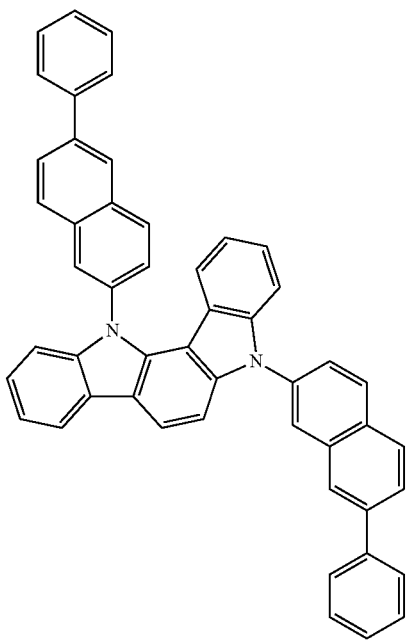

S-11
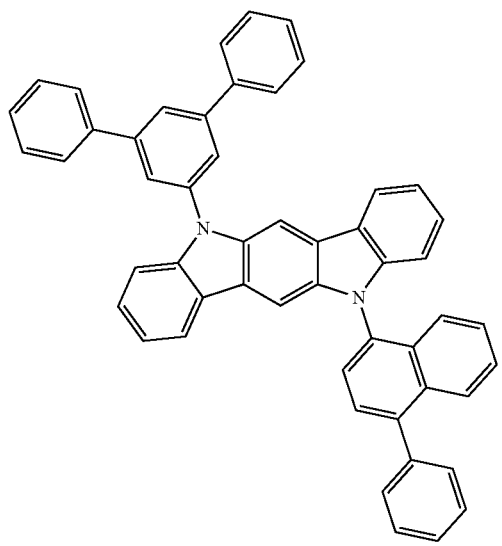
S-12
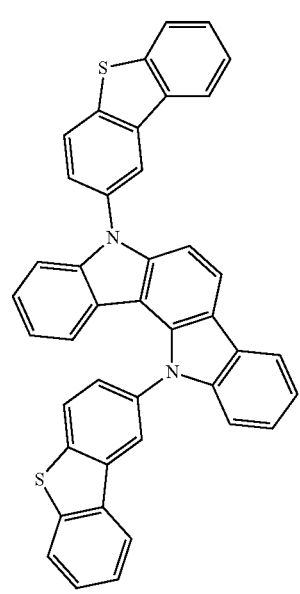
S-13
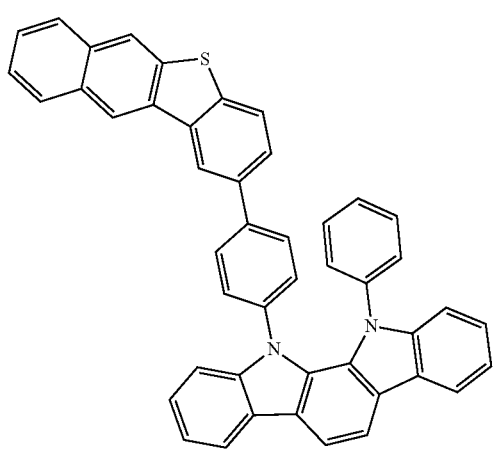
S-14
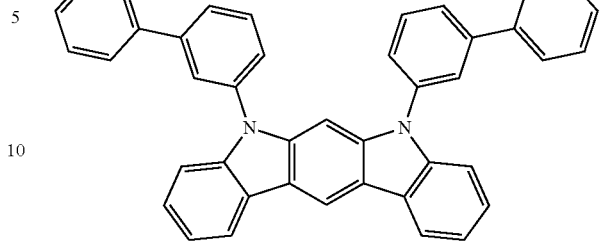
S-15
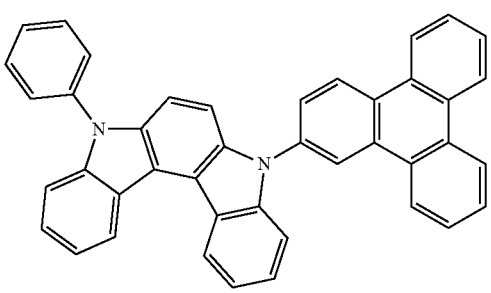
S-16
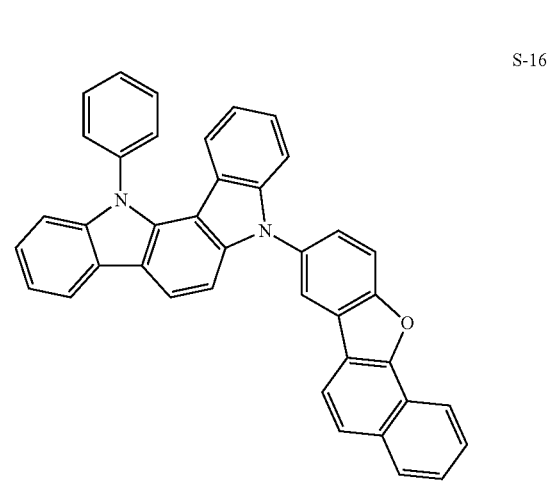
S-17
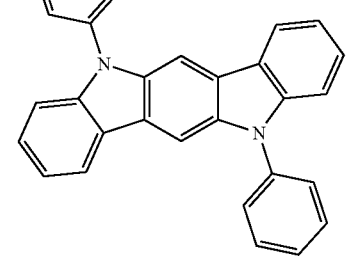

S-18
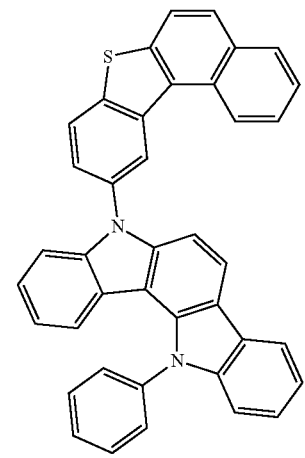
S-19
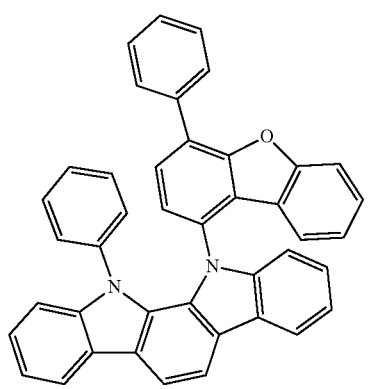
S-20
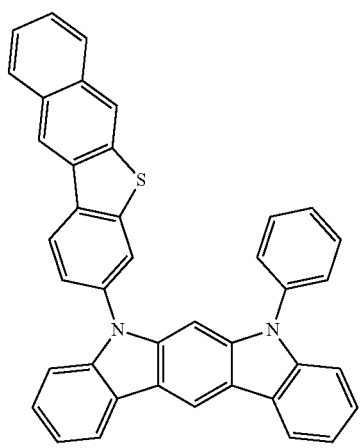
S-21
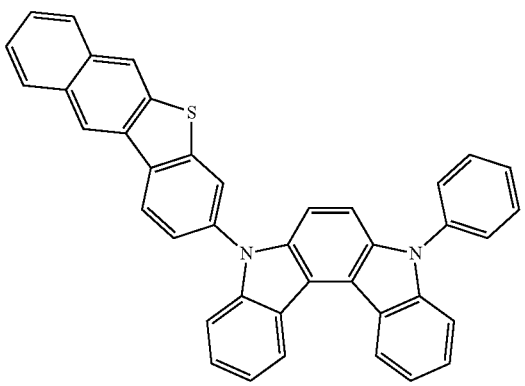
S-22
S-23
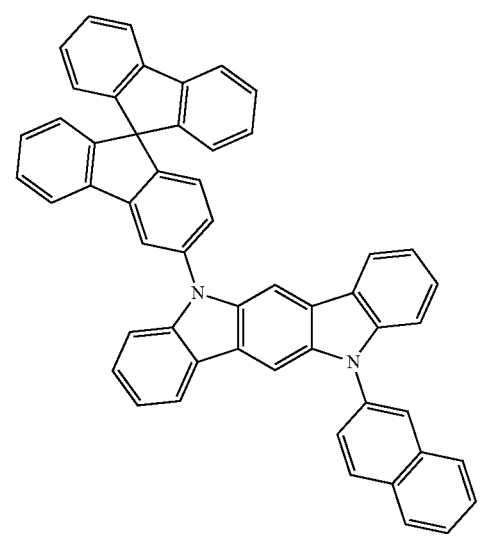

S-24
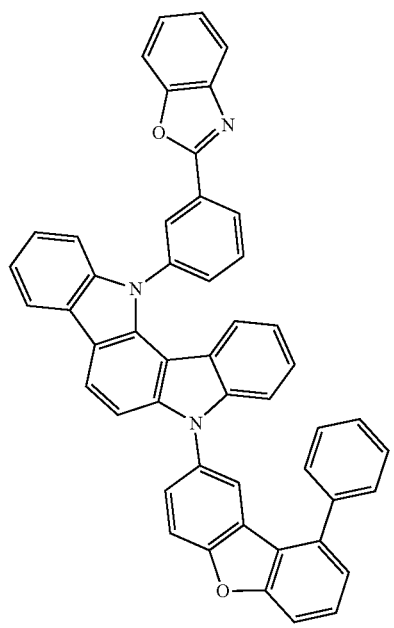
S-27
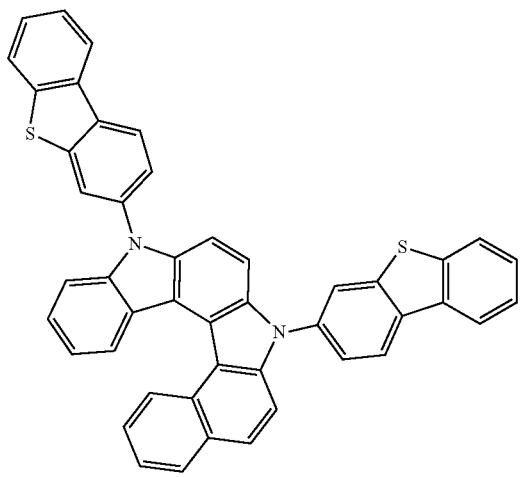
S-25
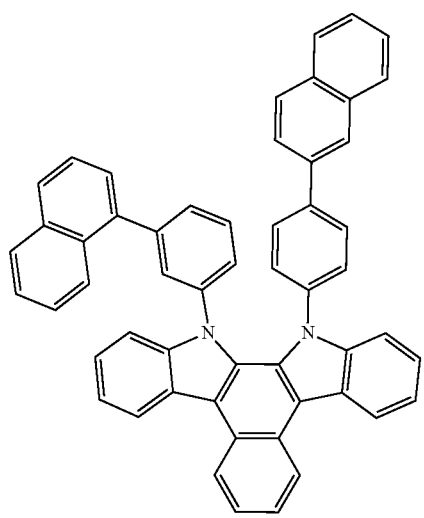
S-28
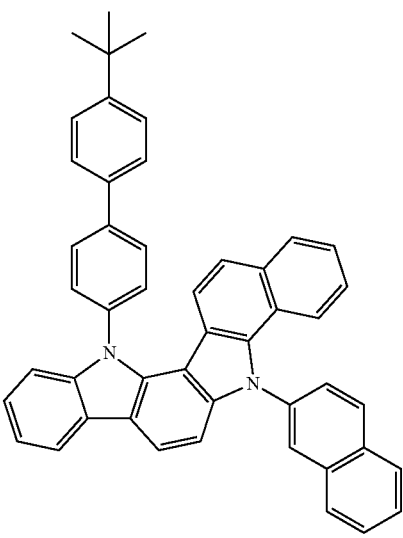
S-26
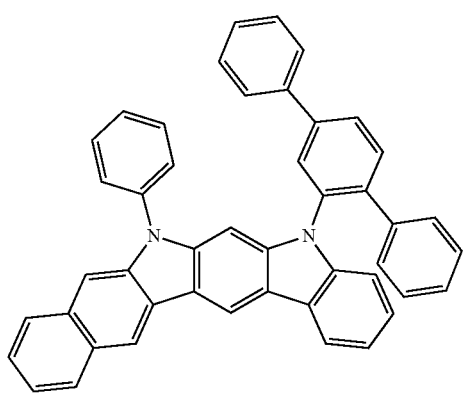
S-29
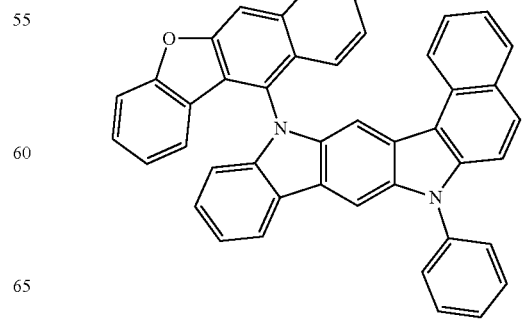

-continued
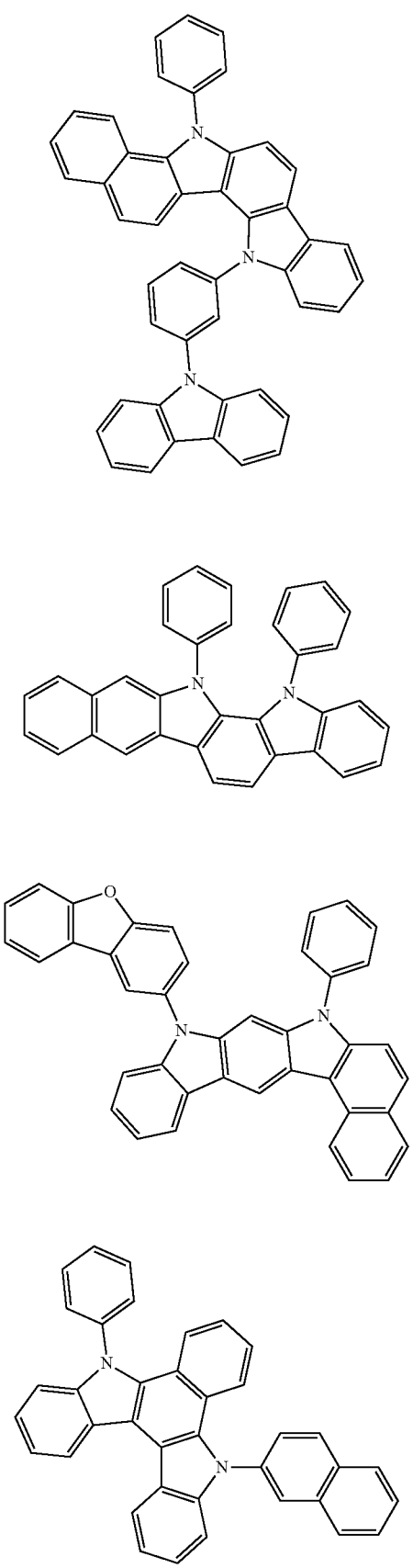
S-30
S-31
S-32
S-33
-continued
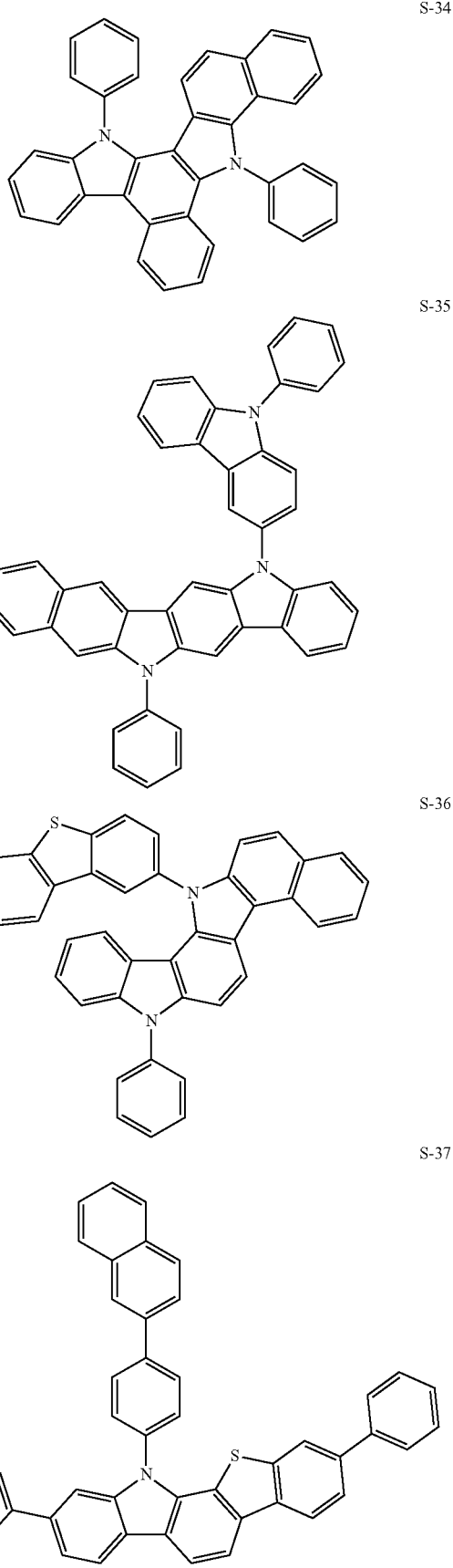
S-34
S-35
S-36
S-37

S-38
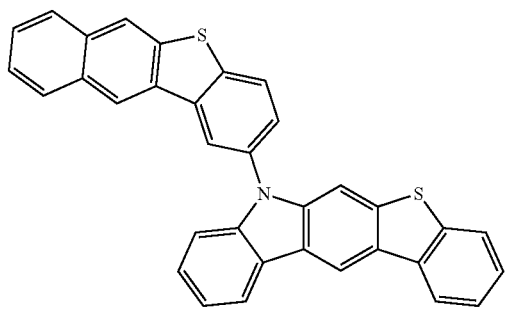
S-39
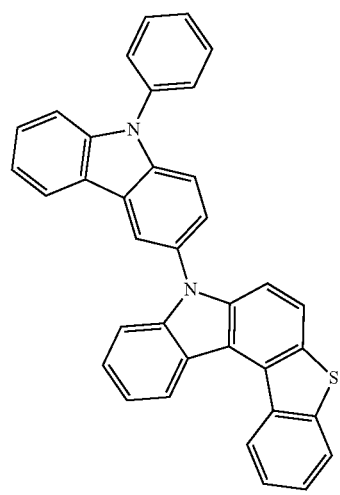
S-40
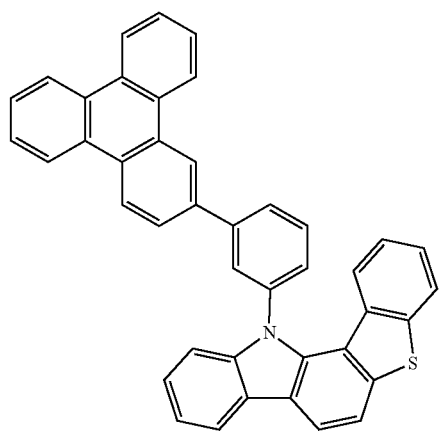
S-41
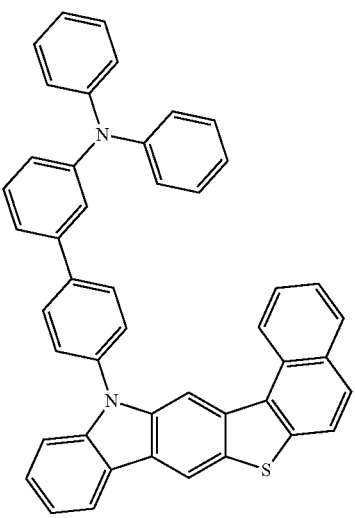
S-42
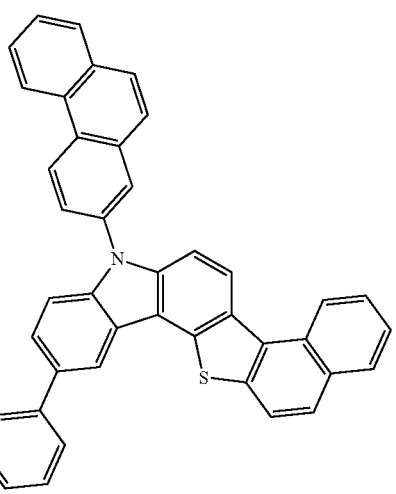
S-43
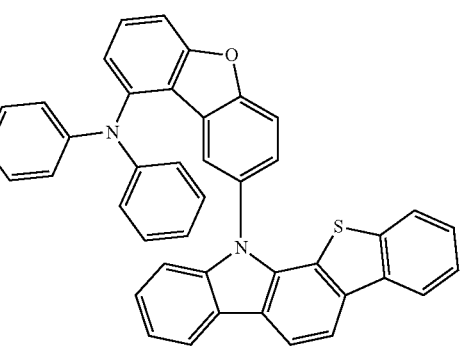

S-44
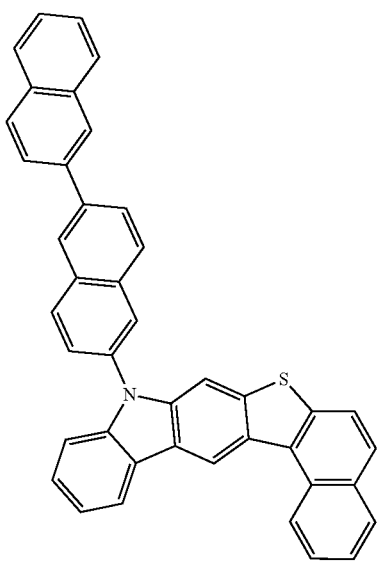
S-45
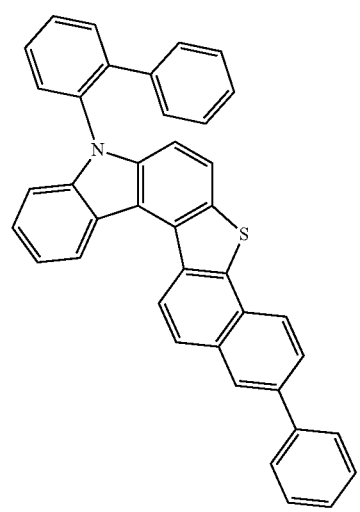
S-46
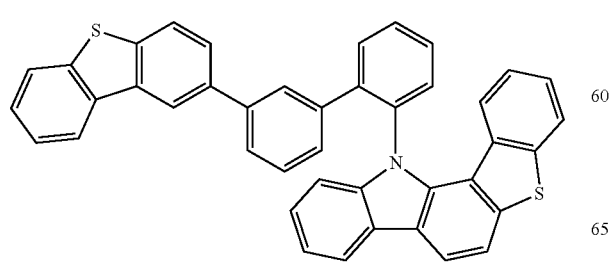
S-47
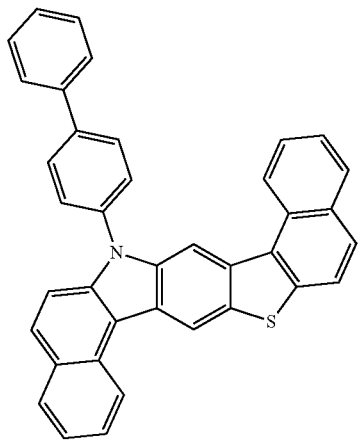
S-48
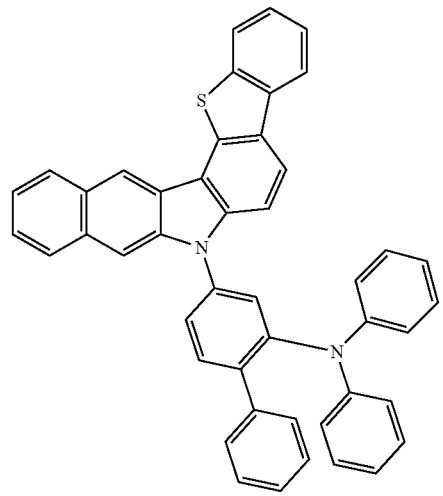
S-49
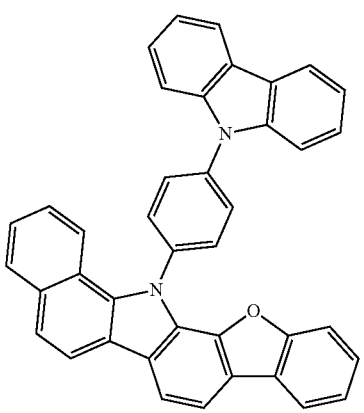

-continued
S-50
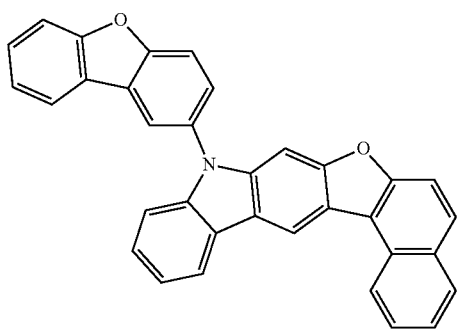
S-51
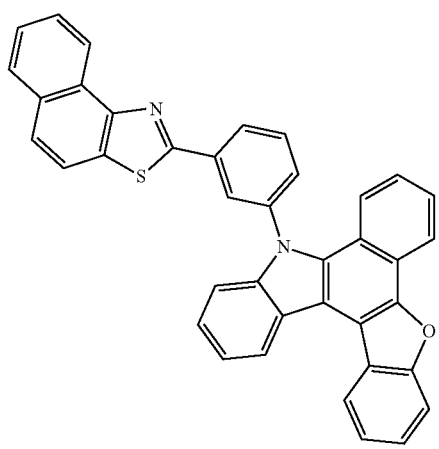
S-52
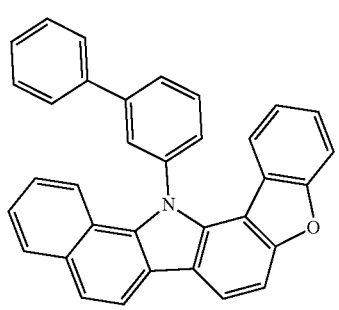
S-53
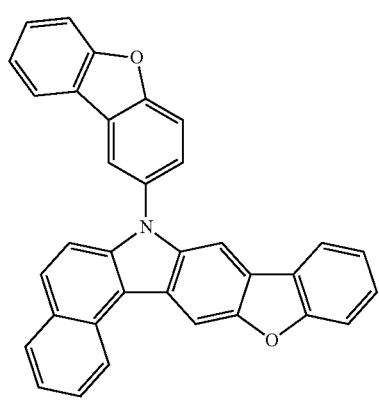
S-54
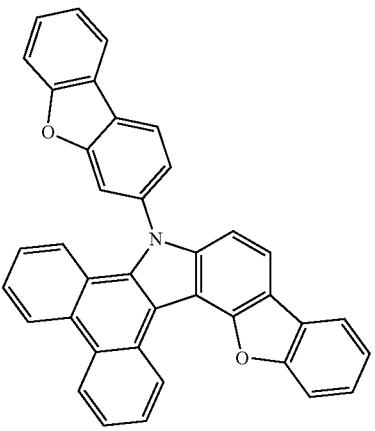
S-55
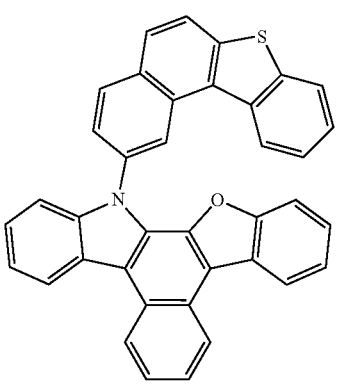
S-56
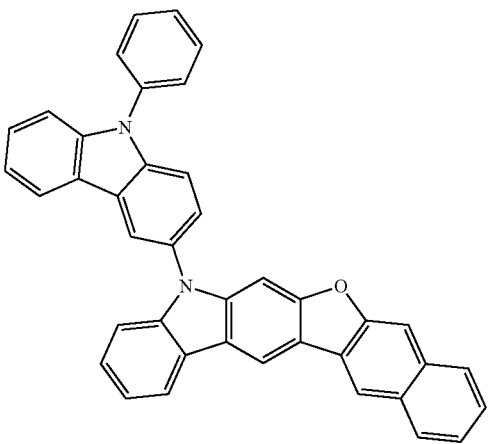
S-57
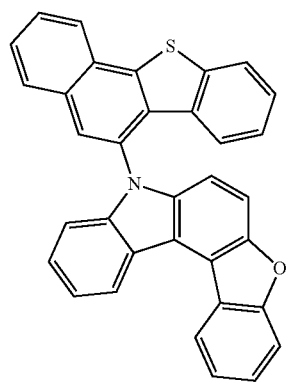

S-58
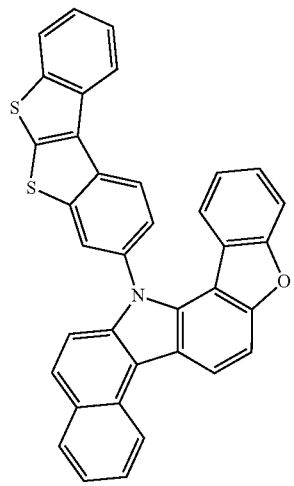
S-59
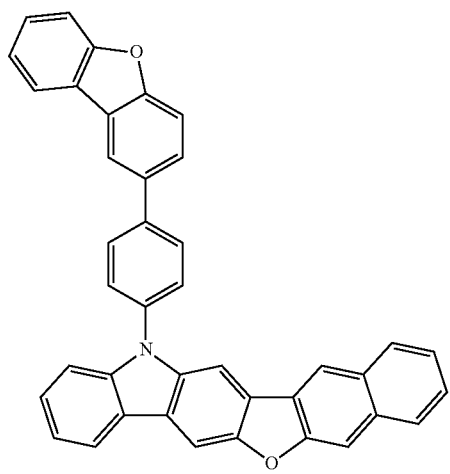
S-60
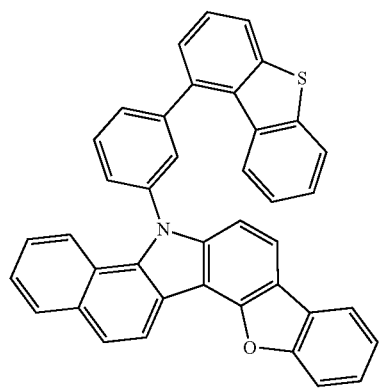
S-61
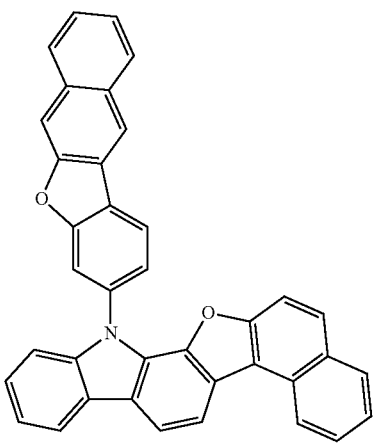
S-62
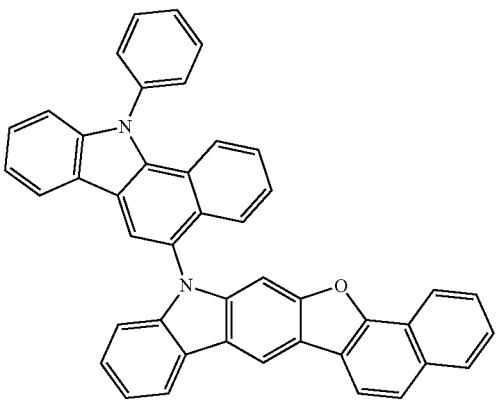
S-63
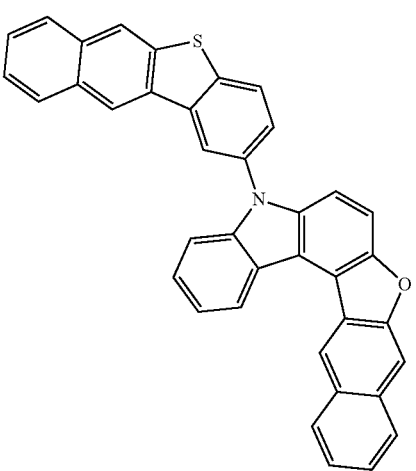

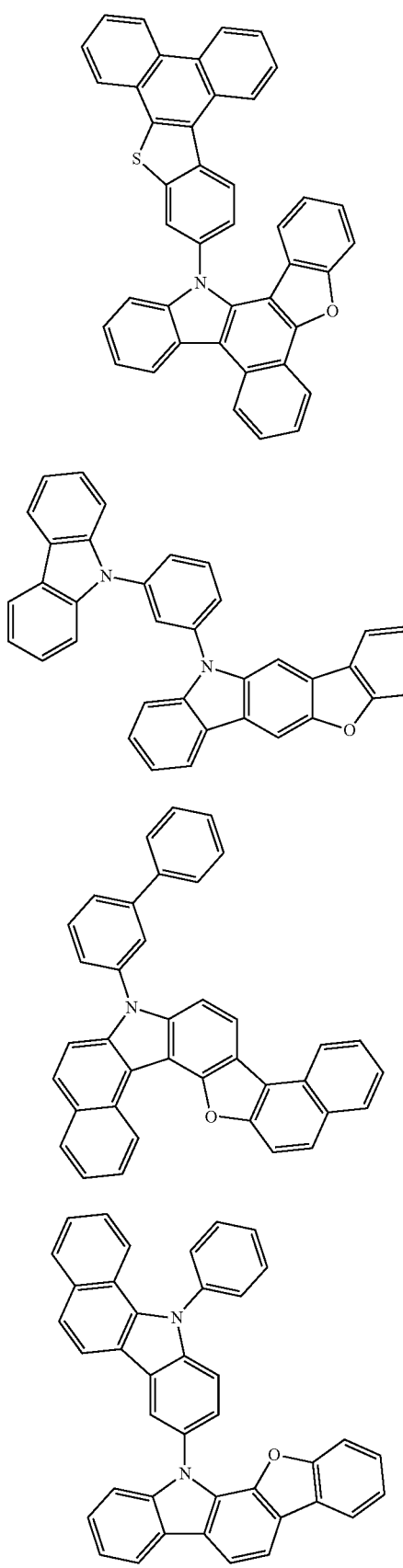
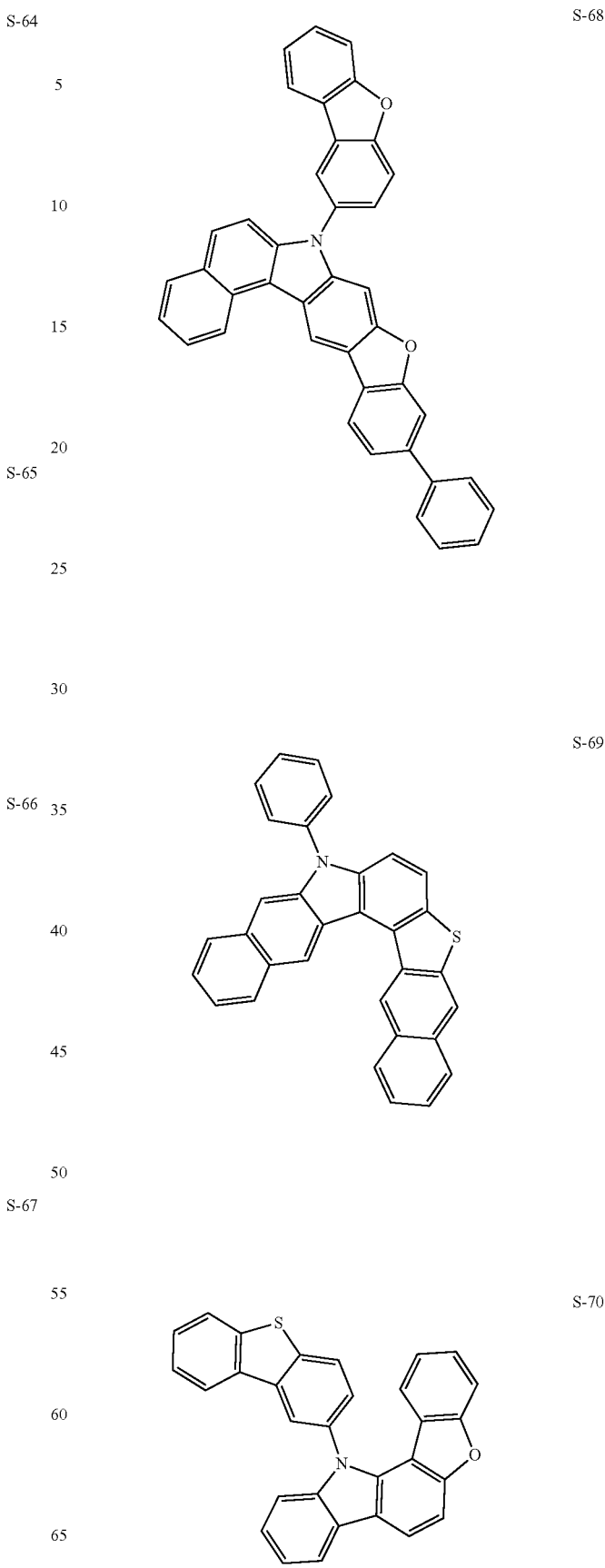

-continued
S-71
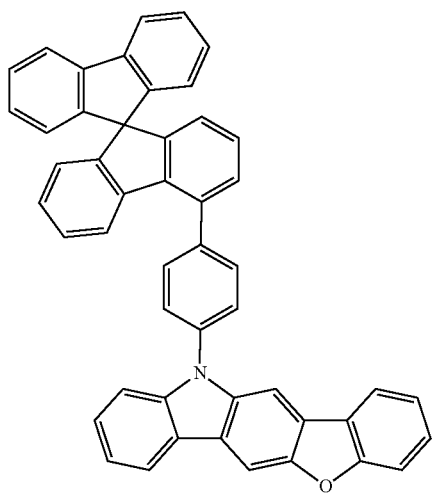
S-72
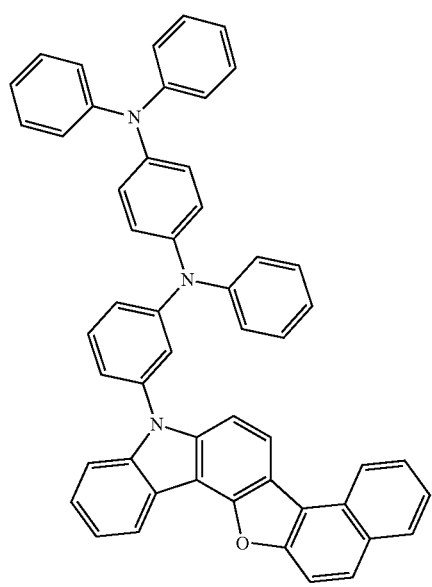
S-73
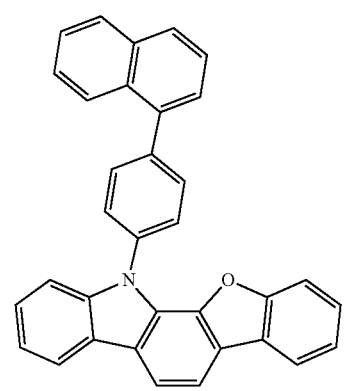
-continued
S-74
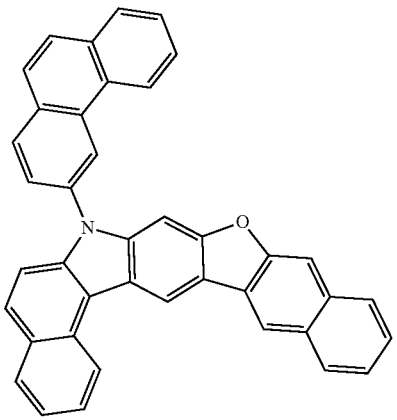
S-75
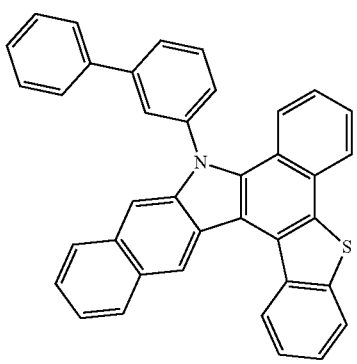
S-76
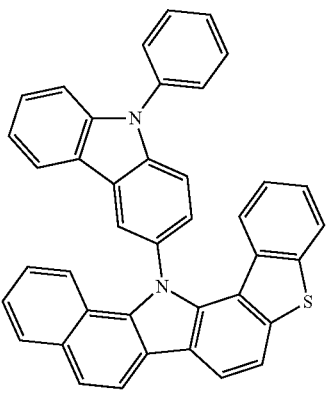
S-77
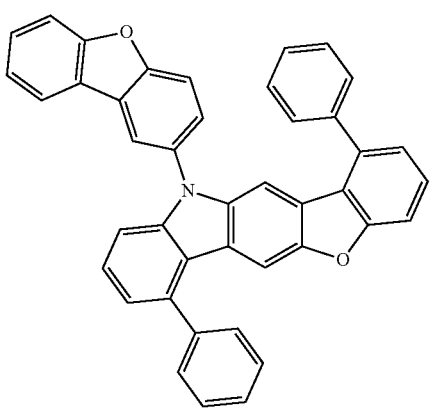

-continued
S-78
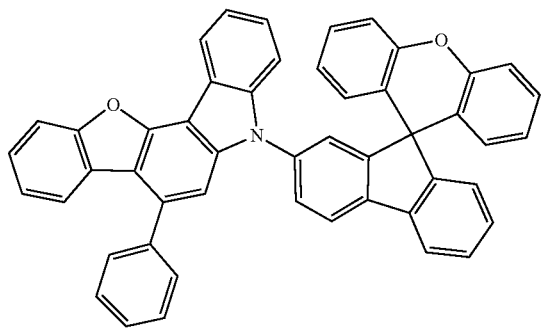
S-79
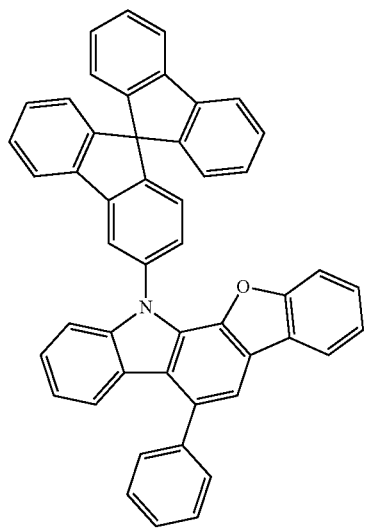
S-80
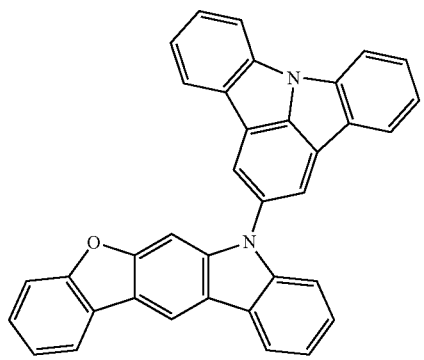
S-81
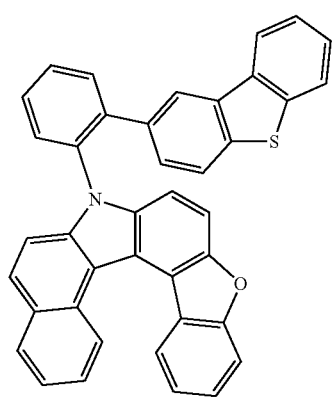
-continued
S-82
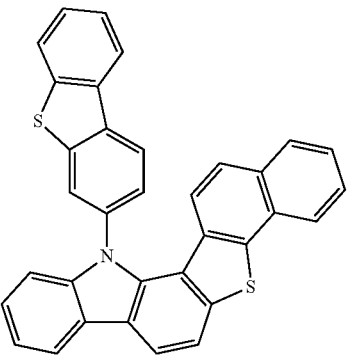
S-83
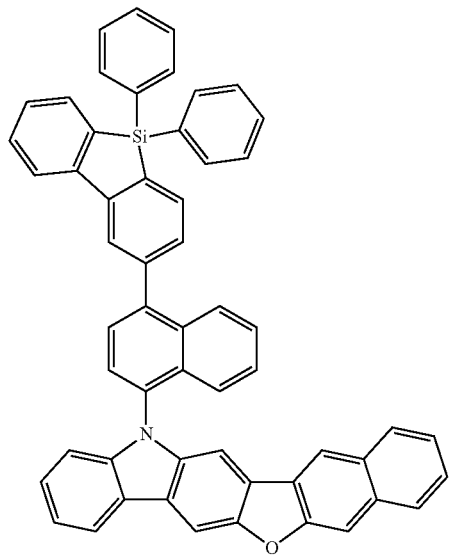
S-84
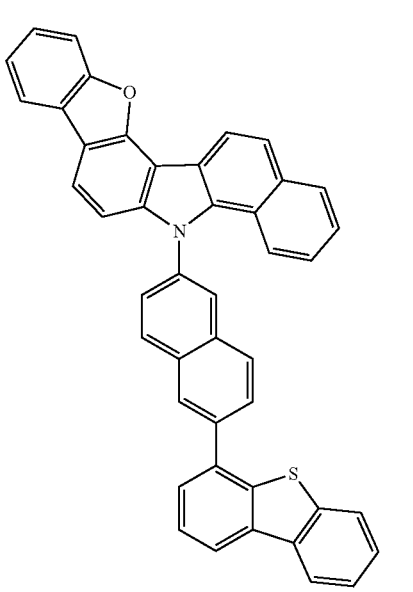

S-85
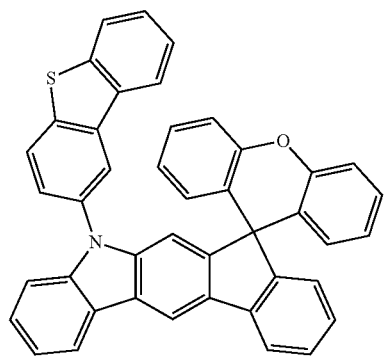
S-86
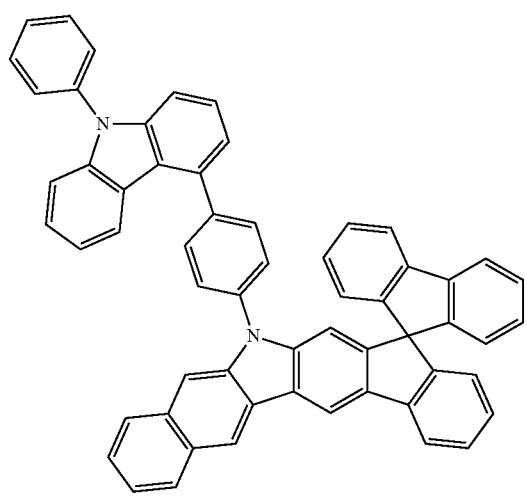
S-87
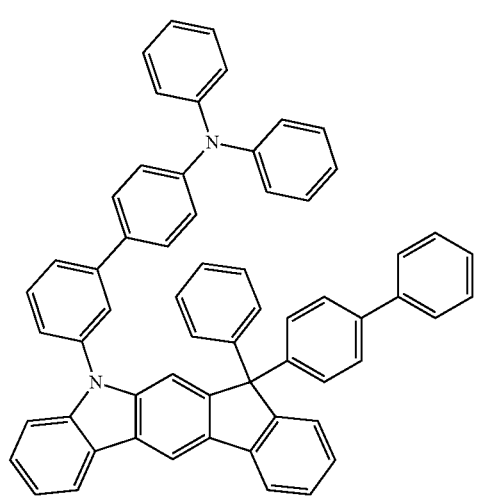
S-88
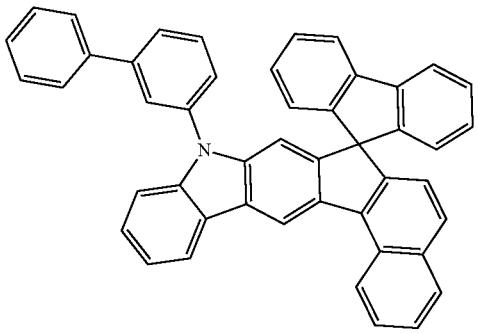
S-89
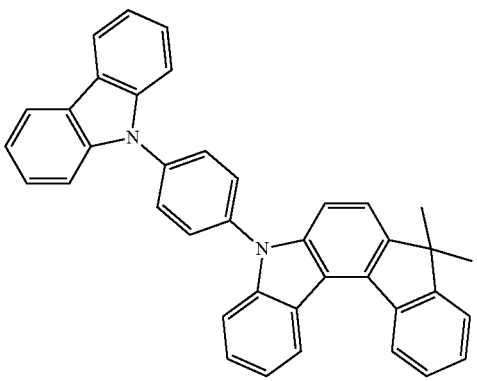
S-90
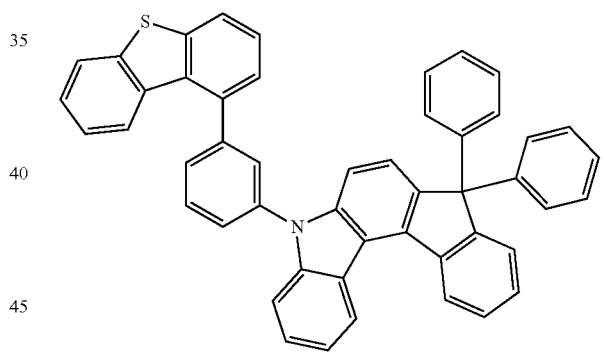
S-91
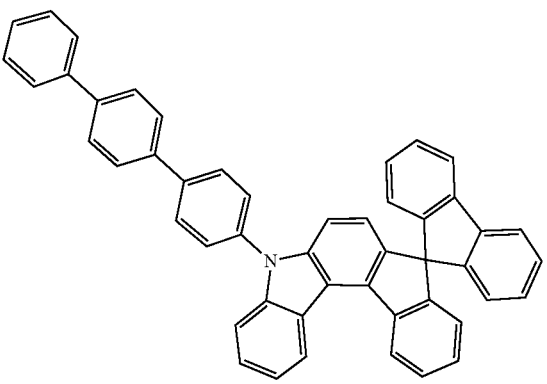

S-92
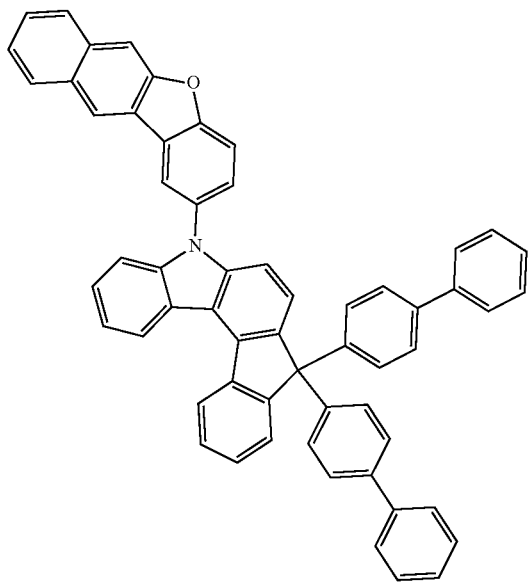
S-93
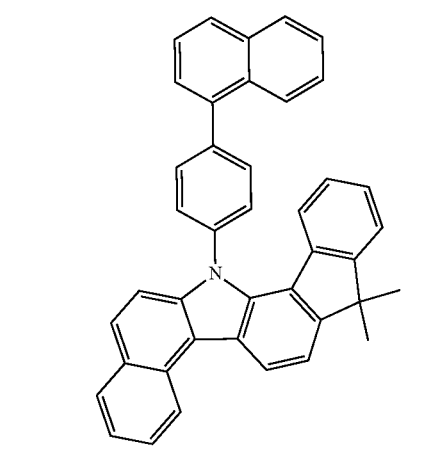
S-94
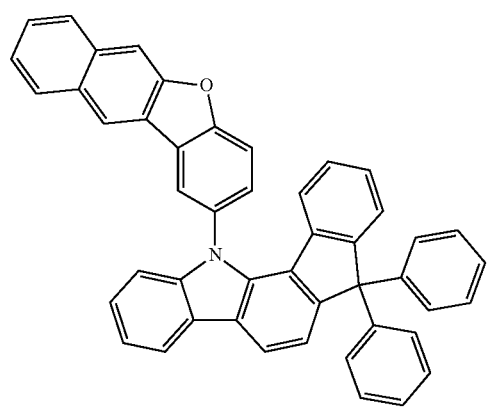
S-95
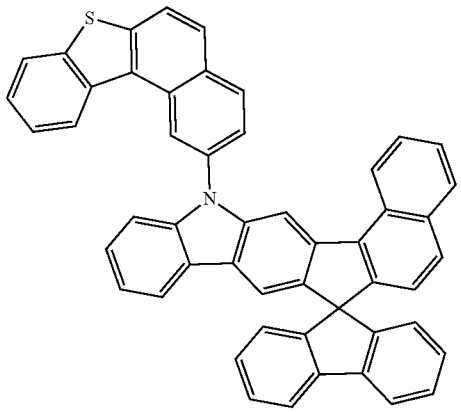
S-96
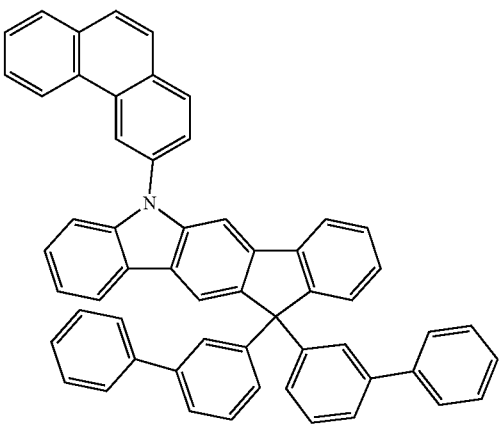
S-97
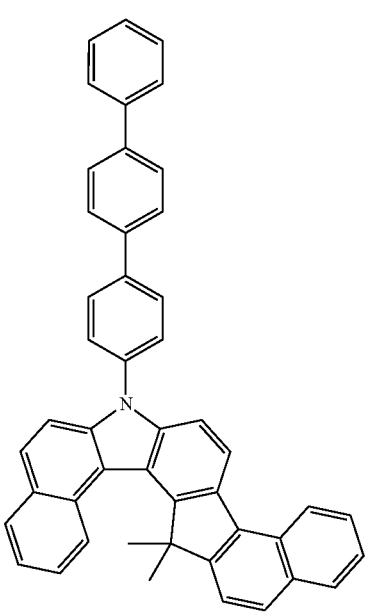

-continued
S-98
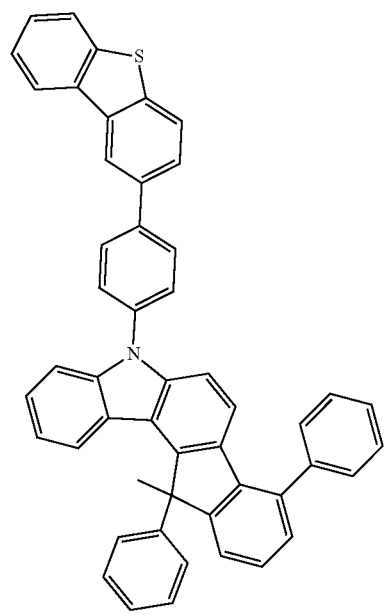
S-99
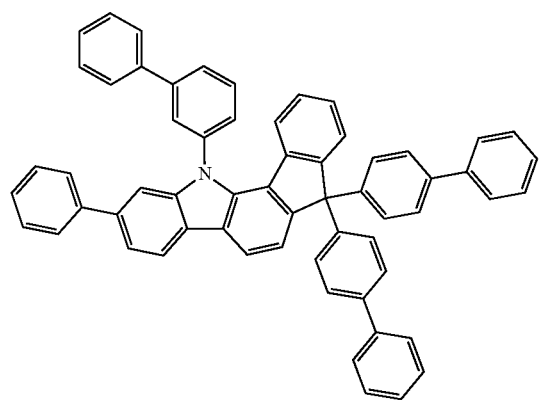
S-100
-continued
S-101
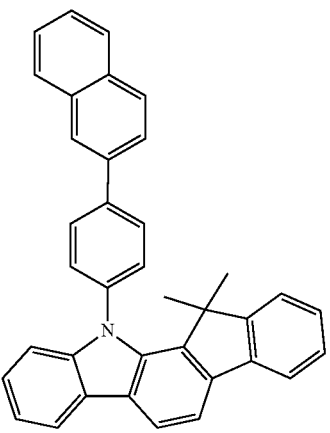
S-102
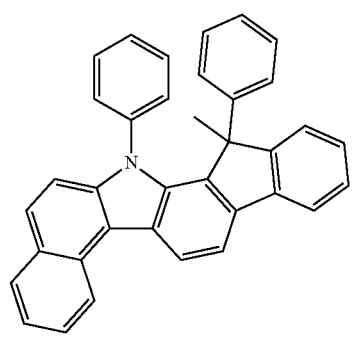
S-103
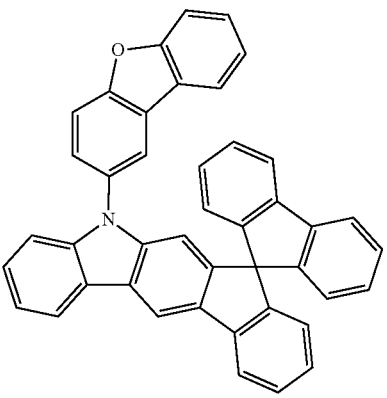
S-104
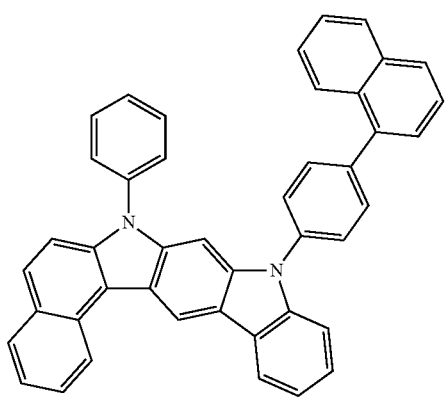

S-105
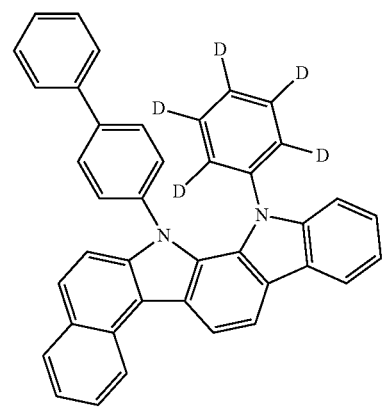
S-106
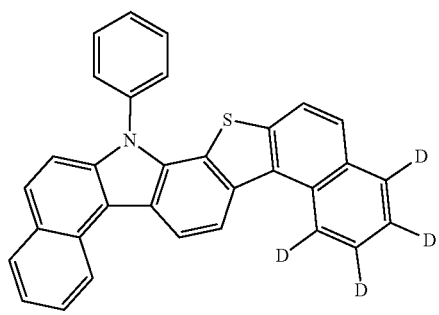
S-107
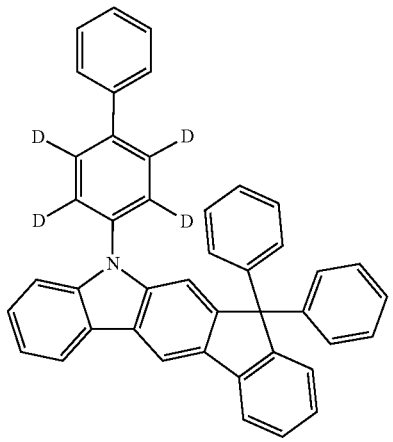
S-108
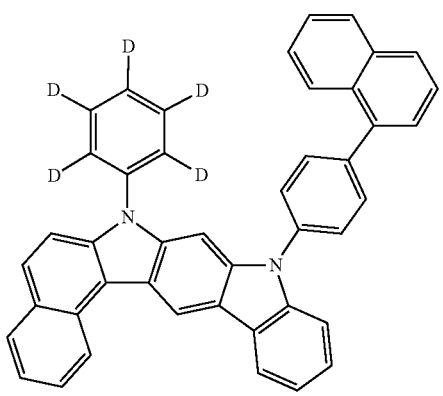
S-109
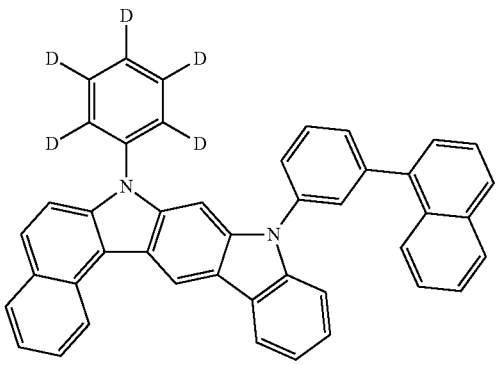
S-110
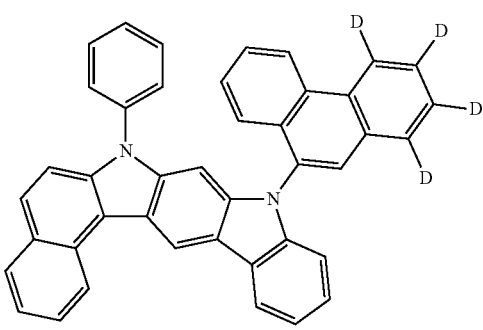
S-111
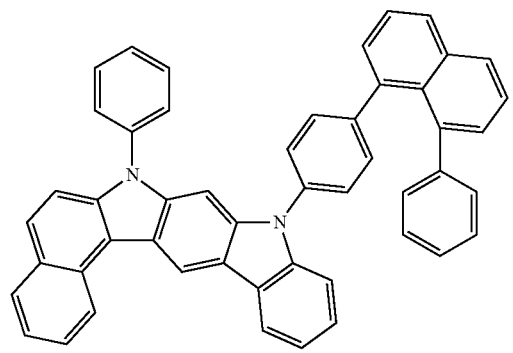
S-112
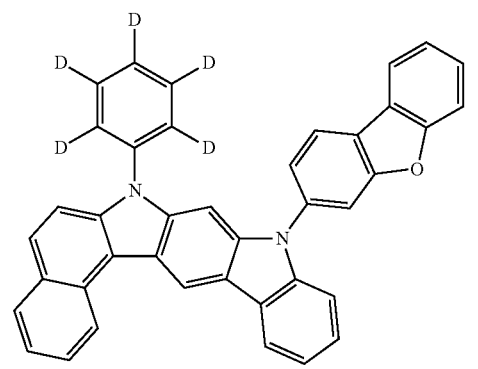

S-113
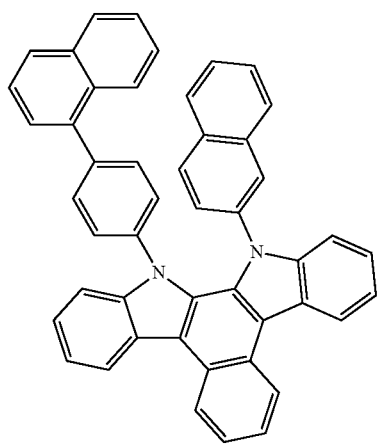
S-114
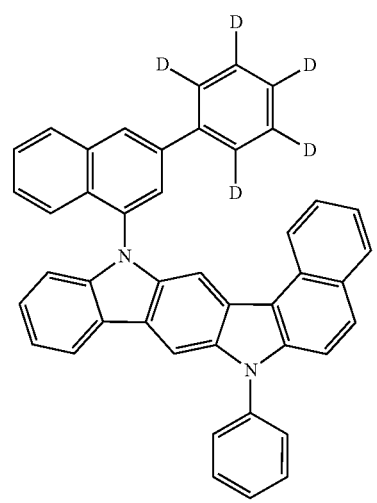
S-115
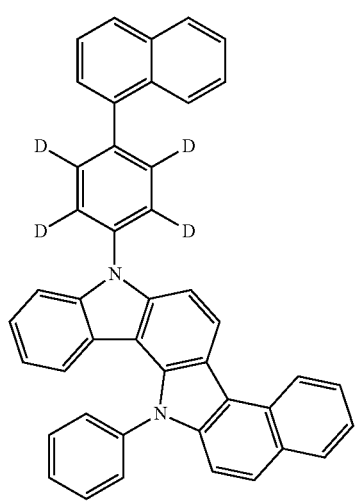
S-116
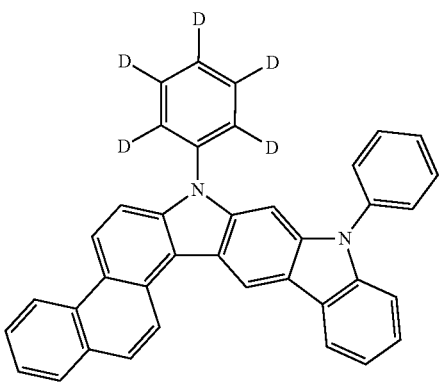
Additionally, the present invention provides compounds selected from the group consisting of the following compounds P-2 to P-16 and compounds P-22 to P-36.
P-2
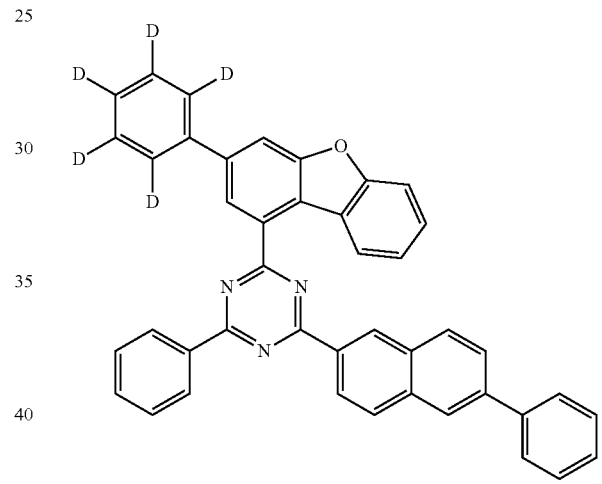
P-3
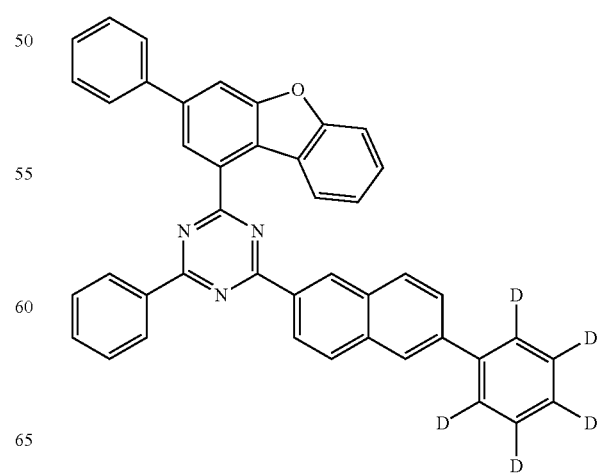

P-4
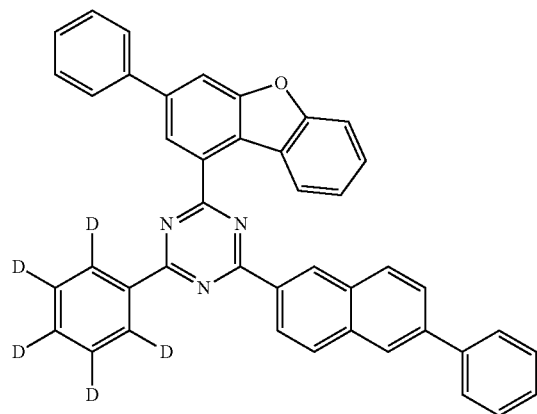
P-7
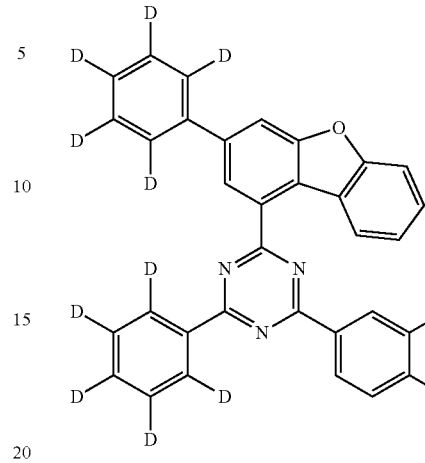
P-5
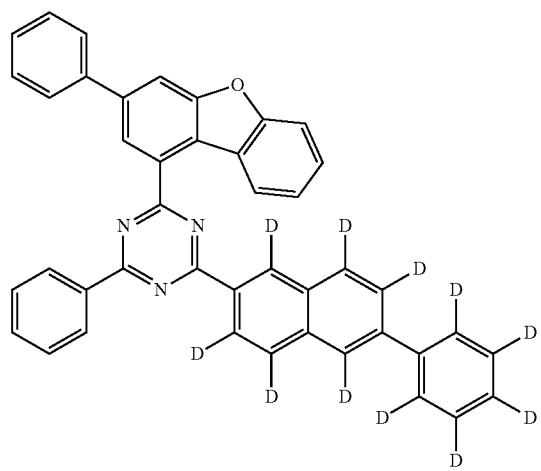
P-8
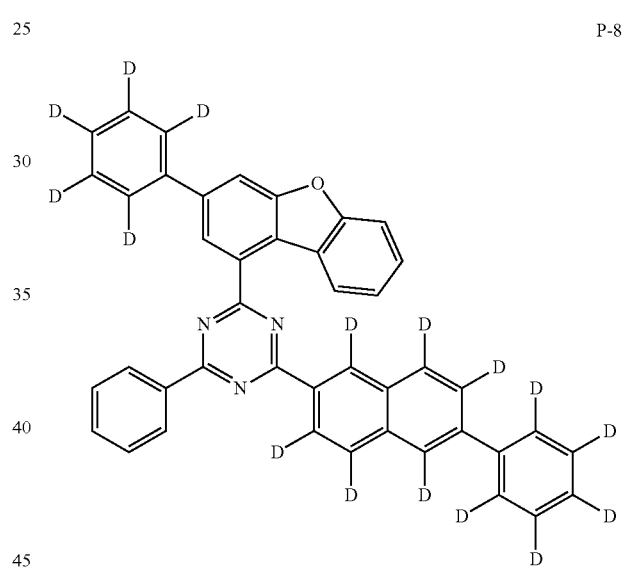
P-6
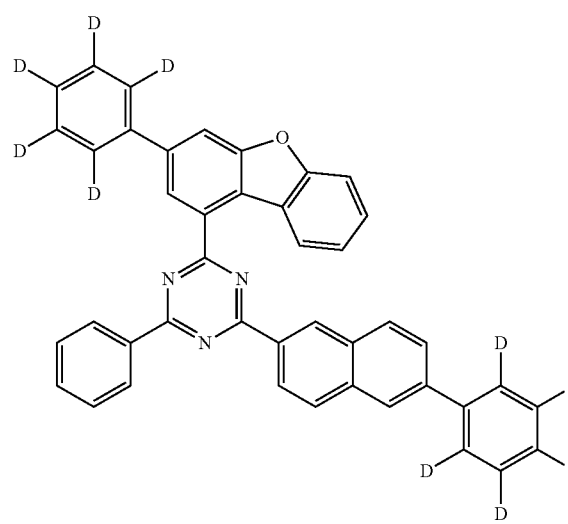
P-9
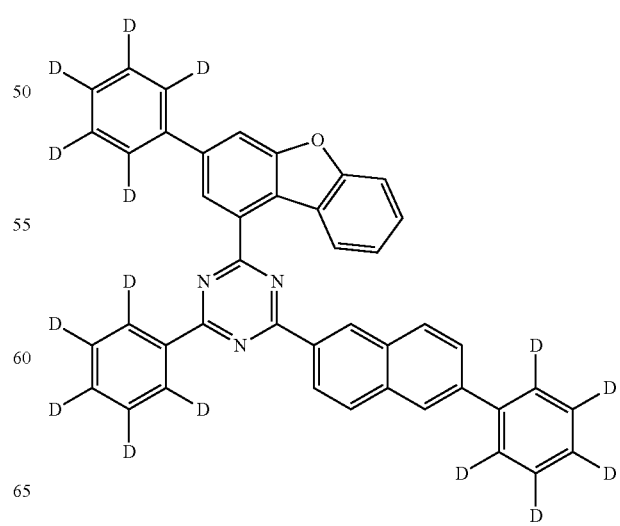

P-10
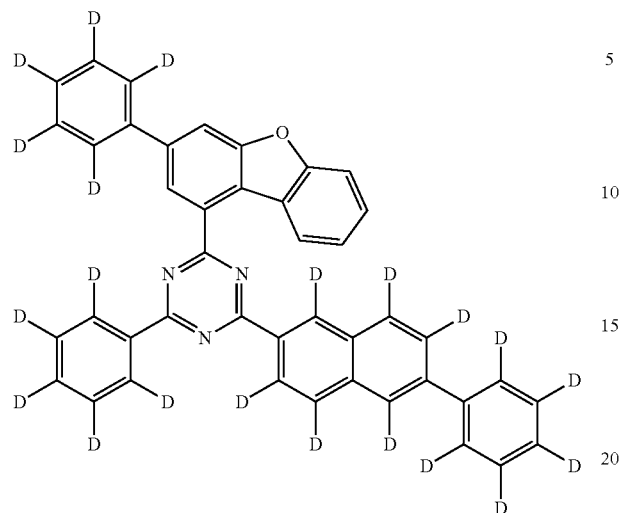
P-11
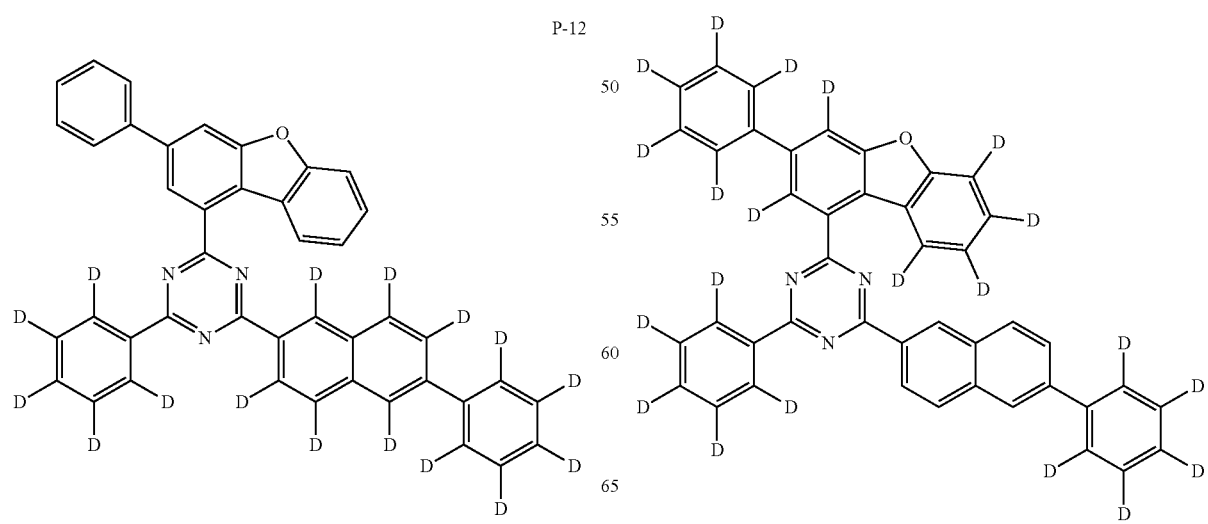
P-12
P-13
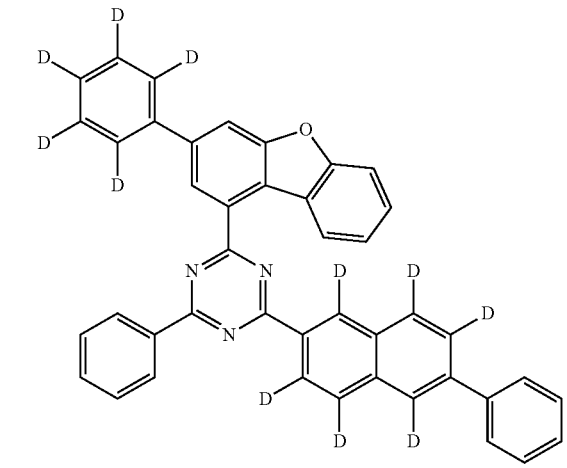
P-14
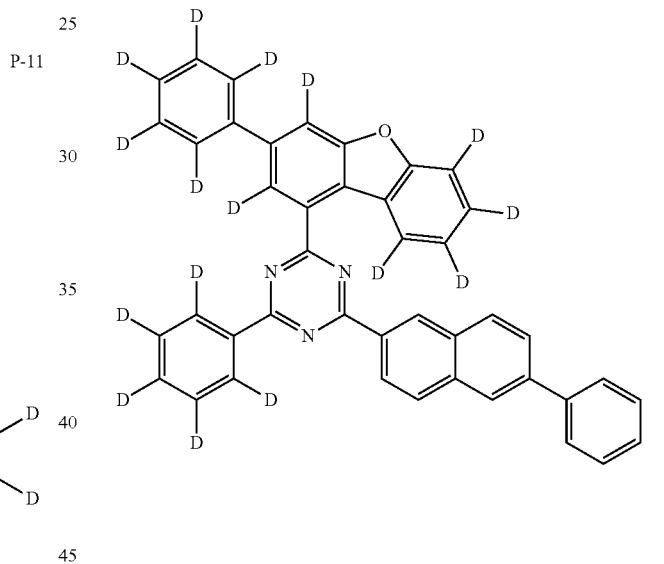
P-15

121
-continued
P-16
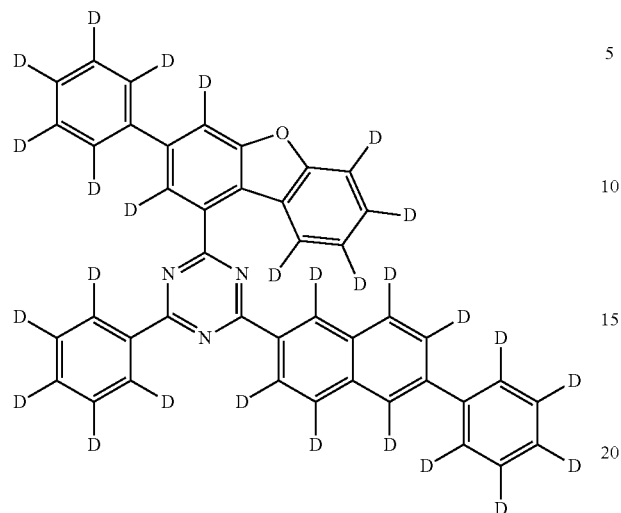
P-22
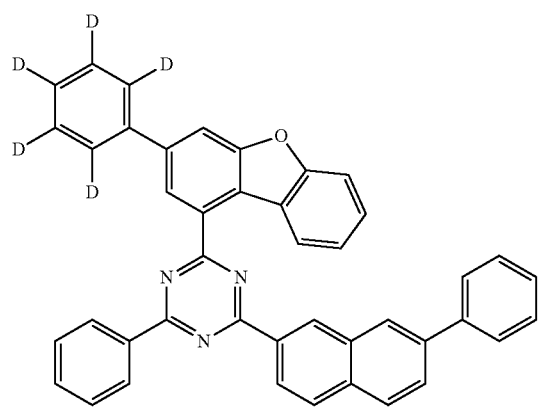
P-23
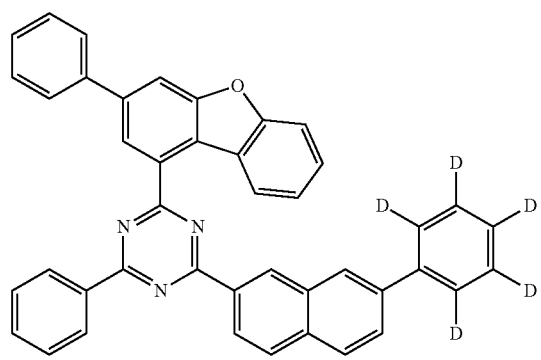
122
-continued
P-24
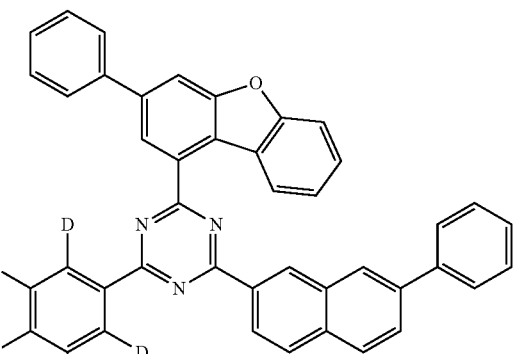
P-25
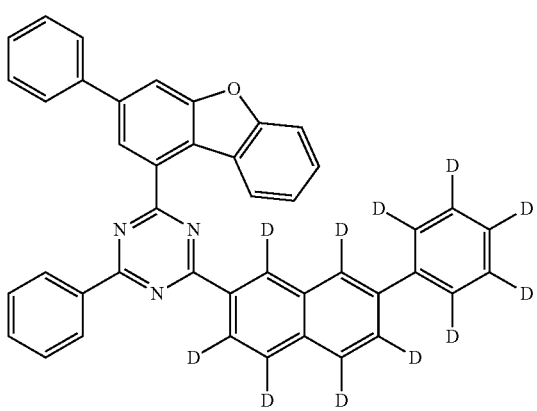
P-26
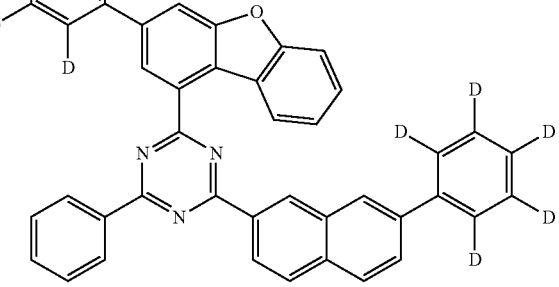

P-27
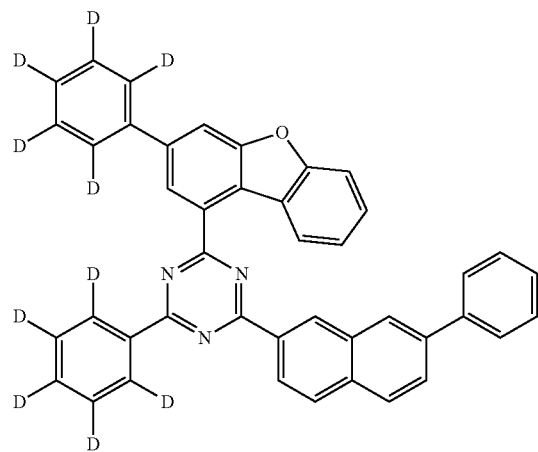
P-28
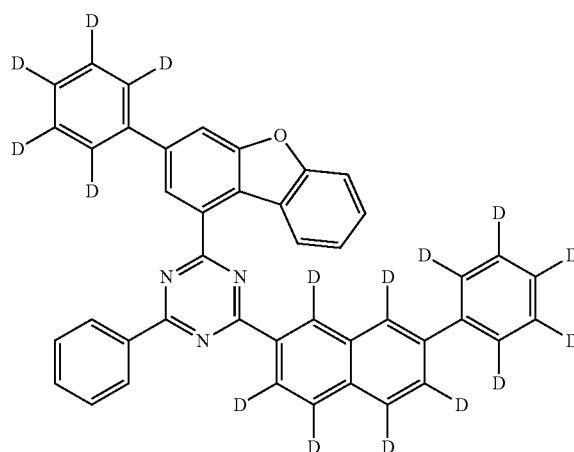
P-29
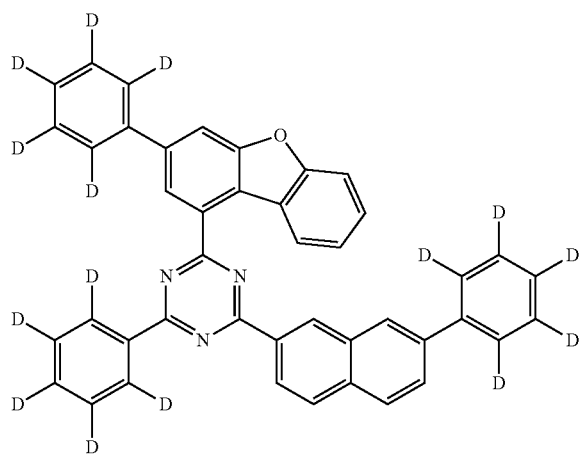
P-30
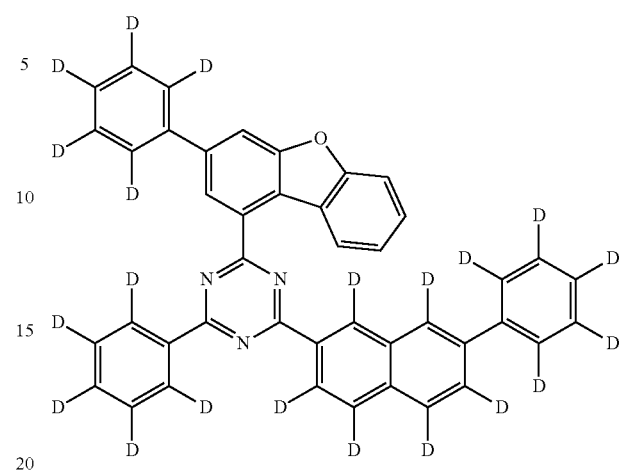
P-31
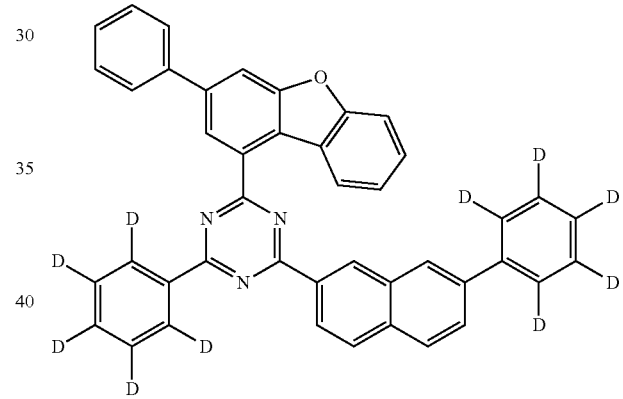
P-32
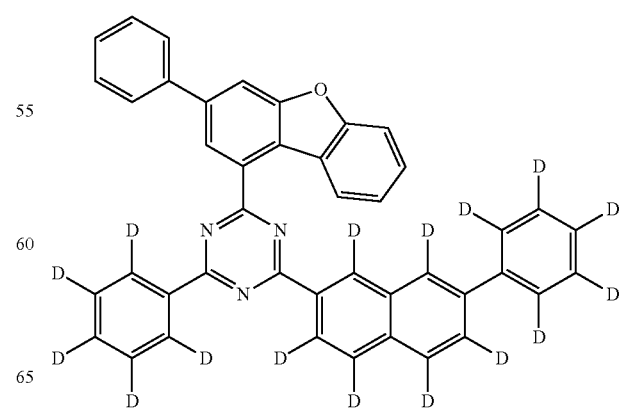

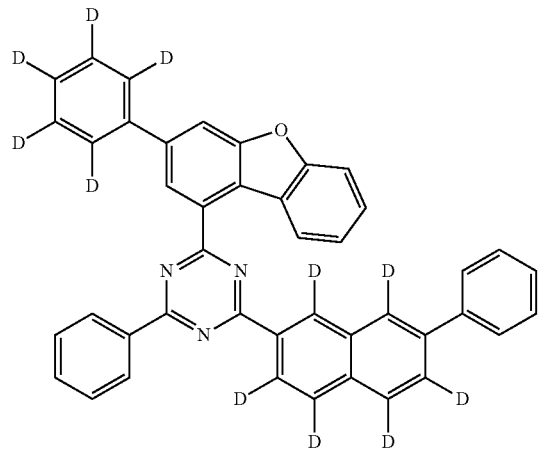

P-33

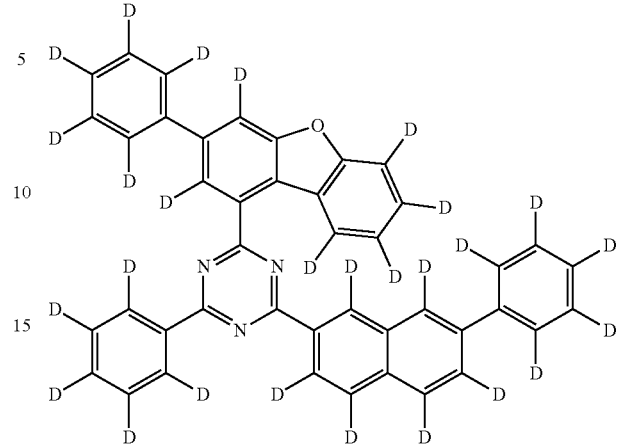

P-36

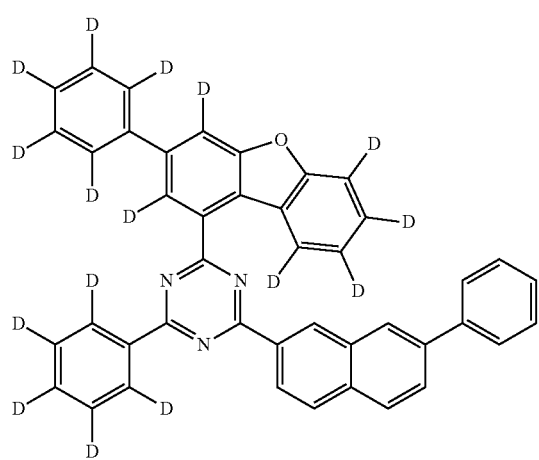

P-34

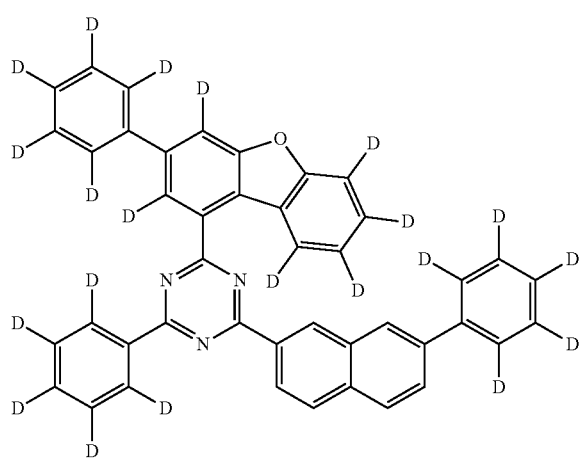

P-35

Also, in another aspect, the present invention provides an organic electronic element comprising a first electrode; a second electrode; and an organic material layer formed between the first electrode and the second electrode; wherein the organic material layer comprises the composition for an organic electronic element or any one of the compounds P-2 to P-16 and compounds P-22 to P-36.

In another aspect, the present invention provides a method for reusing the compounds P-2 to P-16 and compounds P-22 to P-36 comprising:

depositing an organic emitting material comprising any one of the compounds P-2 to P-16 and the compounds P-22 to P-36; to prepare an organic light emitting device;

removing impurities from the crude organic light emitting material;

recovering the organic light emitting material after the impurities are removed; and purifying the recovered organic light emitting material to have a purity of 99.9% or higher.

The step of removing impurities from the crude organic light emitting material recovered from the deposition apparatus may preferably comprise performing a pre-purification process to obtain a purity of 98% or more by recrystallization in a recrystallization solvent.

The recrystallization solvent may be preferably a polar solvent having a polarity index (PI) of 5.5 to 7.2.

The recrystallization solvent may preferably be used by mixing a polar solvent having a polarity value of 5.5 to 7.2 and a non-polar solvent having a polarity value of 2.0 to 4.7.

When a mixture of a polar solvent and a non-polar solvent is used, the recrystallization solvent may be used in an amount of 15% (v/v) or less of the non-polar solvent compared to the polar solvent.

The recrystallization solvent may preferably be used by mixing N-Methylpyrrolidone (NMP) single solvent; or a polar solvent mixed any one selected from the group consisting of 1,3-Dimethyl-2-imidazolidinone, 2-pyrrolidone, N,N-Dimethyl formamide, Dimethyl acetamide, and Dimethyl sulfoxide to the N-Methylpyrrolidone; or alone; or mixed non-polar solvents; selected from the group consisting of Toluene, Dichloromethane (DCM), Dichloroethane (DCE), Tetrahydrofuran (THF), Chloroform, Ethyl acetate and Butanone; or a polar solvent and a non-polar solvent.

The pre-purification process may comprise a step of precipitating crystals of by cooling to 0° C. to 5° C. after dissolving the crude organic light emitting material recovered from the deposition apparatus in a polar solvent at 90° C. to 120° C.

The pre-purification process may comprise a step of precipitating crystals by cooling to 35° C. to 40° C., adding a non-polar solvent, and then cooling to 0° C. to 5° C. after dissolving the crude organic light emitting material recovered from the deposition apparatus in a polar solvent at 90° C. to 120° C.

The pre-purification process may comprise a step of precipitating crystals while concentrating the solvent and removing the non-polar solvent, after dissolving the crude organic light emitting material recovered from the deposition apparatus in a non-polar solvent.

The pre-purification process may comprise a step of recrystallizing again with a non-polar solvent after recrystallizing first with a polar solvent.

The step of purifying the recovered impurities to a purity of 99.9% or higher may comprise performing an adsorption separation process to adsorb and remove impurities by adsorbing on the adsorbent.

The adsorbent may be activated carbon, silica gel, alumina, or a material for known adsorption purposes.

The step of purifying the recovered impurities to a purity of 99.9% or higher may comprise performing sublimation purification.

Referring to FIG. 1, the organic electronic element (100) according to the present invention comprises a first electrode (110), a second electrode (170), an organic material layer comprising a mixture of a compound represented by Formula 1 and a compound represented by Formula 2 or Formula 5, or any one of compounds P-2 to P-16 and compounds P-22 to P-36 between the first electrode (110) and the second electrode (170). Wherein, the first electrode (110) may be an anode or a positive electrode, and the second electrode (170) may be a cathode or a negative electrode. In the case of an inverted organic electronic element, the first electrode may be a cathode, and the second electrode may be an anode.

Figure 2:
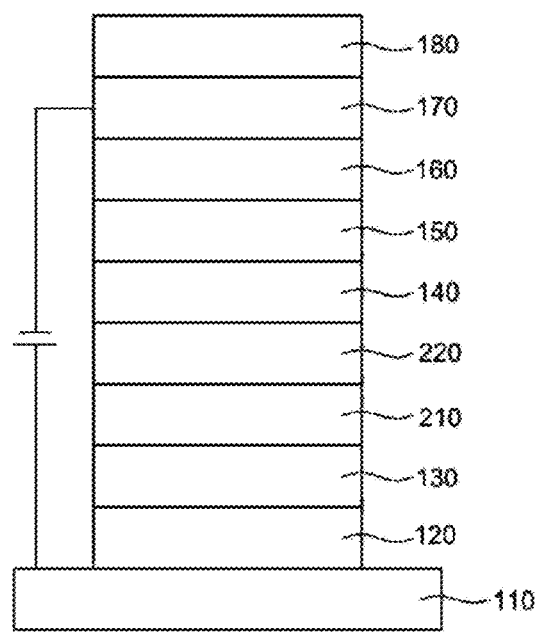

The organic material layer may sequentially comprise a hole injection layer (120), a hole transport layer (130), an emitting layer (140), an electron transport layer (150), and an electron injection layer (160) formed in sequence on the first electrode (110). Here, the remaining layers except the emitting layer (140) may not be formed. The organic material layer may further comprise a hole blocking layer, an electron blocking layer, an emitting-auxiliary layer (220), a buffer layer (210), etc., and the electron transport layer (150) and the like may serve as a hole blocking layer (see FIG. 2).

Also, the organic electronic element according to an embodiment of the present invention may further include a protective layer or a light efficiency enhancing layer (180). The light efficiency enhancing layer may be formed on a surface not in contact with the organic material layer among both surfaces of the first electrode or on a surface not in contact with the organic material layer among both surfaces of the second electrode. The compound or materials for organic electronic element according to an embodiment of the present invention applied to the organic material layer may be used as a material for a hole injection layer (120), a hole transport layer (130), an emitting-auxiliary layer (220), an electron transport auxiliary layer, an electron transport layer (150), an electron injection layer (160), a host or dopant of an emitting layer (140), or the light efficiency enhancing layer. Preferably, for example, the composition for an organic electronic element comprising a mixture of a compound represented by Formula 1 and a compound represented by Formula 2 or Formula 5, or any one of compounds P-2 to P-16 and compounds P-22 to P-36 can be used as a host material for the emitting layer.

Figure 3:
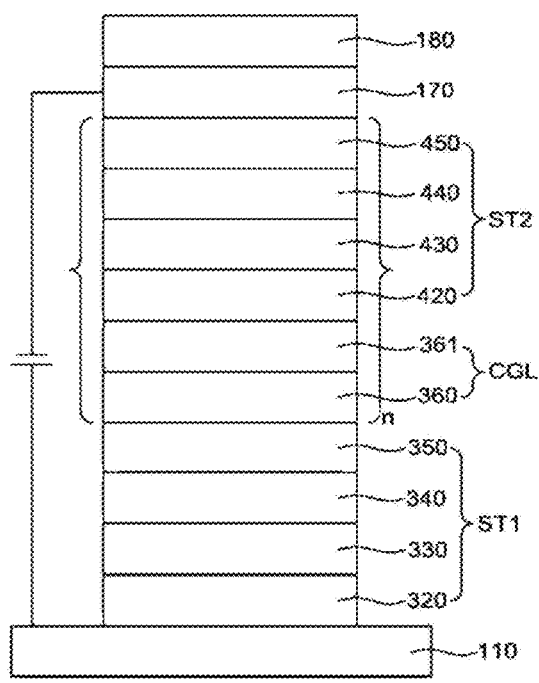

The organic material layer may include 2 or more stacks comprising a hole transport layer, an emitting layer and an electron transport layer sequentially formed on the anode, and may further comprise a charge generation layer formed between the 2 or more stacks (see FIG. 3).

Otherwise, even if the same core is used, the band gap, the electrical characteristics, the interface characteristics, and the like may vary depending on which substituent is bonded at which position, therefore the choice of core and the combination of sub-substituents associated therewith is also very important, and in particular, when the optimal combination of energy levels and T1 values, and unique properties of materials (mobility, interfacial characteristics, etc.) of each organic material layer is achieved, a long life span and high efficiency can be achieved at the same time.

The organic electroluminescent device according to an embodiment of the present invention may be manufactured using a PVD (physical vapor deposition) method. For example, a metal or a metal oxide having conductivity or an alloy thereof is deposited on a substrate to form a cathode, and the organic material layer including the hole injection layer (120), the hole transport layer (130), the emitting layer (140), the electron transport layer (150), and the electron injection layer (160) is formed thereon, and then depositing a material usable as a cathode thereon can manufacture an organic electroluminescent device according to an embodiment of the present invention.

Also, the present invention provides the organic electronic element wherein the organic material layer is formed by one of a spin coating process, a nozzle printing process, an inkjet printing process, a slot coating process, a dip coating process or a roll-to-roll process, and the organic material layer provides an organic electronic element comprising the compound or a composition for an organic electronic element as an electron transport material.

As another specific example, the present invention provides an organic electronic element used by mixing the same or different compounds of the compound represented by Formula 1 to the organic material layer. Preferably, the organic material layer comprises an emitting layer, wherein the emitting layer comprises a composition for an organic electronic element comprising a mixture of a compound represented by Formula 1 and a compound represented by Formula 2 or Formula 5, or any one of compounds P-2 to P-16 and compounds P-22 to P-36.

Also, the present invention provides a composition for an organic electronic element comprising a mixture of a compound represented by Formula 1 and a compound represented by Formula 2 or Formula 5, and provides an organic electronic element comprising the composition.

Also, the present invention provides any one of compounds P-2 to P-16 and compounds P-22 to P-36, and provides an organic electronic element comprising the compound.

Also, the present invention also provides an electronic device comprising a display device comprising the organic electronic element; and a control unit for driving the display device.

According to another aspect, the present invention provides a display device wherein the organic electronic element is at least one of an OLED, an organic solar cell, an organic photo conductor, an organic transistor (organic TFT) and an element for monochromic or white illumination. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, Synthesis examples of the compound represented by Formula 1, Formula 2 and Formula 5 and preparation examples of the organic electronic element according to the present invention will be described in detail by way of example, but are not limited to the following examples.

EXAMPLES

[Synthesis Example 1] Compound Represented by Formula 1

The compound (final products) represented by Formula 1 according to the present invention is synthesized as shown in Reaction Scheme 1, but is not limited thereto.

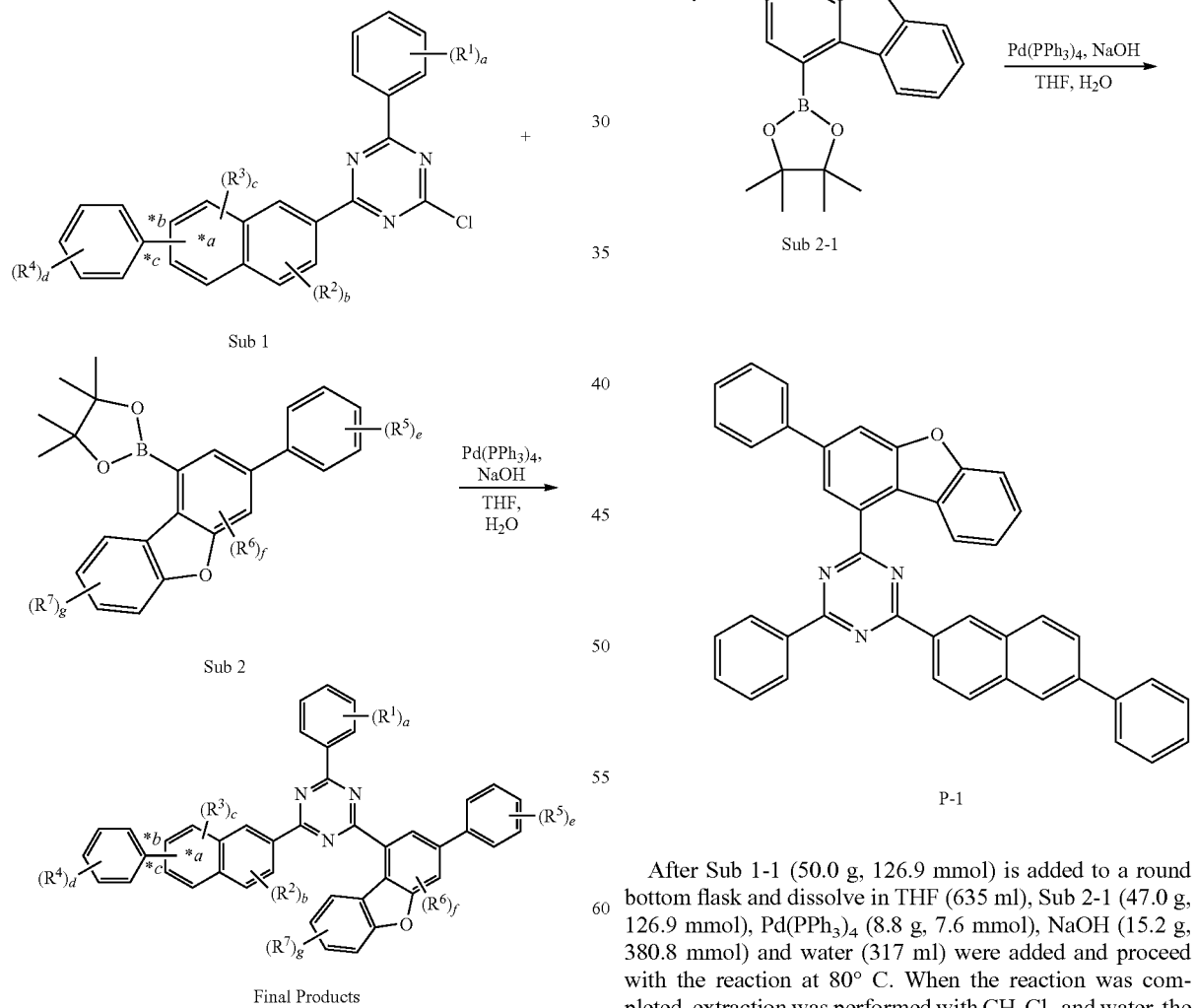

Wherein, $R^1$, $R^2$, $R^3$, $R^4$, $R^5$, $R^6$, $R^7$, a, b, c, d, e, f, g, *a, *b and *c are the same as defined in Formula 1.

I. Synthesis of Final Product

1. Synthesis Example of P-1

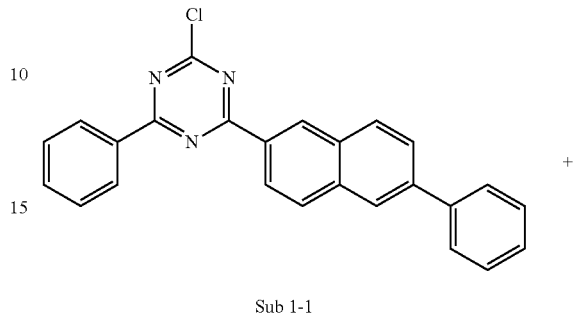

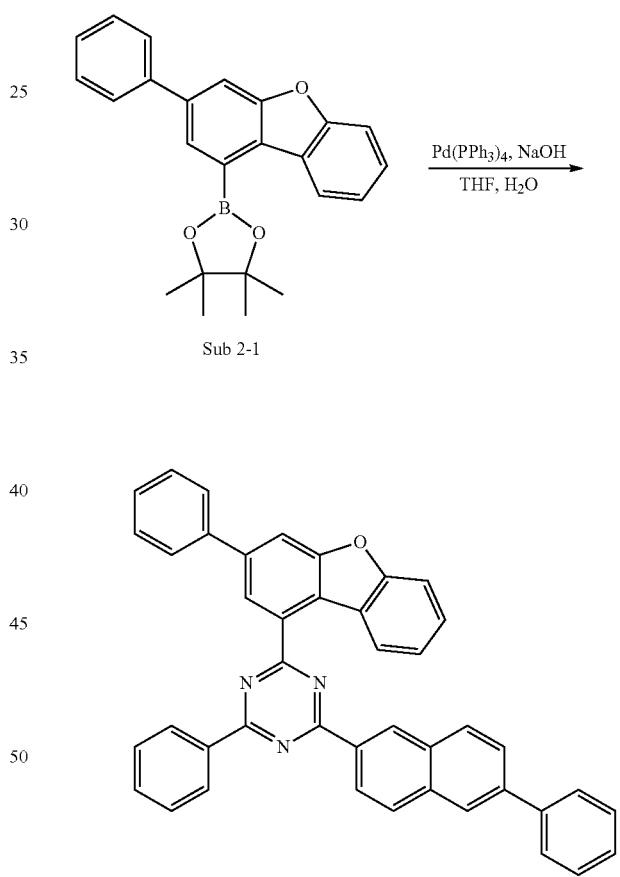

After Sub 1-1 (50.0 g, 126.9 mmol) is added to a round bottom flask and dissolve in THF (635 ml), Sub 2-1 (47.0 g, 126.9 mmol), Pd(PPh$_3$)$_4$ (8.8 g, 7.6 mmol), NaOH (15.2 g, 380.8 mmol) and water (317 ml) were added and proceed with the reaction at 80° C. When the reaction was completed, extraction was performed with CH$_2$Cl$_2$ and water, the organic layer was dried with MgSO$_4$, concentrated, and the resulting organic material was recrystallized using a silica-gel column to obtain 61.7 g of product. (Yield: 80.8%)

2. Synthesis Example of P-5

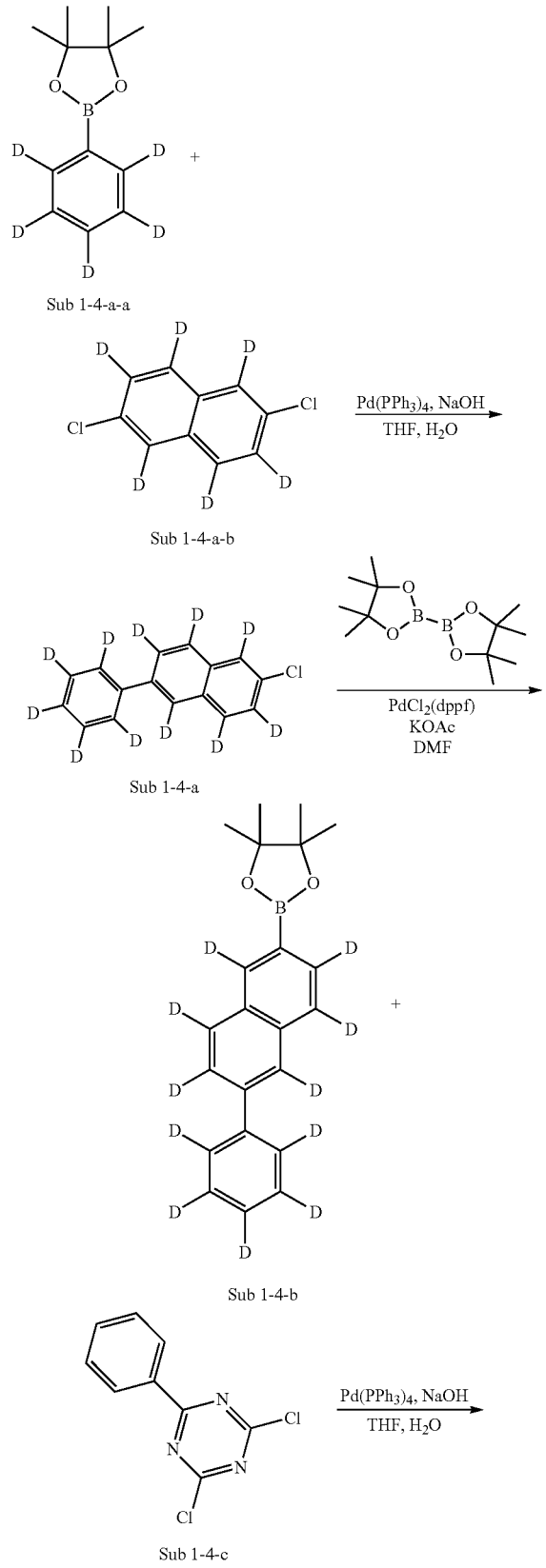

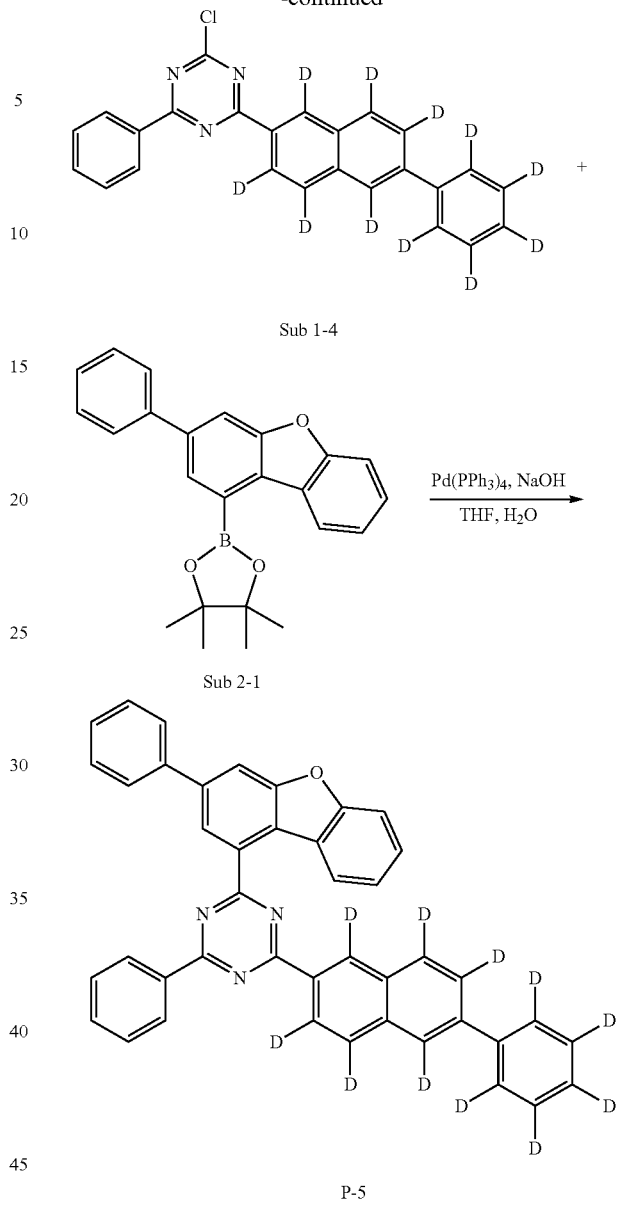

1) Synthesis of Sub 1-4-a

After Sub 1-4-a-a (100.0 g, 478.2 mmol) is added to a round bottom flask and dissolve in THF (2391 ml), Sub 1-4-a-b (97.1 g, 478.2 mmol), Pd(PPh$_3$)$_4$ (33.2 g, 28.7 mmol), NaOH (57.4 g, 1434.7 mmol) and Water (1196 ml) were added and experimented in the same manner as P-1 to obtain 97.2 g of product. (Yield: 81.4%)

2) Synthesis of Sub 1-4-b

Sub 1-4-a (70.0 g, 280.3 mmol) is add to a round bottom flask and dissolve in DMF (1401 ml). 4,4,4',4',5,5,5',5'-octamethyl-2,2'-bi (1,3,2-dioxaborolane) (92.5 g, 364.3 mmol), Pd(dppf)Cl$_2$ (10.3 g, 14.0 mmol), KOAc (82.5 g, 840.7 mmol) were added and stirred at 150° C. for 2 hours. When the reaction was completed, extraction was performed with CH$_2$Cl$_2$ and water, the organic layer was dried with MgSO₄, concentrated, and the resulting organic material was recrystallized using a silicagel column to obtain 76.4 g of product. (Yield: 79.9%)

3) Synthesis of Sub 1-4

After Sub 1-4-b (70.0 g, 205.1 mmol) is added to a round bottom flask and dissolve in THF (1025 ml), Sub 1-4-c (46.4 g, 205.1 mmol), Pd(PPh₃)₄ (14.2 g, 12.3 mmol), NaOH (24.6 g, 615.3 mmol) and Water (513 ml) were added and experimented in the same manner as P-1 to obtain 66.9 g of product. (Yield: 80.5%)

4) Synthesis of P-5

After Sub 1-4 (50.0 g, 123.5 mmol) is added to a round bottom flask and dissolve in THF (617 ml), Sub 2-1 (45.7 g, 123.5 mmol), Pd(PPh₃)₄ (8.6 g, 7.4 mmol), NaOH (14.8 g, 370.4 mmol) and Water (309 ml) were added and experimented in the same manner as P-1 to obtain 61.4 g of product. (Yield: 81.2%)

3. Synthesis of P-26

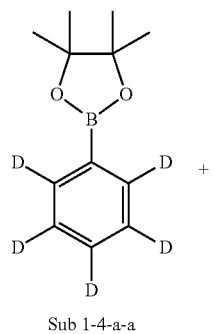

Sub 1-4-a-a

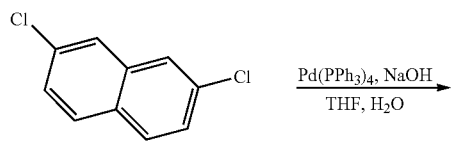

Sub 1-10-a-b

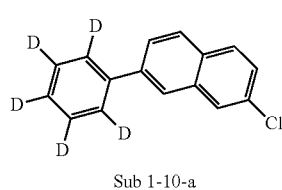

Sub 1-10-a

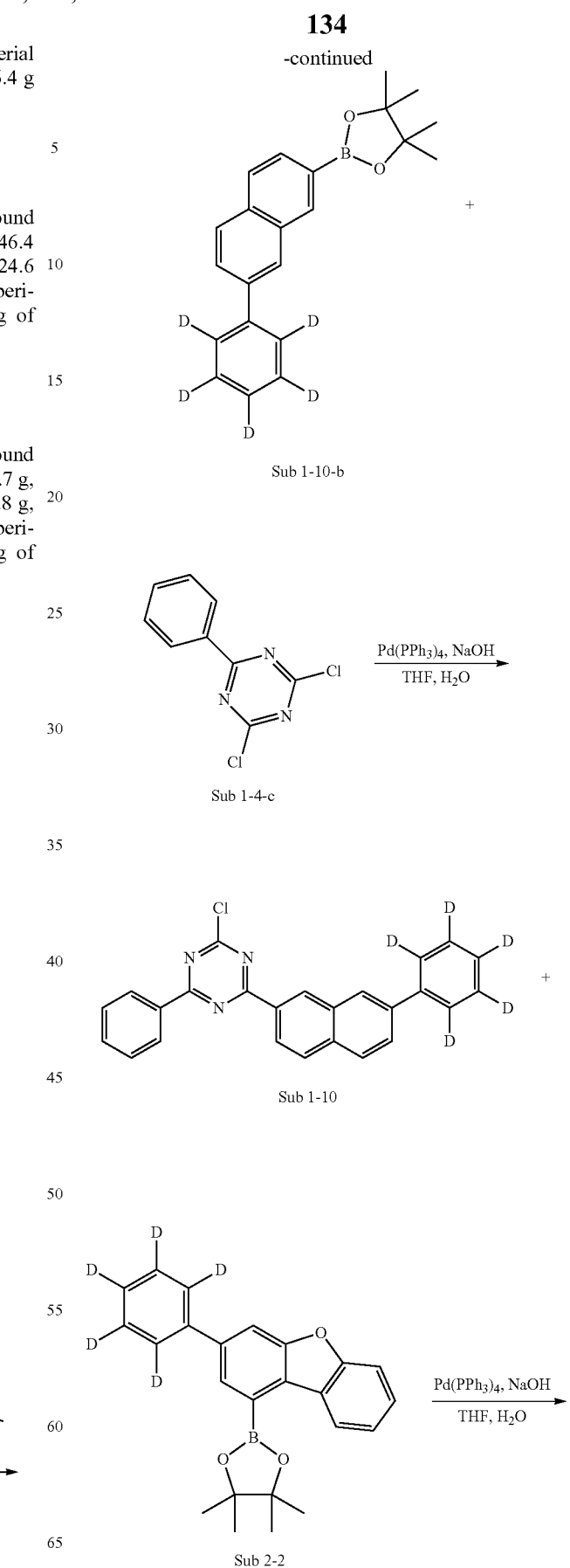

-continued

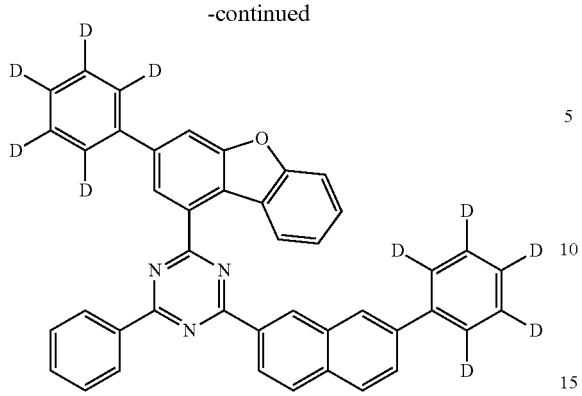

P-26

-continued

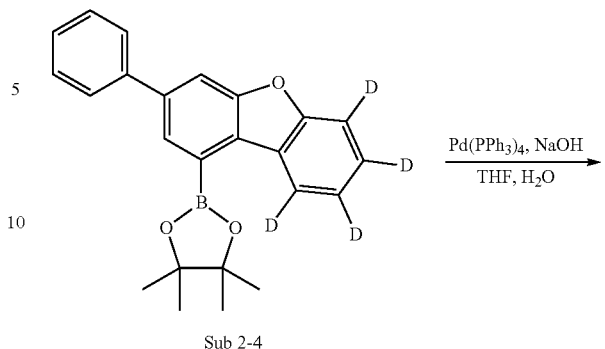

Sub 2-4

1) Synthesis of Sub 1-10-a

After Sub 1-4-a-a (100.0 g, 478.2 mmol) is added to a round bottom flask and dissolve in THF (2391 ml), Sub 1-10-a-b (94.2 g, 478.2 mmol), Pd(PPh₃)₄ (33.2 g, 28.7 mmol), NaOH (57.4 g, 1434.7 mmol) and Water (1196 ml) were added and experimented in the same manner as P-1 to obtain 93.6 g of product. (Yield: 80.3%)

2) Synthesis of Sub 1-10-b

After Sub 1-10-a (70.0 g, 287.2 mmol) is added to a round bottom flask and dissolve in DMF (1436 ml), 4,4,4',4',5,5,5',5'-octamethyl-2,2'-bi (1,3,2-dioxaborolane) (94.8 g, 373.4 mmol), Pd(dppf)Cl₂ (10.5 g, 14.4 mmol), KOAc (84.6 g, 861.6 mmol) were added and experimented in the same manner as Sub 1-4-b to obtain 77.7 g of product. (Yield: 80.7%)

3) Synthesis of Sub 1-10

After Sub 1-10-b (70.0 g, 208.8 mmol) is added to a round bottom flask and dissolve in THF (1044 ml), Sub 1-4-c (47.2 g, 208.8 mmol), Pd(PPh₃)₄ (14.5 g, 12.5 mmol), NaOH (25.1 g, 626.4 mmol) and Water (522 ml) were added and experimented in the same manner as P-1 to obtain 67.5 g of product. (Yield: 81.0%)

4) Synthesis of P-26

After Sub 1-10 (50.0 g, 125.3 mmol) is added to a round bottom flask and dissolve in THF (627 ml), Sub 2-2 (47.0 g, 125.3 mmol), Pd(PPh₃)₄ (8.7 g, 7.5 mmol), NaOH (15.0 g, 376.0 mmol) and Water (313 ml) were added and experimented in the same manner as P-1 to obtain 63.0 g of product. (Yield: 82.2%)

4. Synthesis of P-38

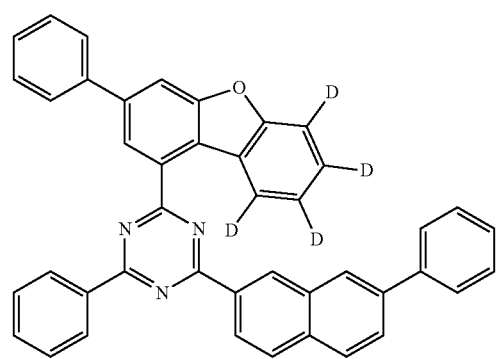

P-38

After Sub 1-9 (50.0 g, 126.9 mmol) is added to a round bottom flask and dissolve in THF (635 ml), Sub 2-4 (47.5 g, 126.9 mmol), Pd(PPh₃)₄ (8.8 g, 7.6 mmol), NaOH (15.2 g, 380.8 mmol) and Water (317 ml) were added and experimented in the same manner as P-1 to obtain 62.8 g of product. (Yield: 81.7%)

Sub 1 in Reaction Scheme 1 may be the following compound, but is not limited thereto, and the FD-MS (Field Desorption-Mass Spectrometry) values of the compounds belonging to Sub 1 are shown in Table 1.

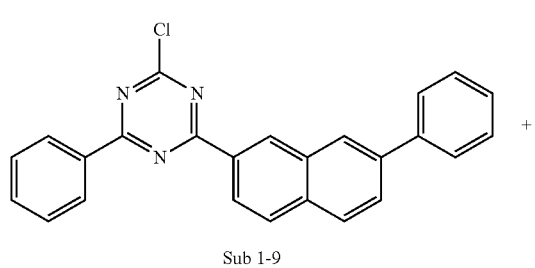

Sub 1-9

+

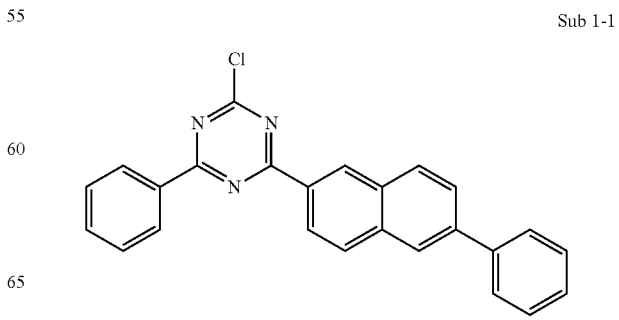

Sub 1-1

-continued
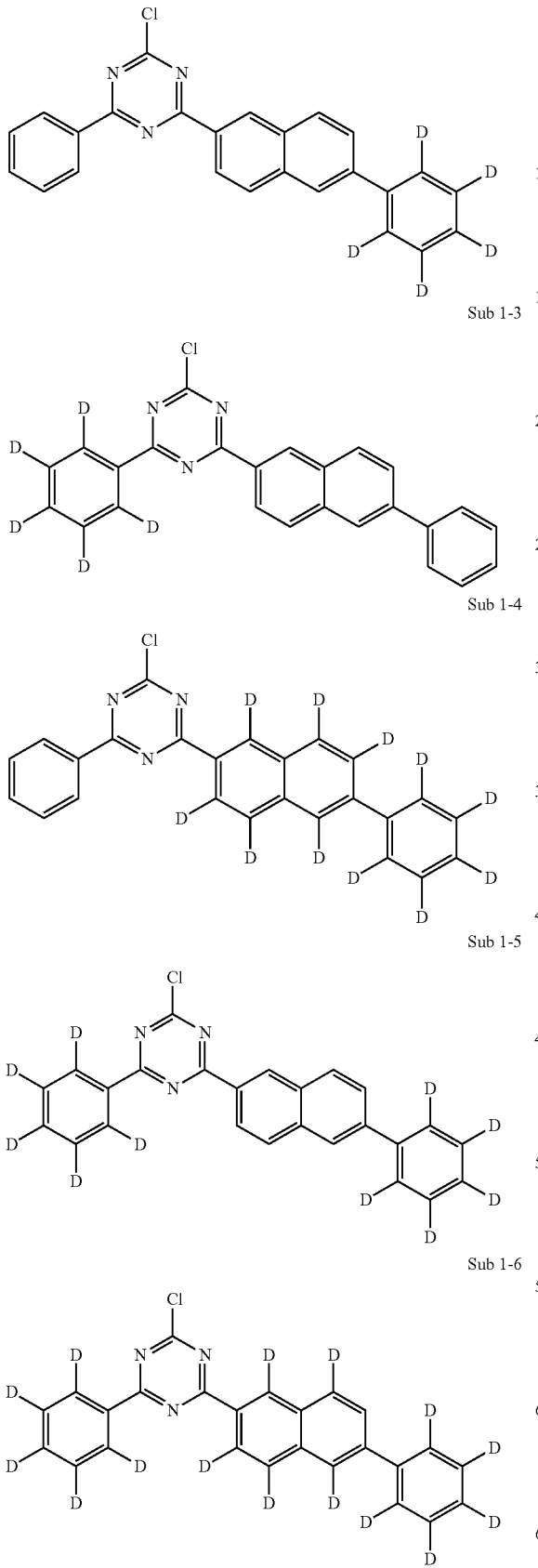
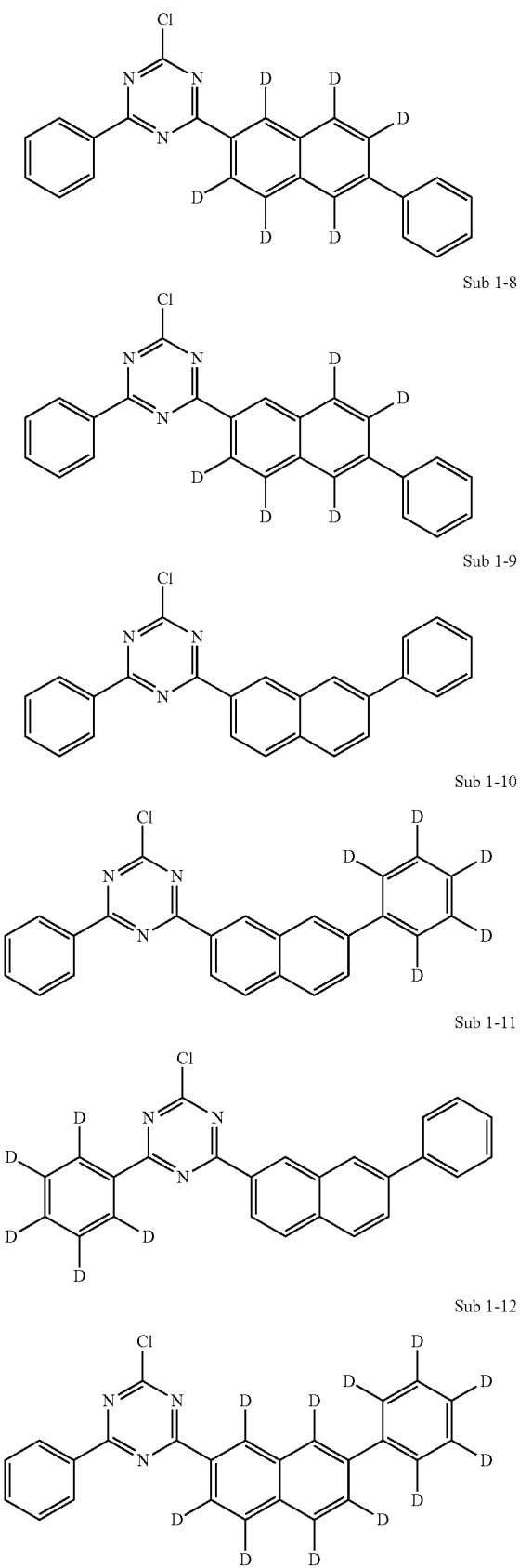

-continued

Sub 1-13
Sub 1-14
Sub 1-15
Sub 1-16

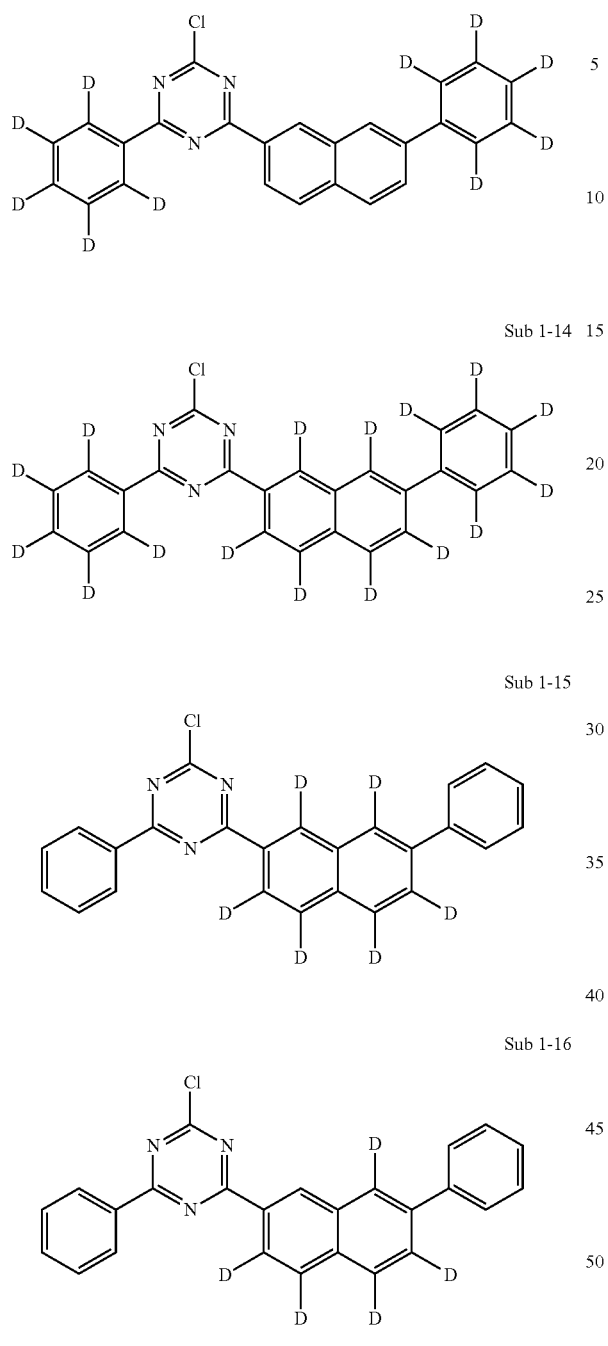

Sub 2 in Reaction Scheme 1 may be a compound as shown below, but is not limited thereto, and the FD-MS (Field Desorption-Mass Spectrometry) values of the compounds belonging to Sub 2 are shown in Table 2.

Sub 2-1
Sub 2-2
Sub 2-3

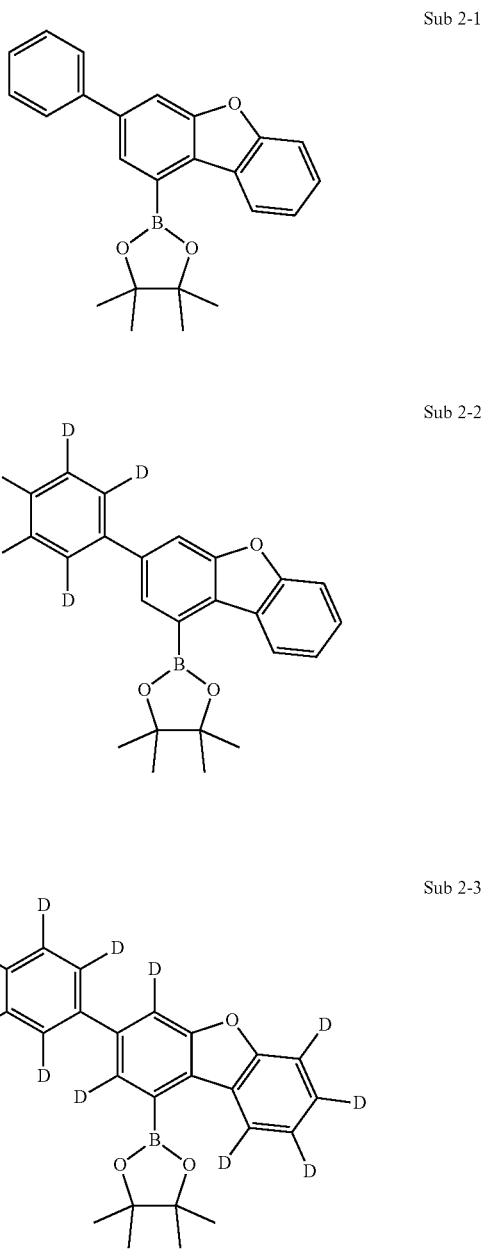

TABLE 1

| Compound | FD-MS | Compound | FD-MS |
| --- | --- | --- | --- |
| Sub 1-1 | m/z = 393.10($C_{25}H_{16}ClN_3$ = 393.87) | Sub 1-2 | m/z = 398.13($C_{25}H_{11}D_5ClN_3$ = 398.90) |
| Sub 1-3 | m/z = 398.13($C_{25}H_{11}D_5ClN_3$ = 398.90) | Sub 1-4 | m/z = 404.17($C_{25}H_5D_{11}ClN_3$ = 404.94) |
| Sub 1-5 | m/z = 403.17($C_{25}H_6D_{10}ClN_3$ = 403.94) | Sub 1-6 | m/z = 409.20($C_{25}D_{16}ClN_3$ = 409.97) |
| Sub 1-7 | m/z = 399.14($C_{25}H_{10}D_6ClN_3$ = 399.91) | Sub 1-8 | m/z = 398.13($C_{25}H_{11}D_5ClN_3$ = 398.90) |
| Sub 1-9 | m/z = 393.10($C_{25}H_{16}ClN_3$ = 393.87) | Sub 1-10 | m/z = 398.13($C_{25}H_{11}D_5ClN_3$ = 398.90) |
| Sub 1-11 | m/z = 398.13($C_{25}H_{11}D_5ClN_3$ = 398.9) | Sub 1-12 | m/z = 404.17($C_{25}H_5D_{11}ClN_3$ = 404.94) |
| Sub 1-13 | m/z = 403.17($C_{25}H_6D_{10}ClN_3$ = 403.94) | Sub 1-14 | m/z = 409.20($C_{25}D_{16}ClN_3$ = 409.97) |
| Sub 1-15 | m/z = 399.14($C_{25}H_{10}D_6ClN_3$ = 399.91) | Sub 1-16 | m/z = 398.13($C_{25}H_{11}D_5ClN_3$ = 398.90) |

-continued

Sub 2-4

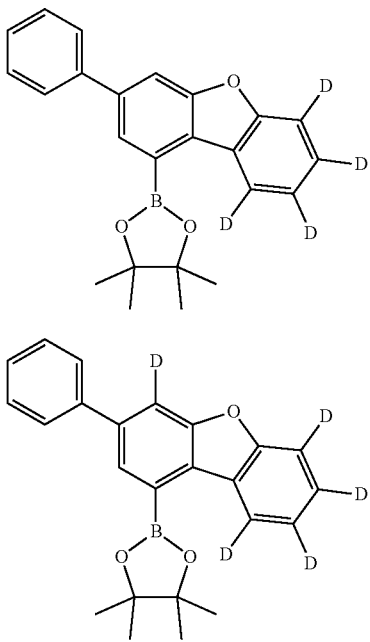

Sub 2-5

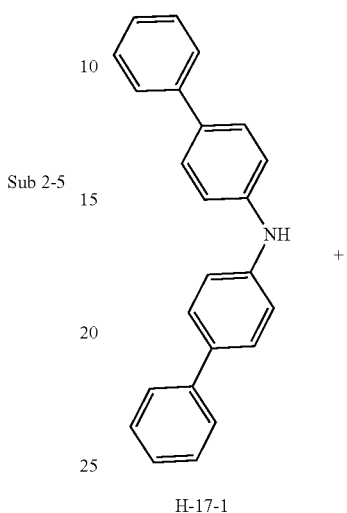

[Synthesis Example 2] Compound Represented by Formula 2

I. Synthesis of Final Product

1. Synthesis Example of H-17

H-17-1

TABLE 2

| Compound | FD-MS | Compound | FD-MS |
|---|---|---|---|
| Sub 2-1 | m/z = 370.17($C_{24}H_{23}BO_3$ = 370.26) | Sub 2-2 | m/z = 375.21($C_{24}H_{18}D_5BO_3$ = 375.29) |
| Sub 2-3 | m/z = 381.24($C_{24}H_{12}D_{11}BO_3$ = 381.32) | Sub 2-4 | m/z = 374.20($C_{24}H_{19}D_4BO_3$ = 374.28) |
| Sub 2-5 | m/z = 375.21($C_{24}H_{18}D_5BO_3$ = 375.29) | | |

The FD-MS (Field Desorption-Mass Spectrometry) values of compounds P-1 to P-40 of the present invention prepared according to the above synthesis examples are shown in Table 3.

TABLE 3

| Compound | FD-MS | Compound | FD-MS |
|---|---|---|---|
| P-1 | m/z = 601.22($C_{43}H_{27}N_3O$ = 601.71) | P-2 | m/z = 606.25($C_{43}H_{22}D_5N_3O$ = 606.74) |
| P-3 | m/z = 606.25($C_{43}H_{22}D_5N_3O$ = 606.74) | P-4 | m/z = 606.25($C_{43}H_{22}D_5N_3O$ = 606.74) |
| P-5 | m/z = 612.28($C_{43}H_{16}D_{11}N_3O$ = 612.78) | P-6 | m/z = 611.28($C_{43}H_{17}D_{10}N_3O$ = 611.77) |
| P-7 | m/z = 611.28($C_{43}H_{17}D_{10}N_3O$ = 611.77) | P-8 | m/z = 617.32($C_{43}H_{11}D_{16}N_3O$ = 617.81) |
| P-9 | m/z = 616.31($C_{43}H_{12}D_{15}N_3O$ = 616.8) | P-10 | m/z = 622.35($C_{43}H_6D_{21}N_3O$ = 622.84) |
| P-11 | m/z = 611.28($C_{43}H_{17}D_{10}N_3O$ = 611.77) | P-12 | m/z = 617.32($C_{43}H_{11}D_{16}N_3O$ = 617.81) |
| P-13 | m/z = 612.28($C_{43}H_{16}D_{11}N_3O$ = 612.78) | P-14 | m/z = 617.32($C_{43}H_{11}D_{16}N_3O$ = 617.81) |
| P-15 | m/z = 622.35($C_{43}H_6D_{21}N_3O$ = 622.84) | P-16 | m/z = 628.38($C_{43}D_{27}N_3O$ = 628.87) |
| P-17 | m/z = 606.25($C_{43}H_{22}D_5N_3O$ = 606.74) | P-18 | m/z = 605.24($C_{43}H_{23}D_4N_3O$ = 605.73) |
| P-19 | m/z = 606.25($C_{43}H_{22}D_5N_3O$ = 606.74) | P-20 | m/z = 612.28($C_{43}H_{16}D_{11}N_3O$ = 612.78) |
| P-21 | m/z = 601.22($C_{43}H_{27}N_3O$ = 601.71) | P-22 | m/z = 606.25($C_{43}H_{22}D_5N_3O$ = 606.74) |
| P-23 | m/z = 606.25($C_{43}H_{22}D_5N_3O$ = 606.74) | P-24 | m/z = 606.25($C_{43}H_{22}D_5N_3O$ = 606.74) |
| P-25 | m/z = 612.28($C_{43}H_{16}D_{11}N_3O$ = 612.78) | P-26 | m/z = 611.28($C_{43}H_{17}D_{10}N_3O$ = 611.77) |
| P-27 | m/z = 611.28($C_{43}H_{17}D_{10}N_3O$ = 611.77) | P-28 | m/z = 617.32($C_{43}H_{11}D_{16}N_3O$ = 617.81) |
| P-29 | m/z = 616.31($C_{43}H_{12}D_{15}N_3O$ = 616.8) | P-30 | m/z = 622.35($C_{43}H_6D_{21}N_3O$ = 622.84) |
| P-31 | m/z = 611.28($C_{43}H_{17}D_{10}N_3O$ = 611.77) | P-32 | m/z = 617.32($C_{43}H_{11}D_{16}N_3O$ = 617.81) |
| P-33 | m/z = 612.28($C_{43}H_{16}D_{11}N_3O$ = 612.78) | P-34 | m/z = 617.32($C_{43}H_{11}D_{16}N_3O$ = 617.81) |
| P-35 | m/z = 622.35($C_{43}H_6D_{21}N_3O$ = 622.84) | P-36 | m/z = 628.38($C_{43}D_{27}N_3O$ = 628.87) |
| P-37 | m/z = 606.25($C_{43}H_{22}D_5N_3O$ = 606.74) | P-38 | m/z = 605.24($C_{43}H_{23}D_4N_3O$ = 605.73) |
| P-39 | m/z = 606.25($C_{43}H_{22}D_5N_3O$ = 606.74) | P-40 | m/z = 612.28($C_{43}H_{16}D_{11}N_3O$ = 612.78) |

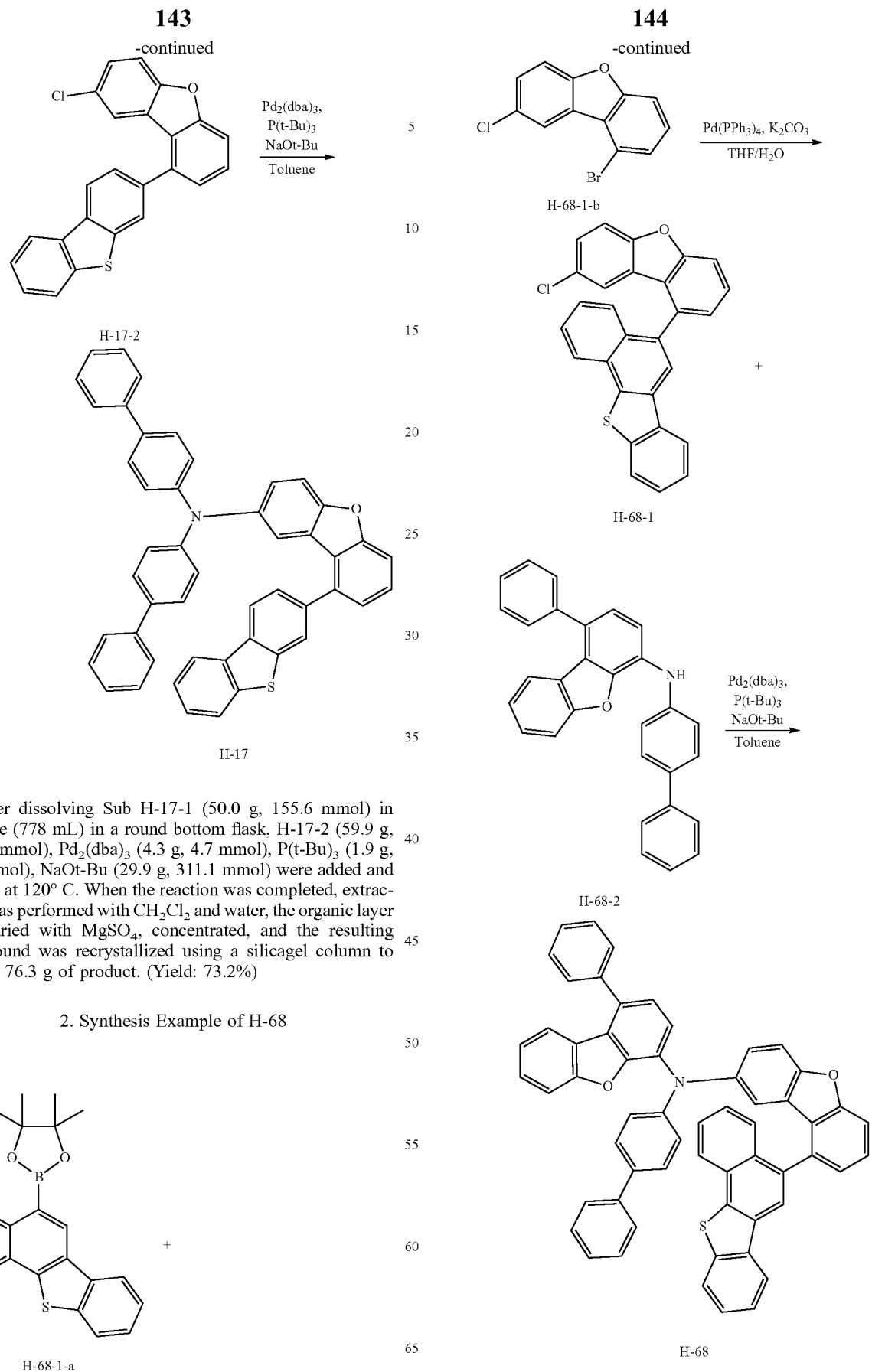

After dissolving Sub H-17-1 (50.0 g, 155.6 mmol) in toluene (778 mL) in a round bottom flask, H-17-2 (59.9 g, 155.6 mmol), Pd₂(dba)₃ (4.3 g, 4.7 mmol), P(t-Bu)₃ (1.9 g, 9.3 mmol), NaOt-Bu (29.9 g, 311.1 mmol) were added and stirred at 120° C. When the reaction was completed, extraction was performed with CH₂Cl₂ and water, the organic layer was dried with MgSO₄, concentrated, and the resulting compound was recrystallized using a silicagel column to obtain 76.3 g of product. (Yield: 73.2%)

2. Synthesis Example of H-68

1) Synthesis of H-68-1

After adding H-68-1-a (35.3 g, 98.0 mmol) to a round bottom flask and dissolving in THF (204 ml), H-68-1-b (23.0 g, 81.7 mmol), Pd(PPh$_3$)$_4$ (2.83 g, 2.45 mmol), K$_2$CO$_3$ (22.58 g, 163.39 mmol) and water (68 ml) were added and proceed with the reaction at 60° C. When the reaction was completed, extraction was performed with CH$_2$Cl$_2$ and water, the organic layer was dried with MgSO$_4$, concentrated, and the resulting compound was recrystallized using a silicagel column to obtain 26.6 g of product. (Yield: 75%)

2) Synthesis of H-68

H-68-1 (20 g, 45.98 mmol), H-68-2 (18.92 g, 45.98 mmol), Pd$_2$(dba)$_3$ (1.26 g, 1.38 mmol), NaOt-Bu (8.84 g, 91.97 mmol), P(t-Bu)$_3$ (1.34 mL, 2.76 mmol), Toluene (153 mL) were added to a round flask in the same manner as in H-1 to obtain 28.7 g of product. (Yield: 77%)

3. Synthesis Example of H-89

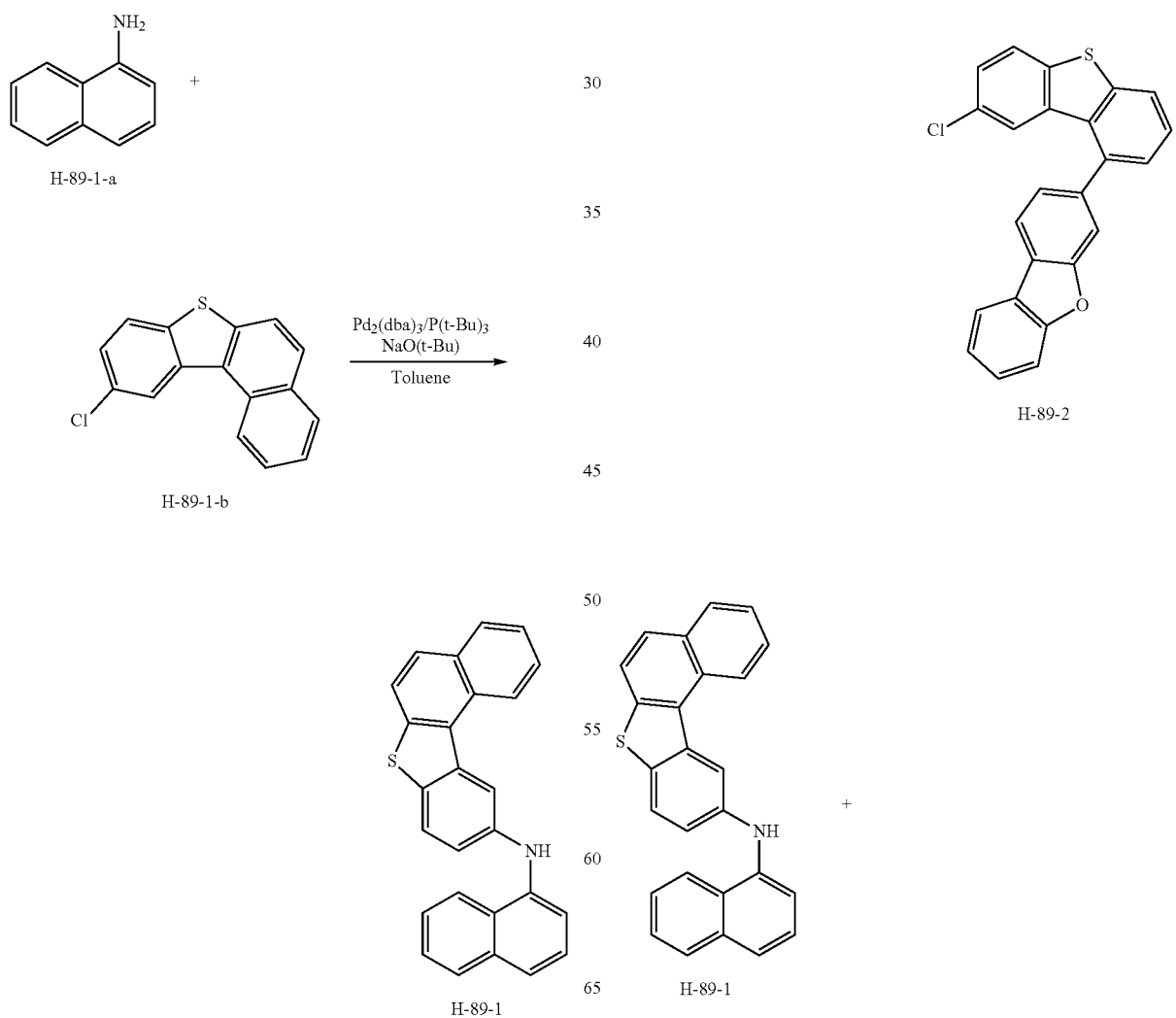

-continued

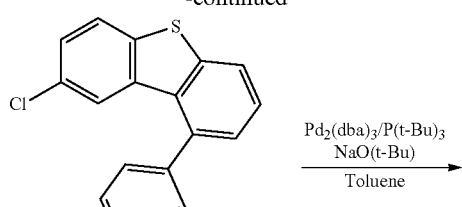

H-89-2

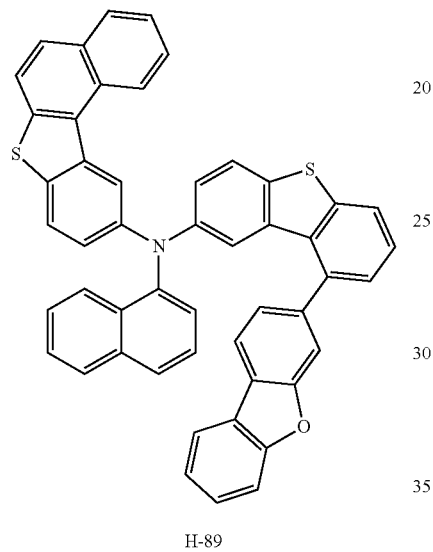

H-89

1) Synthesis of H-89-1

H-89-1-a (50.0 g, 349.2 mmol), H-89-1-b (93.8 g, 349.2 mmol), Pd$_2$(dba)$_3$ (9.6 g, 10.5 mmol), NaOt-Bu (67.1 g, 698.4 mmol), P(t-Bu)$_3$ (4.24 g, 20.9 mmol), Toluene (1746 mL) were added to a round flask in the same manner as in H-1 to obtain 91.1 g of product. (Yield: 69.5%)

2) Synthesis of H-89-2

After adding H-89-2-a (67.4 g, 226.4 mmol) to a round bottom flask and dissolving in THF (755 ml), H-89-2-b (48.0 g, 226.4 mmol), Pd(PPh)$_3$ (7.9 g, 6.8 mmol), K$_2$CO$_3$ (62.6 g, 452.8 mmol), water (252 ml) were added to a round flask in the same manner as in H-69-1 to obtain 58 g of product. (Yield: 69%)

3) Synthesis of H-89

H-89-1 (12.0 g, 32.0 mmol), H-89-2 (12.3 g, 32.0 mmol), Pd$_2$(dba)$_3$ (0.9 g, 1.0 mmol), P(t-Bu)$_3$ (0.47 mL, 1.9 mmol), NaO(t-Bu) (6.1 g, 63.9 mmol), Toluene (107 mL) were added to a round flask in the same manner as in H-1 to obtain 28.7 g of product. (Yield: 77%)

4. Synthesis Example of H-102

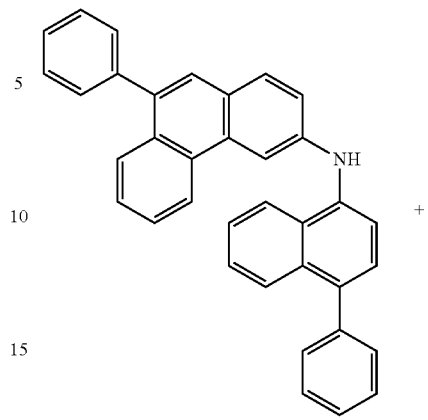

H-102-1

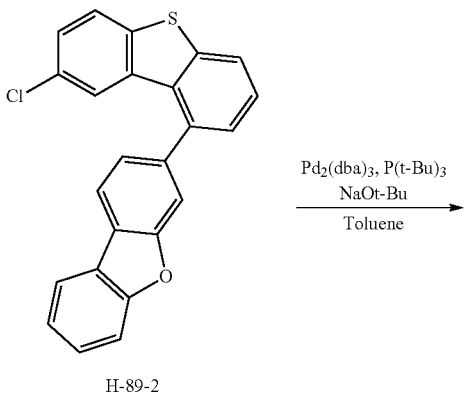

H-89-2

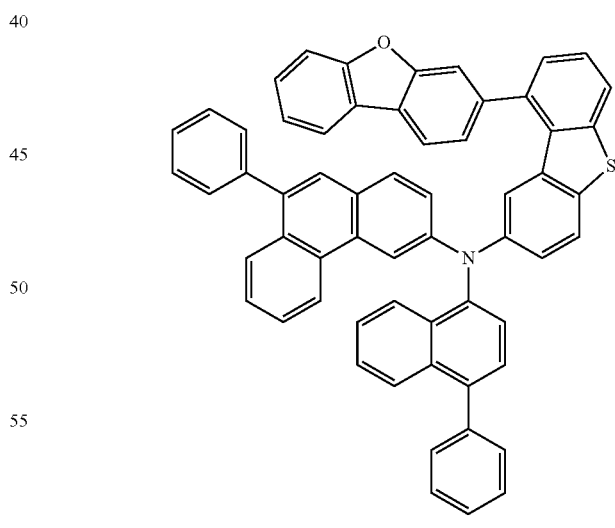

H-102

H-102-1 (21.3 g, 45.2 mmol), H-89-2 (17.4 g, 45.2 mmol), Pd$_2$(dba)$_3$ (1.2 g, 1.4 mmol), NaOt-Bu (8.7 g, 90.3 mmol), P(t-Bu)$_3$, Toluene (150 mL) were added to a round flask in the same manner as in H-1 to obtain 24.4 g of product. (Yield: 66%)

5. Synthesis Example of H-107
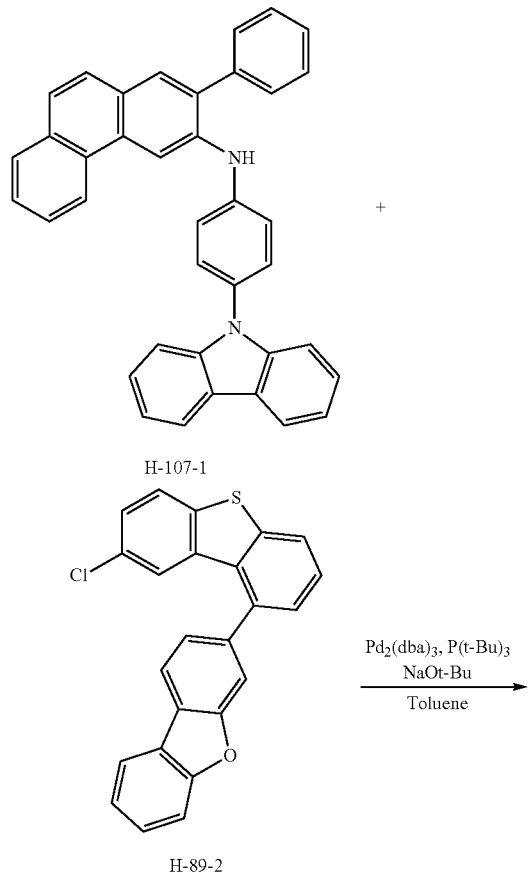
6. Synthesis Example of H-116
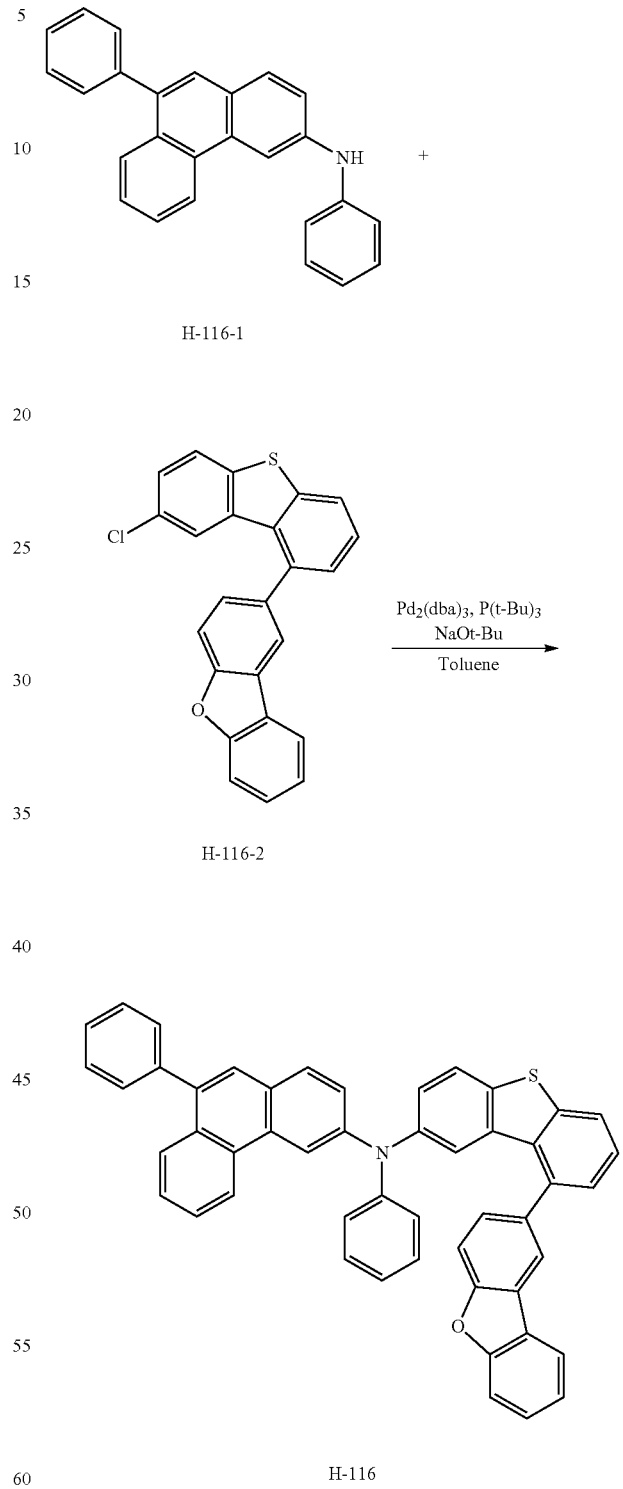
H-107-1 (32.0 g, 62.7 mmol), H-89-2 (24.1 g, 62.7 mmol), Pd$_2$(dba)$_3$ (1.7 g, 1.9 mmol), NaOt-Bu (12.0 g, 125.3 mmol), P(t-Bu)$_3$, Toluene (208 mL) were added to a round flask in the same manner as in H-1 to obtain 25.8 g of product. (Yield: 48%)
H-116-1 (17.4 g, 50.4 mmol), H-116-2 (19.4 g, 50.4 mmol), Pd$_2$(dba)$_3$ (1.4 g, 1.5 mmol), NaOt-Bu (9.7 g, 100.7 mmol), P(t-Bu)$_3$, Toluene (167 mL) were added to a round flask in the same manner as in H-1 to obtain 21.3 g of product. (Yield: 61%)

TABLE 4

| Compound | FD-MS | Compound | FD-MS |
|---|---|---|---|
| H-1 | m/z = 517.15($C_{36}H_{23}NOS$ = 517.65) | H-2 | m/z = 669.21($C_{48}H_{31}NOS$ = 669.84) |
| H-3 | m/z = 617.24($C_{45}H_{31}NO_2$ = 617.75) | H-4 | m/z = 719.23($C_{52}H_{33}NOS$ = 719.90) |
| H-5 | m/z = 693.21($C_{50}H_{31}NOS$ = 693.86) | H-6 | m/z = 643.20($C_{46}H_{29}NOS$ = 643.80) |
| H-7 | m/z = 643.20($C_{46}H_{29}NOS$ = 643.80) | H-8 | m/z = 669.21($C_{48}H_{31}NOS$ = 669.84) |
| H-9 | m/z = 667.20($C_{48}H_{29}NOS$ = 667.83) | H-10 | m/z = 647.25($C_{46}H_{33}NO_3$ = 647.77) |
| H-11 | m/z = 677.24($C_{50}H_{31}NO_2$ = 677.80) | H-12 | m/z = 693.27($C_{51}H_{35}NO_2$ = 693.85) |
| H-13 | m/z = 689.27($C_{49}H_{27}D_6NOS$ = 689.91) | H-14 | m/z = 593.18($C_{42}H_{27}NOS$ = 593.74) |
| H-15 | m/z = 669.21($C_{48}H_{31}NOS$ = 669.84) | H-16 | m/z = 643.20($C_{46}H_{29}NOS$ = 643.80) |
| H-17 | m/z = 669.21($C_{48}H_{31}NOS$ = 669.84) | H-18 | m/z = 785.22($C_{56}H_{35}NS_2$ = 786.02) |
| H-19 | m/z = 617.18($C_{44}H_{27}NOS$ = 617.77) | H-20 | m/z = 601.20($C_{44}H_{27}NO_2$ = 601.70) |
| H-21 | m/z = 643.20($C_{46}H_{29}NOS$ = 643.80) | H-22 | m/z = 703.25($C_{52}H_{33}NO_2$ = 703.84) |
| H-23 | m/z = 633.16($C_{44}H_{27}NS_2$ = 633.83) | H-24 | m/z = 769.24($C_{56}H_{35}NOS$ = 769.96) |
| H-25 | m/z = 690.22($C_{48}H_{26}D_5NS_2$ = 690.93) | H-26 | m/z = 690.22($C_{48}H_{26}D_5NS_2$ = 690.93) |
| H-27 | m/z = 654.23($C_{47}H_{30}N_2O_2$ = 654.77) | H-28 | m/z = 683.19($C_{48}H_{29}NO_2S$ = 683.83) |
| H-29 | m/z = 791.18($C_{54}H_{33}NS_3$ = 792.04) | H-30 | m/z = 745.24($C_{54}H_{35}NOS$ = 745.94) |
| H-31 | m/z = 709.24($C_{51}H_{35}NOS$ = 709.91) | H-32 | m/z = 733.24($C_{53}H_{35}NOS$ = 733.93) |
| H-33 | m/z = 858.27($C_{62}H_{38}N_2OS$ = 859.06) | H-34 | m/z = 643.20($C_{46}H_{29}NOS$ = 643.80) |
| H-35 | m/z = 627.22($C_{46}H_{29}NO_2$ = 627.74) | H-36 | m/z = 759.22($C_{54}H_{33}NO_2S$ = 759.92) |
| H-37 | m/z = 823.33($C_{58}H_{49}NS_2$ = 824.16) | H-38 | m/z = 773.22($C_{55}H_{35}NS_2$ = 774.01) |
| H-39 | m/z = 745.24($C_{54}H_{35}NOS$ = 745.94) | H-40 | m/z = 653.24($C_{48}H_{31}NO_2$ = 653.78) |
| H-41 | m/z = 787.20($C_{55}H_{33}NOS_2$ = 787.99) | H-42 | m/z = 787.20($C_{55}H_{33}NOS_2$ = 787.99) |
| H-43 | m/z = 769.24($C_{56}H_{35}NOS$ = 769.96) | H-44 | m/z = 716.25($C_{52}H_{32}N_2O_2$ = 716.84) |
| H-45 | m/z = 765.16($C_{52}H_{31}NS_3$ = 766.01) | H-46 | m/z = 761.22($C_{54}H_{35}NS_2$ = 762.00) |
| H-47 | m/z = 733.21($C_{52}H_{31}NO_2S$ = 733.89) | H-48 | m/z = 669.21($C_{48}H_{31}NOS$ = 669.84) |
| H-49 | m/z = 667.2($C_{48}H_{29}NOS$ = 667.83) | H-50 | m/z = 717.21($C_{52}H_{31}NOS$ = 717.89) |
| H-51 | m/z = 743.23($C_{54}H_{33}NOS$ = 743.92) | H-52 | m/z = 769.24($C_{56}H_{35}NOS$ = 769.96) |
| H-53 | m/z = 693.21($C_{50}H_{31}NOS$ = 693.86) | H-54 | m/z = 719.23($C_{52}H_{33}NOS$ = 719.90) |
| H-55 | m/z = 710.20($C_{49}H_{30}N_2O_2S$ = 710.85) | H-56 | m/z = 657.18($C_{46}H_{27}NO_2S$ = 657.79) |
| H-57 | m/z = 763.22($C_{53}H_{33}NO_3S$ = 763.91) | H-58 | m/z = 959.29($C_{70}H_{41}NO2S$ = 960.16) |
| H-59 | m/z = 763.20($C_{53}H_{33}NOS_2$ = 763.97) | H-60 | m/z = 811.23($C_{58}H_{34}FNOS$ = 811.97) |
| H-61 | m/z = 721.22($C_{50}H_{31}N_3OS$ = 721.88) | H-62 | m/z = 793.28($C_{56}H_{40}FNOS$ = 794.00) |
| H-63 | m/z = 708.22($C_{50}H_{32}N_2OS$ = 708.88) | H-64 | m/z = 1001.28($C_{72}H_{43}NOS_2$ = 1002.26) |
| H-65 | m/z = 1022.33($C_{75}H_{46}N_2OS$ = 1023.27) | H-66 | m/z = 794.24($C_{57}H_{34}N_2OS$ = 794.97) |
| H-67 | m/z = 919.29($C_{68}H_{41}NOS$ = 920.14) | H-68 | m/z = 809.24($C_{58}H_{35}NO_2S$ = 809.98) |
| H-69 | m/z = 759.21($C_{54}H_{33}NS_2$ = 759.98) | H-70 | m/z = 759.21($C_{54}H_{33}NS_2$ = 759.98) |
| H-71 | m/z = 699.17($C_{48}H_{29}NOS_2$ = 699.89) | H-72 | m/z = 699.17($C_{48}H_{29}NOS_2$ = 699.89) |
| H-73 | m/z = 699.17($C_{48}H_{29}NOS_2$ = 699.89) | H-74 | m/z = 699.17($C_{48}H_{29}NOS_2$ = 699.89) |
| H-75 | m/z = 749.18($C_{52}H_{31}NOS_2$ = 749.95) | H-76 | m/z = 749.18($C_{52}H_{31}NOS_2$ = 749.95) |
| H-77 | m/z = 749.18($C_{52}H_{31}NOS_2$ = 749.95) | H-78 | m/z = 749.18($C_{52}H_{31}NOS_2$ = 749.95) |
| H-79 | m/z = 749.18($C_{52}H_{31}NOS_2$ = 749.95) | H-80 | m/z = 749.18($C_{52}H_{31}NOS_2$ = 749.95) |
| H-81 | m/z = 799.20($C_{56}H_{33}NOS_2$ = 800.01) | H-82 | m/z = 799.20($C_{56}H_{33}NOS_2$ = 800.01) |
| H-83 | m/z = 799.20($C_{56}H_{33}NOS_2$ = 800.01) | H-84 | m/z = 825.22($C_{58}H_{35}NOS_2$ = 826.04) |
| H-85 | m/z = 699.17($C_{48}H_{29}NOS_2$ = 699.89) | H-86 | m/z = 699.17($C_{48}H_{29}NOS_2$ = 699.89) |
| H-87 | m/z = 699.17($C_{48}H_{29}NOS_2$ = 699.89) | H-88 | m/z = 699.17($C_{48}H_{29}NOS_2$ = 699.89) |
| H-89 | m/z = 727.91($C_{50}H_{29}NOS_2$ = 723.91) | H-90 | m/z = 727.91($C_{50}H_{29}NOS_2$ = 723.91) |
| H-91 | m/z = 727.91($C_{50}H_{29}NOS_2$ = 723.91) | H-92 | m/z = 727.91($C_{50}H_{29}NOS_2$ = 723.91) |
| H-93 | m/z = 727.91($C_{50}H_{29}NOS_2$ = 723.91) | H-94 | m/z = 727.91($C_{50}H_{29}NOS_2$ = 723.91) |
| H-95 | m/z = 773.18($C_{54}H_{31}NOS_2$ = 773.97) | H-96 | m/z = 773.18($C_{54}H_{31}NOS_2$ = 773.97) |
| H-97 | m/z = 773.18($C_{54}H_{31}NOS_2$ = 773.97) | H-98 | m/z = 773.18($C_{54}H_{31}NOS_2$ = 773.97) |
| H-99 | m/z = 673.15($C_{46}H_{27}NOS_2$ = 673.85) | H-100 | m/z = 773.18($C_{54}H_{31}NOS_2$ = 773.97) |
| H-101 | m/z = 819.26($C_{60}H_{37}NOS$ = 820.02) | H-102 | m/z = 819.26($C_{60}H_{37}NOS$ = 820.02) |
| H-103 | m/z = 819.26($C_{60}H_{37}NOS$ = 820.02) | H-104 | m/z = 819.26($C_{60}H_{37}NOS$ = 820.02) |
| H-105 | m/z = 819.26($C_{60}H_{37}NOS$ = 820.02) | H-106 | m/z = 858.27($C_{62}H_{38}N_2OS$ = 859.06) |
| H-107 | m/z = 858.27($C_{62}H_{38}N_2OS$ = 859.06) | H-108 | m/z = 858.27($C_{62}H_{38}N_2OS$ = 859.06) |
| H-109 | m/z = 858.27($C_{62}H_{38}N_2OS$ = 859.06) | H-110 | m/z = 858.27($C_{62}H_{38}N_2OS$ = 859.06) |
| H-111 | m/z = 858.27($C_{62}H_{38}N_2OS$ = 859.06) | H-112 | m/z = 858.27($C_{62}H_{38}N_2OS$ = 859.06) |
| H-113 | m/z = 858.27($C_{62}H_{38}N_2OS$ = 859.06) | H-114 | m/z = 858.27($C_{62}H_{38}N_2OS$ = 859.06) |
| H-115 | m/z = 693.21($C_{50}H_{31}NOS$ = 693.86) | H-116 | m/z = 693.21($C_{50}H_{31}NOS$ = 693.86) |
| H-117 | m/z = 693.21($C_{50}H_{31}NOS$ = 693.86) | H-118 | m/z = 769.24($C_{56}H_{35}NOS$ = 769.96) |
| H-119 | m/z = 693.21($C_{50}H_{31}NOS$ = 693.86) | H-120 | m/z = 693.21($C_{50}H_{31}NOS$ = 693.86) |
| H-121 | m/z = 669.21($C_{48}H_{31}NOS$ = 669.84) | H-122 | m/z = 785.22($C_{56}H_{35}NS_2$ = 786.02) |
| H-123 | m/z = 617.18($C_{44}H_{27}NOS$ = 617.77) | H-124 | m/z = 601.20($C_{44}H_{27}NO_2$ = 601.70) |
| H-125 | m/z = 709.24($C_{51}H_{35}NOS$ = 709.91) | H-126 | m/z = 861.25($C_{62}H_{39}NS_2$ = 862.12) |
| H-127 | m/z = 663.21($C_{50}H_{31}NOS$ = 693.86) | H-128 | m/z = 677.24($C_{50}H_{31}NO_2$ = 677.80) |
| H-129 | m/z = 745.24($C_{54}H_{35}NOS$ = 745.94) | H-130 | m/z = 709.19($C_{50}H_{31}NS_2$ = 709.93) |
| H-131 | m/z = 667.20($C_{48}H_{29}NOS$ = 667.83) | H-132 | m/z = 601.20($C_{44}H_{27}NO_2$ = 601.70) |

The compound represented by Formula 5 is manufactured by using a known synthetic method (named reaction) or by referring to published patent publications, such as Korean Patent Registration No. 10-2395819, U.S. Patent Publication No. 2023-0129535, etc., but it is not limited to.

Meanwhile, the FD-MS (Field Desorption-Mass Spectrometry) values of the compounds S-1 to S-116 of the present invention are shown in Table 5.

In the above, exemplary synthesis examples of the present invention represented by Formula 1, Formula 2, and Formula 5 have been described, but these are all based on the Buchwald-Hartwig cross coupling reaction, Miyaura boration reaction, Suzuki cross-coupling reaction, Intramolecular acid-induced cyclization reaction (*J. mater. Chem.* 1999, 9, 2095.), Pd(II)-catalyzed oxidative cyclization reaction (*Org. Lett.* 2011, 13, 5504), and PPh$_3$-mediated reductive

TABLE 5

| Compound | FD-MS | Compound | FD-MS |
|---|---|---|---|
| S-1 | m/z = 408.16($C_{30}H_{20}N_2$ = 408.50) | S-2 | m/z = 534.21 ($C_{40}H_{26}N_2$ = 534.66) |
| S-3 | m/z = 560.23($C_{42}H_{28}N_2$ = 560.70) | S-4 | m/z = 584.23($C_{44}H_{28}N_2$ = 584.72) |
| S-5 | m/z = 560.23($C_{42}H_{28}N_2$ = 560.70) | S-6 | m/z = 634.24($C_{48}H_{30}N_2$ = 634.78) |
| S-7 | m/z = 610.24($C_{46}H_{30}N_2$ = 610.76) | S-8 | m/z = 498.17($C_{36}H_{22}N_2O$ = 498.59) |
| S-9 | m/z = 574.20($C_{42}H_{26}N_2O$ = 574.68) | S-10 | m/z = 660.26($C_{50}H_{32}N_2$ = 660.82) |
| S-11 | m/z = 686.27($C_{52}H_{34}N_2$ = 686.86) | S-12 | m/z = 620.14($C_{42}H_{24}N_2S_2$ = 620.79) |
| S-13 | m/z = 640.20($C_{46}H_{28}N_2S$ = 640.80) | S-14 | m/z = 560.23($C_{42}H_{28}N_2$ = 560.70) |
| S-15 | m/z = 558.21($C_{42}H_{26}N_2$ = 558.68) | S-16 | m/z = 548.19($C_{40}H_{24}N_2O$ = 548.65) |
| S-17 | m/z = 573.22($C_{42}H_{27}N_3$ = 573.70) | S-18 | m/z = 564.17($C_{40}H_{24}N_2S$ = 564.71) |
| S-19 | m/z = 574.20($C_{42}H_{26}N_2O$ = 574.68) | S-20 | m/z = 564.17($C_{40}H_{24}N_2S$ = 564.71) |
| S-21 | m/z = 564.17($C_{40}H_{24}N_2S$ = 564.71) | S-22 | m/z = 813.31($C_{61}H_{39}N_3$ = 814.00) |
| S-23 | m/z = 696.26($C_{53}H_{32}N_2$ = 696.85) | S-24 | m/z = 691.23($C_{49}H_{29}N_3O_2$ = 691.79) |
| S-25 | m/z = 710.27($C_{54}H_{34}N_2$ = 710.88) | S-26 | m/z = 610.24($C_{46}H_{30}N_2$ = 610.76) |
| S-27 | m/z = 670.15($C_{46}H_{26}N_2S_2$ = 670.85) | S-28 | m/z = 640.29($C_{48}H_{36}N_2$ = 640.83) |
| S-29 | m/z = 598.20($C_{44}H_{26}N_2O$ = 598.71) | S-30 | m/z = 623.24($C_{46}H_{29}N_3$ = 623.76) |
| S-31 | m/z = 458.18($C_{34}H_{22}N_2$ = 458.56) | S-32 | m/z = 548.19($C_{40}H_{24}N_2O$ = 548.65) |
| S-33 | m/z = 508.19($C_{38}H_{24}N_2$ = 508.62) | S-34 | m/z = 508.19($C_{38}H_{24}N_2$ = 508.62) |
| S-35 | m/z = 623.24($C_{46}H_{29}N_3$ = 623.76) | S-36 | m/z = 564.17($C_{40}H_{24}N_2S$ = 564.71) |
| S-37 | m/z = 627.20($C_{46}H_{29}NS$ = 627.81) | S-38 | m/z = 505.10($C_{34}H_{19}NS_2$ = 505.65) |
| S-39 | m/z = 514.15($C_{36}H_{22}N_2S$ = 514.65) | S-40 | m/z = 575.17($C_{42}H_{25}NS$ = 575.73) |
| S-41 | m/z = 642.21($C_{46}H_{30}N_2S$ = 642.82) | S-42 | m/z = 575.17($C_{42}H_{25}NS$ = 575.73) |
| S-43 | m/z = 606.18($C_{42}H_{26}N_2OS$ = 606.74) | S-44 | m/z = 575.17($C_{42}H_{25}NS$ = 575.73) |
| S-45 | m/z = 551.17($C_{40}H_{25}NS$ = 551.71) | S-46 | m/z = 607.14($C_{42}H_{25}NS_2$ = 607.79) |
| S-47 | m/z = 525.16($C_{38}H_{23}NS$ = 525.67) | S-48 | m/z = 642.21($C_{46}H_{30}N_2S$ = 642.82) |
| S-49 | m/z = 548.19($C_{40}H_{24}N_2O$ = 548.65) | S-50 | m/z = 473.14($C_{34}H_{19}NO_2$ = 473.53) |
| S-51 | m/z = 566.15($C_{39}H_{22}N_2OS$ = 566.68) | S-52 | m/z = 459.16($C_{34}H_{21}NO$ = 459.55) |
| S-53 | m/z = 473.14($C_{34}H_{19}NO_2$ = 473.53) | S-54 | m/z = 523.16($C_{38}H_{21}NO_2$ = 523.59) |
| S-55 | m/z = 539.13($C_{38}H_{21}NOS$ = 539.65) | S-56 | m/z = 548.19($C_{40}H_{24}N_2O$ = 548.65) |
| S-57 | m/z = 489.12($C_{34}H_{19}NOS$ = 489.59) | S-58 | m/z = 545.09($C_{36}H_{19}NOS_2$ = 545.67) |
| S-59 | m/z = 549.17($C_{40}H_{23}NO_2$ = 549.63) | S-60 | m/z = 565.15($C_{40}H_{23}NOS$ = 565.69) |
| S-61 | m/z = 523.16($C_{38}H_{21}NO_2$ = 523.59) | S-62 | m/z = 598.2($C_{44}H_{26}N_2O$ = 598.71) |
| S-63 | m/z = 539.13($C_{38}H_{21}NOS$ = 539.65) | S-64 | m/z = 589.15($C_{42}H_{23}NOS$ = 589.71) |
| S-65 | m/z = 498.17($C_{36}H_{22}N_2O$ = 498.59) | S-66 | m/z = 509.18($C_{38}H_{23}NO$ = 509.61) |
| S-67 | m/z = 548.19($C_{40}H_{24}N_2O$ = 548.65) | S-68 | m/z = 549.17($C_{40}H_{23}NO_2$ = 549.63) |
| S-69 | m/z = 449.12($C_{32}H_{19}NS$ = 449.57) | S-70 | m/z = 439.1($C_{30}H_{17}NOS$ = 439.53) |
| S-71 | m/z = 647.22($C_{49}H_{29}NO$ = 647.78) | S-72 | m/z = 717.28($C_{52}H_{35}N_3O$ = 717.87) |
| S-73 | m/z = 459.16($C_{34}H_{21}NO$ = 459.55) | S-74 | m/z = 533.18($C_{40}H_{23}NO$ = 533.63) |
| S-75 | m/z = 525.16($C_{38}H_{23}NS$ = 525.67) | S-76 | m/z = 564.17($C_{40}H_{24}N_2S$ = 564.71) |
| S-77 | m/z = 575.19($C_{42}H_{25}NO_2$ = 575.67) | S-78 | m/z = 663.22($C_{49}H_{29}NO_2$ = 663.78) |
| S-79 | m/z = 647.22($C_{49}H_{29}NO$ = 647.78) | S-80 | m/z = 496.16($C_{36}H_{20}N_2O$ = 496.57) |
| S-81 | m/z = 565.15($C_{40}H_{23}NOS$ = 565.69) | S-82 | m/z = 505.1($C_{34}H_{19}NS_2$ = 505.65) |
| S-83 | m/z = 765.25($C_{56}H_{35}NOSi$ = 765.99) | S-84 | m/z = 615.17($C_{44}H_{25}NOS$ = 615.75) |
| S-85 | m/z = 603.17($C_{43}H_{25}NOS$ = 603.74) | S-86 | m/z = 772.29($C_{59}H_{36}N_2$ = 772.95) |
| S-87 | m/z = 802.33($C_{61}H_{42}N_2$ = 803.02) | S-88 | m/z = 607.23($C_{47}H_{29}N$ = 607.76) |
| S-89 | m/z = 524.23($C_{39}H_{28}N_2$ = 524.67) | S-90 | m/z = 665.22($C_{49}H_{31}NS$ = 665.85) |
| S-91 | m/z = 633.25($C_{49}H_{31}N$ = 633.79) | S-92 | m/z = 775.29($C_{59}H_{37}NO$ = 775.95) |
| S-93 | m/z = 535.23($C_{41}H_{29}N$ = 535.69) | S-94 | m/z = 623.22($C_{47}H_{29}NO$ = 623.76) |
| S-95 | m/z = 687.20($C_{51}H_{29}NS$ = 687.86) | S-96 | m/z = 735.29($C_{57}H_{37}N$ = 735.93) |
| S-97 | m/z = 611.26($C_{47}H_{33}N$ = 611.79) | S-98 | m/z = 679.23($C_{50}H_{33}NS$ = 679.88) |
| S-99 | m/z = 787.32($C_{61}H_{41}N$ = 788.01) | S-100 | m/z = 743.33($C_{55}H_{41}N_3$ = 743.95) |
| S-101 | m/z = 485.21($C_{37}H_{27}N$ = 485.63) | S-102 | m/z = 471.20($C_{36}H_{25}N$ = 471.60) |
| S-103 | m/z = 571.19($C_{43}H_{25}NO$ = 571.68) | S-104 | m/z = 584.23($C_{44}H_{28}N_2$ = 584.72) |
| S-105 | m/z = 539.24($C_{40}H_{21}D_5N_2$ = 539.69) | S-106 | m/z = 453.15($C_{32}H_{15}NS$ = 471.6) |
| S-107 | m/z = 563.26($C_{43}H_{26}D_4NO$ = 563.74) | S-108 | m/z = 589.26($C_{44}H_{23}D_5N_2$ = 584.72) |
| S-109 | m/z = 589.26($C_{44}H_{23}D_5N_2$ = 589.75) | S-110 | m/z = 562.23($C_{42}H_{22}D_4N_2$ = 562.71) |
| S-111 | m/z = 660.26($C_{50}H_{32}N_2$ = 660.82) | S-112 | m/z = 553.22($C_{40}H_{19}D_5N_2O$ = 553.68) |
| S-113 | m/z = 634.24($C_{48}H_{30}N_2$ = 634.78) | S-114 | m/z = 589.26($C_{44}H_{23}D_5N_2$ = 589.75) |
| S-115 | m/z = 588.25($C_{44}H_{24}D_4N_2$ = 588.75) | S-116 | m/z = 513.23($C_{38}H_{19}D_5N_2$ = 513.65) | cyclization reaction (*J. Org. Chem.* 2005, 70, 5014.), and it will be easily understood by those skilled in the art that the reaction proceeds even when other substituents defined in Formula 1, Formula 2 and Formula 5 are bonded in addition to the substituents specified in the specific synthesis examples.

Manufacturing Evaluation of Organic Electronic Elements

[Example 1] Red Organic Light Emitting Device (Phosphorescent Host)

Compound A and Compound B were used on the ITO layer (anode) formed on the glass substrate, and a hole injection layer with a thickness 10 nm was formed by doping Compound B at a weight ratio of 98:2, and Compound A was vacuum deposited on the hole injection layer to a thickness of 110 nm to form a hole transport layer. Next, compound C-R was vacuum deposited to a thickness of 10 nm on the hole transport layer to form an emitting auxiliary layer. Thereafter, the host material of the emitting layer uses Compound P-1, a compound of the present invention, as the first host, and Compound H-35, a compound of the present invention, as the second host, and a mixture of the first host and the second host in a weight ratio of 5:5 is used.

Bis-(1-phenylisoquinolyl) iridium (III) acetylacetonate (hereinafter, '(piq)$_2$Ir(acac)' was used as a dopant material, and the dopant was doped so that the weight ratio of the host to the dopant was 95:5 to form an emitting layer with a thickness 30 nm.

Next, Compound E is vacuum deposited on the emitting layer to form a hole blocking layer with a thickness of 10 nm, and an electron transport layer with a thickness of 30 nm was formed on the hole blocking layer using a mixture of Compound F and Compound G at a weight ratio of 5:5. Afterwards, Compound G was deposited on the electron transport layer to form an electron injection layer with a thickness of 0.2 nm, and then Al was deposited to form a cathode with a thickness of 150 nm.

Compound A: N-([1,1'-biphenyl]-4-yl)-9,9-dimethyl-N-(4-(9-phenyl-9H-carbazol-3-yl)phenyl)-9H-fluoren-2-amine Compound B: 4,4',4''-((1E,1'E,1''E)-cyclopropane-1,2,3-triylidenetris(cyanomethaneylylidene))tris(2,3,5,6-tetrafluorobenzonitrile)

Compound C-R: N$^7$-(dibenzo[b,d]thiophen-2-yl)-N$^2$,N$^2$,N$^7$-triphenyldibenzo[b,d]thiophene-2,7-diamine Compound E: 2-(4'-(9,9-dimethyl-9H-fluoren-2-yl)-[1,1'-biphenyl]-3-yl)-4,6-diphenyl-1,3,5-triazine Compound F: 2,7-bis(4-(4,6-diphenyl-1,3,5-triazin-2-yl)phenyl)naphthalene Compound G: (8-quinolinolato)lithium

[Example 2] to [Example 63]

An organic electroluminescent device was manufactured in the same manner as Example 1, except that the compound of the present invention shown in Table 6 was used as the host material of the emitting layer.

[Comparative Example 1] to [Comparative Example 20]

An organic electroluminescent device was manufactured in the same manner as in Example 1, except that Comparative Compounds 1 to 6 as the host material of the emitting layer were used as the first host, or Comparative Compounds A to Comparative Compound D were used as the second host.

[Comparative Compound 1]

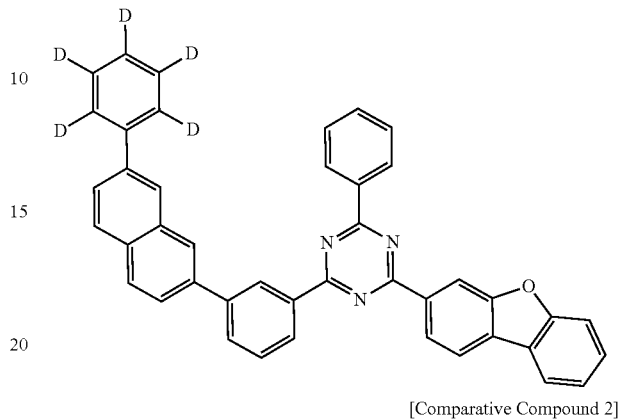

[Comparative Compound 2]

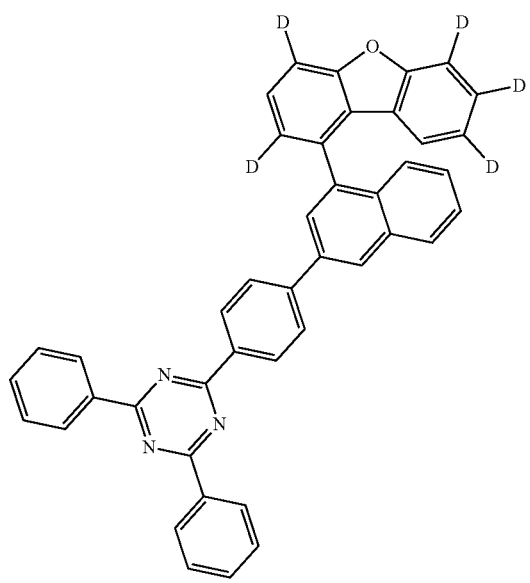

[Comparative Compound 3]

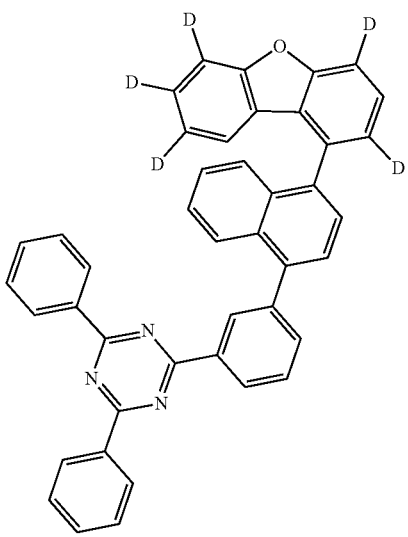

[Comparative Compound 4]
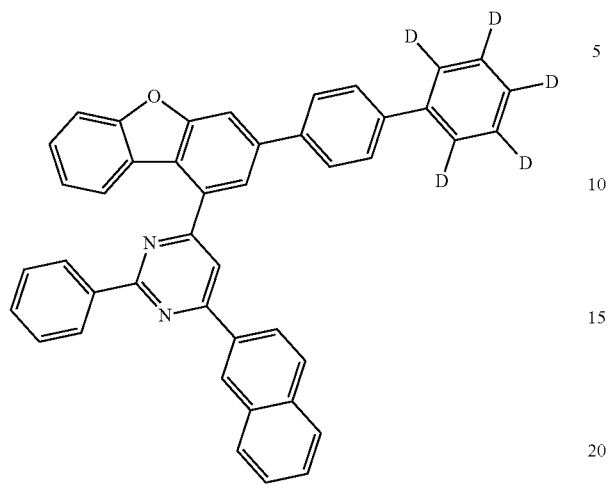
[Comparative Compound A]
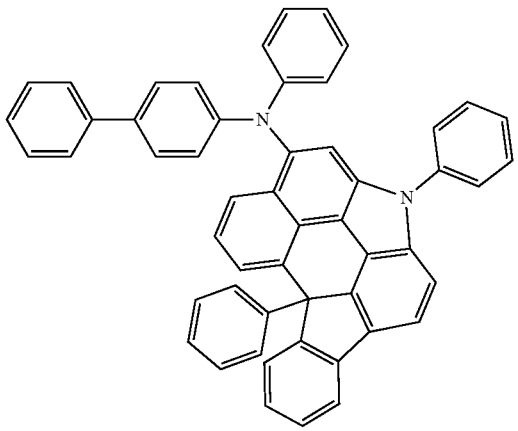
[Comparative Compound 5]
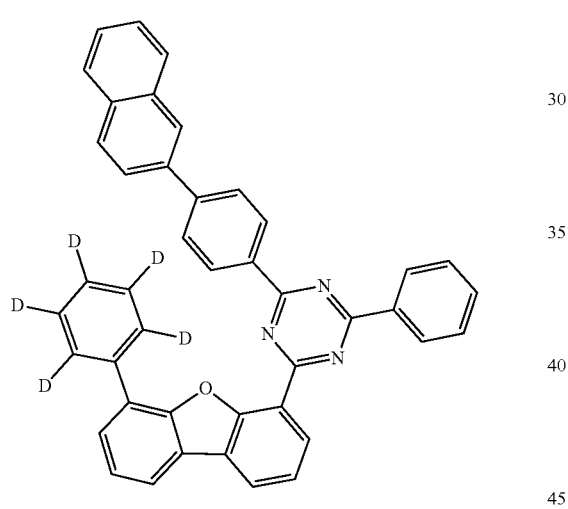
[Comparative Compound B]
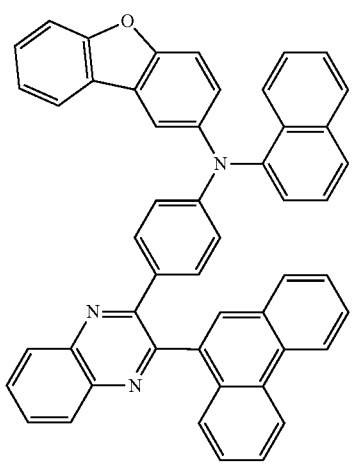
[Comparative Compound 6]
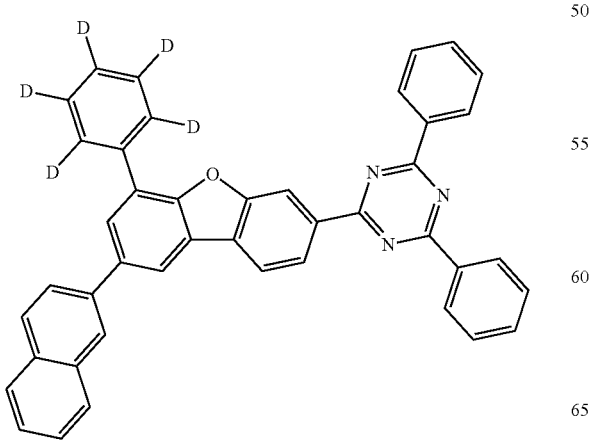
[Comparative Compound C]
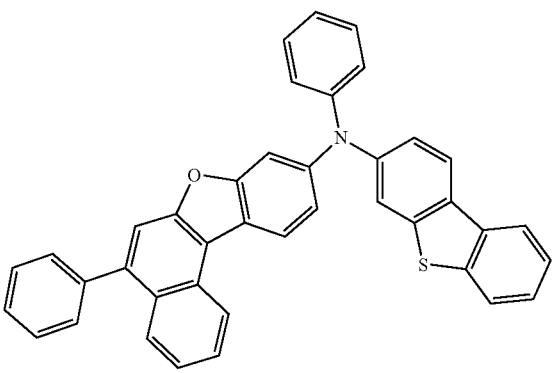

-continued

[Comparative Compound D]

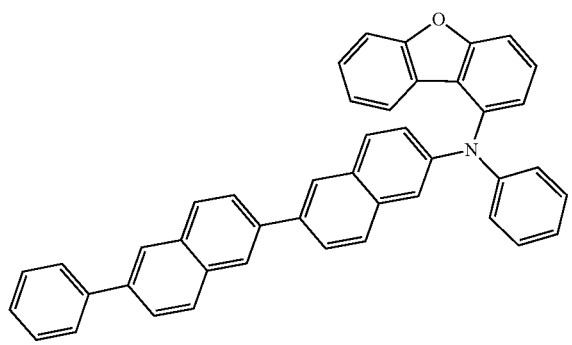

Example 64

An organic electroluminescent device was manufactured in the same manner as Example 1, except that Compound P-1 of the present invention was used as the host material of the emitting layer without a second host.

[Example 65] to [Example 85]

An organic electroluminescent device was manufactured in the same manner as Example 64, except that the compound of the present invention shown in Table 7 was used as the host material of the emitting layer.

[Comparative Example 21] to [Comparative Example 26]

An organic electroluminescent device was manufactured in the same manner as Example 64, except that Comparative Compounds 1 to 6 shown in Table 7 were used as the host material of the emitting layer.

To the organic electroluminescent device manufactured by Examples 1 to 85 and Comparative Examples 1 to 26 of the present invention, Electroluminescence (EL) characteristics were measured with a PR-650 of Photoresearch Co., by applying a forward bias DC voltage. As a result of the measurement, T95 life was measured at a standard luminance of 2,500 cd/m² through life measuring apparatus manufactured by McScience. Table 6 and Table 7 show the results of device fabrication and evaluation according to the examples.

The measuring apparatus can evaluate the performance of new materials compared to comparative compounds under identical conditions, without being affected by possible daily fluctuations in deposition rate, vacuum quality or other parameters.

During the evaluation, one batch contains 4 identically prepared OLEDs including a comparative compound, and the performance of a total of 12 OLEDs is evaluated in 3 batches, so the value of the experimental results obtained in this way indicates statistical significance.

TABLE 6

| | Frist host | Second host | | Voltage (v) | Current Density (mA/cm²) | Brightness (cd/m²) | Efficiency (cd/A) | T(95) |
|---|---|---|---|---|---|---|---|---|
| Comparative example 1 | Comparative Compound 1 | H-35 | | 5.2 | 11.4 | 2500.0 | 22.0 | 93.7 |
| Comparative example2 | Comparative Compound 2 | | | 5.3 | 12.9 | 2500.0 | 19.4 | 91.8 |
| Comparative example3 | Comparative Compound 3 | | | 5.2 | 11.7 | 2500.0 | 21.3 | 90.1 |
| Comparative example4 | Comparative Compound 4 | | | 5.1 | 11.5 | 2500.0 | 21.7 | 92.3 |
| Comparative example5 | Comparative Compound 5 | | | 5.2 | 12.8 | 2500.0 | 19.5 | 91.4 |
| Comparative example6 | Comparative Compound 6 | | | 5.2 | 11.7 | 2500.0 | 21.3 | 100.4 |
| Comparative example7 | Comparative Compound 1 | S-40 | | 5.5 | 12.0 | 2500.0 | 20.9 | 99.0 |
| Comparative example8 | Comparative Compound 2 | | | 5.5 | 12.0 | 2500.0 | 20.8 | 100.4 |
| Comparative example9 | Comparative Compound 3 | | | 5.4 | 12.1 | 2500.0 | 20.7 | 95.9 |
| Comparative example10 | Comparative Compound 4 | | | 5.4 | 12.2 | 2500.0 | 20.5 | 101.3 |
| Comparative example11 | Comparative Compound 5 | | | 5.3 | 12.5 | 2500.0 | 20.0 | 95.2 |
| Comparative example12 | Comparative Compound 6 | | | 5.4 | 12.0 | 2500.0 | 20.8 | 95.8 |
| Comparative example13 | P-1 | Comparative Compound A | | 5.3 | 10.3 | 2500.0 | 24.2 | 102.0 |
| Comparative example14 | | Comparative Compound B | | 5.3 | 11.2 | 2500.0 | 22.3 | 104.0 |
| Comparative example15 | | Comparative Compound C | | 5.4 | 10.3 | 2500.0 | 24.2 | 104.5 |
| Comparative example16 | | Comparative Compound D | | 5.2 | 10.0 | 2500.0 | 25.0 | 102.8 |
| Comparative example17 | Comparative Compound 1 | Comparative Compound A | | 5.2 | 12.4 | 2500.0 | 20.1 | 93.8 |
| Comparative example18 | | Comparative Compound B | | 5.3 | 12.3 | 2500.0 | 20.3 | 95.3 |
| Comparative example19 | | Comparative Compound C | | 5.2 | 12.0 | 2500.0 | 20.8 | 93.5 |

TABLE 6-continued

| | Frist host | Second host | Voltage (v) | Current Density (mA/cm$^2$) | Brightness (cd/m$^2$) | Efficiency (cd/A) | T(95) |
|---|---|---|---|---|---|---|---|
| Comparative example20 | | Comparative Compound D | 5.4 | 12.0 | 2500.0 | 20.9 | 94.2 |
| Example 1 | P-1 | H-35 | 4.2 | 6.9 | 2500.0 | 36.4 | 129.8 |
| Example 2 | P-2 | | 4.0 | 6.2 | 2500.0 | 40.5 | 134.5 |
| Example 3 | P-4 | | 4.1 | 6.0 | 2500.0 | 41.4 | 134.5 |
| Example 4 | P-6 | | 4.1 | 5.8 | 2500.0 | 43.4 | 130.6 |
| Example 5 | P-7 | | 4.1 | 5.9 | 2500.0 | 42.4 | 134.8 |
| Example 6 | P-16 | | 4.3 | 6.7 | 2500.0 | 37.2 | 125.8 |
| Example 7 | P-17 | | 4.2 | 6.6 | 2500.0 | 37.8 | 128.1 |
| Example 8 | P-18 | | 4.2 | 6.7 | 2500.0 | 37.3 | 126.0 |
| Example 9 | P-21 | | 4.4 | 6.6 | 2500.0 | 38.1 | 130.0 |
| Example 10 | P-22 | | 4.2 | 6.9 | 2500.0 | 36.1 | 127.7 |
| Example 11 | P-23 | | 4.2 | 6.5 | 2500.0 | 38.7 | 128.8 |
| Example 12 | P-25 | | 4.2 | 6.7 | 2500.0 | 37.4 | 129.3 |
| Example 13 | P-28 | | 4.3 | 6.9 | 2500.0 | 36.5 | 127.5 |
| Example 14 | P-34 | | 4.3 | 6.4 | 2500.0 | 39.0 | 129.7 |
| Example 15 | P-38 | | 4.2 | 6.6 | 2500.0 | 37.6 | 127.6 |
| Example 16 | P-39 | | 4.3 | 6.7 | 2500.0 | 37.4 | 127.4 |
| Example 17 | P-1 | S-40 | 4.6 | 6.7 | 2500.0 | 37.1 | 131.6 |
| Example 18 | P-3 | | 4.2 | 6.2 | 2500.0 | 40.1 | 141.8 |
| Example 19 | P-4 | | 4.2 | 6.2 | 2500.0 | 40.1 | 144.4 |
| Example 20 | P-7 | | 4.2 | 5.6 | 2500.0 | 44.8 | 144.3 |
| Example 21 | P-9 | | 4.1 | 5.6 | 2500.0 | 44.6 | 141.7 |
| Example 22 | P-17 | | 4.5 | 6.5 | 2500.0 | 38.5 | 129.9 |
| Example 23 | P-18 | | 4.5 | 6.5 | 2500.0 | 38.3 | 128.8 |
| Example 24 | P-21 | | 4.7 | 6.8 | 2500.0 | 36.6 | 133.7 |
| Example 25 | P-22 | | 4.3 | 6.4 | 2500.0 | 39.0 | 135.8 |
| Example 26 | P-24 | | 4.4 | 6.9 | 2500.0 | 36.2 | 134.3 |
| Example 27 | P-25 | | 4.4 | 6.8 | 2500.0 | 37.0 | 132.3 |
| Example 28 | P-34 | | 4.5 | 6.9 | 2500.0 | 36.4 | 136.6 |
| Example 29 | P-37 | | 4.7 | 6.6 | 2500.0 | 38.0 | 132.7 |
| Example 30 | P-39 | | 4.6 | 6.7 | 2500.0 | 37.2 | 131.3 |
| Example 31 | P-1 | H-49 | 4.3 | 6.0 | 2500.0 | 41.4 | 129.6 |
| Example 32 | P-3 | | 4.1 | 5.9 | 2500.0 | 42.3 | 130.2 |
| Example 33 | P-6 | | 4.0 | 5.9 | 2500.0 | 42.4 | 133.8 |
| Example 34 | P-9 | | 4.1 | 5.7 | 2500.0 | 43.5 | 131.7 |
| Example 35 | P-17 | | 4.2 | 6.6 | 2500.0 | 38.0 | 125.2 |
| Example 36 | P-19 | | 4.3 | 6.6 | 2500.0 | 38.1 | 129.5 |
| Example 37 | P-21 | H-122 | 4.4 | 6.9 | 2500.0 | 36.5 | 128.8 |
| Example 38 | P-23 | | 4.2 | 6.9 | 2500.0 | 36.5 | 127.1 |
| Example 39 | P-25 | | 4.2 | 6.5 | 2500.0 | 38.7 | 127.4 |
| Example 40 | P-34 | | 4.5 | 6.8 | 2500.0 | 36.7 | 127.5 |
| Example 41 | P-38 | | 4.3 | 6.7 | 2500.0 | 37.3 | 128.0 |
| Example 42 | P-2 | S-55 | 4.2 | 6.1 | 2500.0 | 41.1 | 142.1 |
| Example 43 | P-4 | | 4.1 | 6.2 | 2500.0 | 40.5 | 144.7 |
| Example 44 | P-7 | | 4.1 | 5.7 | 2500.0 | 43.8 | 143.6 |
| Example 45 | P-16 | | 4.0 | 5.6 | 2500.0 | 44.4 | 143.2 |
| Example 46 | P-18 | | 4.5 | 7.0 | 2500.0 | 35.5 | 131.3 |
| Example 47 | P-20 | | 4.4 | 6.9 | 2500.0 | 36.5 | 131.8 |
| Example 48 | P-22 | S-60 | 4.4 | 6.5 | 2500.0 | 38.3 | 135.5 |
| Example 49 | P-24 | | 4.4 | 6.9 | 2500.0 | 36.4 | 135.8 |
| Example 50 | P-28 | | 4.5 | 6.8 | 2500.0 | 36.7 | 137.9 |
| Example 51 | P-37 | | 4.4 | 6.9 | 2500.0 | 36.5 | 136.1 |
| Example 52 | P-39 | | 4.5 | 6.5 | 2500.0 | 38.3 | 132.7 |
| Example 53 | P-2 | S-109 | 4.1 | 5.7 | 2500.0 | 43.6 | 142.0 |
| Example 54 | P-4 | | 4.2 | 6.2 | 2500.0 | 40.0 | 144.1 |
| Example 55 | P-7 | | 4.3 | 5.8 | 2500.0 | 43.1 | 140.9 |
| Example 56 | P-16 | | 4.2 | 6.4 | 2500.0 | 39.1 | 140.3 |
| Example 57 | P-18 | | 4.5 | 7.1 | 2500.0 | 35.3 | 128.2 |
| Example 58 | P-20 | | 4.6 | 6.4 | 2500.0 | 39.0 | 131.7 |
| Example 59 | P-22 | S-112 | 4.4 | 6.5 | 2500.0 | 38.5 | 131.1 |
| Example 60 | P-24 | | 4.5 | 6.9 | 2500.0 | 36.4 | 138.0 |
| Example 61 | P-28 | | 4.3 | 6.8 | 2500.0 | 36.8 | 135.4 |
| Example 62 | P-37 | | 4.7 | 6.7 | 2500.0 | 37.1 | 134.5 |
| Example 63 | P-39 | | 4.6 | 6.9 | 2500.0 | 36.5 | 130.3 |

TABLE 7

| | compound | Voltage | Current Density (mA/cm²) | Brightness (cd/m²) | Efficiency (cd/A) | T(95) |
|---|---|---|---|---|---|---|
| Comparative example21 | Comparative Compound 1 | 5.5 | 14.4 | 2500.0 | 17.4 | 97.2 |
| Comparative example22 | Comparative Compound 2 | 5.4 | 14.9 | 2500.0 | 16.8 | 93.4 |
| Comparative example23 | Comparative Compound 3 | 5.4 | 12.6 | 2500.0 | 19.9 | 89.6 |
| Comparative example24 | Comparative Compound 4 | 5.4 | 14.0 | 2500.0 | 17.9 | 97.1 |
| Comparative example25 | Comparative Compound 5 | 5.5 | 13.2 | 2500.0 | 18.9 | 94.5 |
| Comparative example26 | Comparative Compound 6 | 5.4 | 12.6 | 2500.0 | 19.9 | 93.7 |
| Example 64 | P-1 | 4.6 | 8.0 | 2500.0 | 31.2 | 110.4 |
| Example 65 | P-2 | 4.1 | 6.3 | 2500.0 | 39.6 | 129.9 |
| Example 66 | P-3 | 4.2 | 6.3 | 2500.0 | 39.4 | 129.4 |
| Example 67 | P-4 | 4.1 | 6.7 | 2500.0 | 37.3 | 124.1 |
| Example 68 | P-5 | 4.1 | 6.8 | 2500.0 | 36.7 | 127.6 |
| Example 69 | P-6 | 4.2 | 6.8 | 2500.0 | 36.9 | 125.7 |
| Example 70 | P-7 | 4.1 | 6.9 | 2500.0 | 36.3 | 125.9 |
| Example 71 | P-8 | 4.1 | 6.8 | 2500.0 | 36.9 | 124.7 |
| Example 72 | P-9 | 4.1 | 6.4 | 2500.0 | 38.9 | 127.9 |
| Example 73 | P-10 | 4.1 | 6.4 | 2500.0 | 39.3 | 123.8 |
| Example 74 | P-11 | 4.1 | 6.7 | 2500.0 | 37.2 | 123.5 |
| Example 75 | P-12 | 4.2 | 6.4 | 2500.0 | 38.8 | 123.6 |
| Example 76 | P-13 | 4.2 | 6.3 | 2500.0 | 39.6 | 124.9 |
| Example 77 | P-14 | 4.1 | 6.4 | 2500.0 | 38.9 | 127.4 |
| Example 78 | P-15 | 4.2 | 6.9 | 2500.0 | 36.4 | 125.2 |
| Example 79 | P-16 | 4.3 | 6.3 | 2500.0 | 40.0 | 124.8 |
| Example 80 | P-17 | 4.5 | 7.8 | 2500.0 | 31.9 | 111.9 |
| Example 81 | P-18 | 4.6 | 8.7 | 2500.0 | 28.7 | 111.4 |
| Example 82 | P-19 | 4.8 | 9.4 | 2500.0 | 26.7 | 110.8 |
| Example 83 | P-21 | 4.6 | 8.6 | 2500.0 | 29.2 | 109.2 |
| Example 84 | P-22 | 4.3 | 7.4 | 2500.0 | 33.6 | 115.3 |
| Example 85 | P-23 | 4.4 | 7.3 | 2500.0 | 34.2 | 116.0 |

First, the results in Table 6 are explained.

As can be seen from the results in Table 6, when a red organic electroluminescent device was manufactured using the material for an organic electroluminescent device of the present invention as a host material for the emitting layer, compared to the comparative examples using Comparative Compounds 1 to 6, which have a similar basic skeleton to the compound of the present invention as the first host, or Comparative Compounds A to Comparative Compound D as the second host, the driving voltage, efficiency and lifespan of the organic electroluminescent device can be improved.

Comparative Compounds 1 to 6 can be considered as structural isomers with similar molecular weight and skeleton to the compound represented by Formula 1 of the present invention, but do not have the same composition as Formula 1 of the present invention.

In order to confirm the difference in the energy level of the compound due to this difference, the data measured using the DFT method (B3LYP/6-31g(D)) of the Gaussian program is shown in Table 8.

TABLE 8

| Compound | LUMO(eV) |
|---|---|
| P-1 | −2.041 |
| P-21 | −2.016 |
| Comparative Compound 1 | −1.968 |
| Comparative Compound 2 | −1.942 |
| Comparative Compound 3 | −1.854 |
| Comparative Compound 4 | −1.979 |

TABLE 8-continued

| Compound | LUMO(eV) |
|---|---|
| Comparative Compound 5 | −1.872 |
| Comparative Compound 6 | −1.982 |

As can be seen from the results in Table 8, it can be seen that the LUMO energy levels of the compound represented by Formula 1 of the present invention and Comparative Compounds 1 to 6 are formed differently.

To explain in more detail, as the compound represented by Formula 1 of the present invention forms a deeper LUMO level than Comparative Compound 1 to Comparative Compound 6, injection of electrons from the electron transport region into the emitting layer occurs more smoothly when applied to a device. As a result, it is judged that electrons become more abundant in the emitting layer when the compound represented by Formula 1 of the present invention is applied to the device than when Comparative Compound 1 to Comparative Compound 6 is applied to the device.

However, in the emitting layer, it is important to form exciton by balancing electrons and holes, and if electrons and holes are unbalanced, the performance of the device deteriorates due to excess polaron. Therefore, as the first host has excellent electron transport ability, the hole transport ability of the second host is important.

When the compound represented by Formula 2 of the present invention is used as a second host, the planarity of the molecule is poor and the degree of distortion is large, as is the case with amine compounds such as Comparative Compound A to Comparative Compound D. As the compound represented by Formula 2 has an additional substituent called Ar³ introduced into the ring containing X¹, the Ar³ moiety can form additional π orbital overlap with the Ar¹ moiety or Ar² moiety within the molecule, so it has more π orbital overlap in the structure compared to Comparative Compounds A to Comparative Compounds D. As a result, when using the compound represented by Formula 2 of the present invention, the intermolecular distance becomes closer during device fabrication than Comparative Compound A to Comparative Compound D, so that dexter energy transfer occurs more smoothly and as a result, it is believed that the hole injection characteristics into the emitting layer are significantly improved.

When using the compound represented by Formula 5 of the present invention as a second host, compared to comparative compounds having an amine skeleton, the degree of intramolecular distortion is relatively small and the planarity is relatively large, so the intermolecular hole transfer characteristics and hole injection characteristics are judged to be greater than those of Comparative Compounds A to D.

Therefore, when a composition comprising a mixture of a compound represented by Formula 1 and a compound represented by Formula 2 or Formula 5 of the present invention is applied as a host of an organic electronic element, especially an emitting layer, it has improved electron transfer characteristics and hole transfer characteristics compared to when comparative compounds are applied to the device, which increases exciton formation in the emitting layer and, as a result, maximizes the luminous efficiency of the element and improves charge balance of the entire element, it is believed that the driving voltage and lifespan of the element have been significantly improved.

Next, the results in Table 7 are explained.

Comparative Compounds 1 to 6 used in Comparative Examples 21 to 26 are composed of fragments similar to the compounds of the present invention, but are different in whether deuterium is substituted or the substitution position of the substituent.

In order to check changes depending on the position at which the substituent is substituted, despite being a structural isomer, Data measuring the IR spectrum using the DFT method (B3LYP/6-31g(D)) of the Gaussian program are shown in FIGS. 4 to 16.

Figure 4:
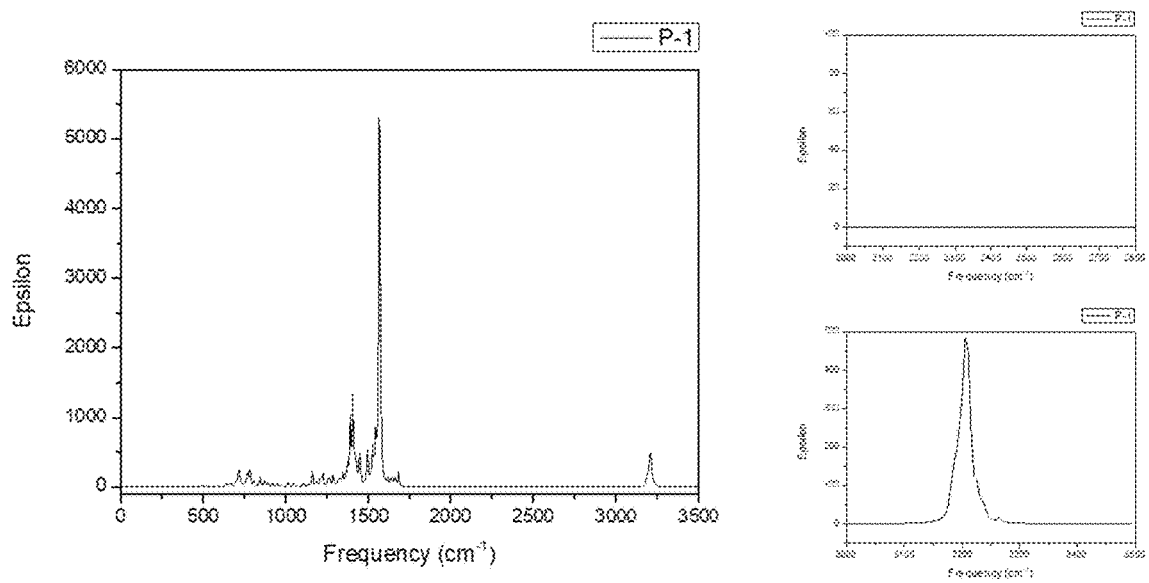
Figure 5:
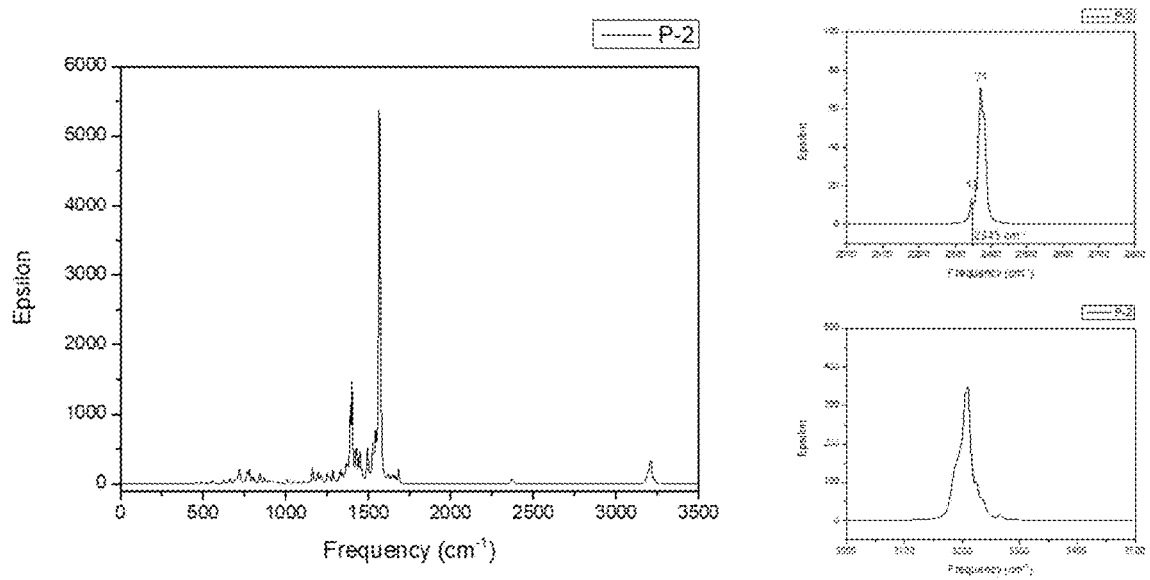
Figure 6:
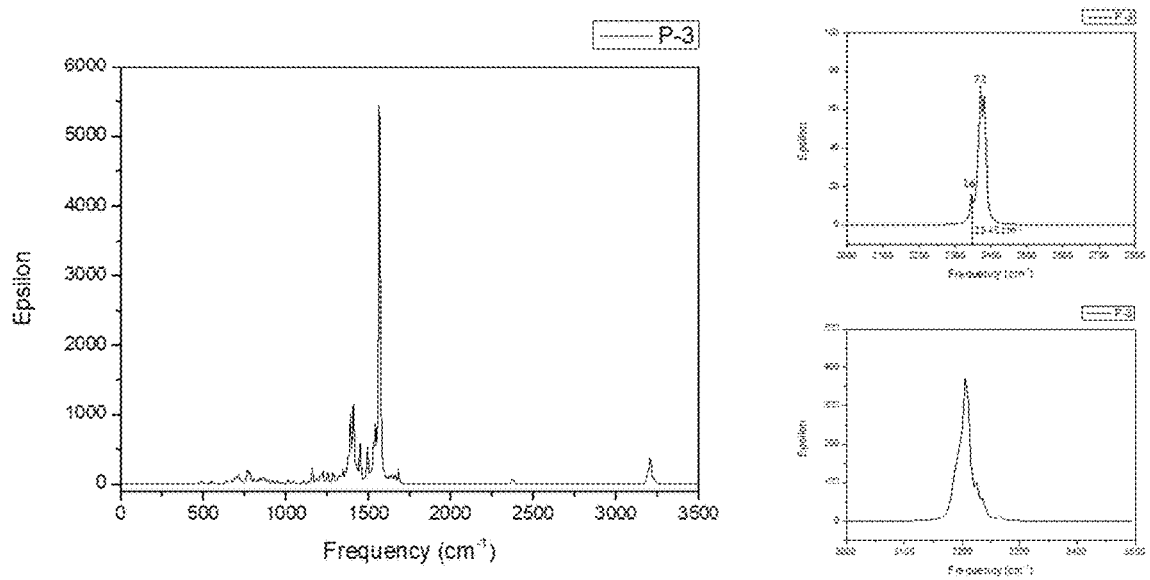
Figure 7:
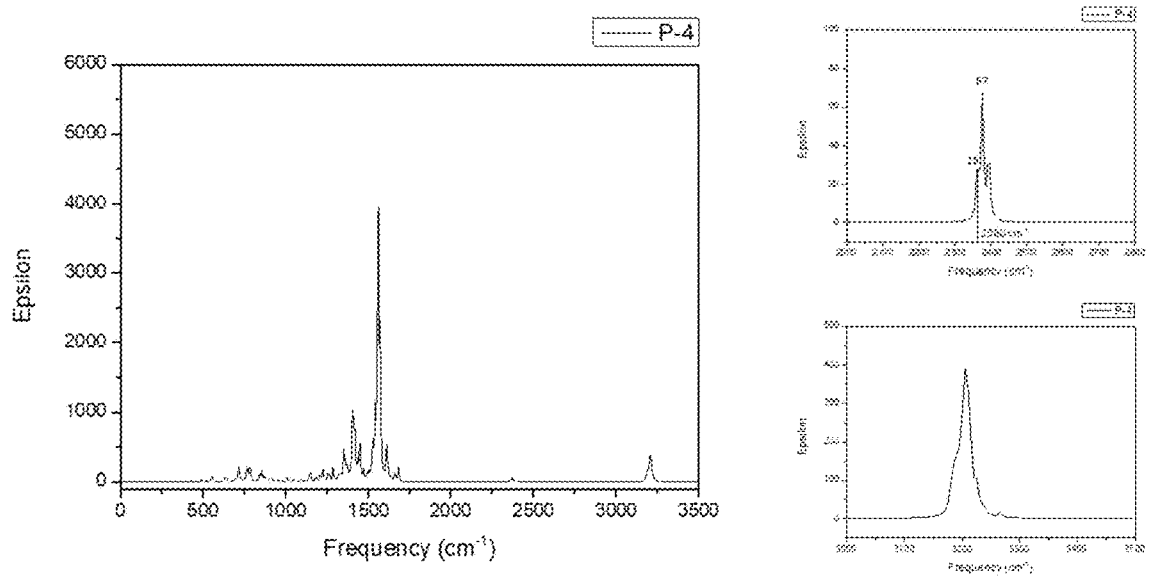
Figure 8:
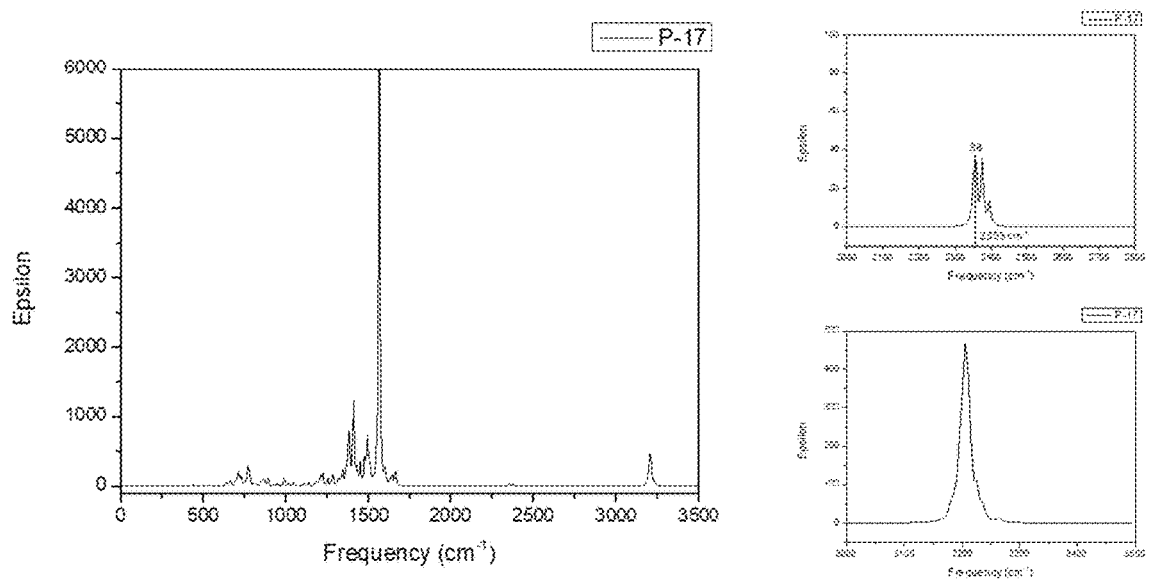
Figure 9:
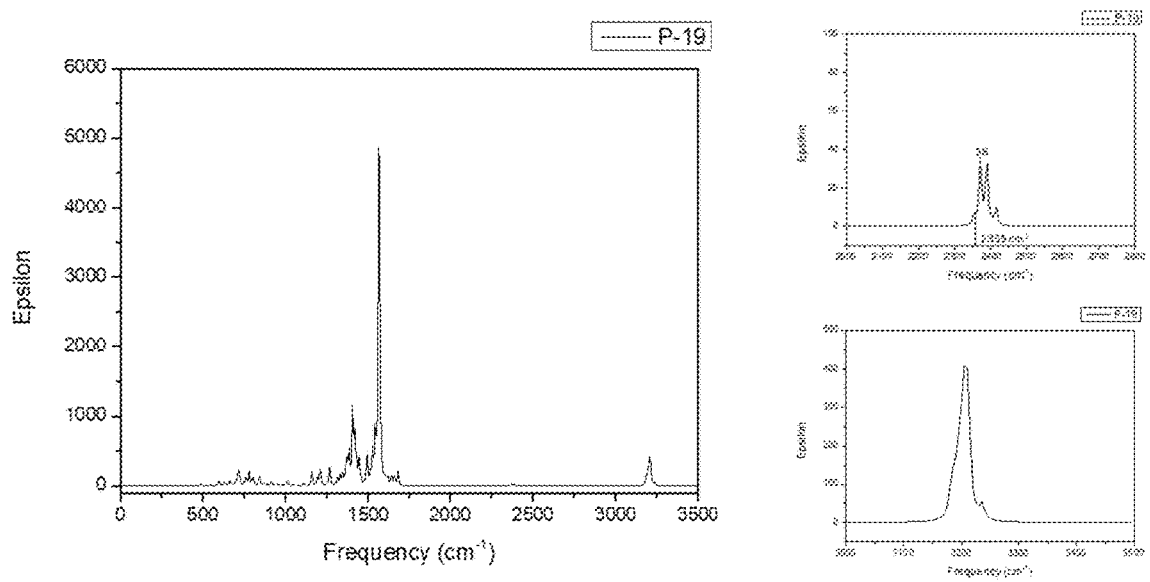
Figure 10:
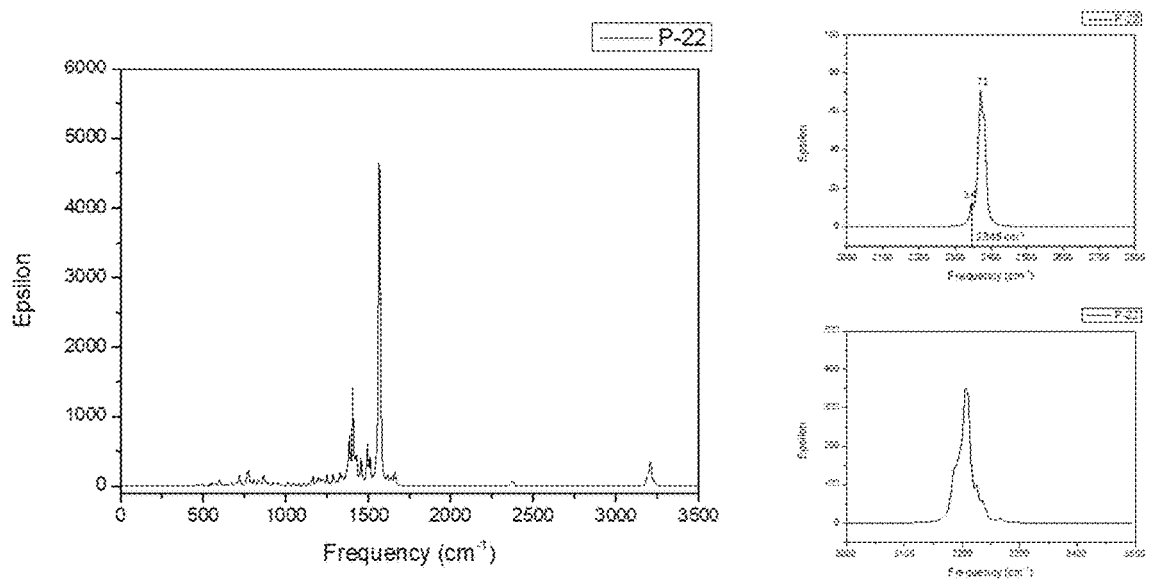
Figure 11:
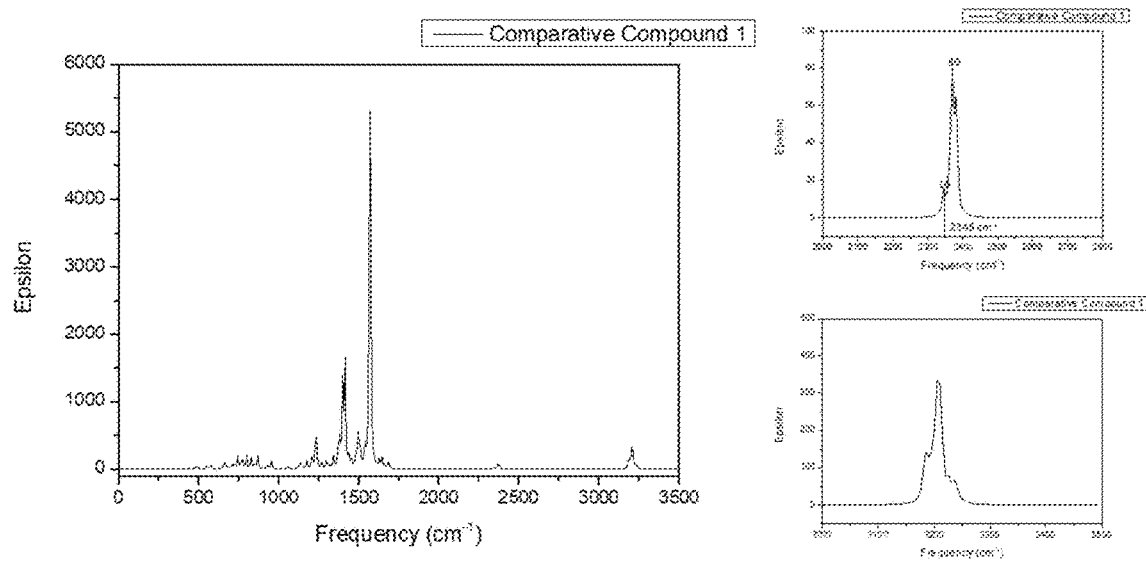
Figure 12:
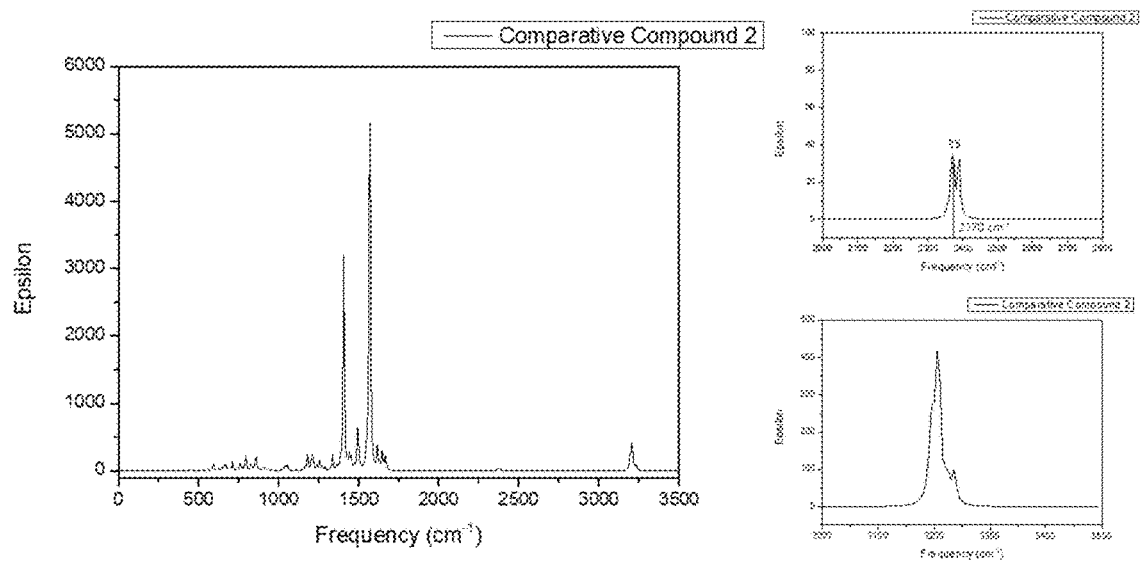
Figure 15:
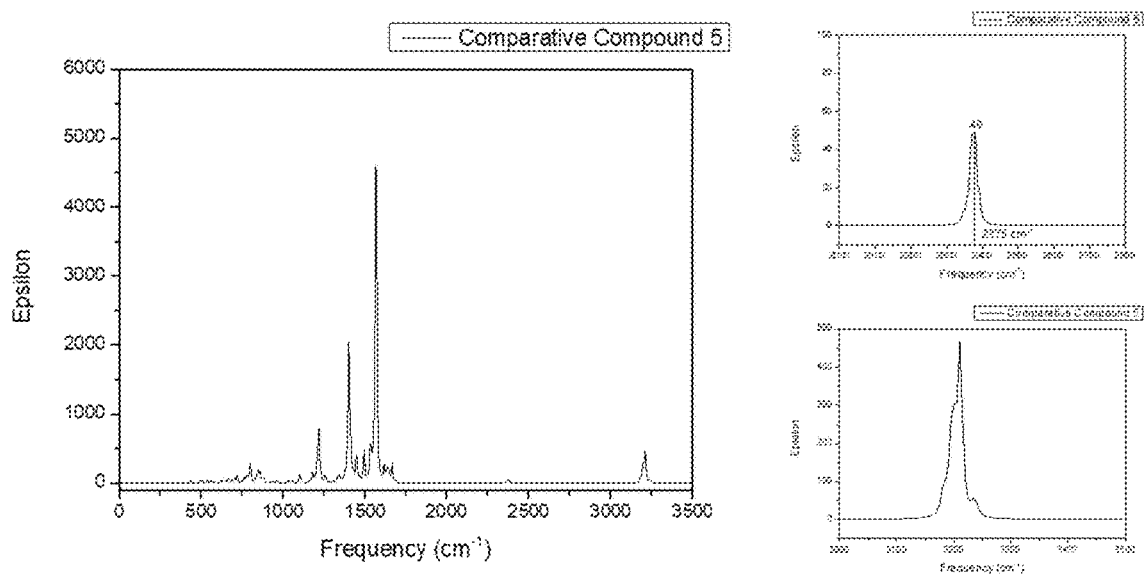
Figure 16:
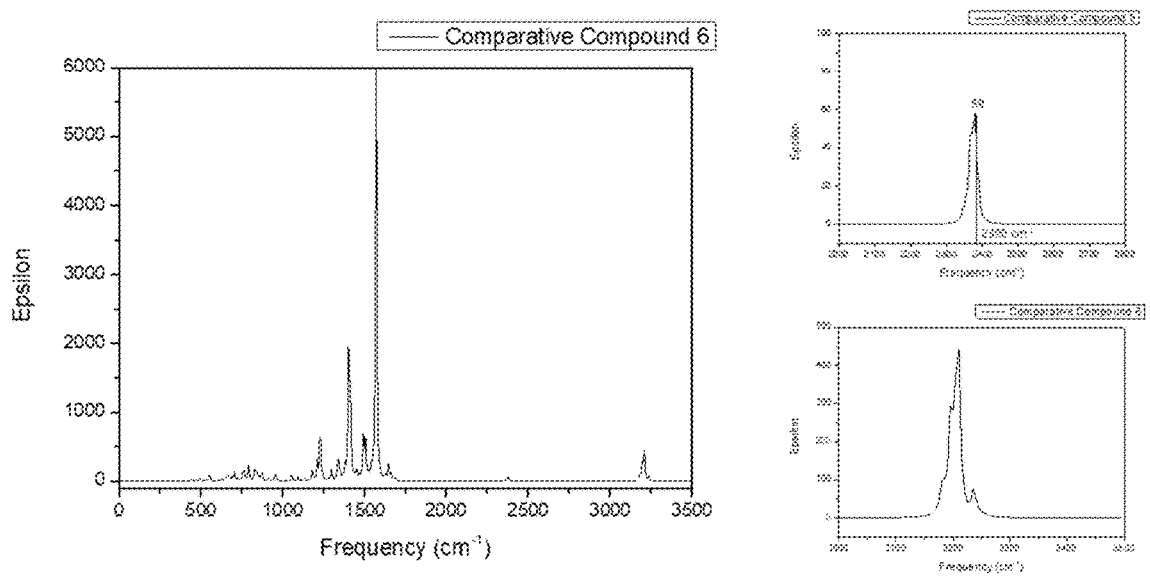

As can be seen from FIGS. 4 to 16, there is a difference in IR Spectrum depending on the position of deuterium substitution in the compound. FIG. 4 (Compound P-1) to FIG. 16 (Comparative Compound 6) all have a peak around 3,200 cm⁻¹ due to C—H Stretching mode, but Compound P-1 and Compound P-21 without deuterium substitution, have the highest epsilon value around 3,200 cm⁻¹. On the contrary, in the case of Comparative Compound 1 to Comparative Compound 6 with deuterium substitution and the compounds of the present invention with deuterium substitution, the epsilon value around 3,200 cm⁻¹ decreases and a peak is generated around 2,400 cm⁻¹ by C-D stretching mode.

That is, compared to Compound P-1 and Compound P-21 in which deuterium is not substituted, Comparative Compounds 1 to 6 in which deuterium is substituted and the compounds of the present invention in which deuterium is substituted are structurally more stable because high frequency vibration is suppressed, and non-radiative decay is reduced, thereby increasing the lifespan and efficiency of the element.

In the compounds of the present invention, when comparing compounds P-2 to P-4 and P-17 and P-19, which have the same basic structure but different positions of deuterium substitution, the epsilon values around 2,400 cm-1 are different.

To explain in more detail, the epsilon value around 2,400 cm-1 was greater for compounds P-2 to P-4 than for compounds P-17 and P-19, and as a result, it can be seen that the high frequency vibration suppression effect of compounds P-2 to P-4 was greater, and the performance of the element was further improved. In other words, even for compounds with the same skeleton, the high frequency vibration suppression effect may be different depending on the position at which deuterium is substituted, which suggests that even structural isomers may have significant effects that are difficult to predict.

However, although Comparative Compound 1 and Comparative Compound 4 have a higher epsilon value around 2,400 cm⁻¹ than Comparative Compound P-2 of the present invention, the element data of the compound of the present invention shows a better effect. To interpret this phenomenon, the average value of TT-TT interaction in the amorphous state of the compounds of the present invention and the comparative compounds was measured using molecular simulation (Schrodinger Maestro Materials Science 5.2.135). The results are shown in Table 9.

TABLE 9

| Compound | average value of $_{TT\text{-}TT}$ interaction |
| --- | --- |
| P-2 | 2322 |
| P-3 | 2369 |
| P-4 | 2311 |
| P-22 | 2306 |
| P-23 | 2335 |
| P-24 | 2365 |
| Comparative Compound 1 | 2251 |
| Comparative Compound 2 | 2274 |
| Comparative Compound 3 | 2264 |
| Comparative Compound 4 | 2293 |
| Comparative Compound 5 | 2291 |
| Comparative Compound 6 | 2186 |

As can be seen from the results in Table 9, it can be seen that the average values of TT-TT interaction between the compounds of the present invention and the comparative compounds are significantly different. As a result, the compound of the present invention, which has a large average value of IT-IT interaction, has a shorter intermolecular distance during device deposition compared to comparative compounds. As a result, Dexter Energy Transfer occurs more smoothly than in comparative compounds, and electron mobility is greatly improved. As exciton formation in the emitting layer increases significantly compared to comparative compounds, it is believed that the performance of the element is improved.

That is, as can be seen from the results of Tables 6 to 9 and FIGS. 4 to 16, even if it is a compound with a similar composition, it can be confirmed that the compound of the present invention, which satisfies all complex factors such as the type of specific substituent and the substitution position of the substituent, shows a significant effect compared to other comparative compounds in organic electronic elements. Through this, it can be seen that the compound of the present invention exhibits a more significant effect in organic electronic elements than simple structural isomers or compounds with similar compositions not described in this specification.

These results show that even in compounds with similar molecular components, the properties of compounds such as the hole characteristics, light efficiency characteristics, energy level, hole injection and mobility characteristics, charge balance of holes and electrons, volume density, and intermolecular distance of the molecule depending on the type and substitution position of the substituents being substituted, may vary significantly enough to be difficult to predict and additionally, suggest that a single configuration does not affect the overall results of the element, but that the performance of the element can vary due to complex factors.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

What is claimed is:

1. A composition for an organic electronic element comprising a mixture of a compound represented by Formula 1 and a compound represented by Formula 2 or Formula 5:

Formula 1

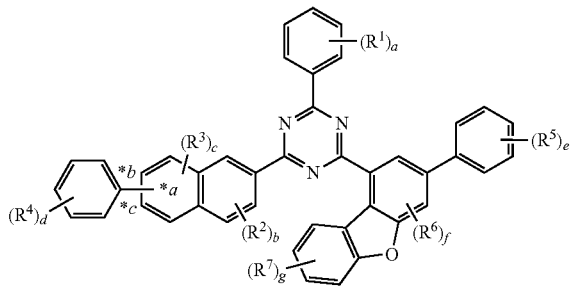

Formula 2

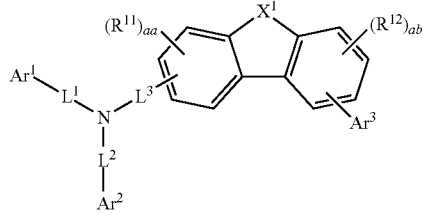

Formula 2-1

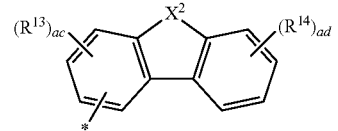

wherein:
$R^1$, $R^2$, $R^3$, $R^4$, $R^5$, $R^6$ and $R^7$ are, being the same or different from each other, each independently hydrogen or deuterium, $R^{11}$, $R^{12}$, $R^{13}$ and $R^{14}$ are each independently same or different, and each independently selected from the group consisting of hydrogen; deuterium; $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and a $C_3$-$C_{60}$ aliphatic ring, or may form a ring by combining with an adjacent group(s), $Ar^1$ and $Ar^2$ are each independently selected from the group consisting of an $C_6$-$C_{60}$ aryl group; a fluorenyl group; a $C_2$-$C_{60}$ heterocyclic group including at least one heteroatom of O, N, S, Si or P; a $C_1$-$C_{50}$ alkyl group; and a $C_3$-$C_{60}$ aliphatic ring;

$Ar^3$ is a substituent represented by Formula 2-1, $L^1$, $L^2$ and $L^3$ are each selected from the group consisting of single bond; an arylene group; a fluorenylene group; a $C_2$-$C_{60}$ heterocyclic group including at least one heteroatom of O, N, S, Si or P, $X^1$ is O or S, $X^2$ is O, S or CR'R'', R' and R'' are selected from the group consisting of a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; and a $C_1$-$C_{50}$ alkyl group, a, d and e are independently an integer of 0 to 5, b, c, aa, ab and ac are independently an integer of 0 to 3, f is an integer of 0 to 2, and g and ad are independently an integer of 0 to 4,

*a is bonded to *b or *c,

Formula 5

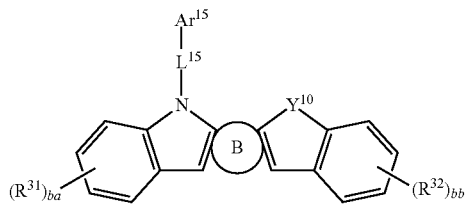

wherein:
$L^{15}$ is selected from the group consisting of a single bond; an $C_6$-$C_{60}$ arylene group; a fluorenylene group; a $C_2$-$C_{60}$ heterocyclic group including at least one heteroatom of O, N, S, Si or P; and a fused ring group of a $C_3$-$C_{60}$ aliphatic ring and an $C_6$-$C_{60}$ aromatic ring, $Ar^{15}$ is selected from the group consisting of an $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; and -L'-N($R^a$)($R^b$), $Y^{10}$ is O, S, C($R^{51}$) ($R^{52}$) or $NR^{53}$, Ring B is an $C_6$~$C_{20}$ aryl group, $R^{31}$ and $R^{32}$ are each the same or different, and each independently selected from the group consisting of hydrogen; deuterium; halogen; cyano group; a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group; or an adjacent plurality of $R^{31}$ or plurality of $R^{32}$ may be bonded to each other to form a ring, ba and bb are each an integer of 0 to 4, L' is selected from the group consisting of a single bond; an $C_6$-$C_{60}$ arylene group; a fluorenylene group; a $C_2$-$C_{60}$ heterocyclic group including at least one heteroatom of O, N, S, Si or P; and a $C_3$-$C_{60}$ aliphatic ring, $R^{51}$, $R^{52}$, $R^{53}$, $R^a$ and $R^b$ are each independently selected from the group consisting of a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and a $C_3$-$C_{60}$ aliphatic ring; or $R^{51}$ and $R^{52}$ can be bonded to each other to form a spiro ring, \* refers to position to be bonded, wherein the aryl group, arylene group, heterocyclic group, fluorenyl group, fluorenylene group, fused ring group, aliphatic ring group, alkyl group, alkenyl group, alkynyl group, alkoxy group and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; a $C_3$-$C_{20}$ aliphatic ring; $C_7$-$C_{20}$ arylalkyl group; $C_8$-$C_{20}$ arylalkenyl group; $C_7$-$C_{20}$ alkylaryl group; also the hydrogen of these substituents may be further substituted with one or more deuteriums, and the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

2. The composition for an organic electronic element of claim 1, wherein Formula 1 is represented by Formula 1-1 or Formula 1-2:

Formula 1-1

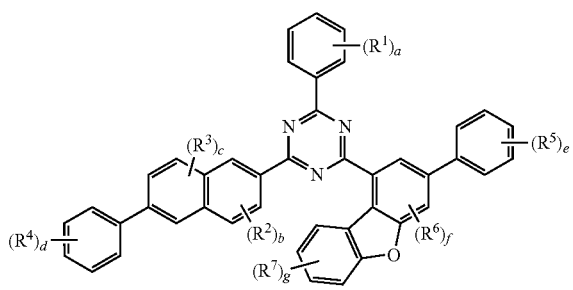

Formula 1-2 wherein: $R^1$, $R^2$, $R^3$, $R^4$, $R^5$, $R^6$, $R^7$, a, b, c, d, e, f and g are the same as defined in claim 1.

3. The composition for an organic electronic element of claim 1, wherein any one of $R^1$, $R^2$, $R^3$, $R^4$, $R^5$, $R^6$ and $R^7$ is deuterium.

4. The composition for an organic electronic element of claim 1, wherein Formula 1 is selected from the group consisting of Compounds P-1 to P-40:

P-1

P-2

P-3

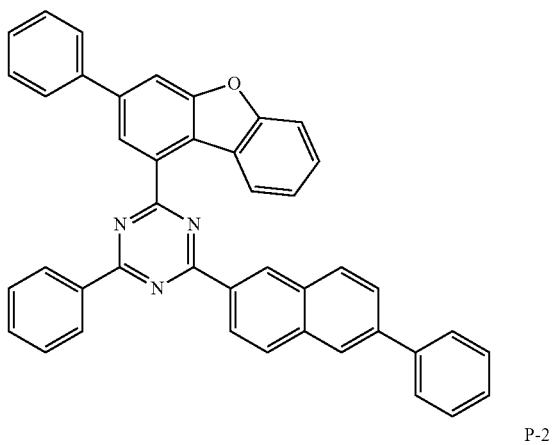

P-4
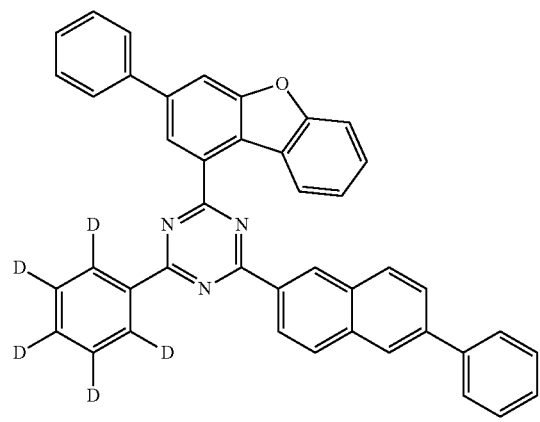
P-7
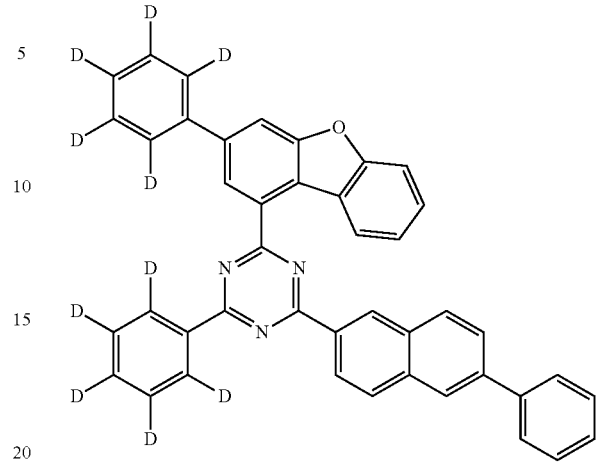
P-5
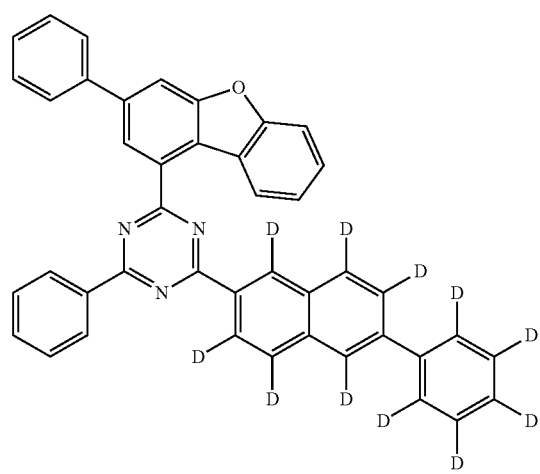
P-8
P-6
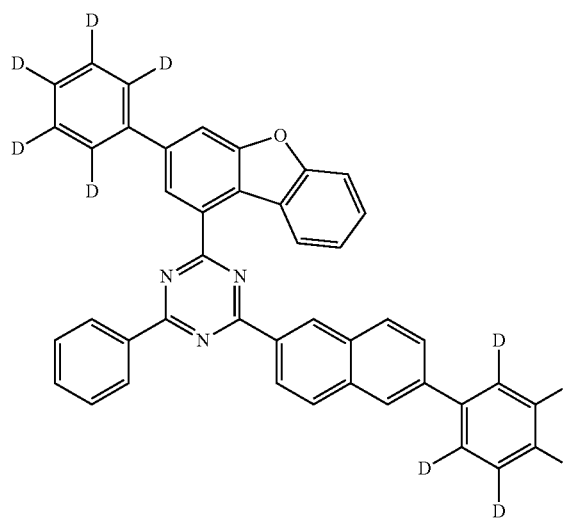
P-9

P-10
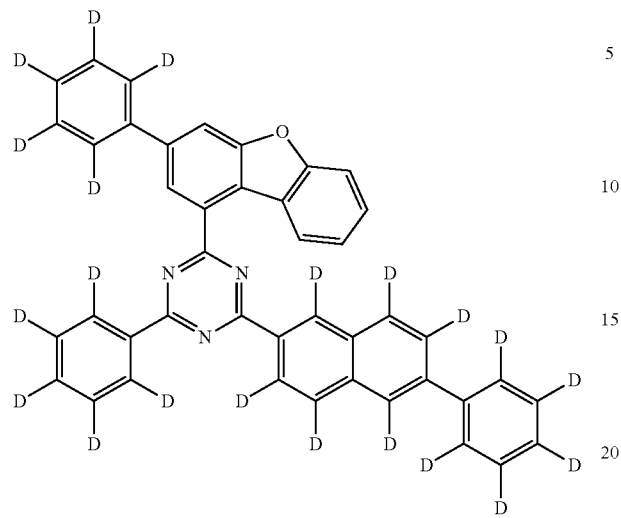
P-13
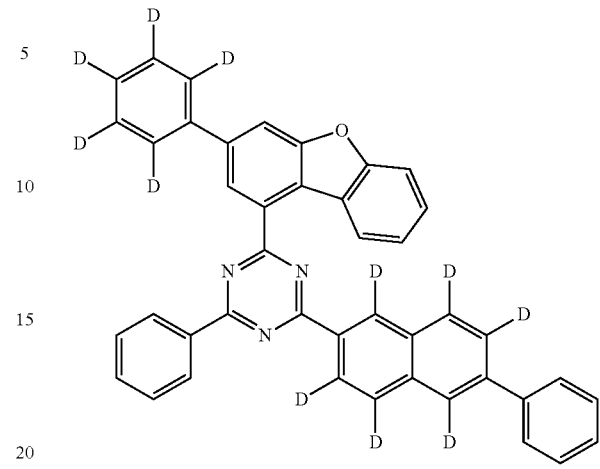
P-11
P-14
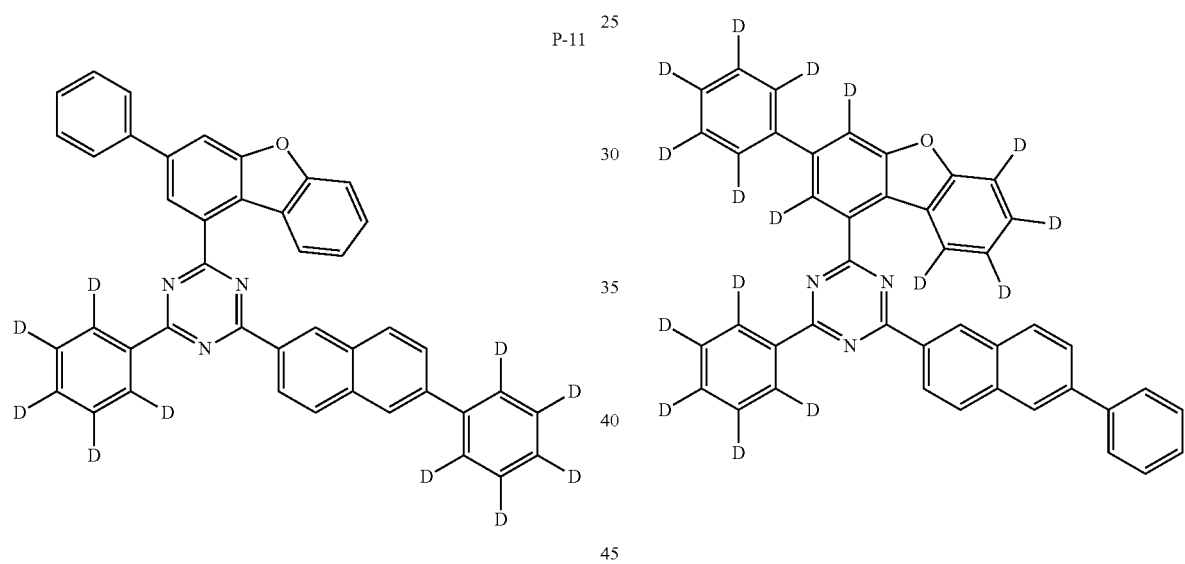
P-12
P-15
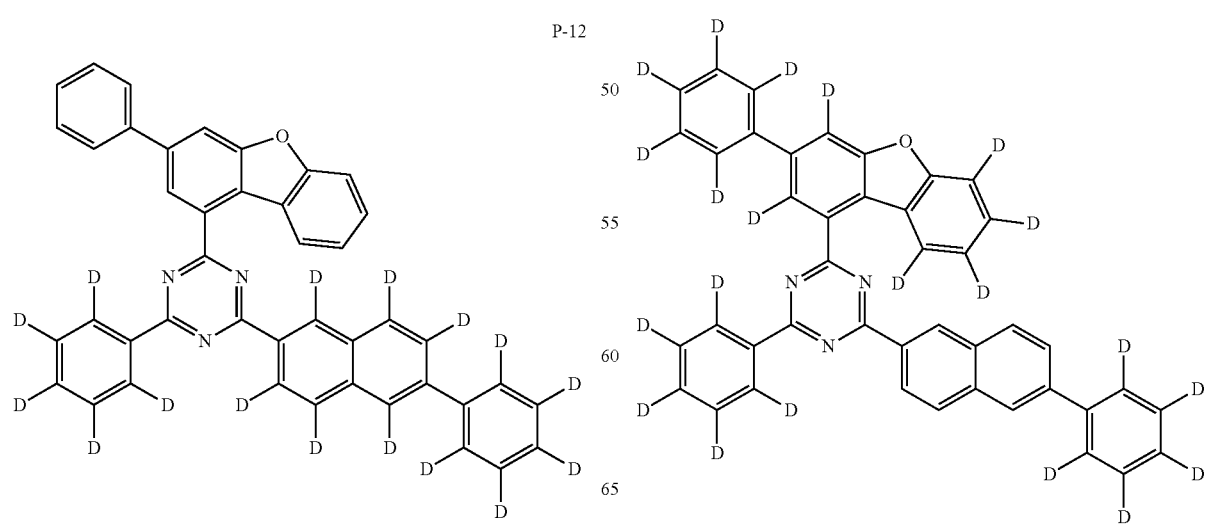

P-16
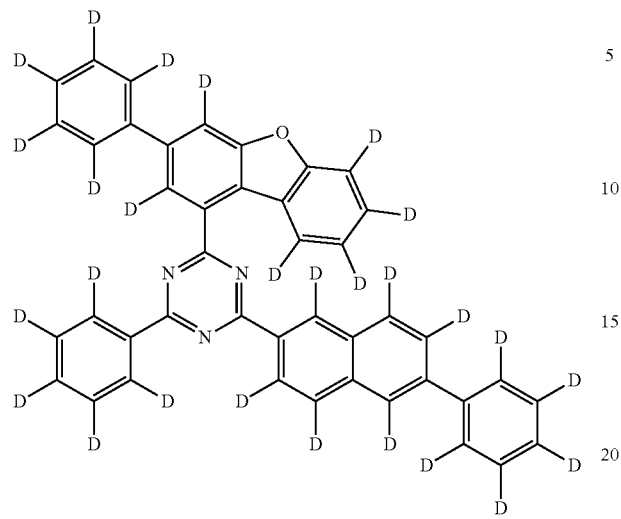
P-17
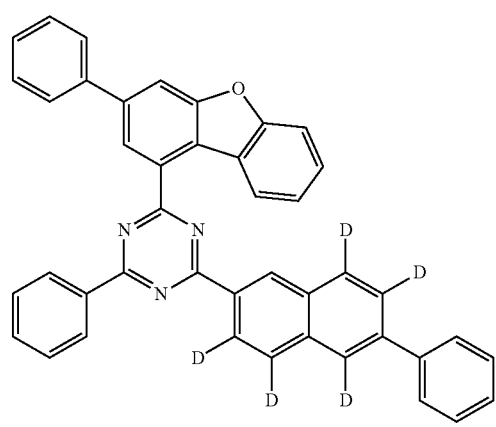
P-18
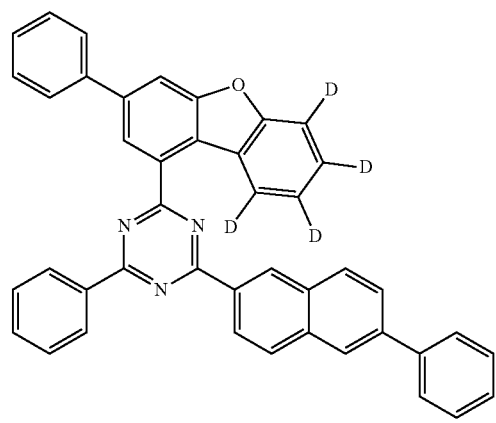
P-19
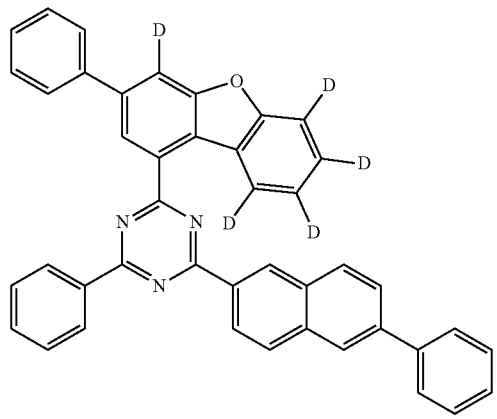
P-20
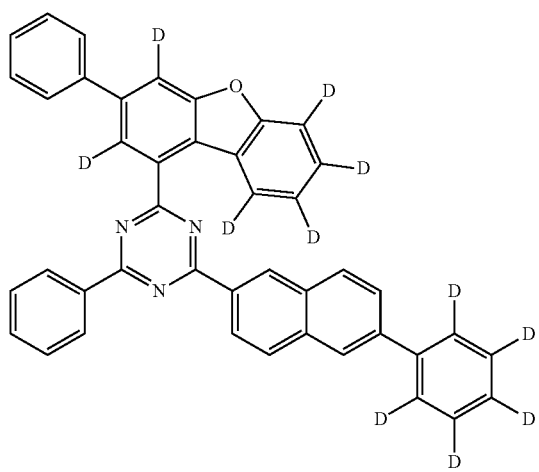
P-21
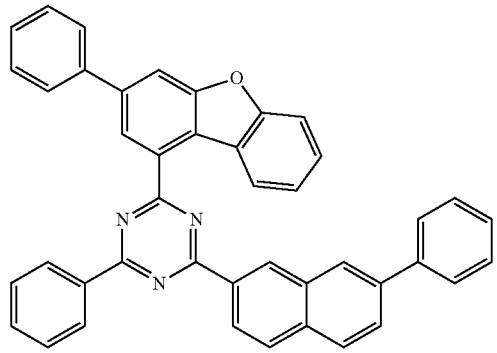

P-22
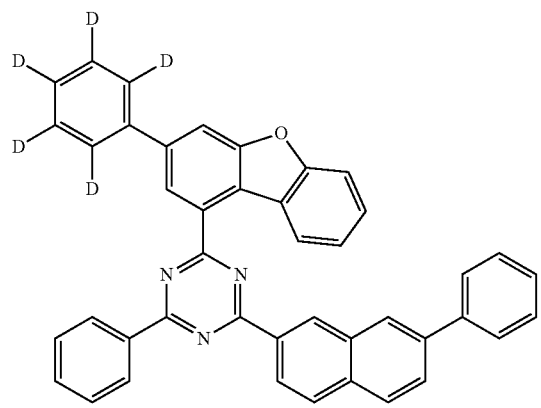
P-23
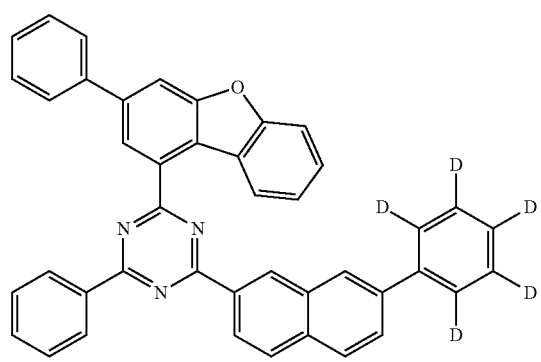
P-24
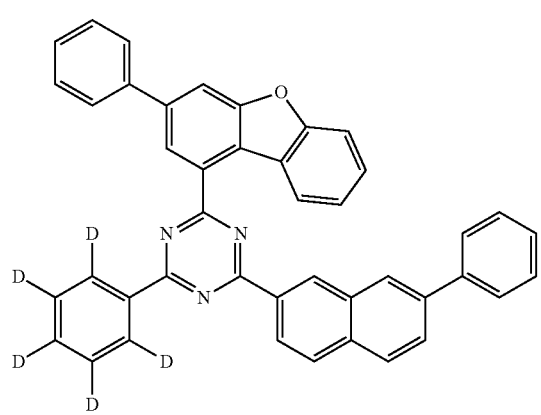
P-25
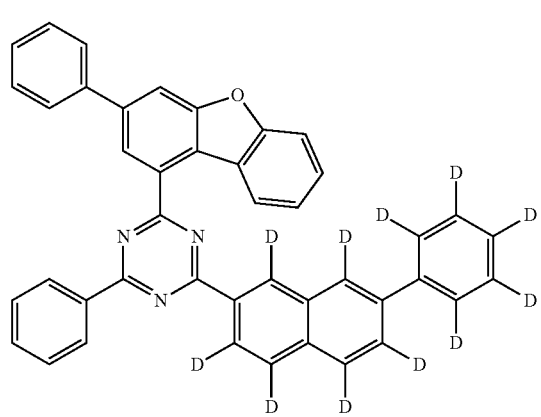
P-26
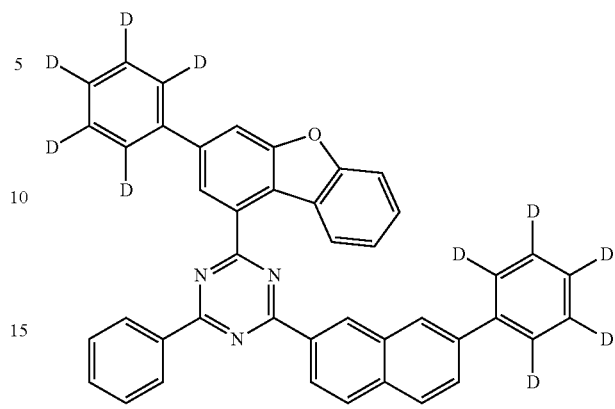
P-27
P-28

-continued
P-29
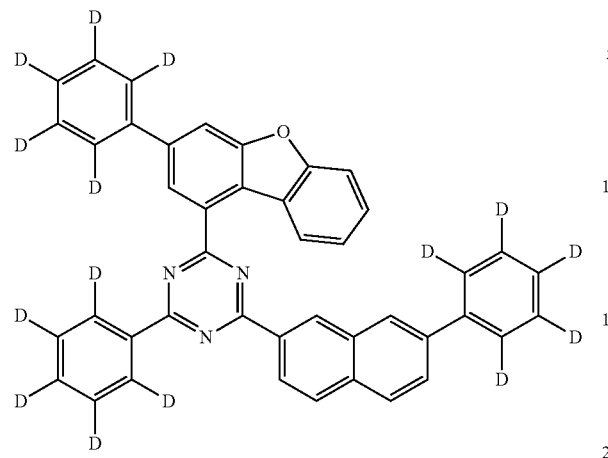
P-32
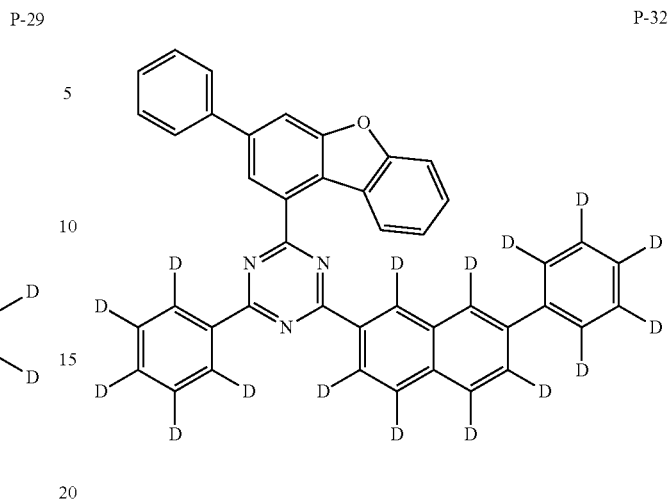
P-30
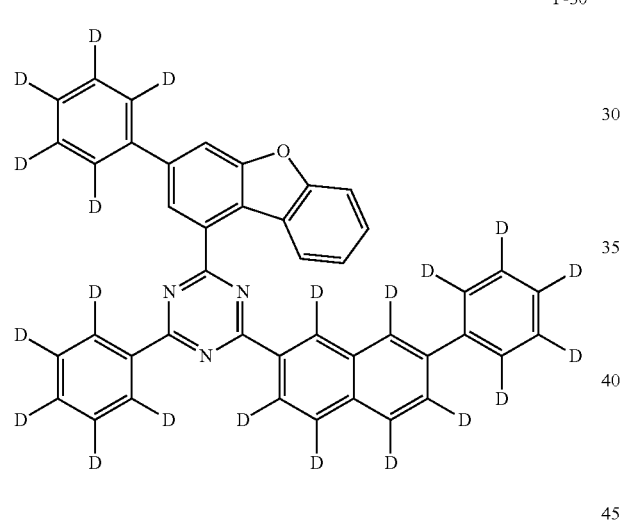
P-33
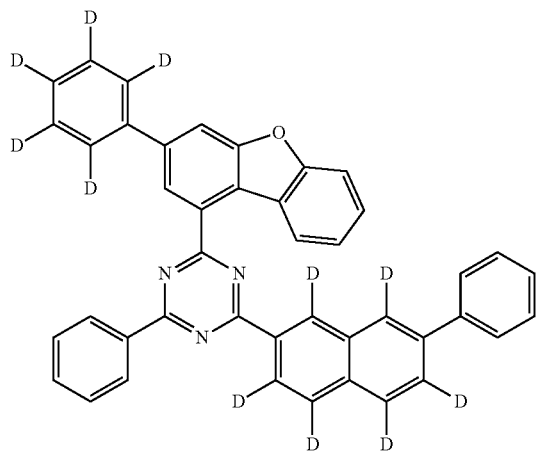
P-31
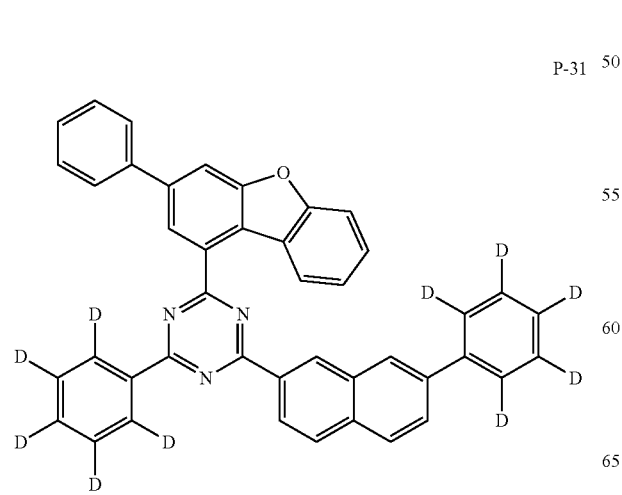
P-34
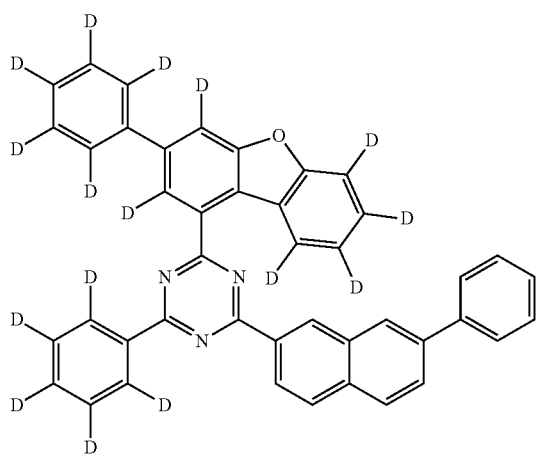

P-35
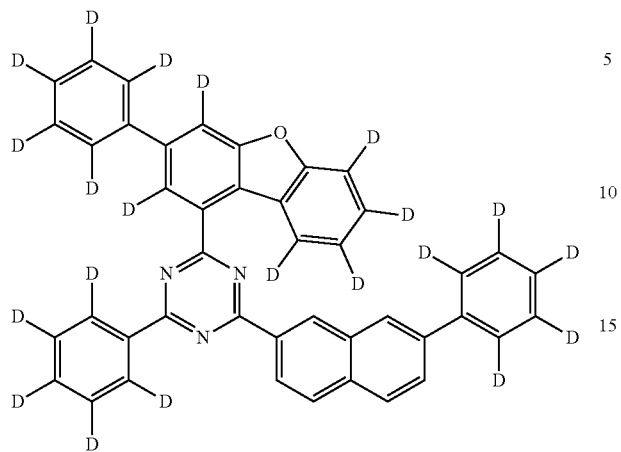
P-36
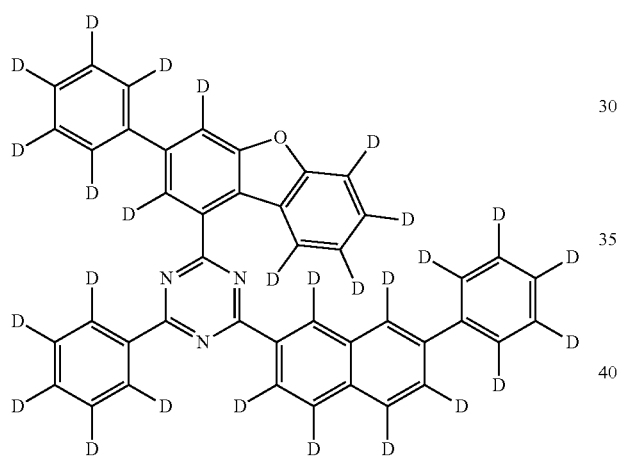
P-37
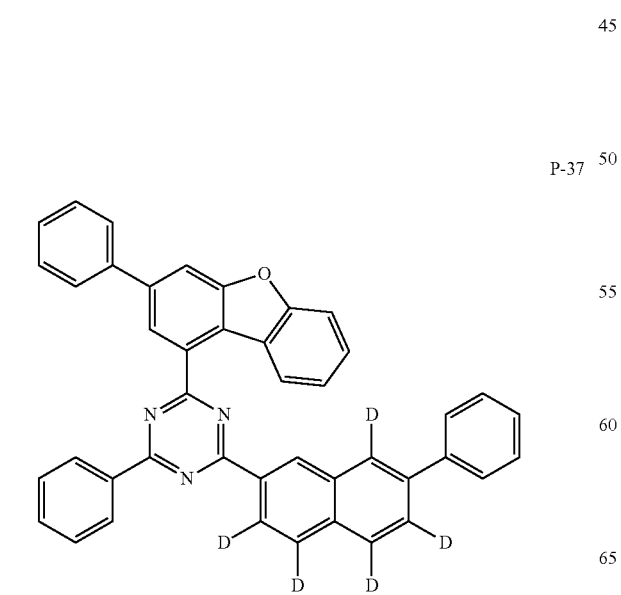
P-38
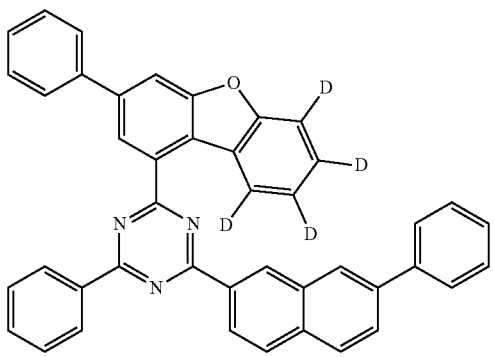
P-39
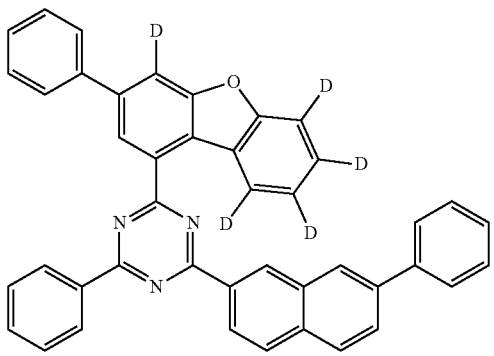
P-40
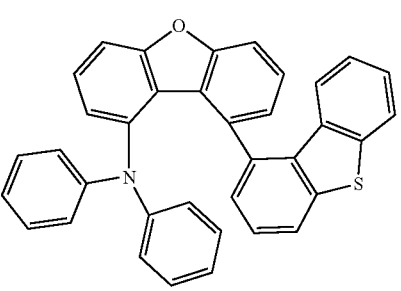
5. The composition for an organic electronic element of claim 1, wherein Formula 2 is selected from the group consisting of Compounds H-1 to H-132:
H-1

H-2
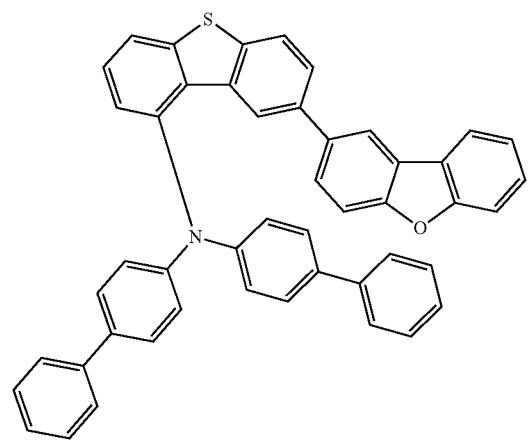
H-3
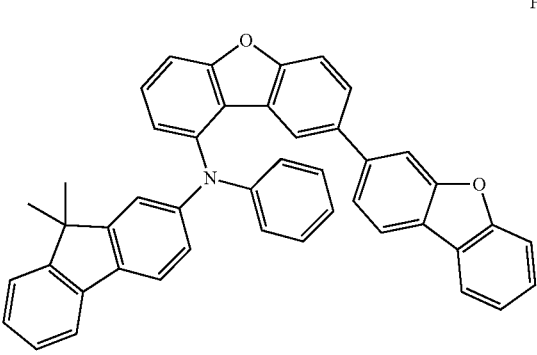
H-4
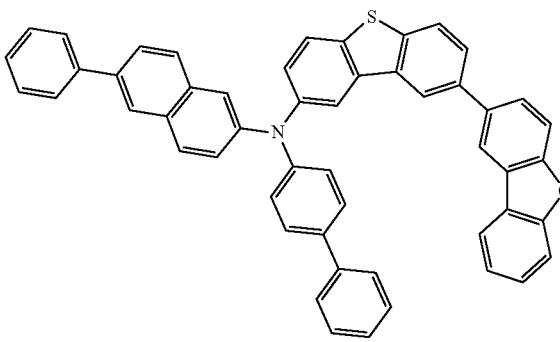
H-5
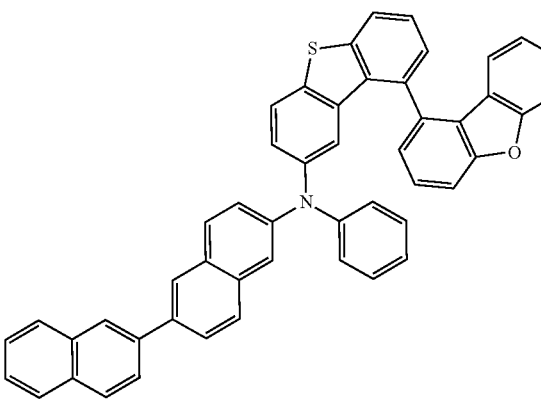
H-6
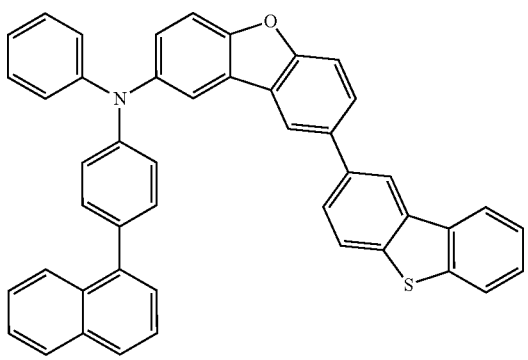
H-7
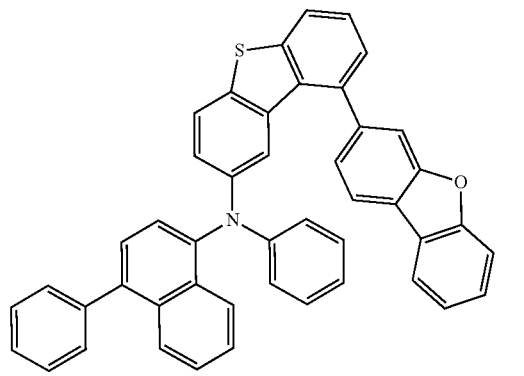
H-8
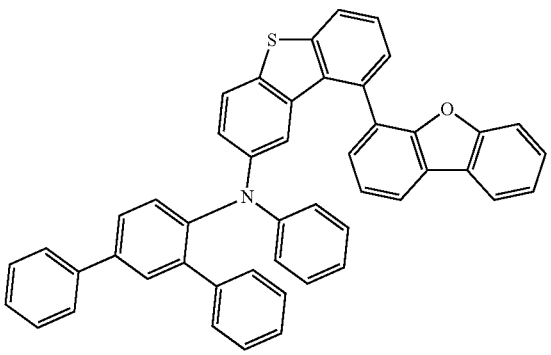
H-9
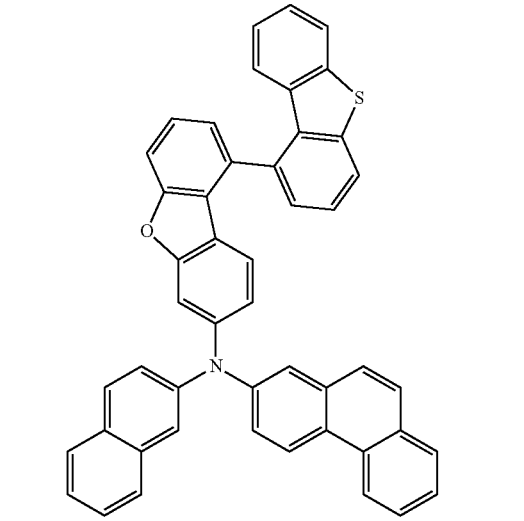

H-10
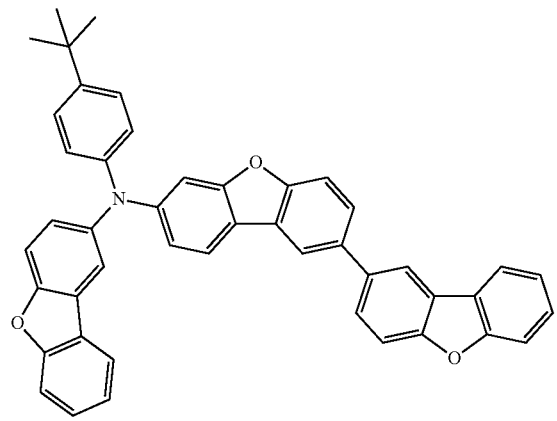
H-11
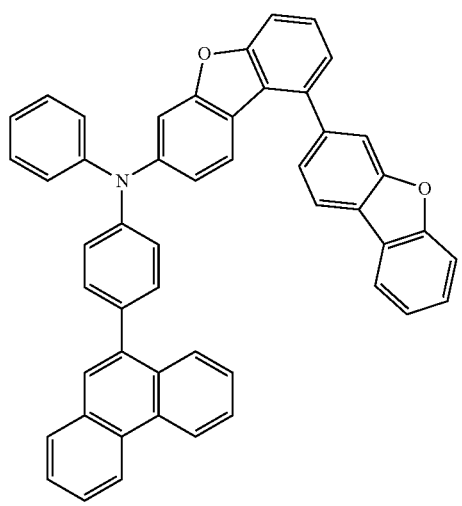
H-12
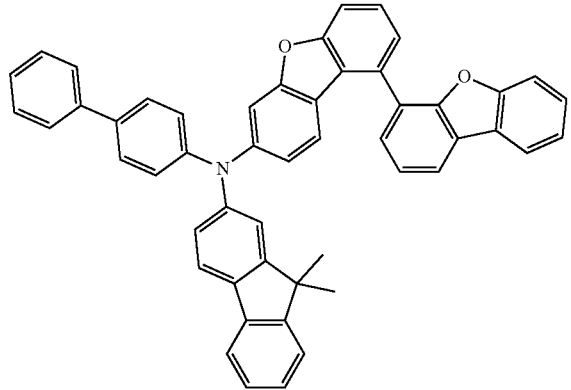
H-13
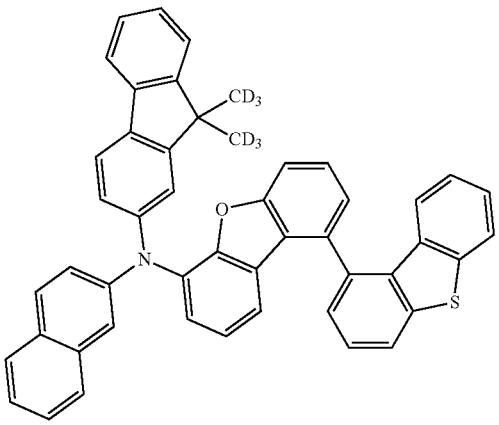
H-14
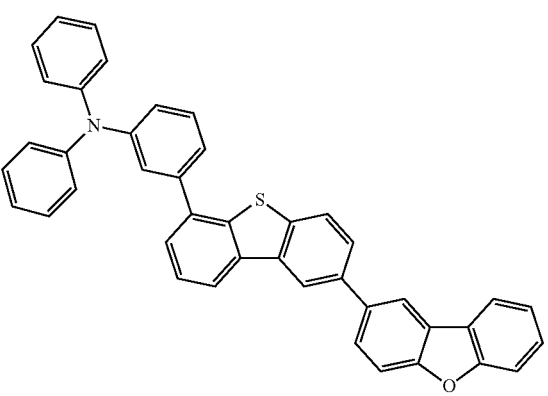
H-15
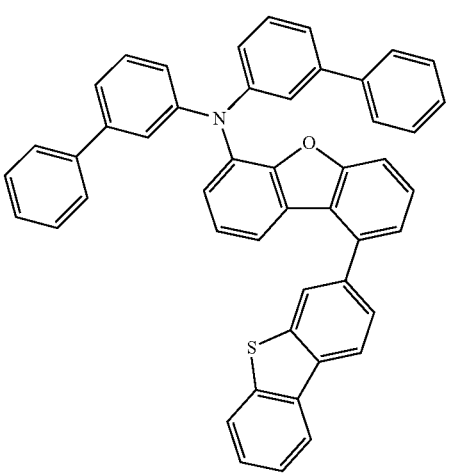

-continued
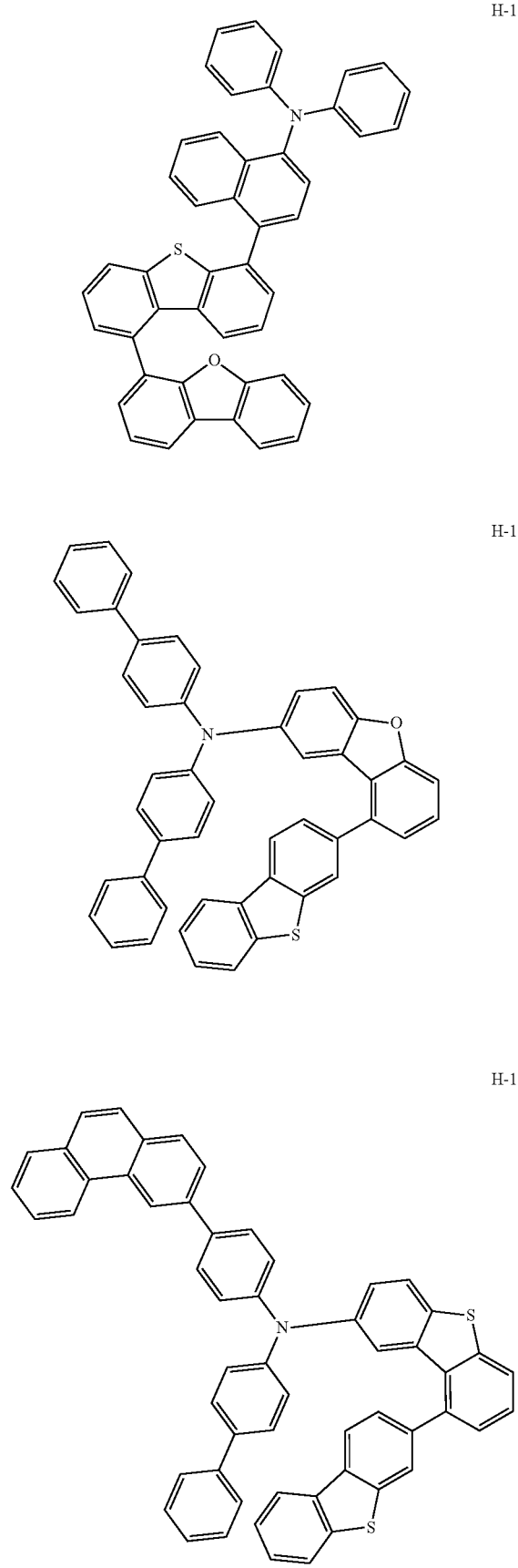
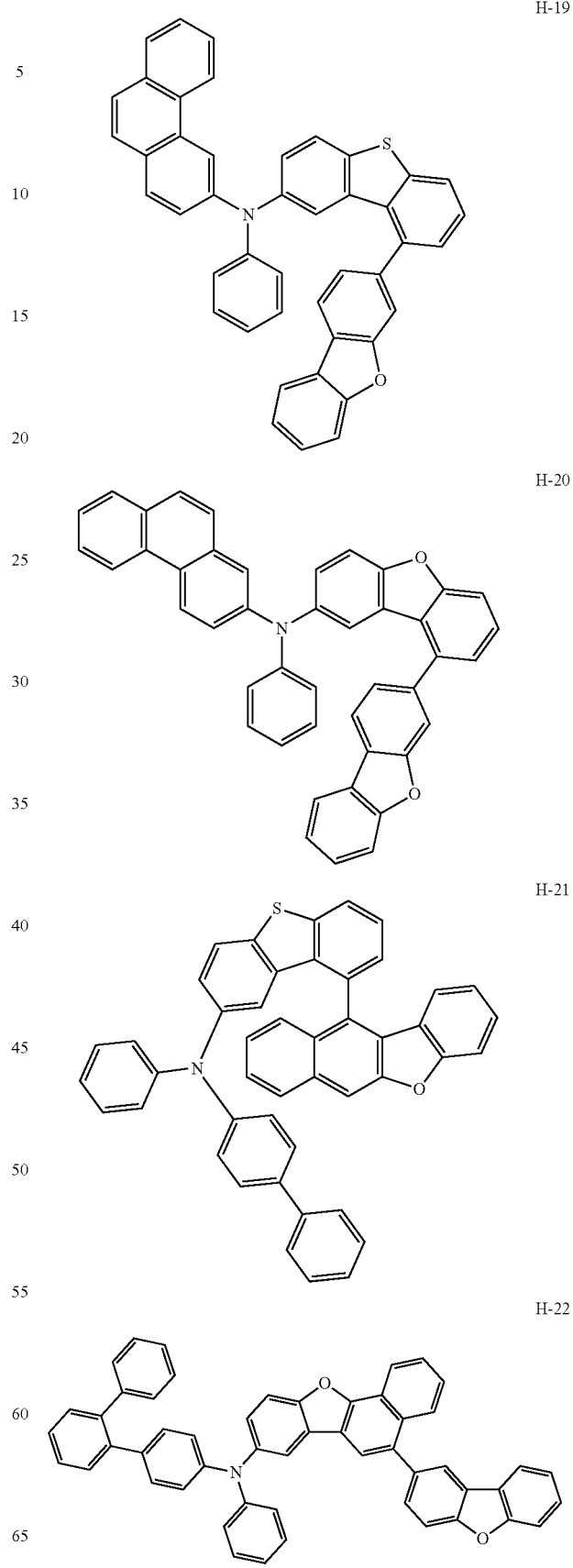

H-23
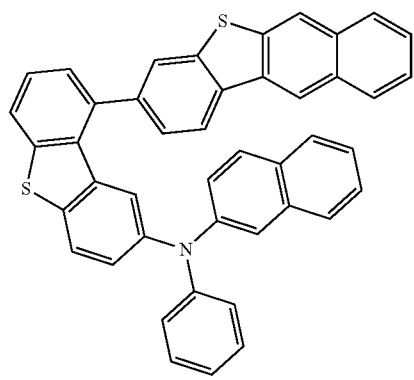
H-24
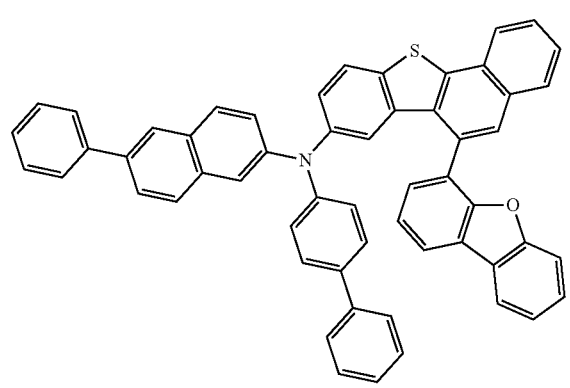
H-25
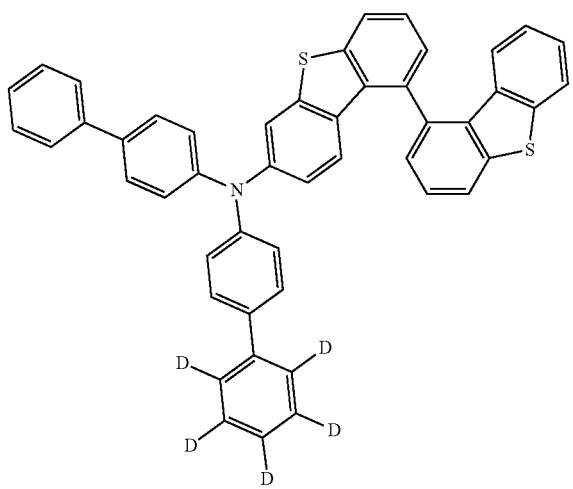
H-26
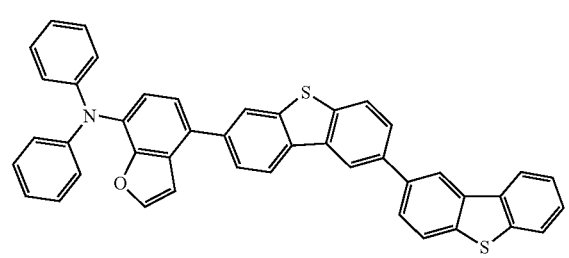
H-27
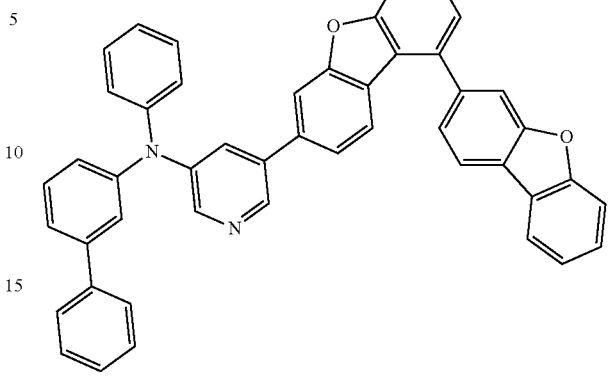
H-28
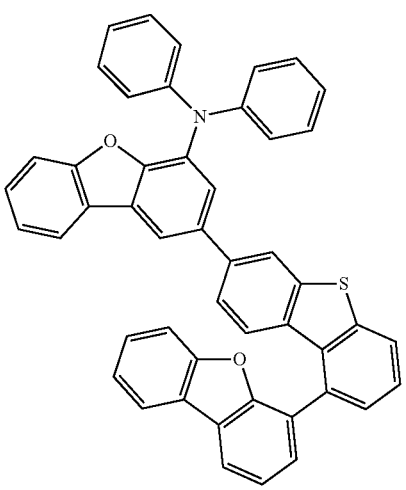
H-29
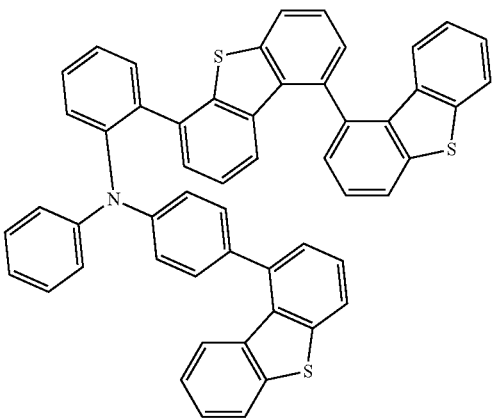

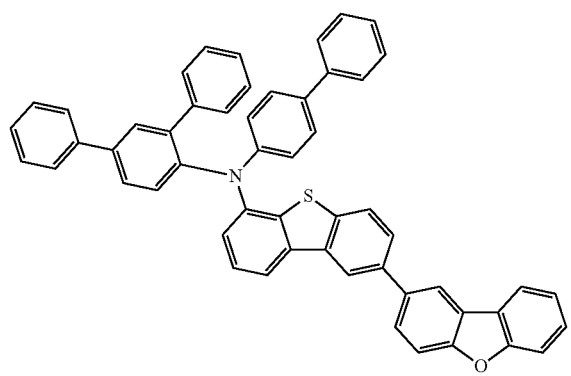
H-30
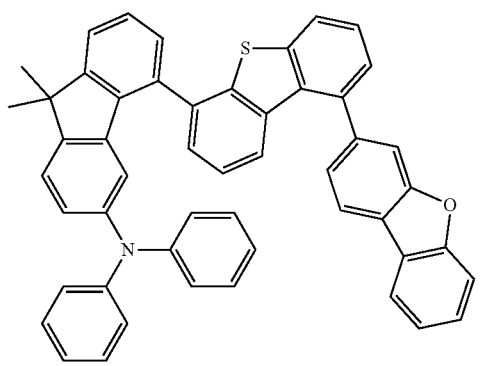
H-31
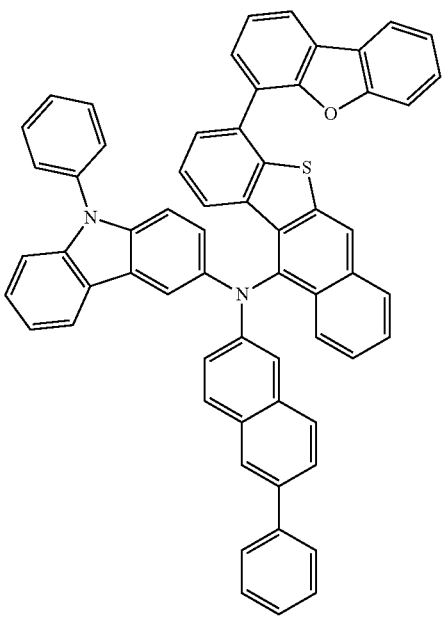
H-33
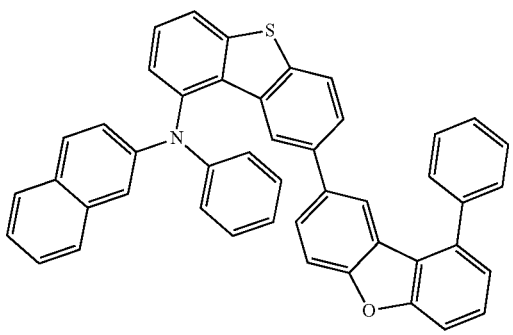
H-34
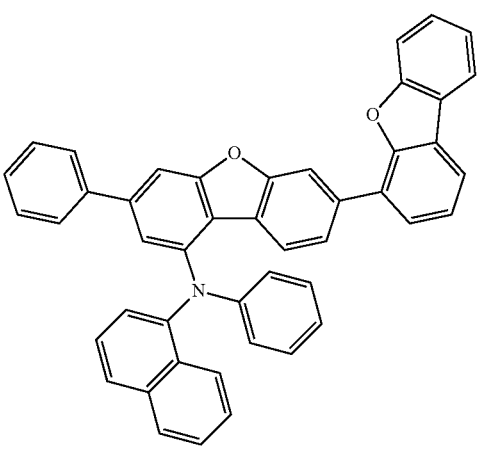
H-35
H-32

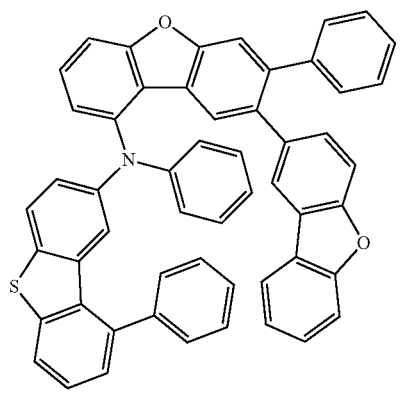
H-36
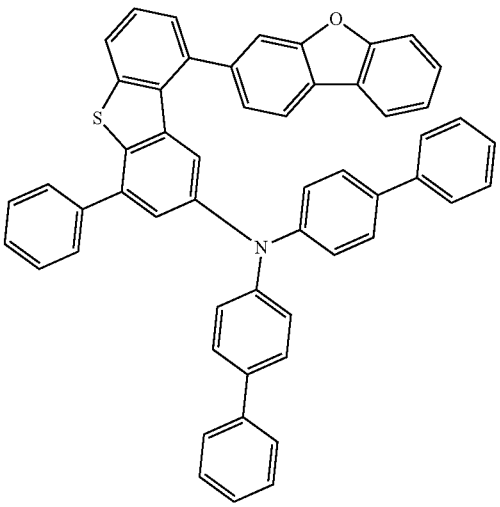
H-39
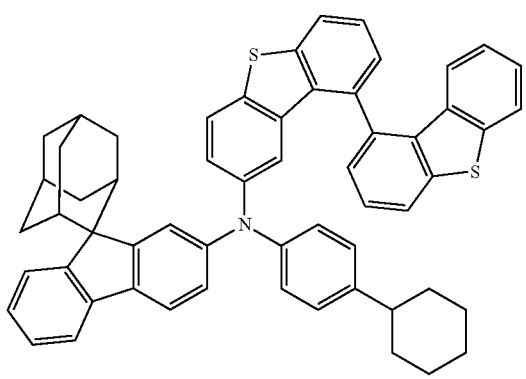
H-37
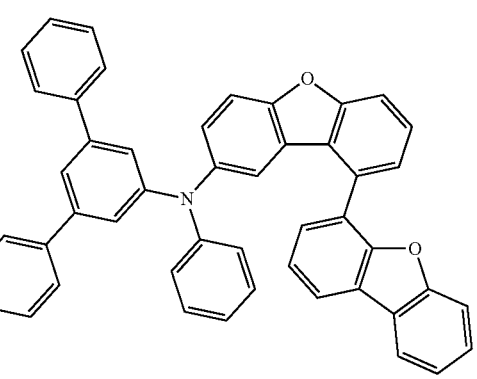
H-40
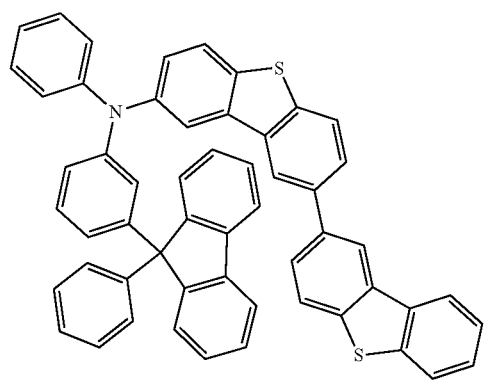
H-38
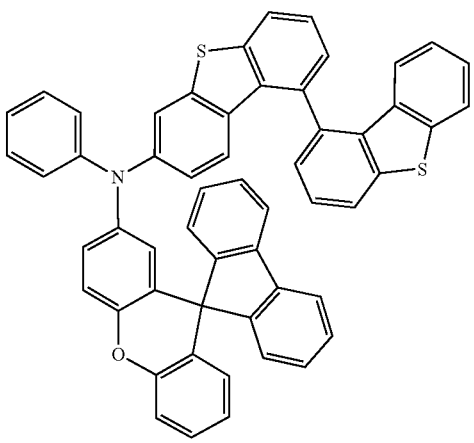
H-41

H-42
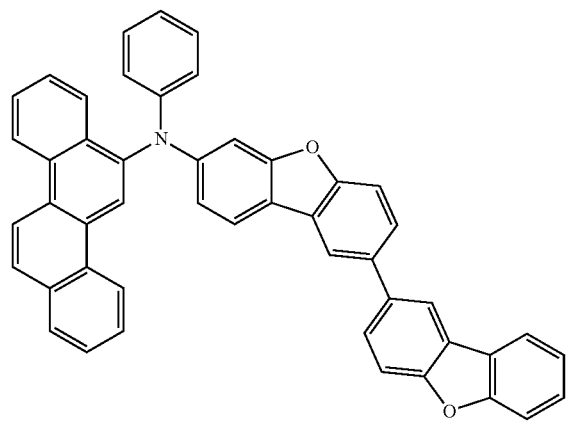
H-43
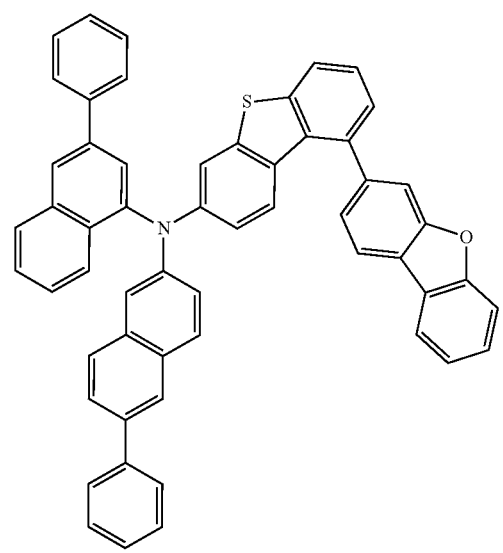
H-44
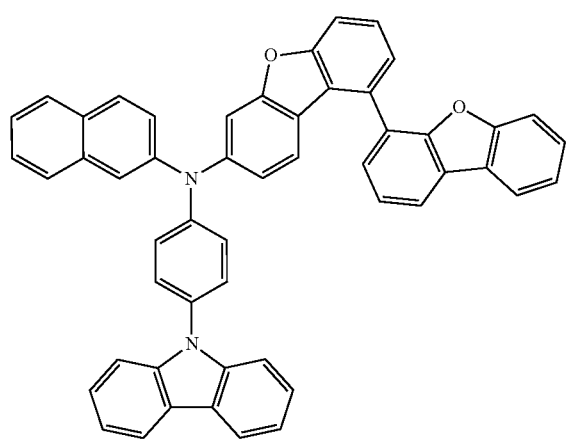
H-45
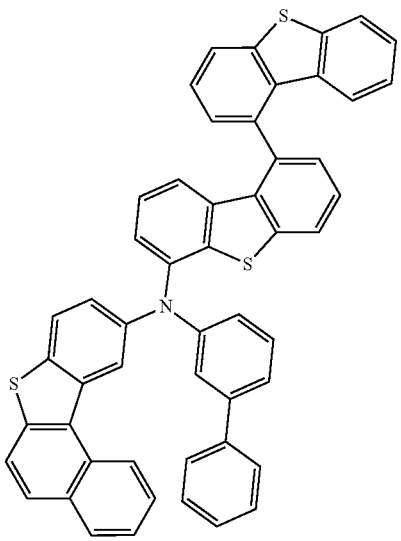
H-46
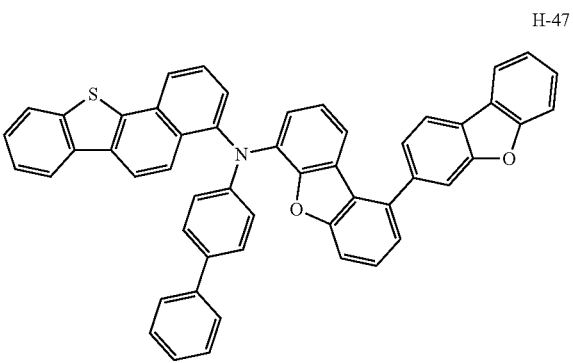
H-47

H-48
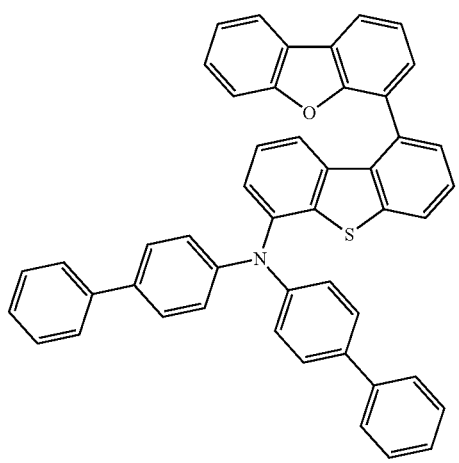
H-49
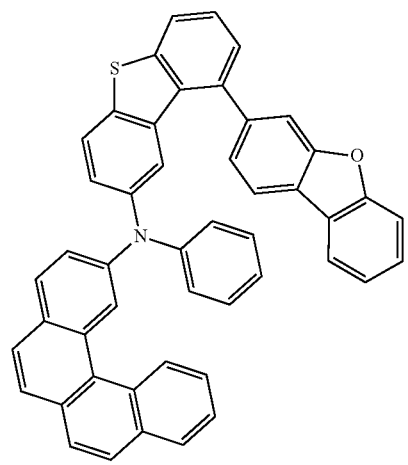
H-50
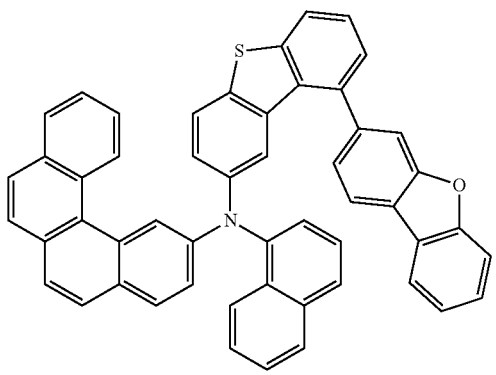
H-51
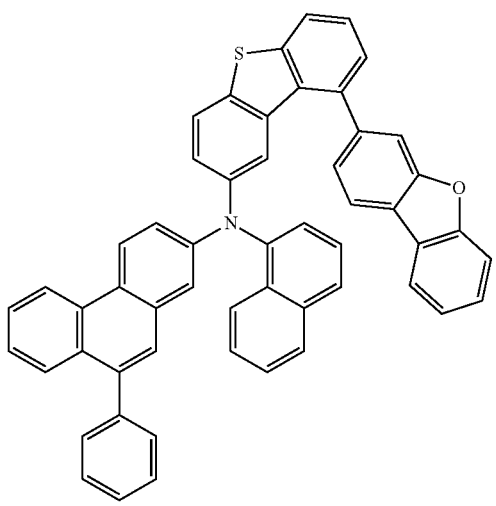
H-52
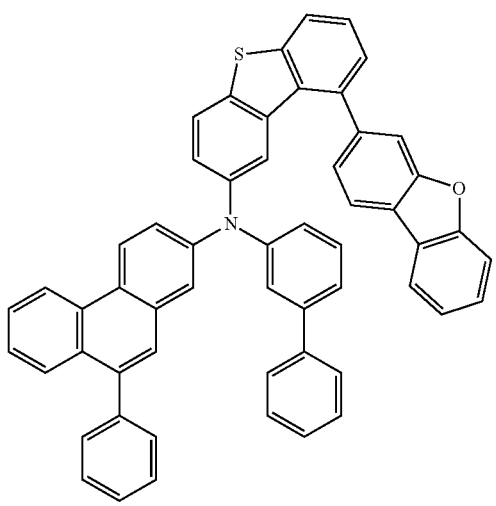
H-53
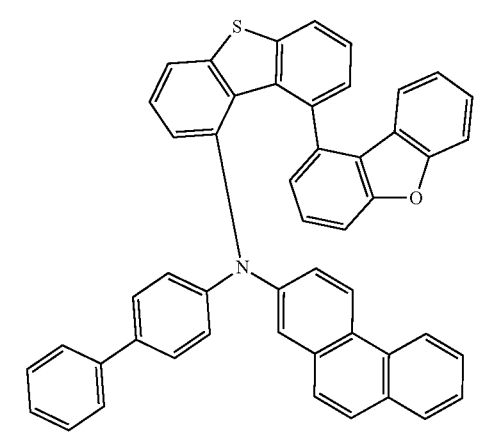

-continued
H-54
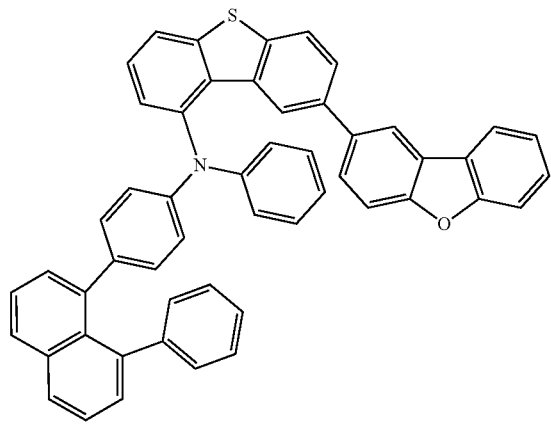
H-55
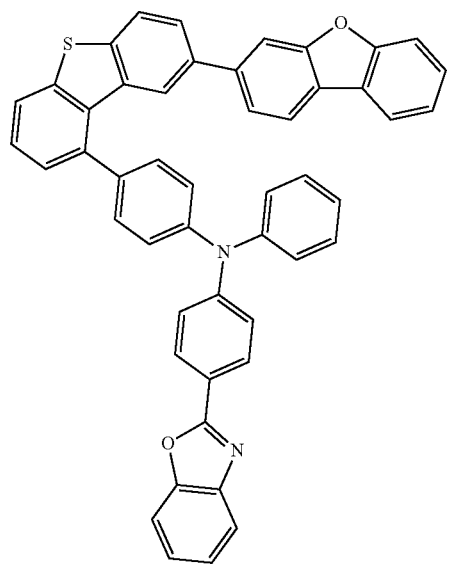
H-56
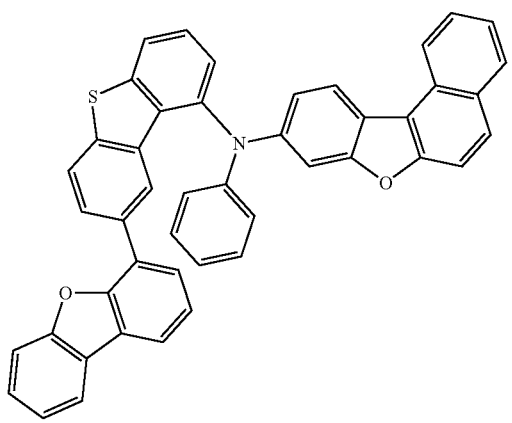
-continued
H-57
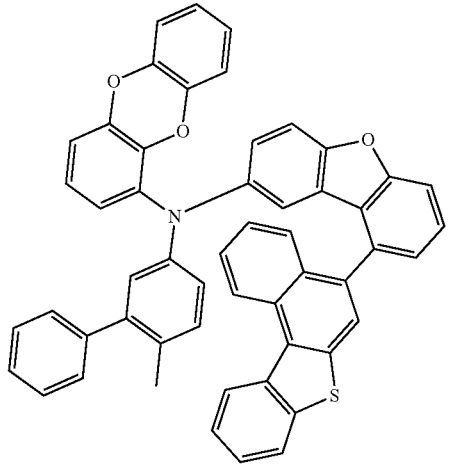
H-58
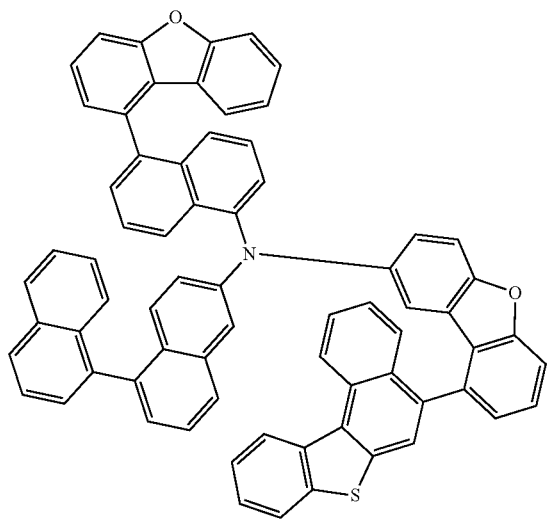
H-59
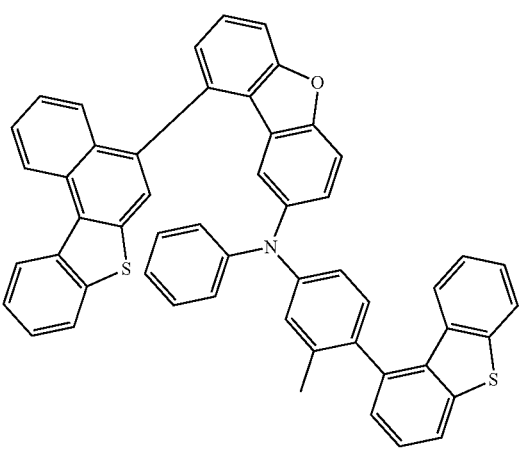

H-60
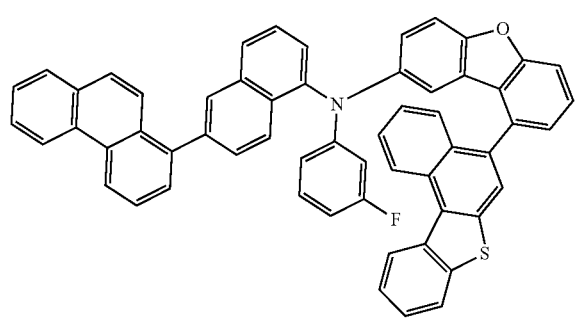
H-61
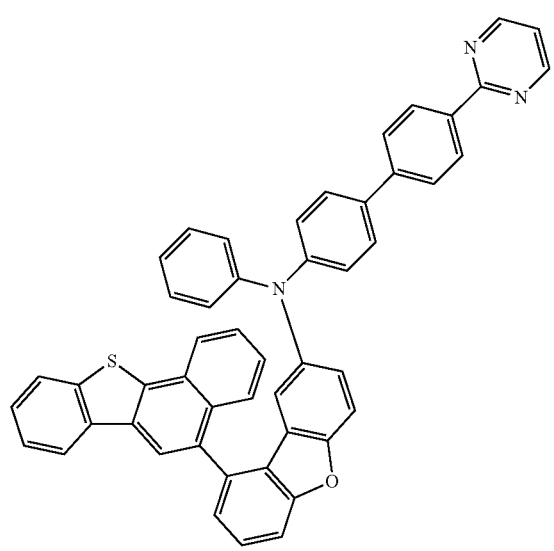
H-62
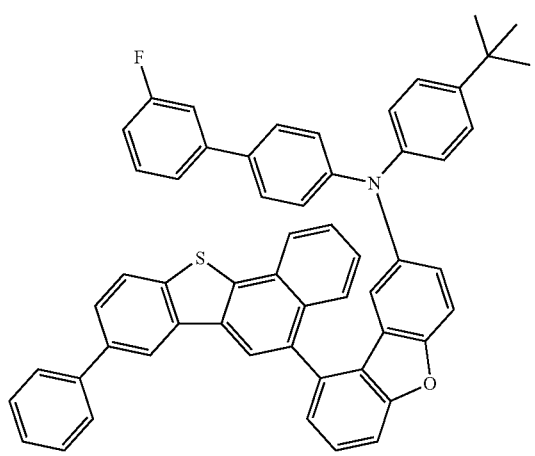
H-63
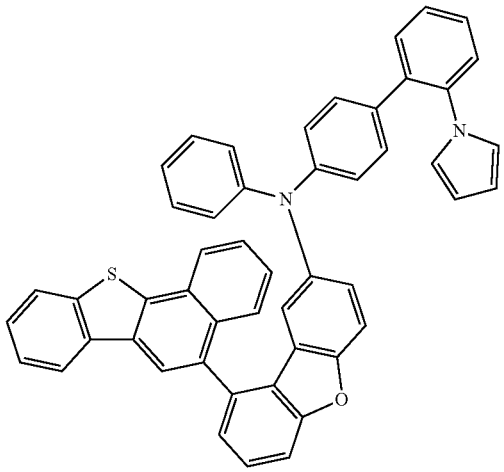
H-64
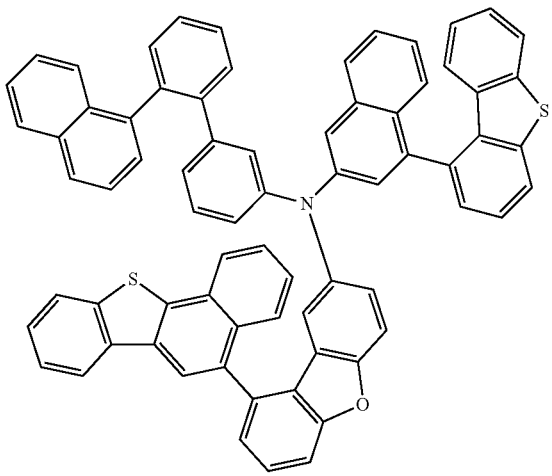
H-65
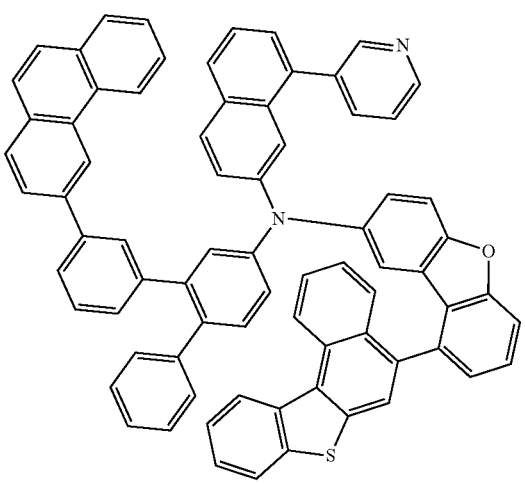

H-66
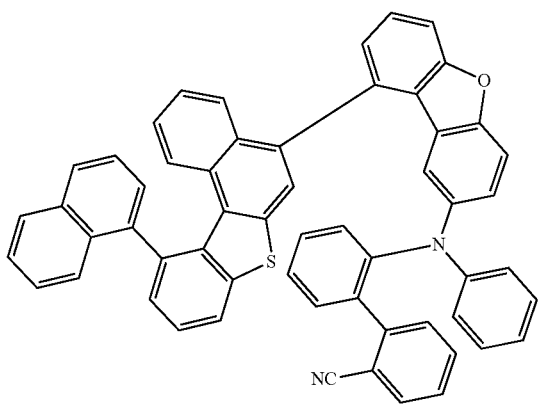
H-67
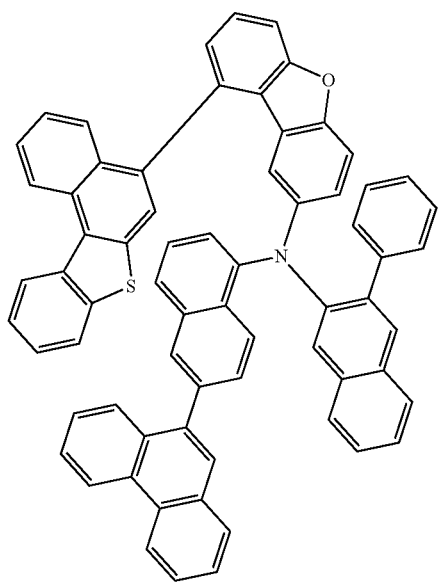
H-68
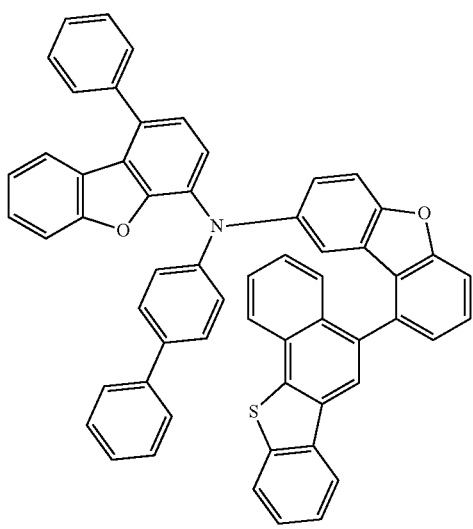
H-69
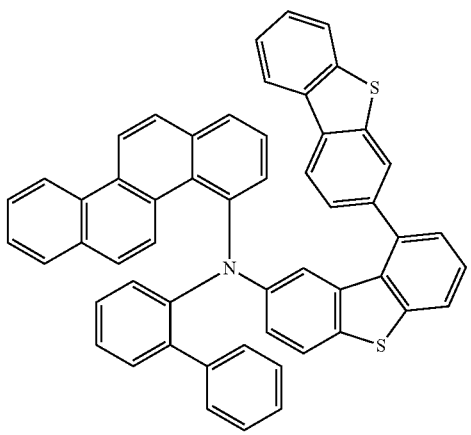
H-70
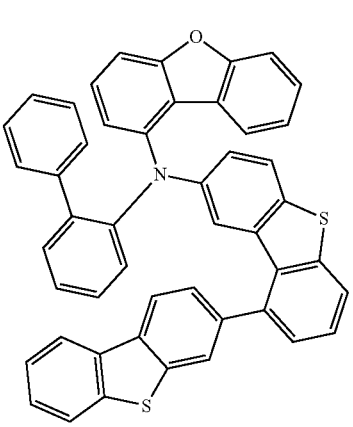
H-71

H-72
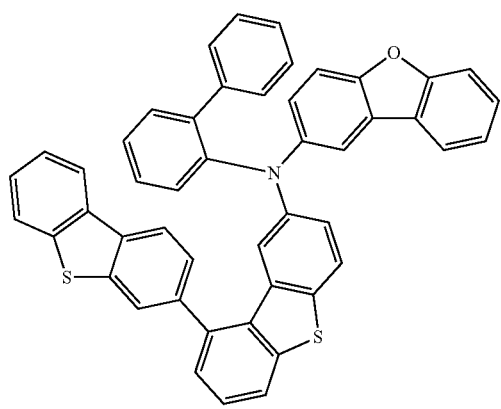
H-73
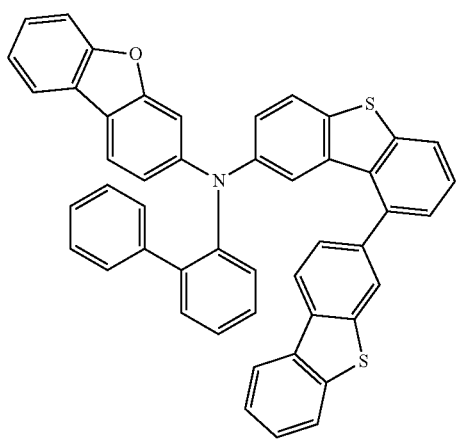
H-74
H-75
H-76
H-77
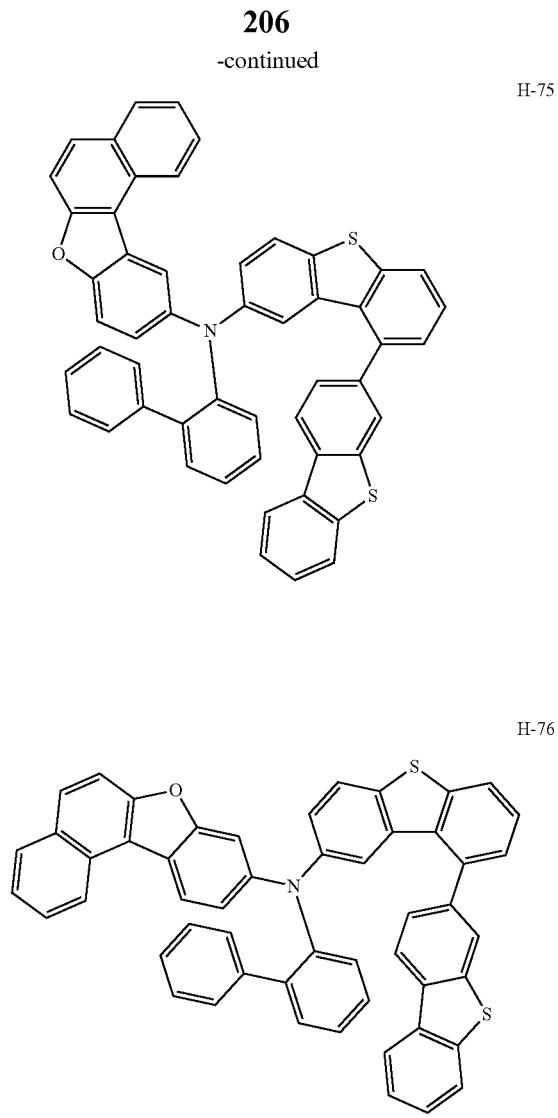

H-78
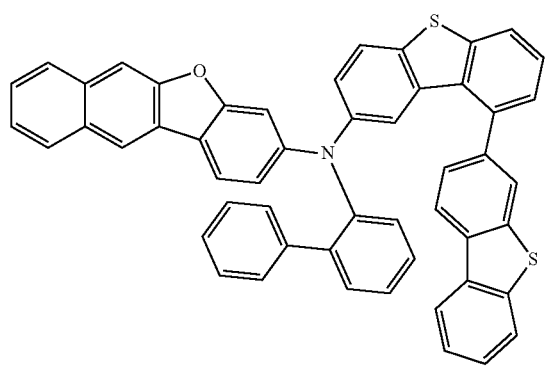
H-79
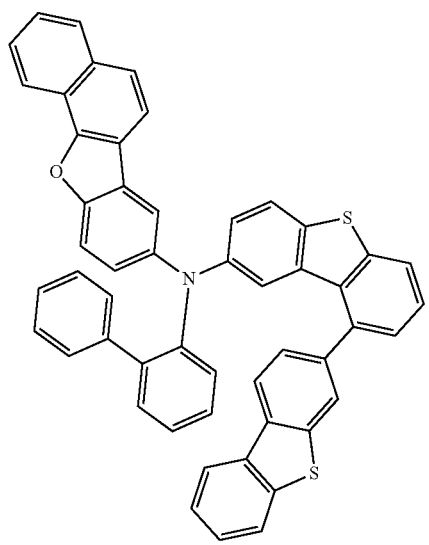
H-80
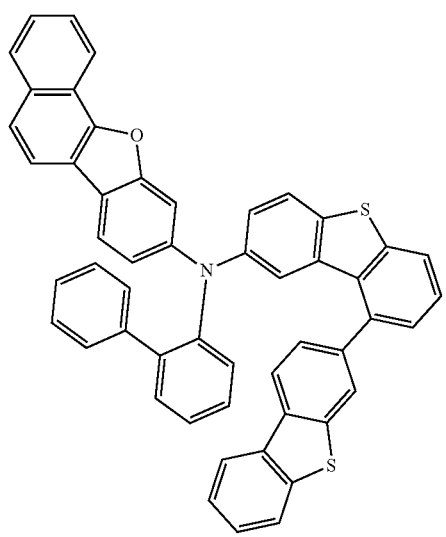
H-81
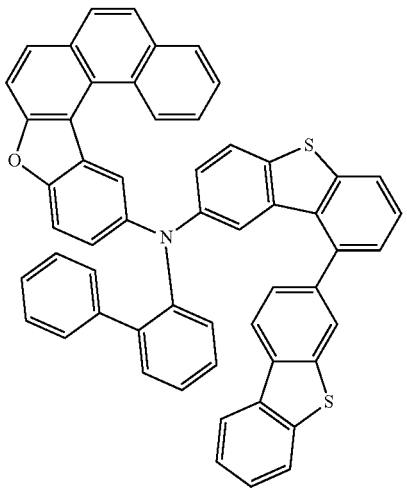
H-82
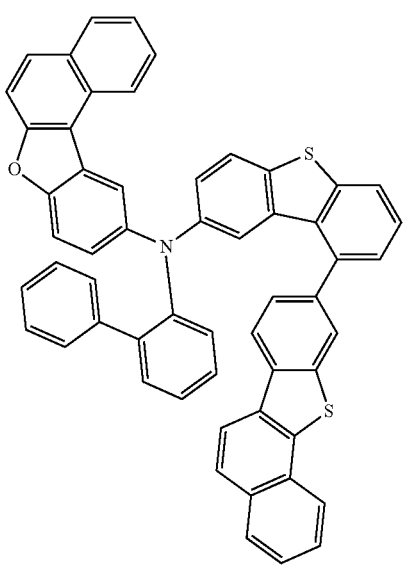
H-83
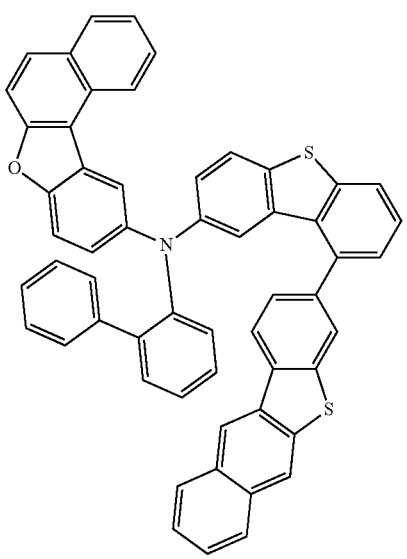

H-84
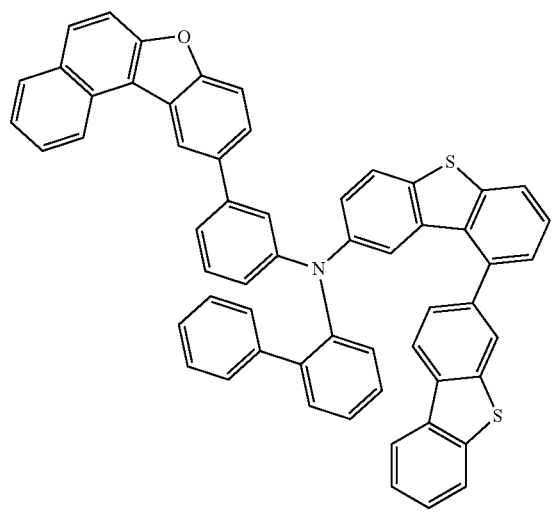
H-87
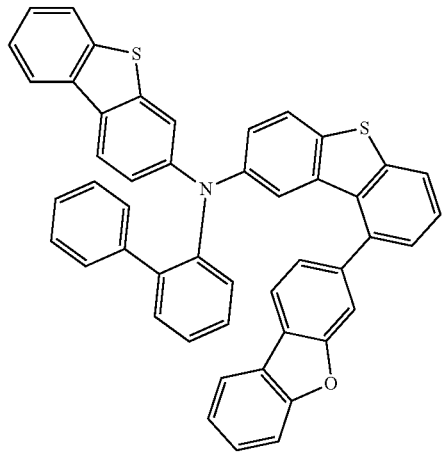
H-85
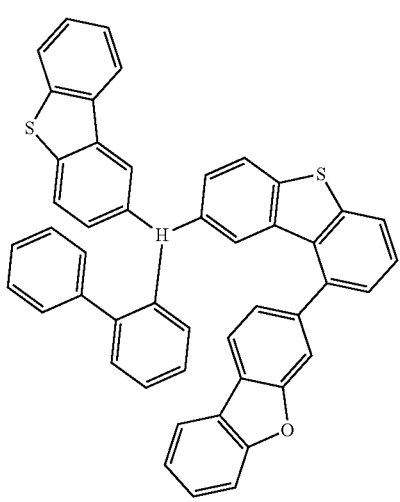
H-88
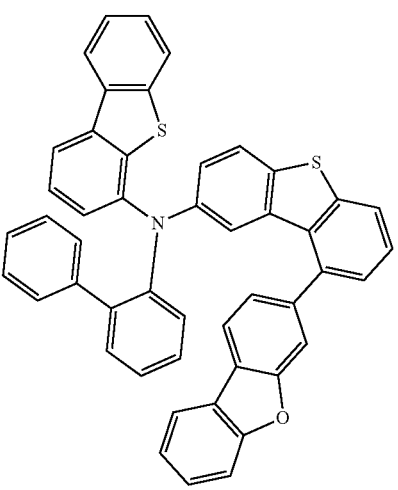
H-86
H-89
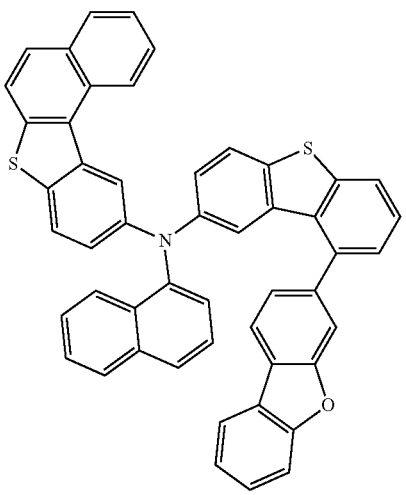

-continued
H-90
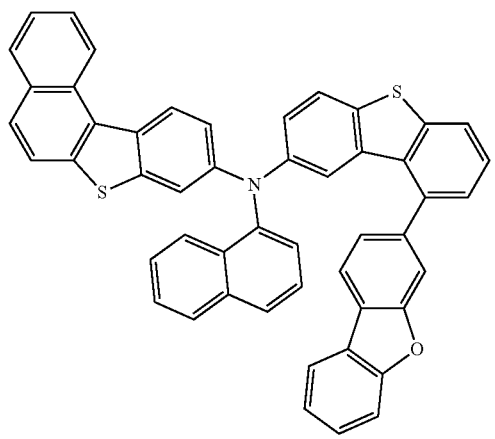
H-91
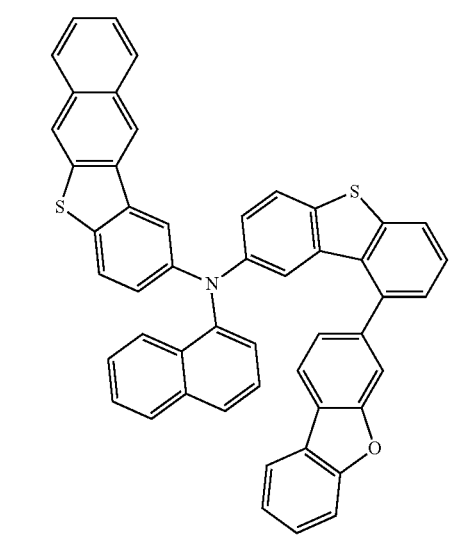
H-92
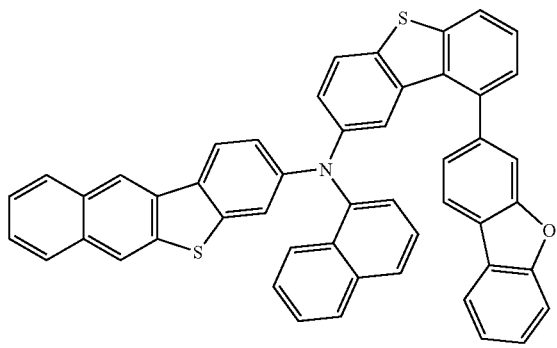
-continued
H-93
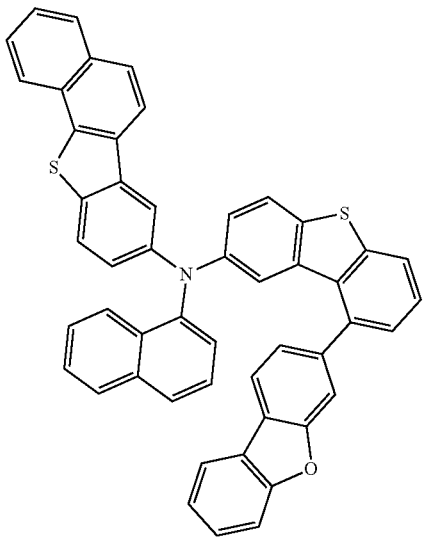
H-94
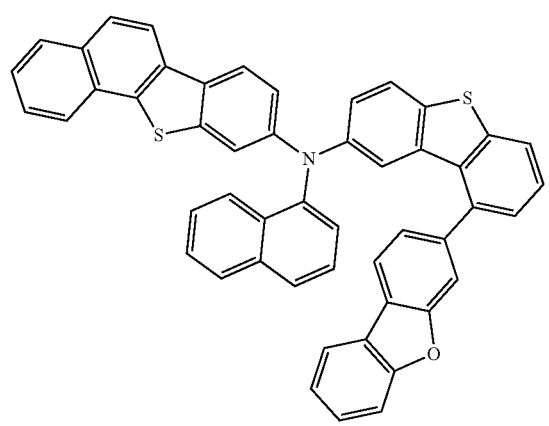
H-95
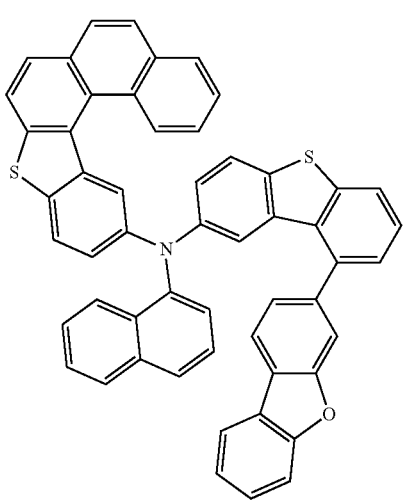

H-96
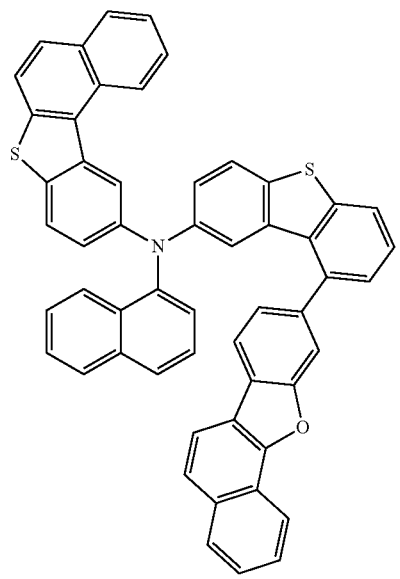
H-97
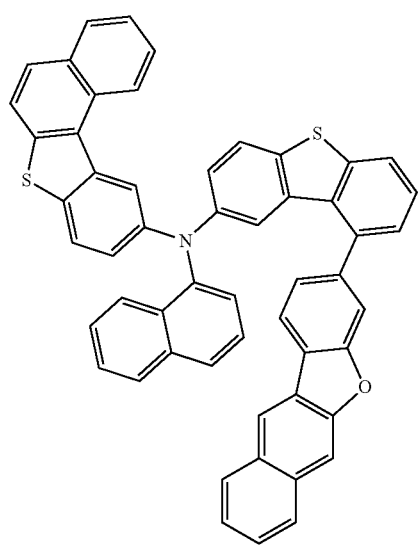
H-98
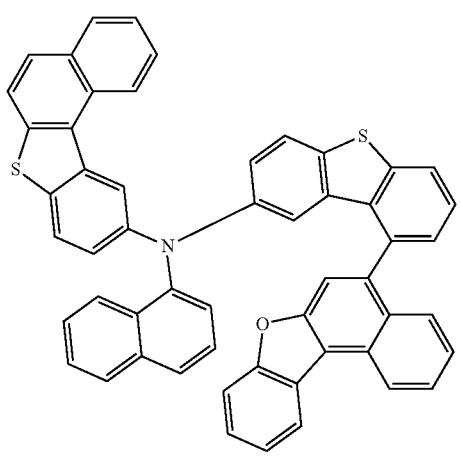
H-99
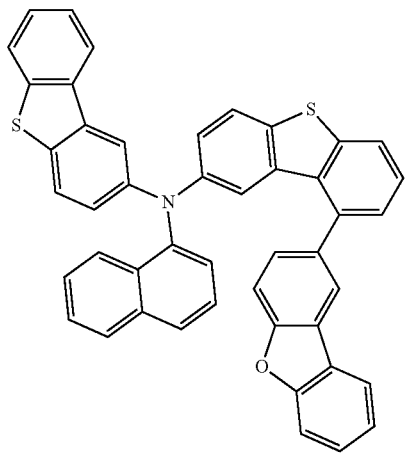
H-100
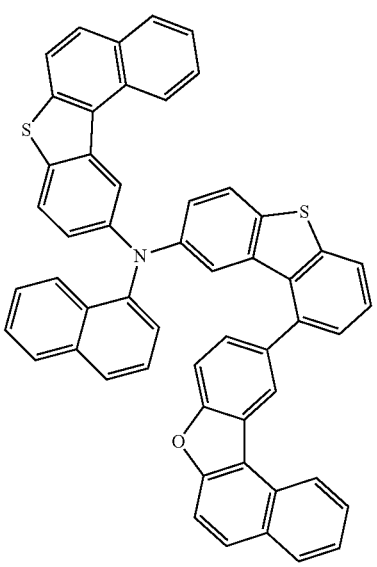
H-101
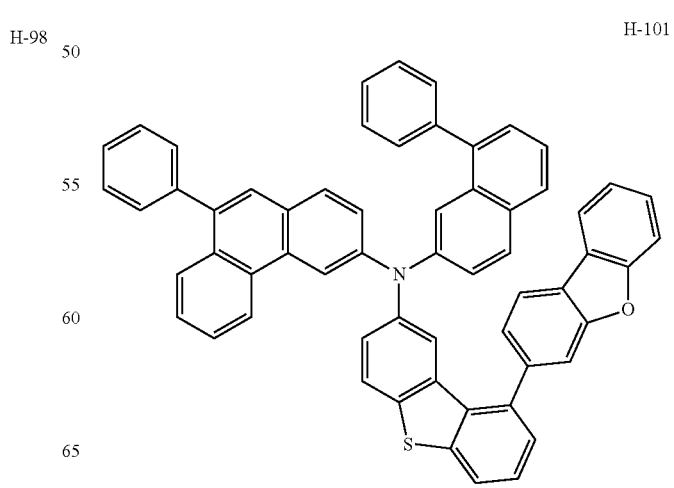

H-102
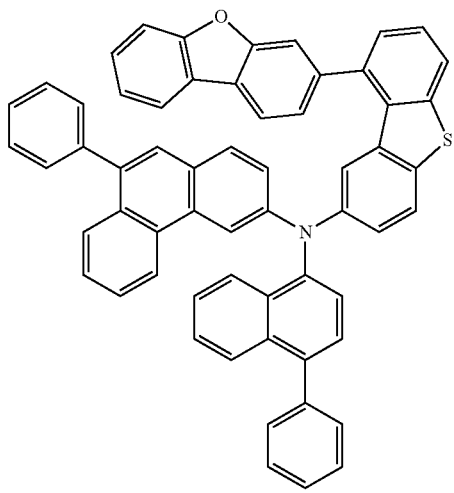
H-103
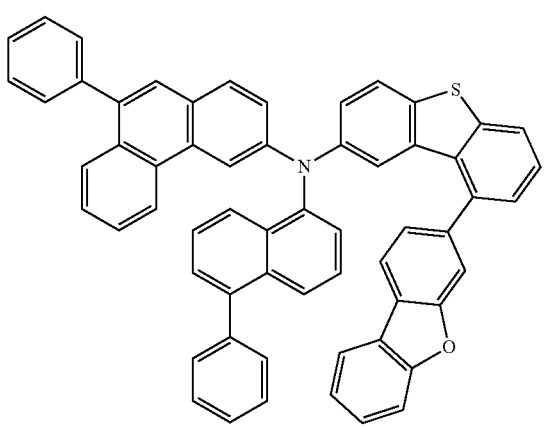
H-104
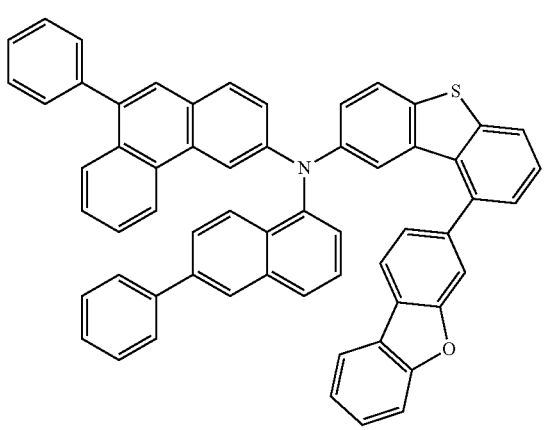
H-105
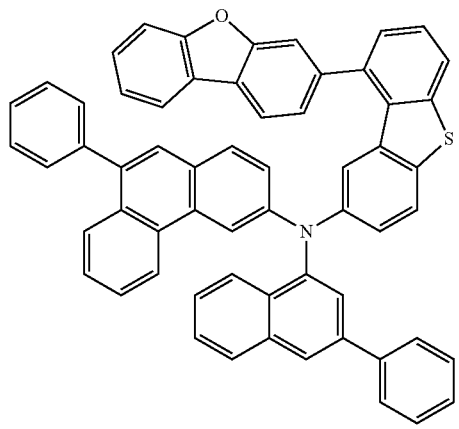
H-106
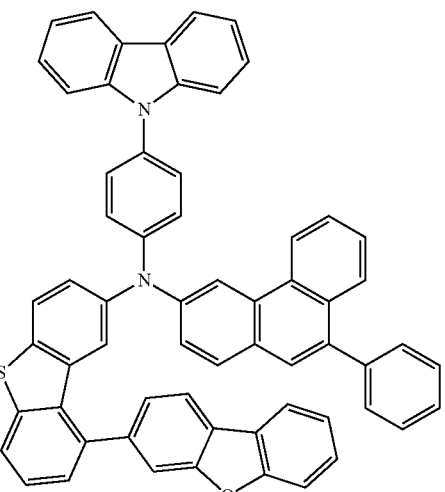
H-107
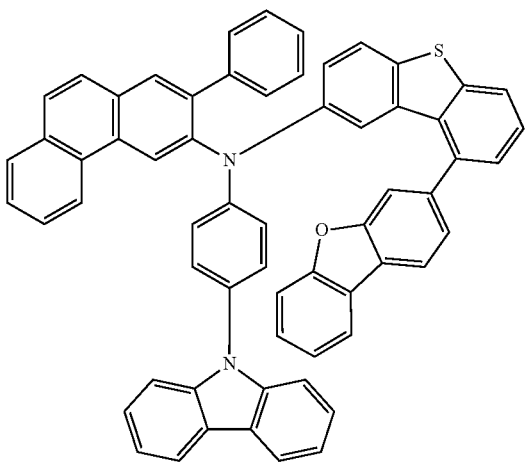

H-108
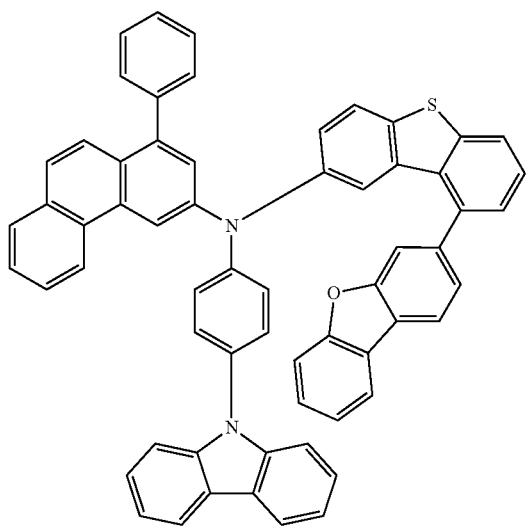
H-109
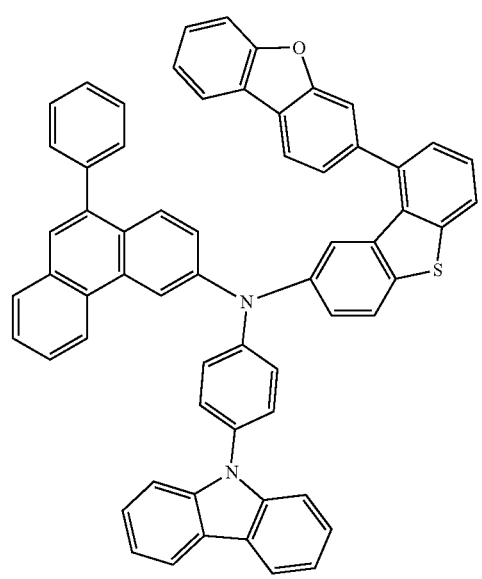
H-110
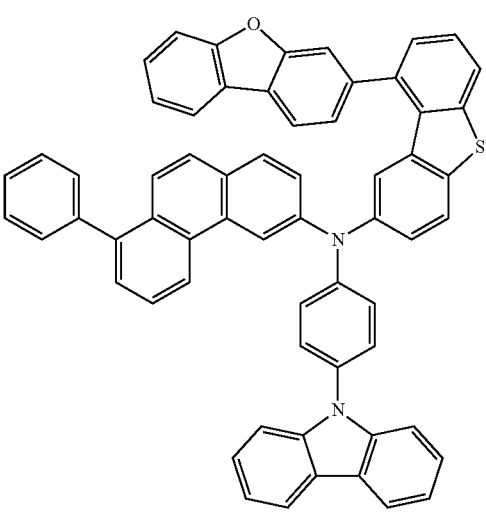
H-111
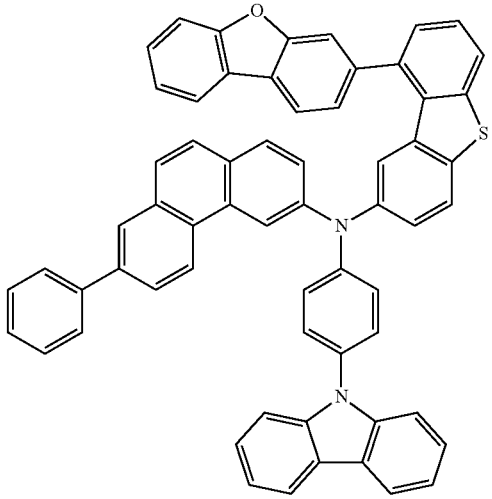
H-112
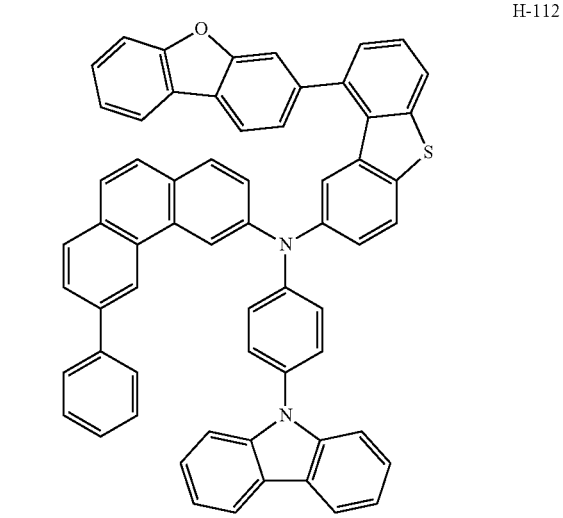
H-113
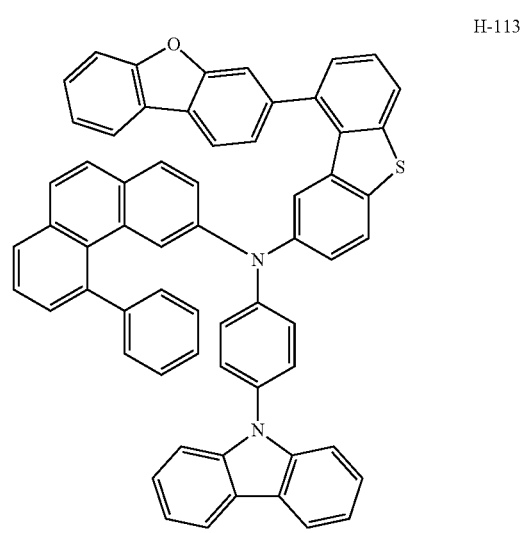

H-114
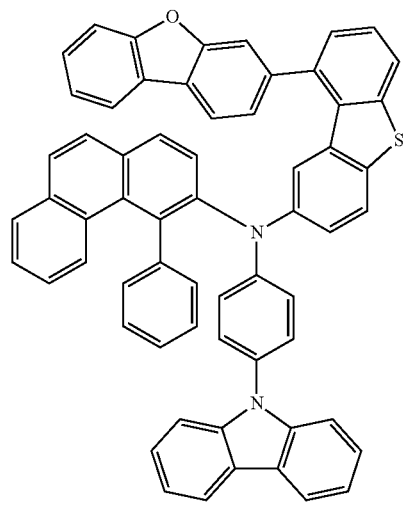
H-115
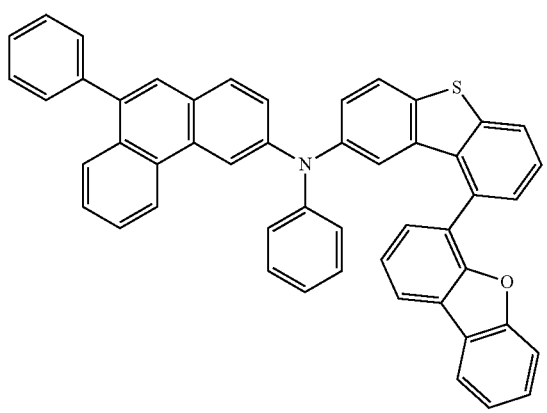
H-116
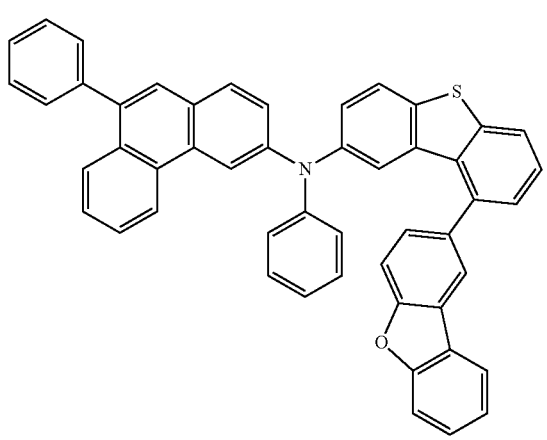
H-117
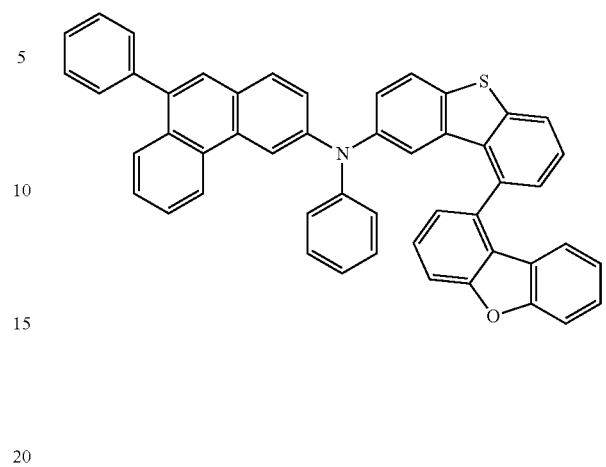
H-118
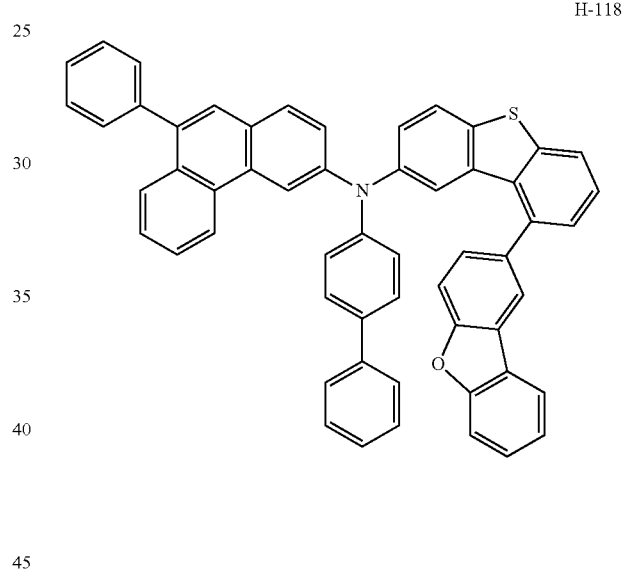
H-119
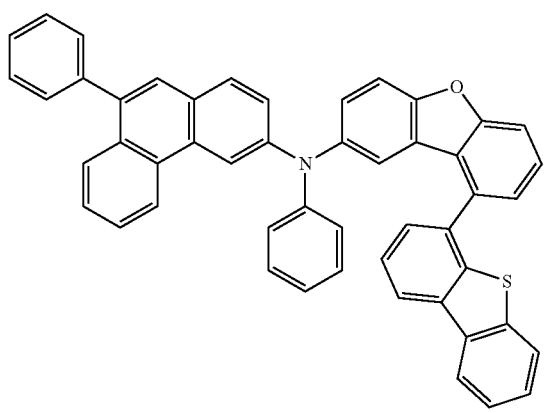

H-120
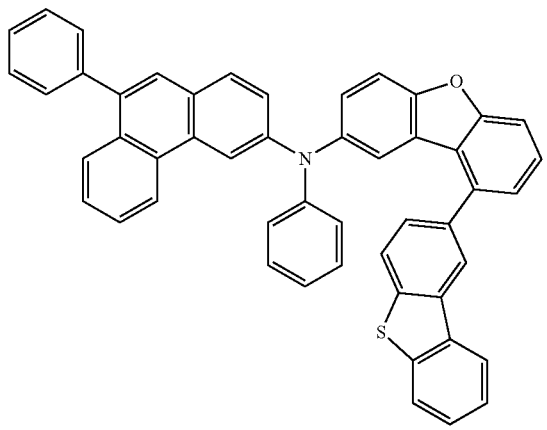
H-121
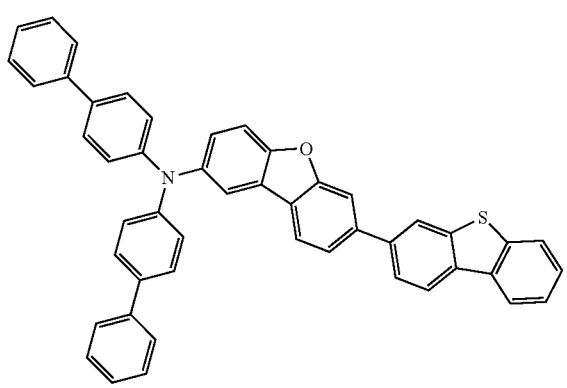
H-122
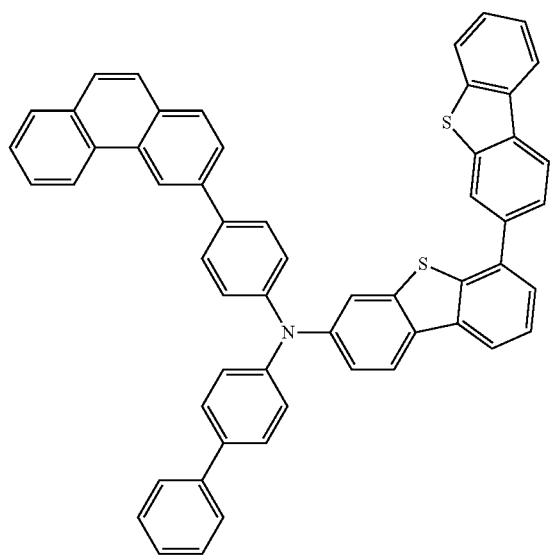
H-123
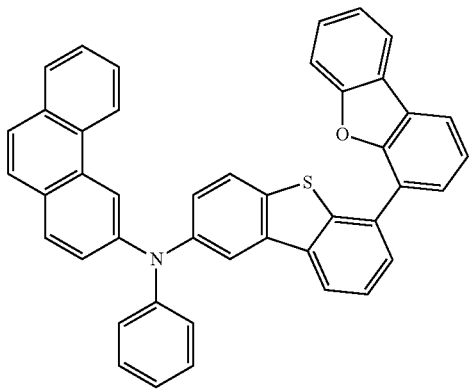
H-124
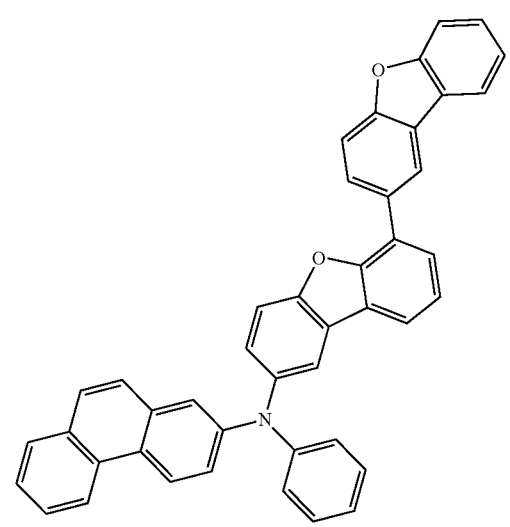
H-125
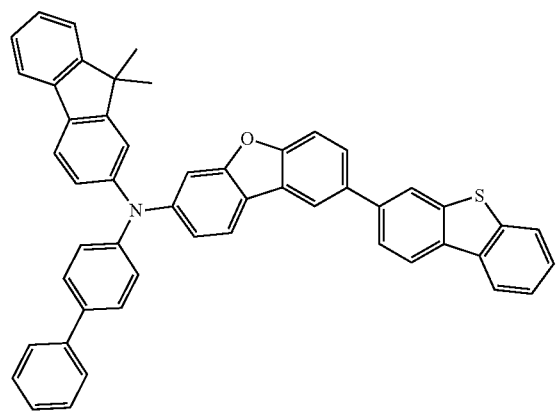

H-126
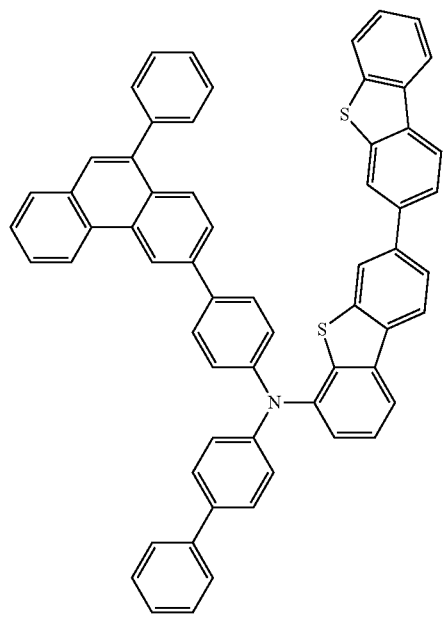
H-127
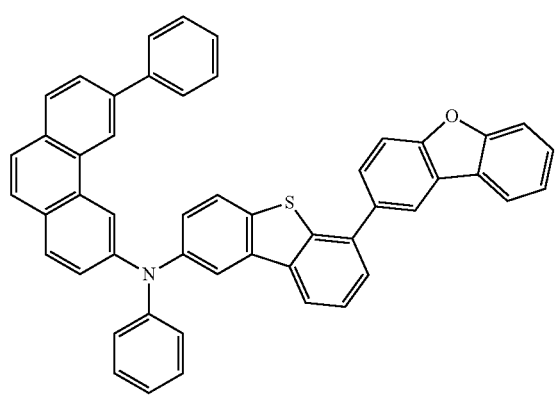
H-128
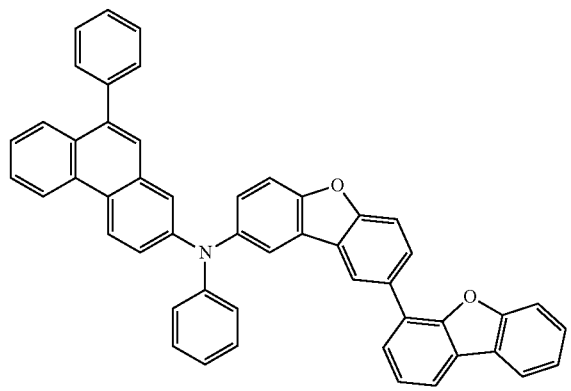
H-129
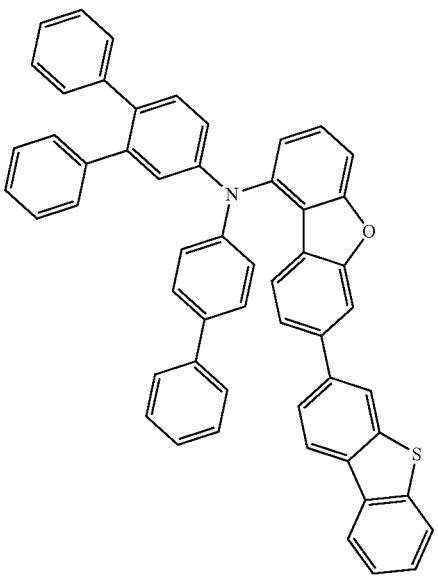
H-130
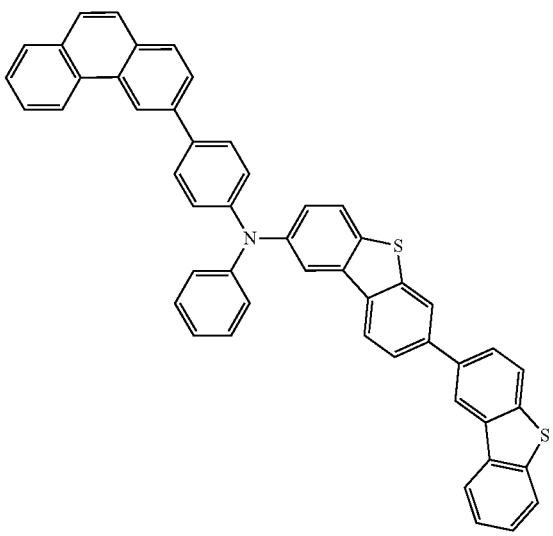
H-131
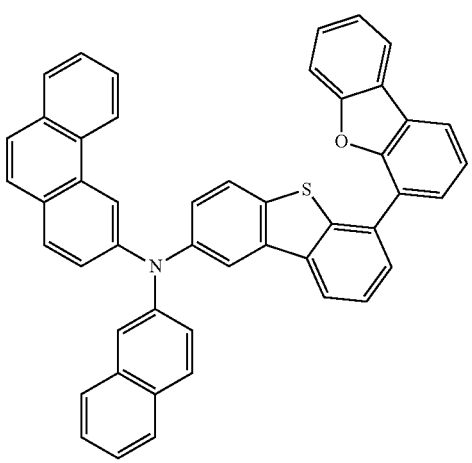

H-132
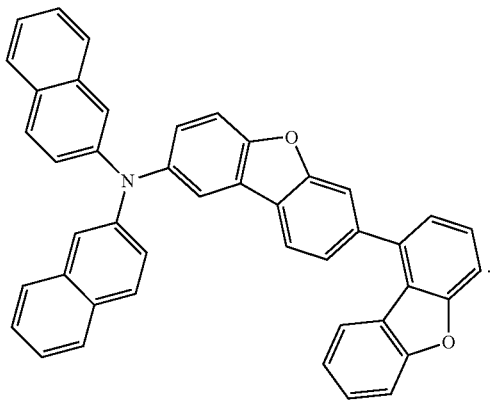
S-4
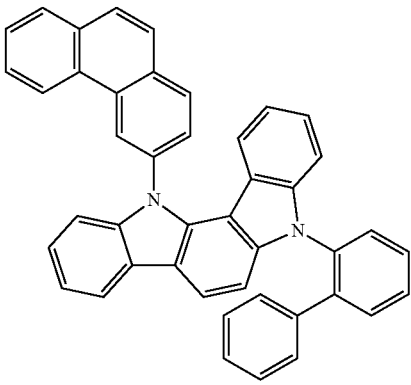
6. The composition for an organic electronic element of claim 1, wherein Formula 5 is selected from the group consisting of Compounds S-1 to S-116:
S-1
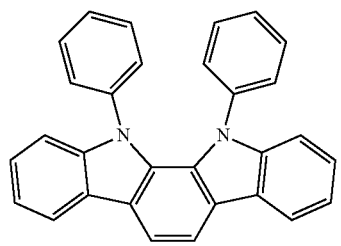
S-5
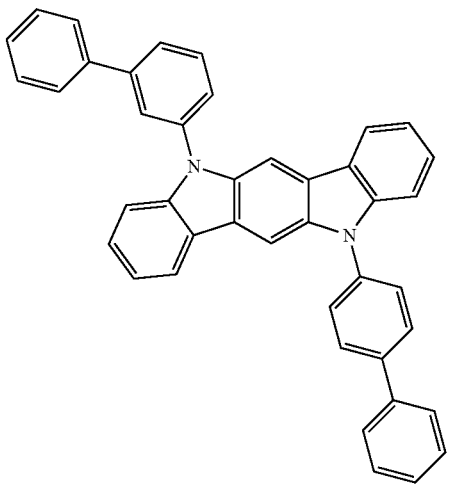
S-2
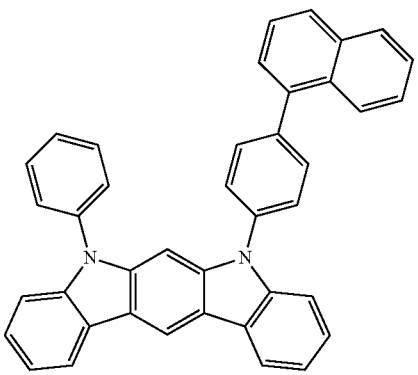
S-3
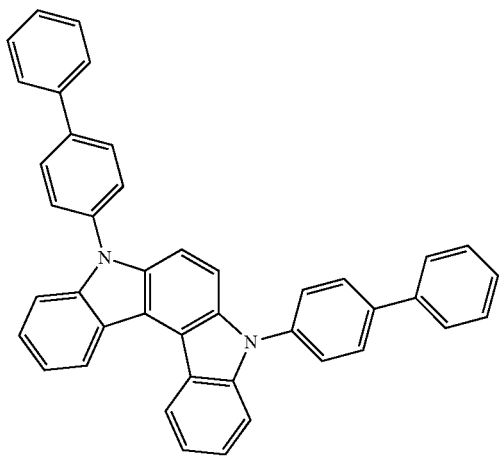
S-6
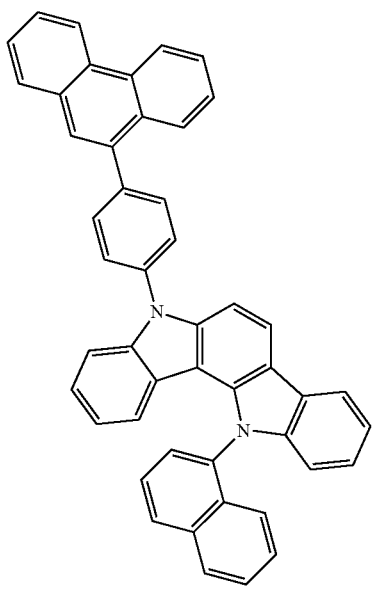

-continued
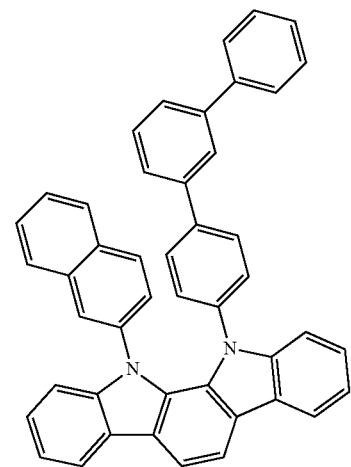
S-7
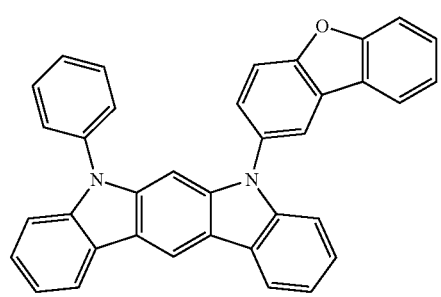
S-8
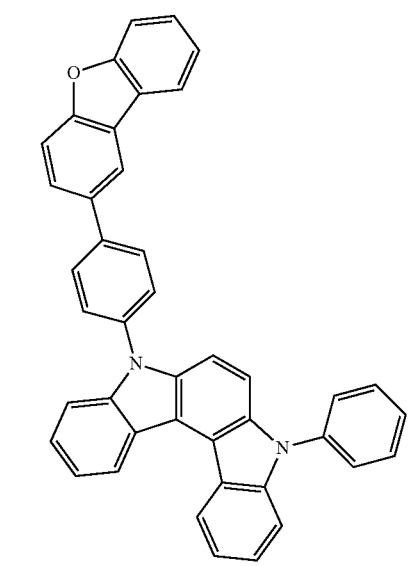
S-9
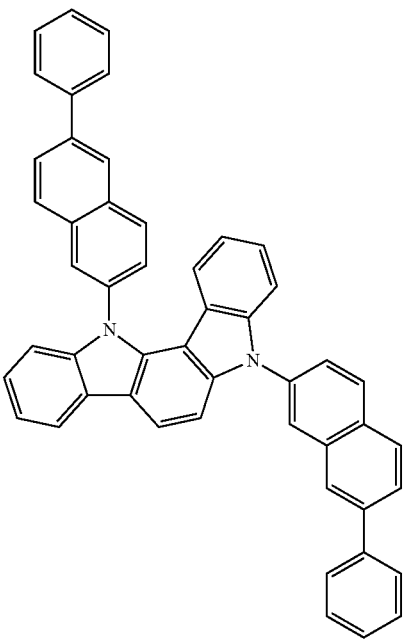
S-10
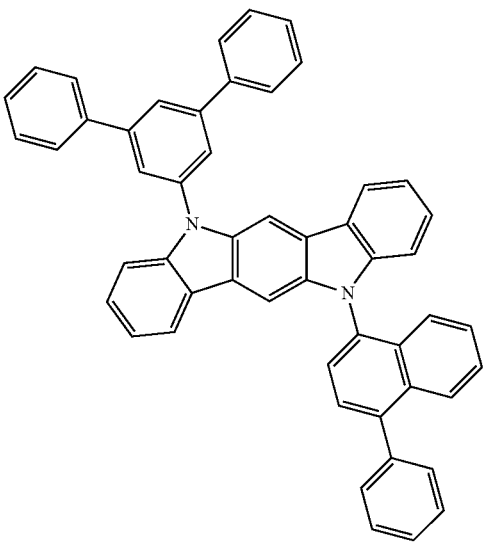
S-11

S-12
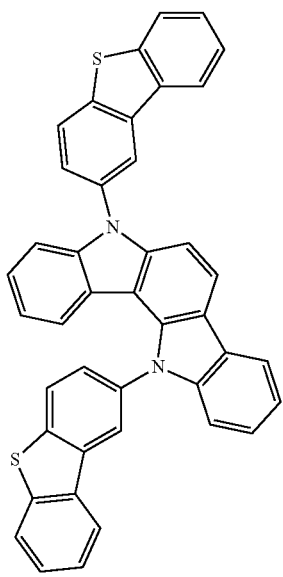
S-13
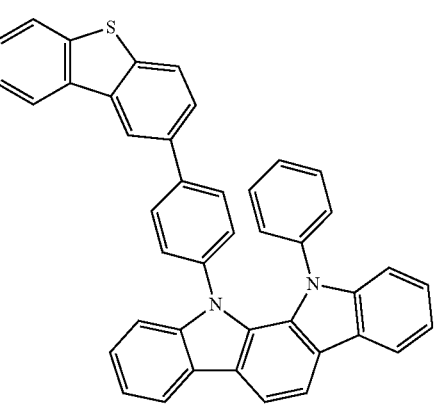
S-14
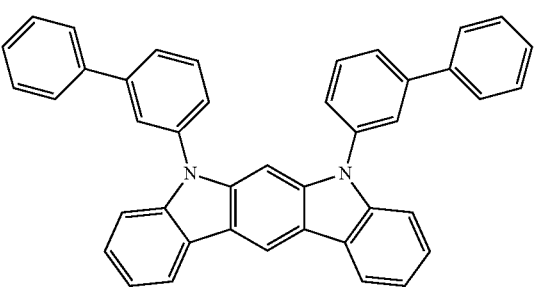
S-15
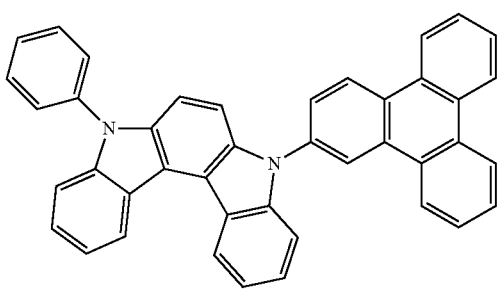
S-16
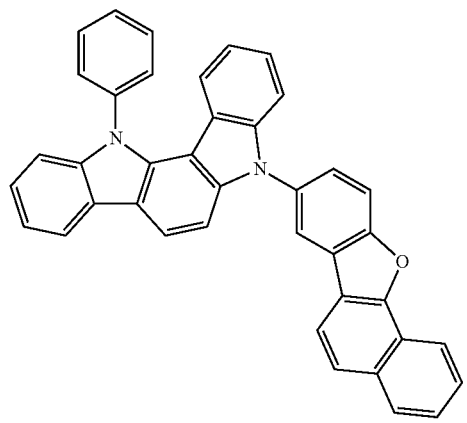
S-17
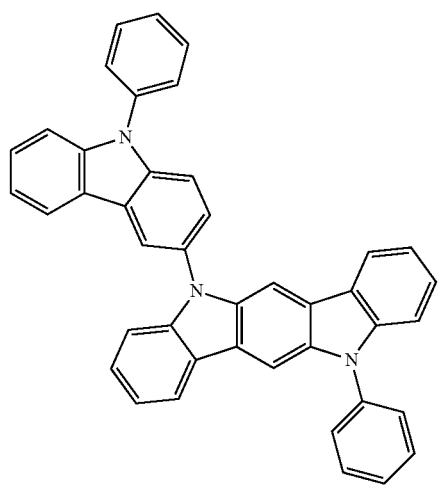
S-18
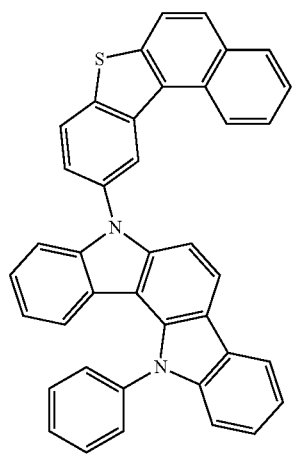

S-19
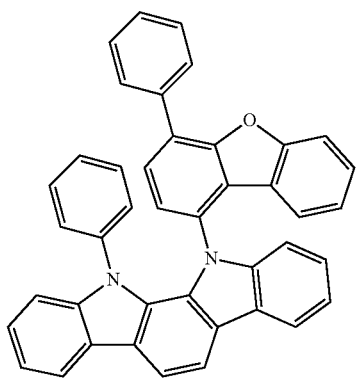
S-20
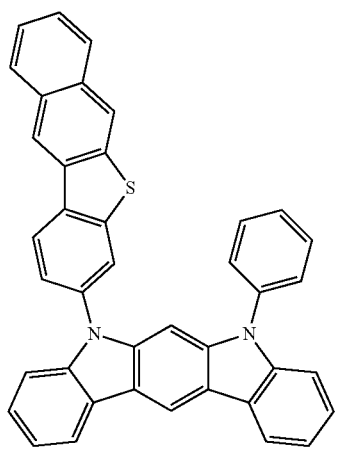
S-21
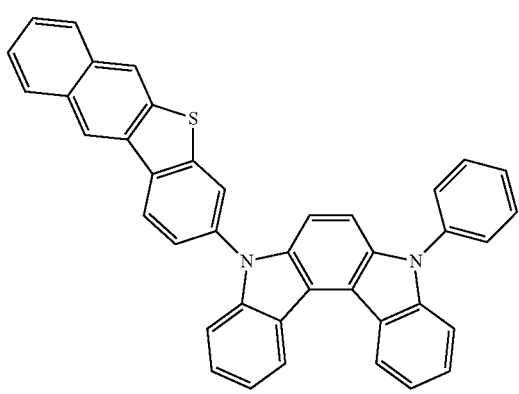
S-22
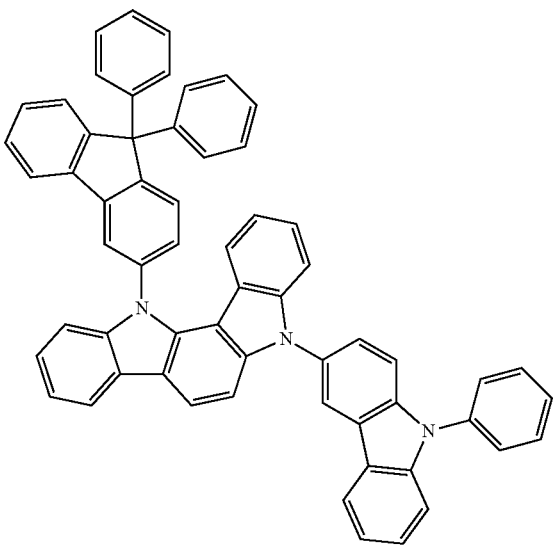
S-23
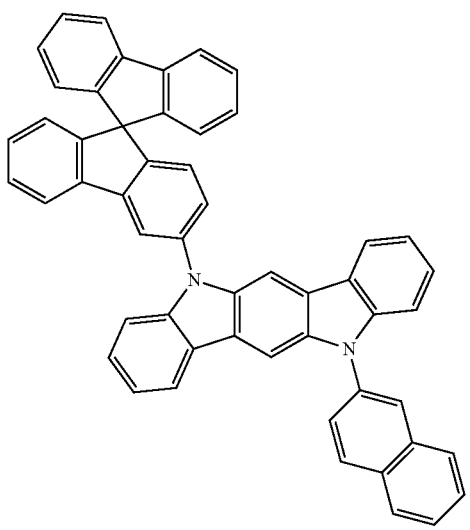

S-24
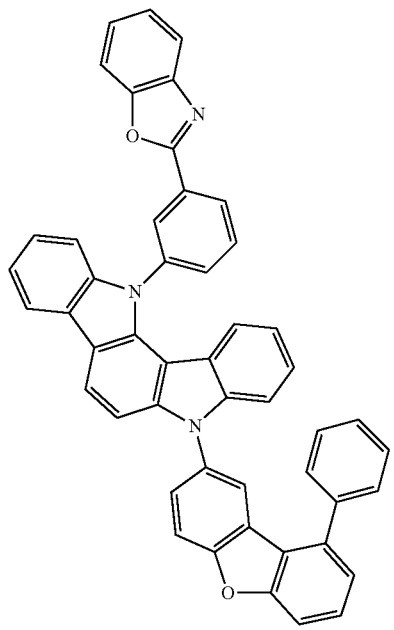
S-25
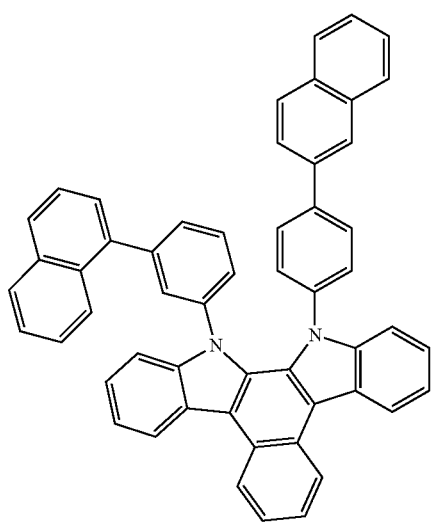
S-26
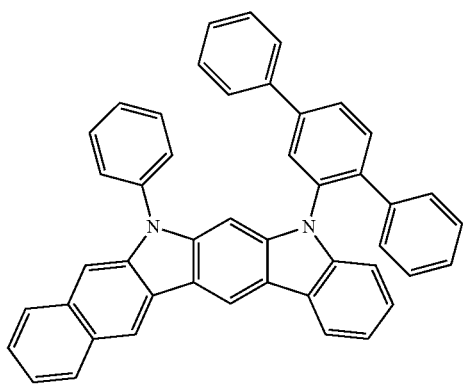
S-27
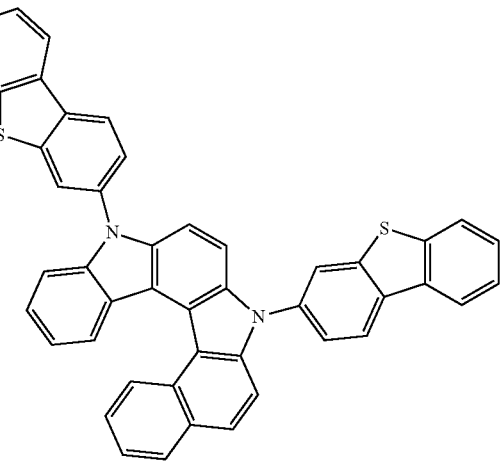
S-28
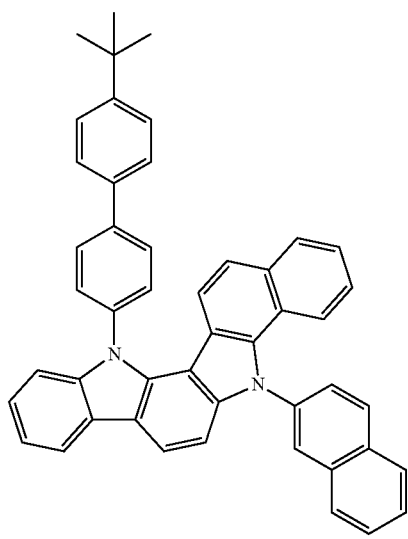
S-29
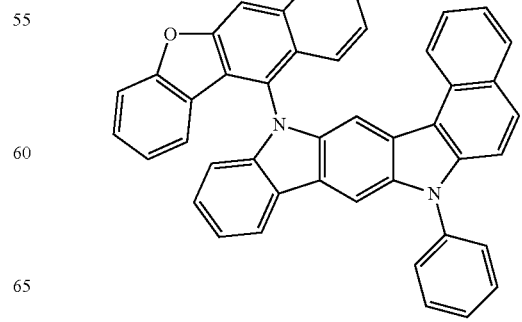

-continued
S-30
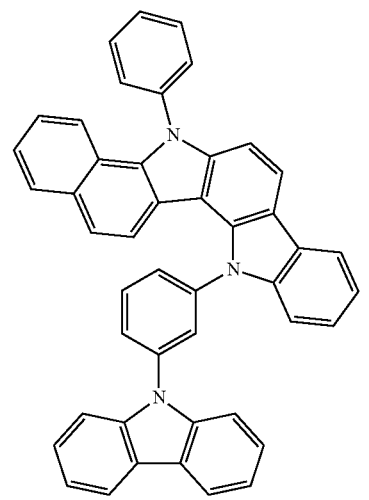
S-31
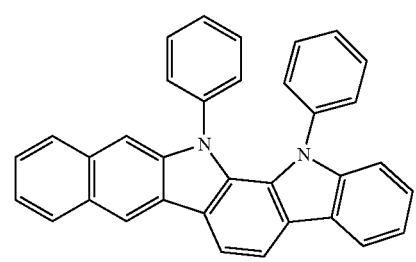
S-32
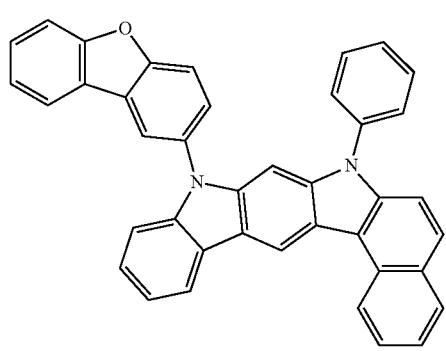
S-33
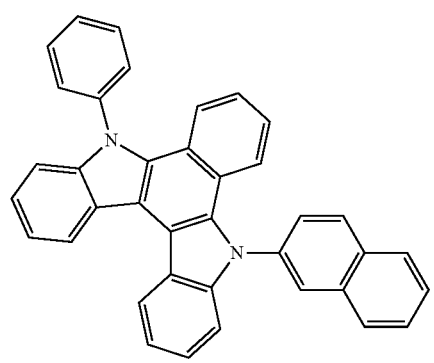
S-34
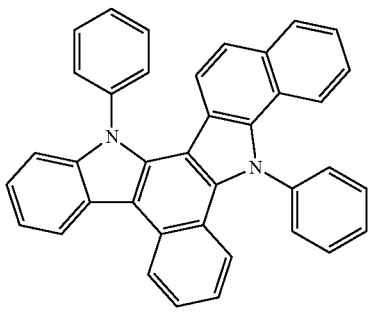
S-35
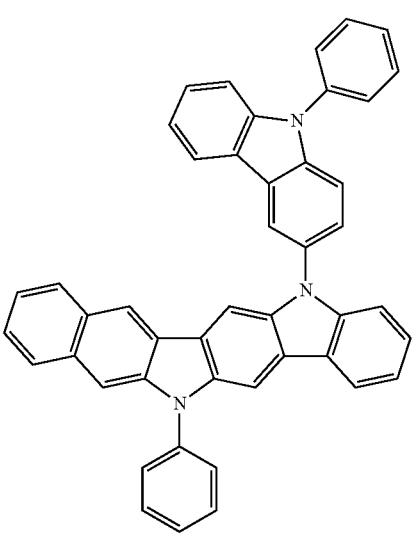
S-36
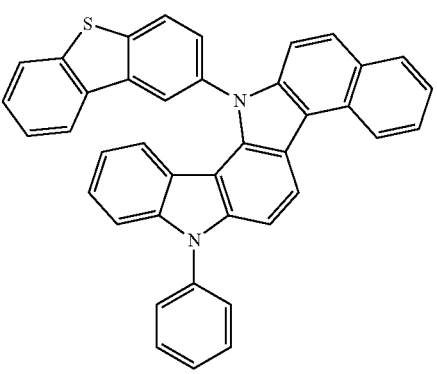
S-37
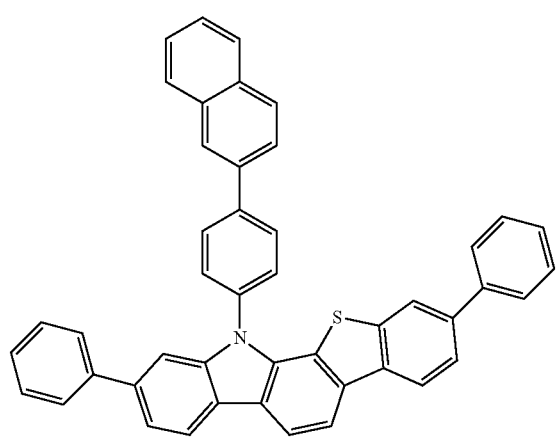

-continued
S-38
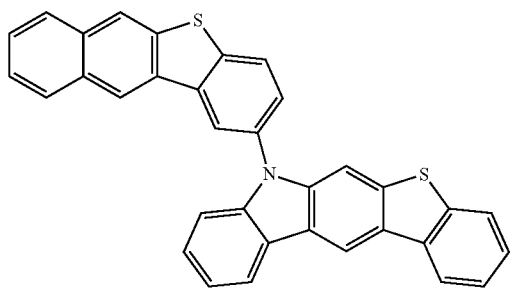
S-39
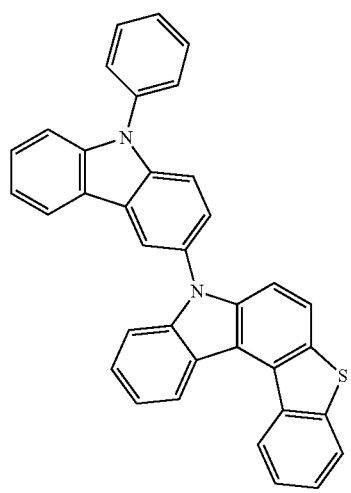
S-40
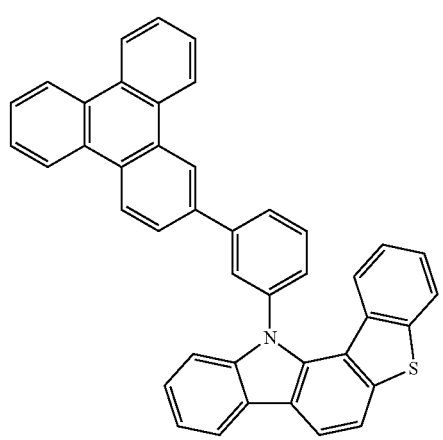
-continued
S-41
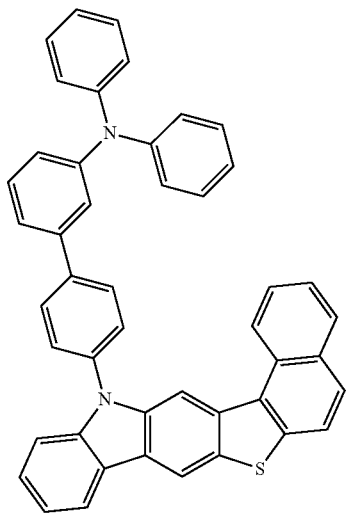
S-42
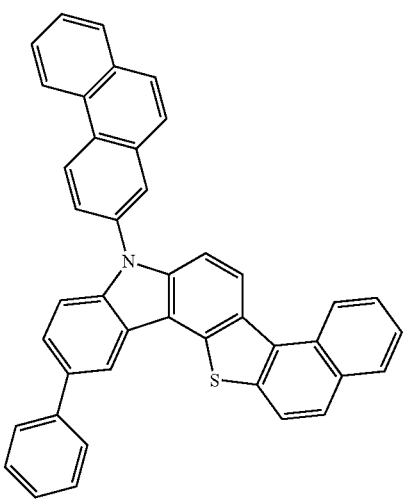
S-43
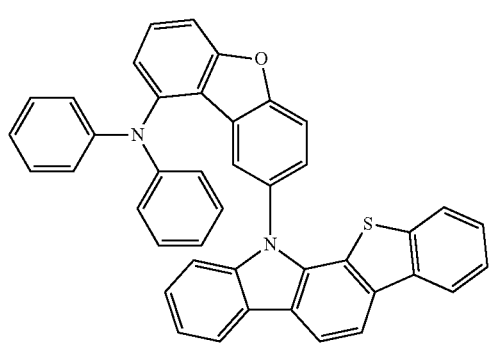

-continued
S-44
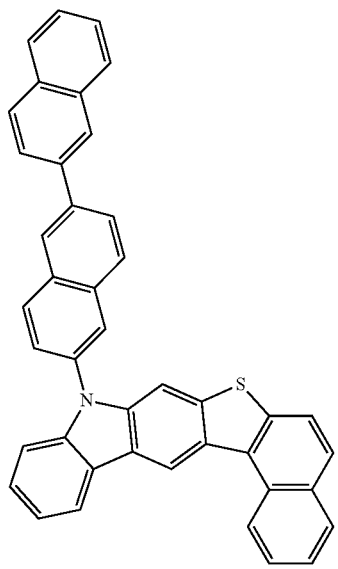
S-45
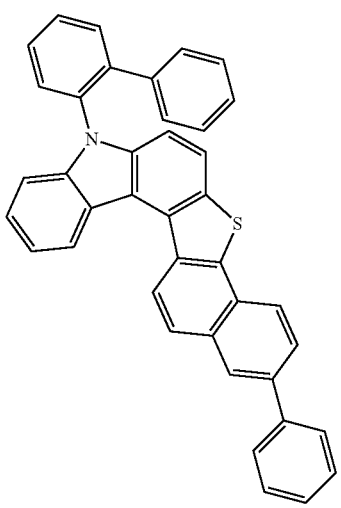
S-46
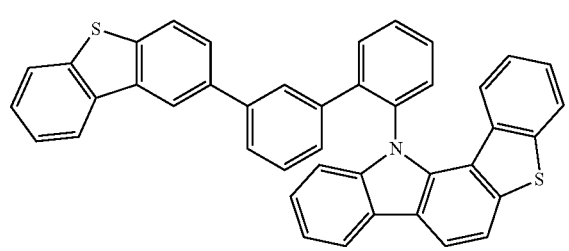
-continued
S-47
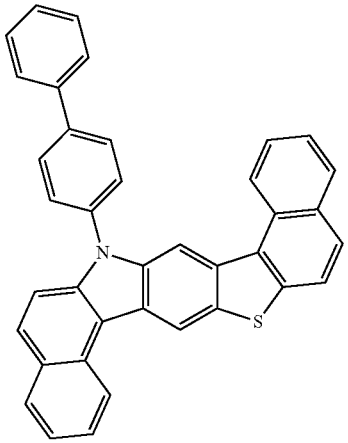
S-48
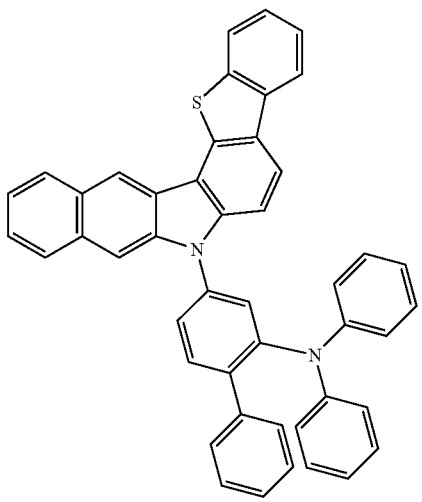
S-49
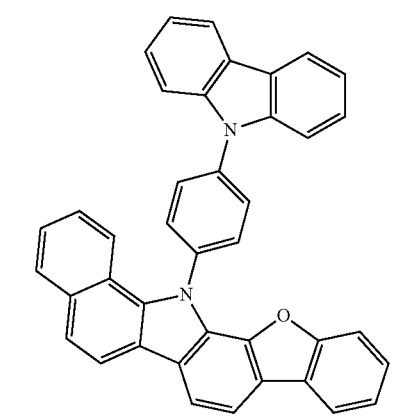

-continued
S-50
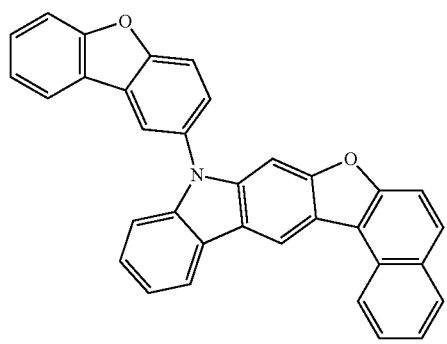
S-51
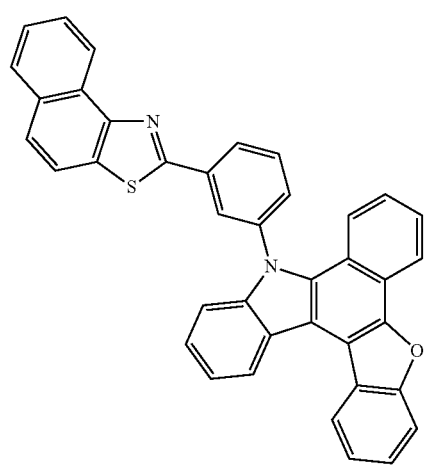
S-52
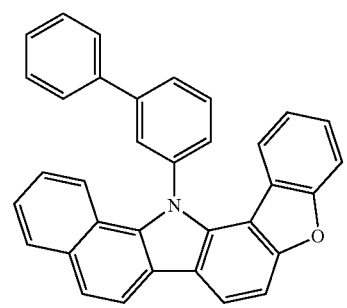
S-53
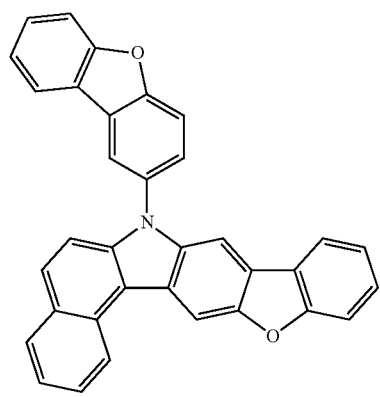
-continued
S-54
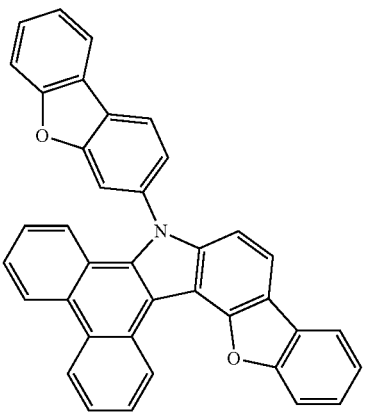
S-55
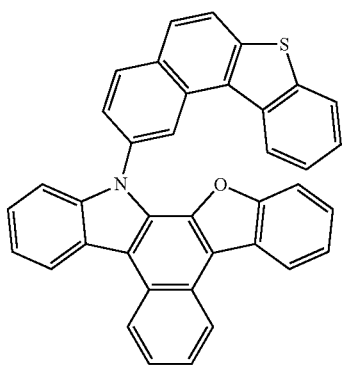
S-56
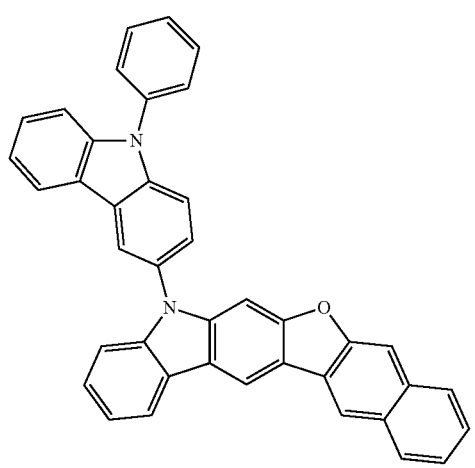
S-57
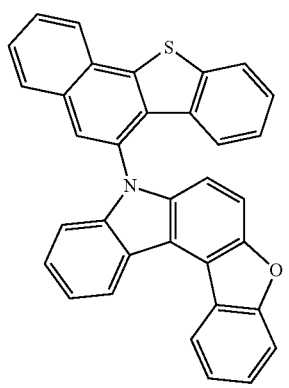

-continued
S-58
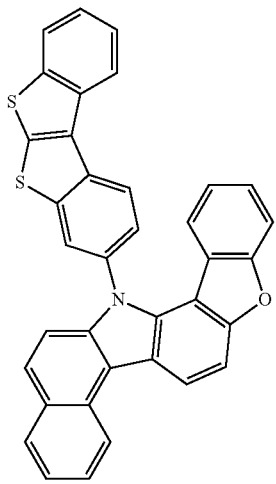
S-59
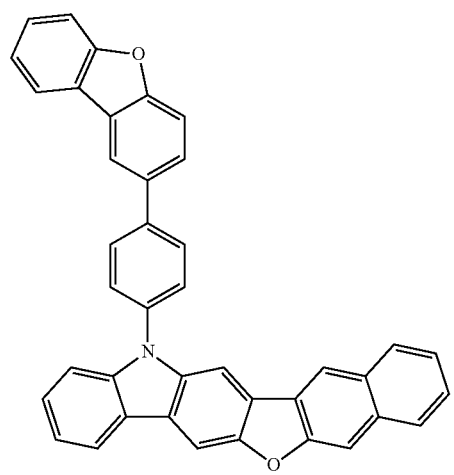
S-60
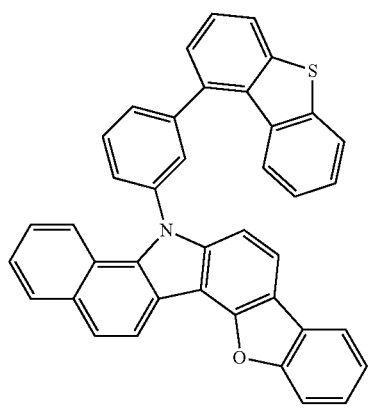
-continued
S-61
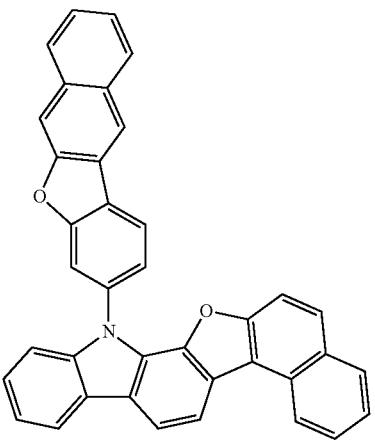
S-62
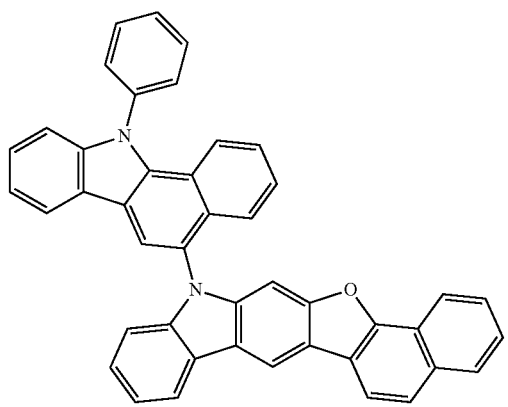
S-63
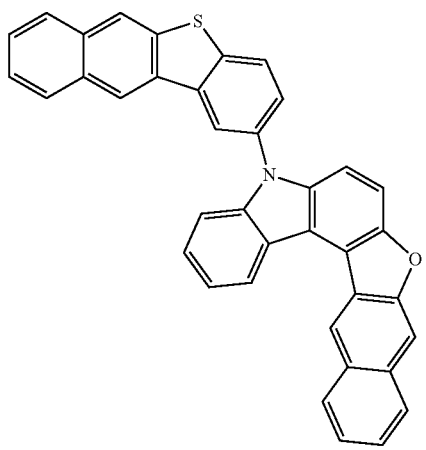

-continued
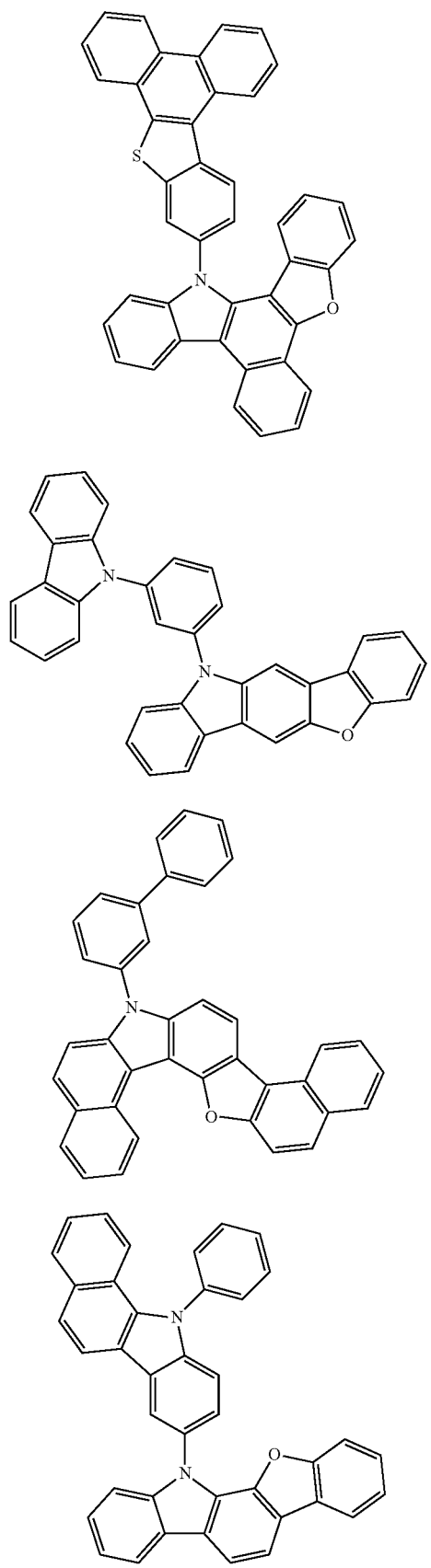
S-64
S-65
S-66
S-67
-continued
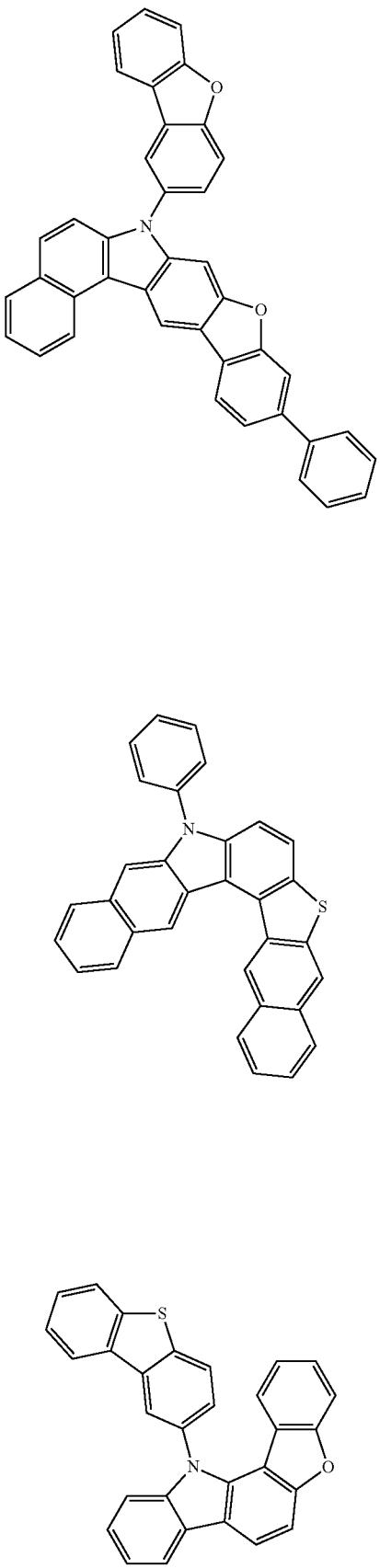
S-68
S-69
S-70

S-71
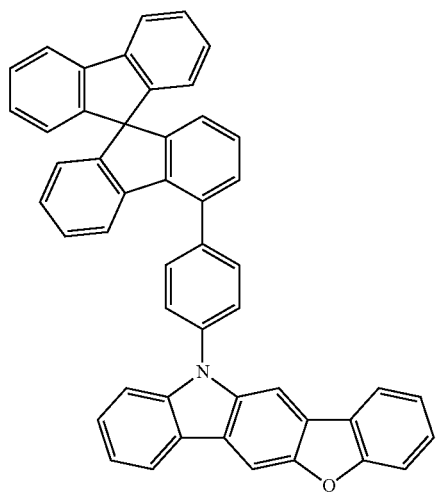
S-72
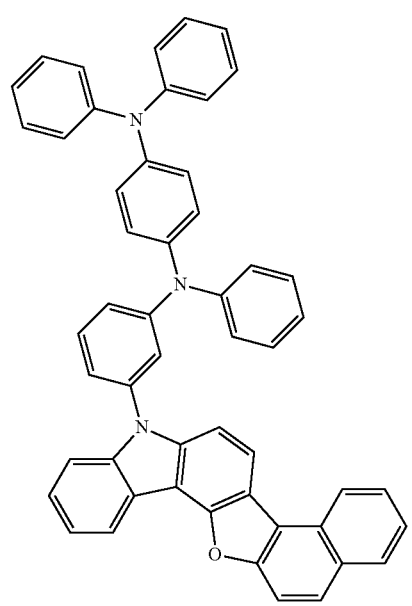
S-73
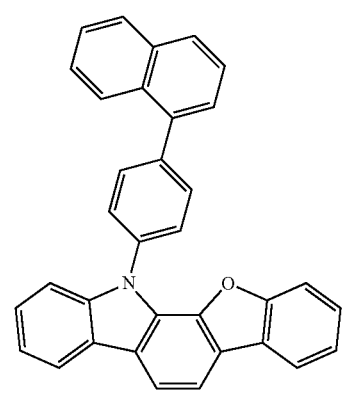
S-74
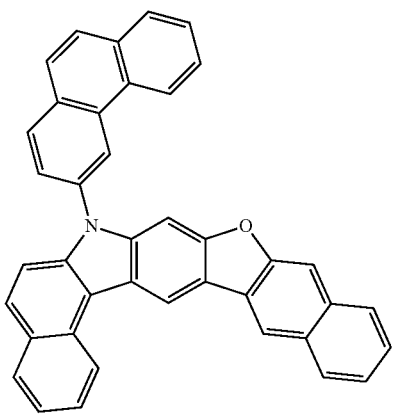
S-75
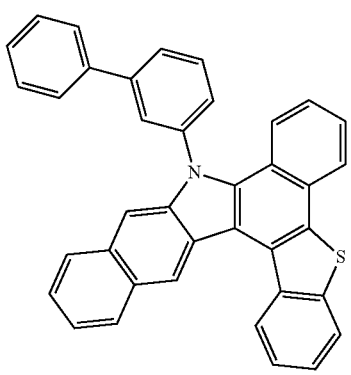
S-76
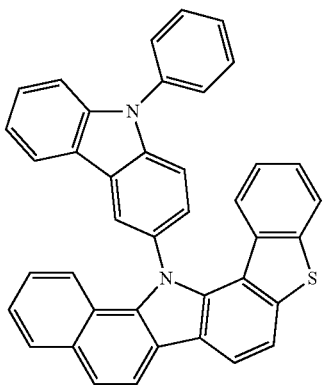
S-77
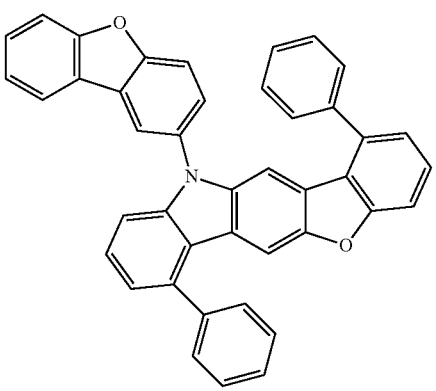

-continued
S-78
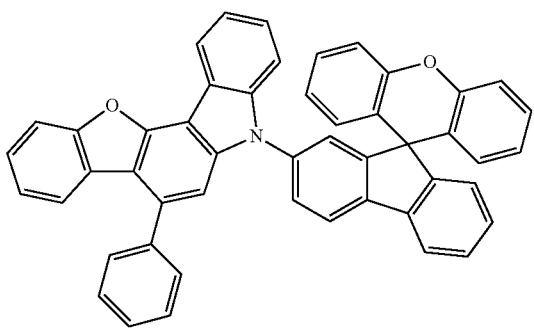
S-79
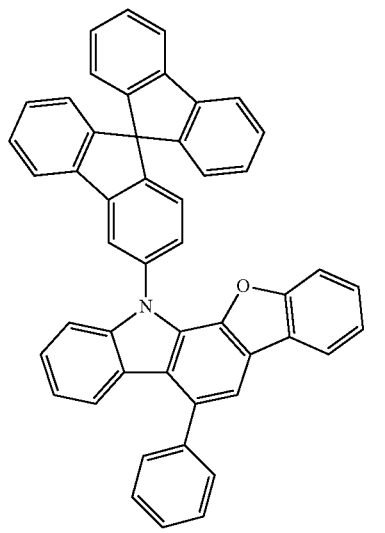
S-80
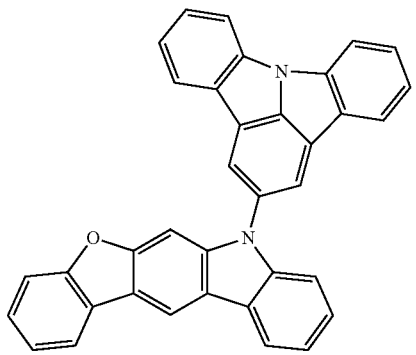
S-81
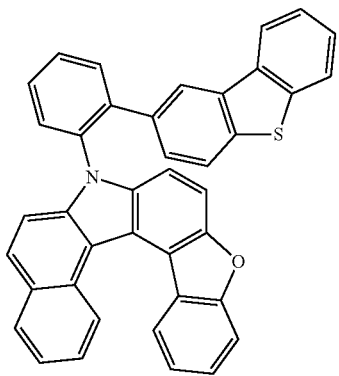
S-82
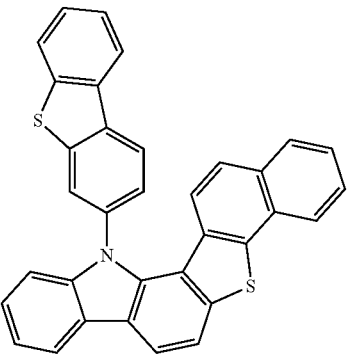
S-83
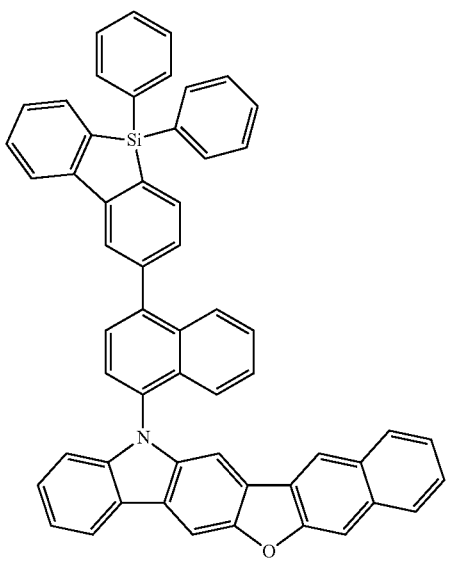
S-84
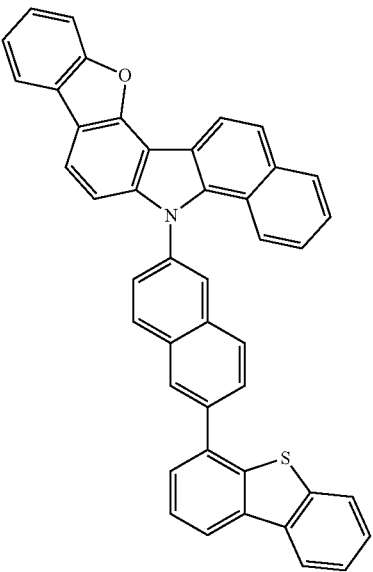

S-85
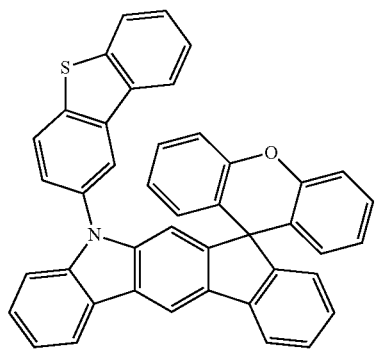
S-86
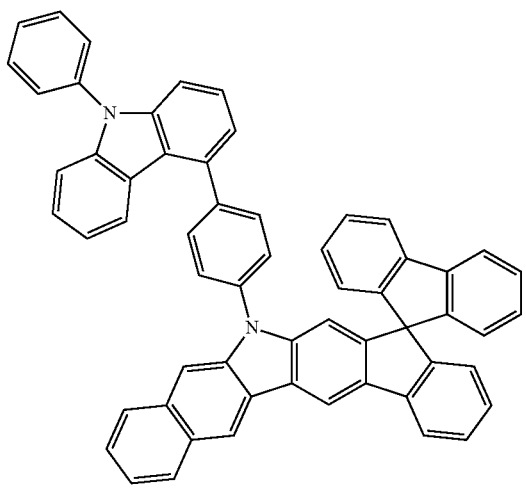
S-87
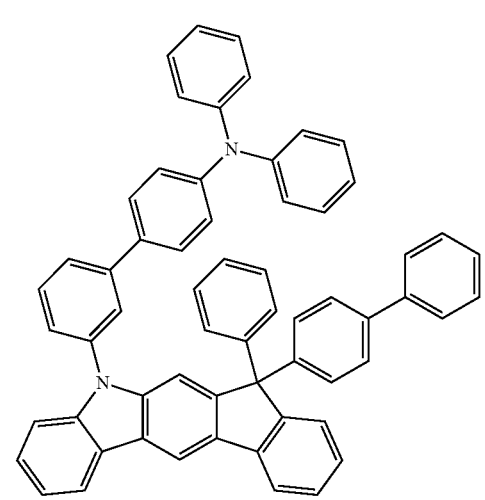
S-88
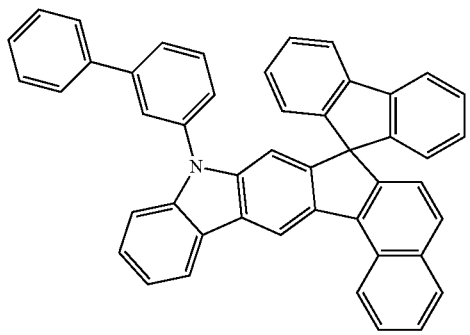
S-89
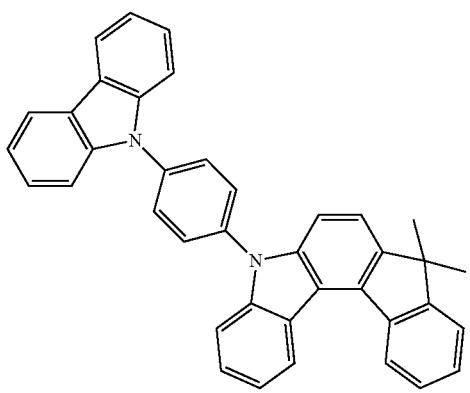
S-90
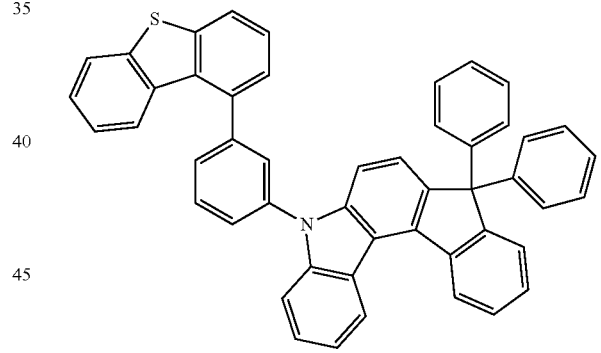
S-91
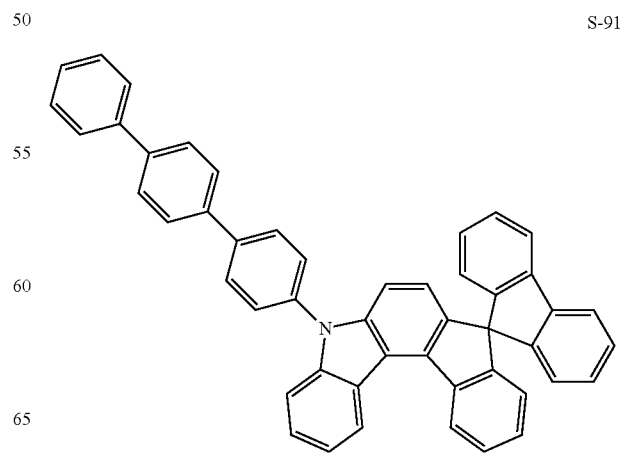

-continued
S-92
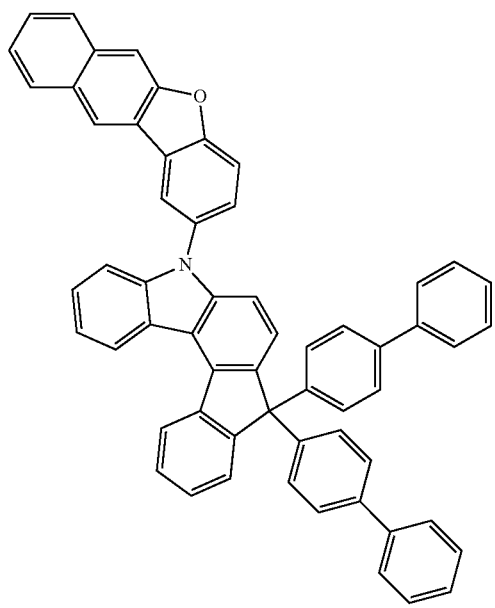
S-93
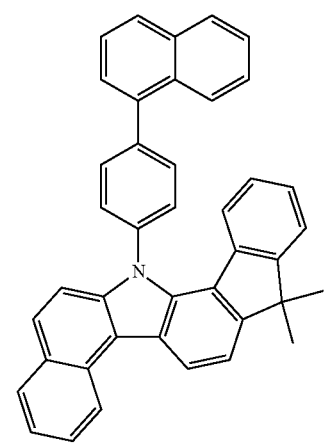
S-94
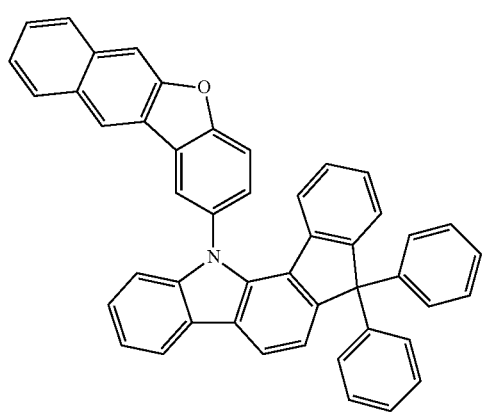
S-95
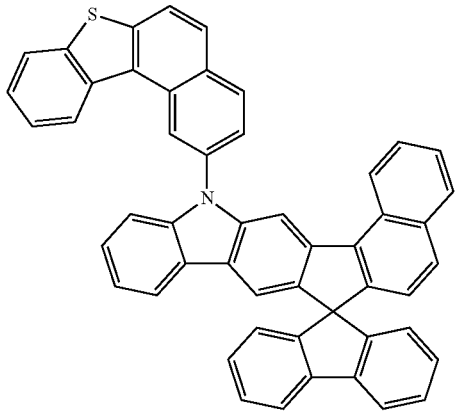
S-96
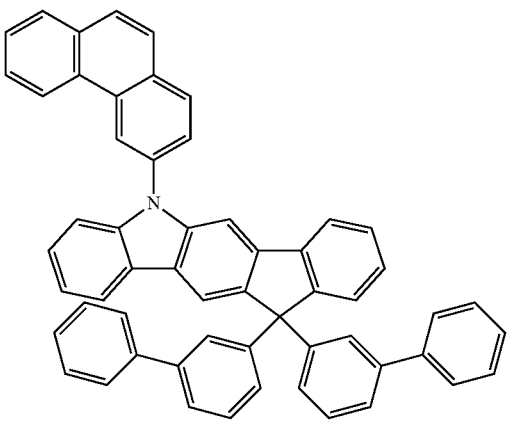
S-97
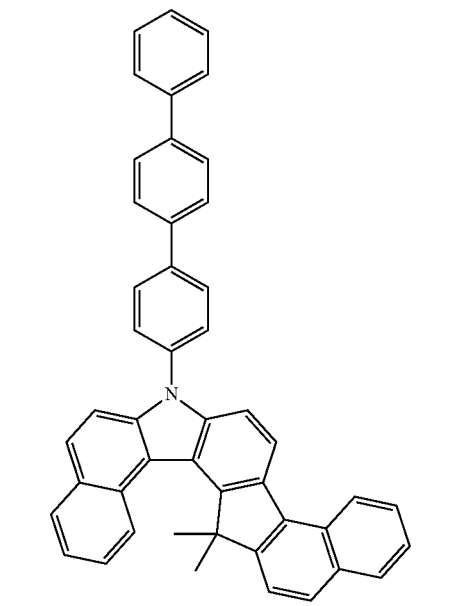

S-98
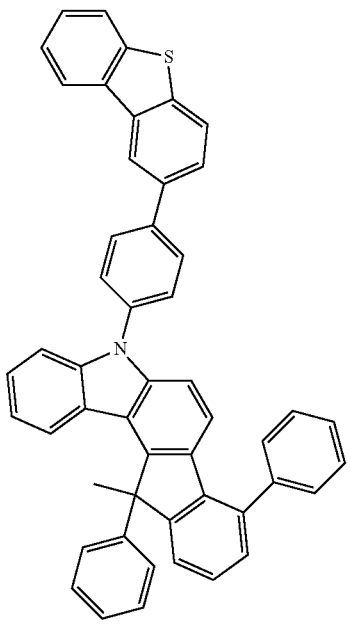
S-99
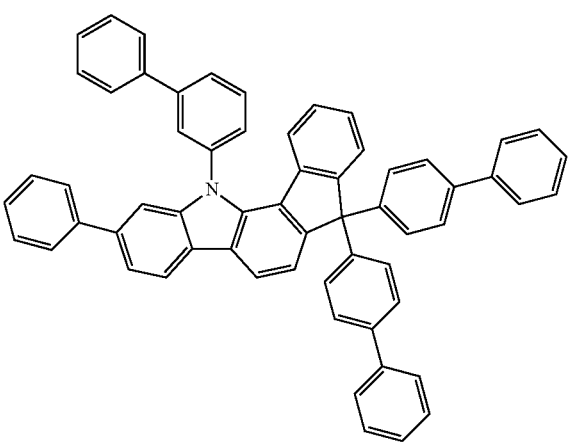
S-100
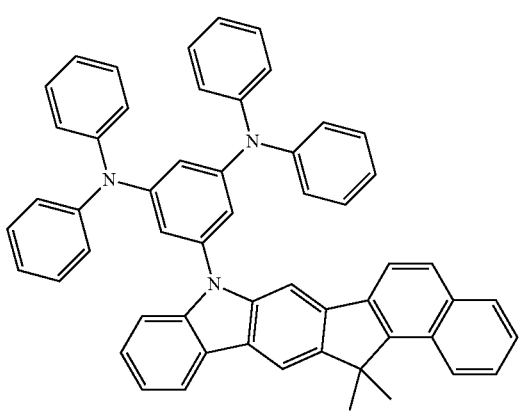
S-101
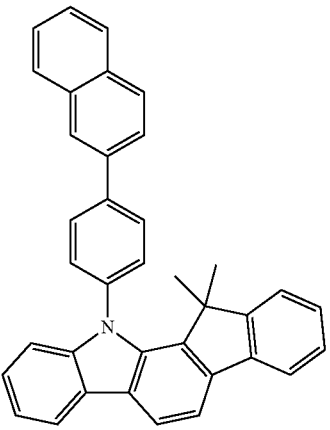
S-102
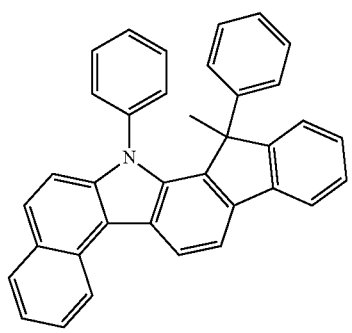
S-103
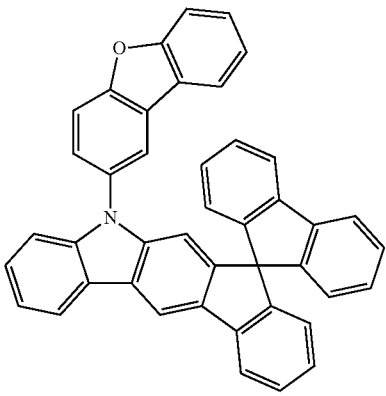
S-104
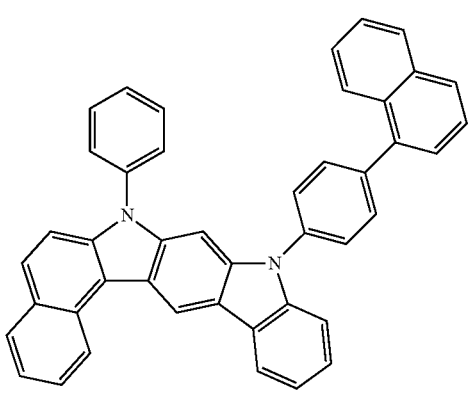

S-105
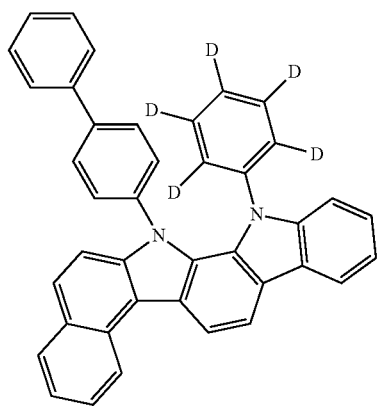
S-106
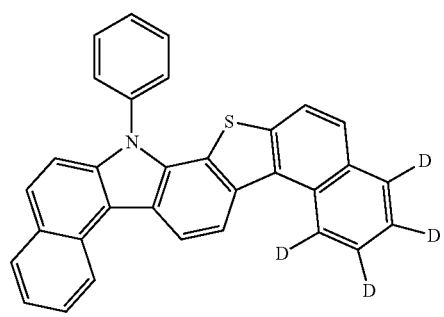
S-107
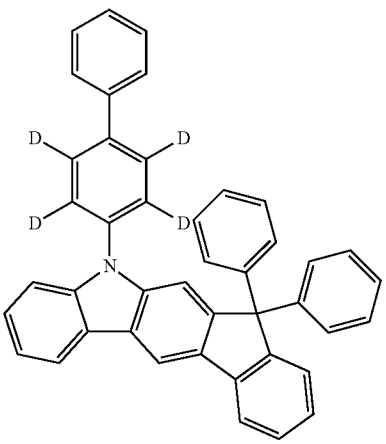
S-108
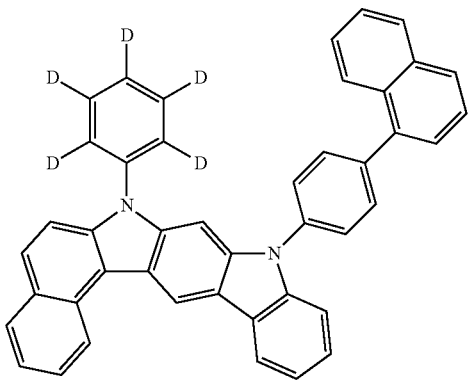
S-109
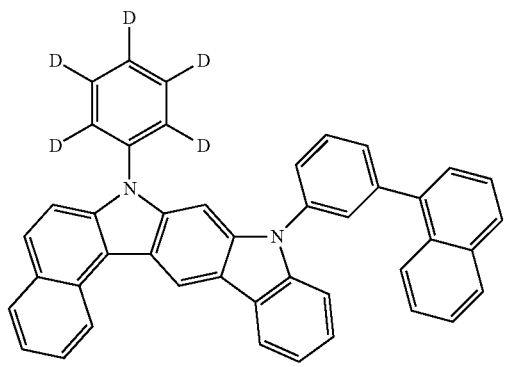
S-110
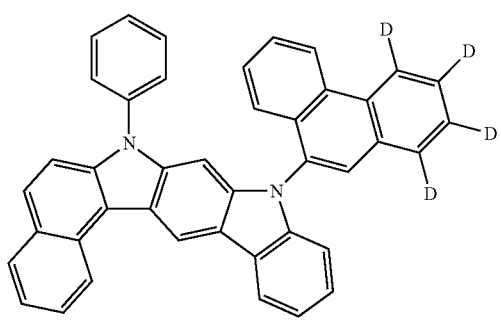
S-111
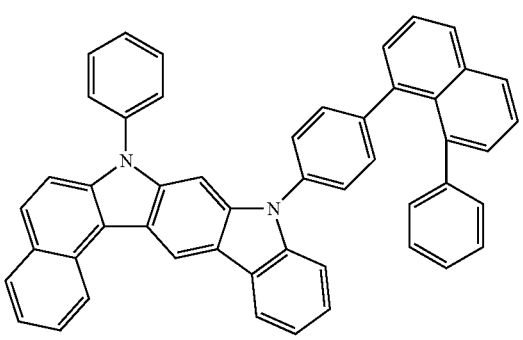
S-112
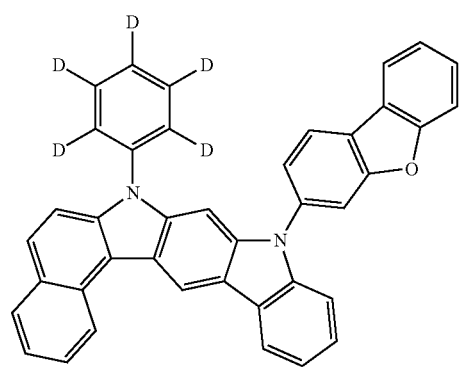

S-113
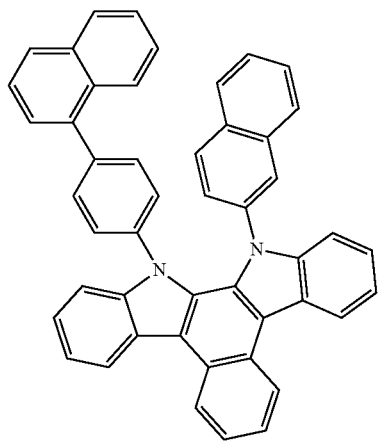
S-114
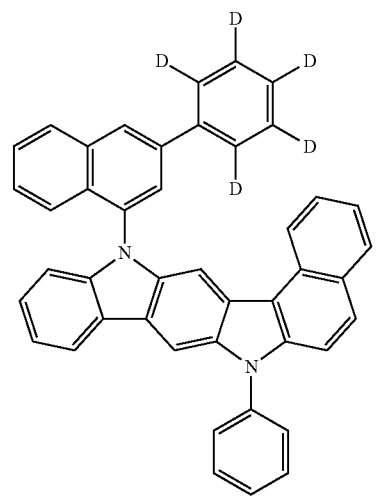
S-115
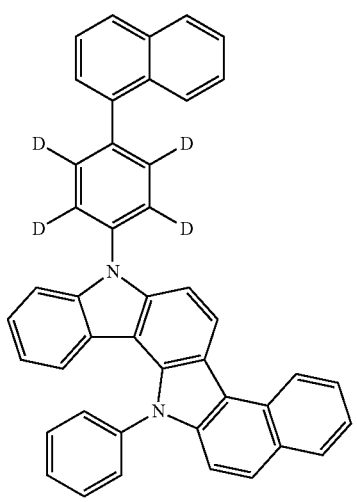
S-116
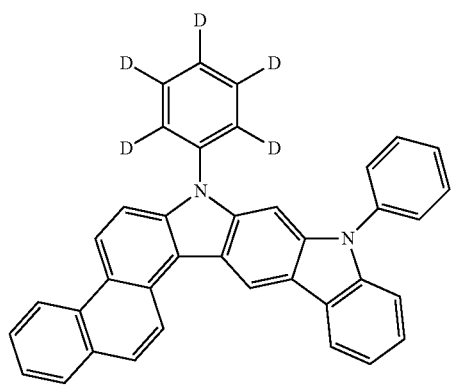
7. A compound selected from the group consisting of Compounds P-2 to P-16 and Compounds P-22 to P-36:
P-2
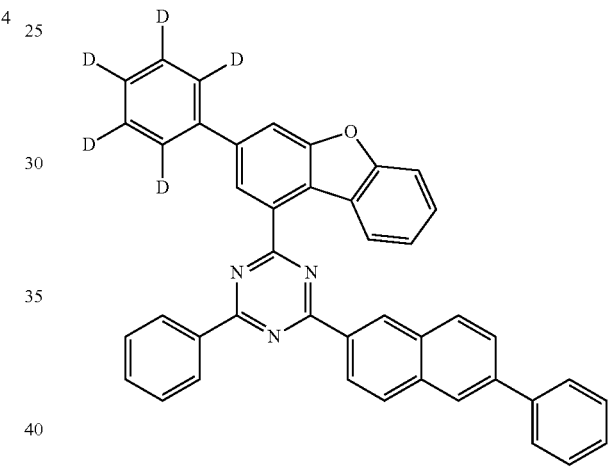
P-3
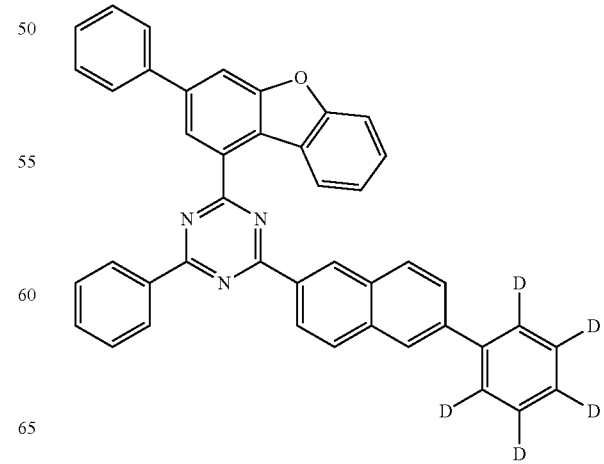

P-4
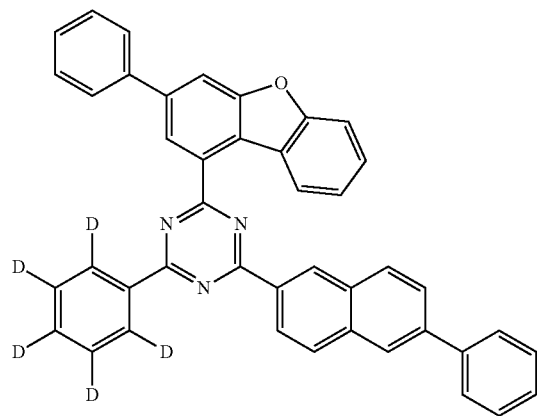
P-5
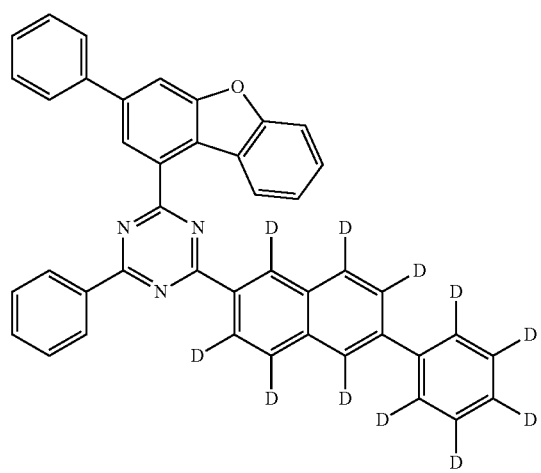
P-6
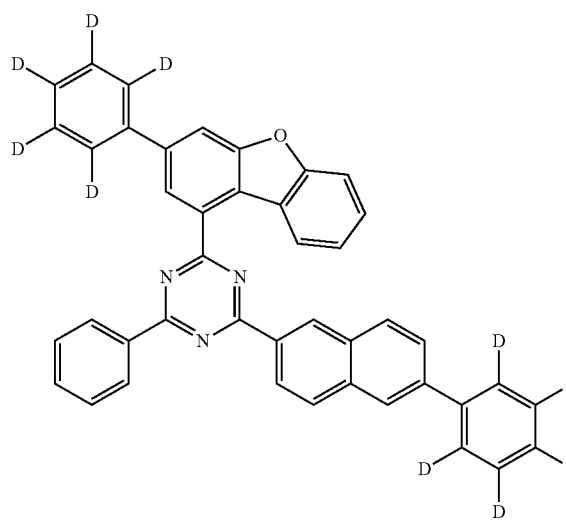
P-7
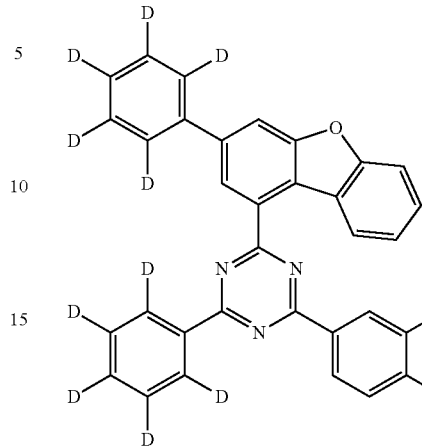
P-8
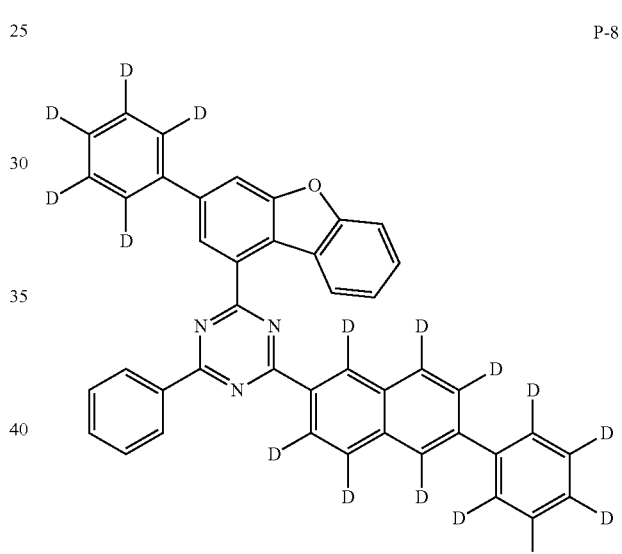
P-9
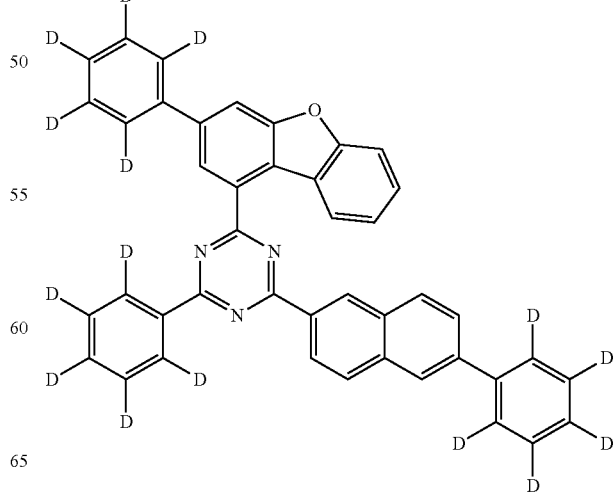

263
-continued
P-10
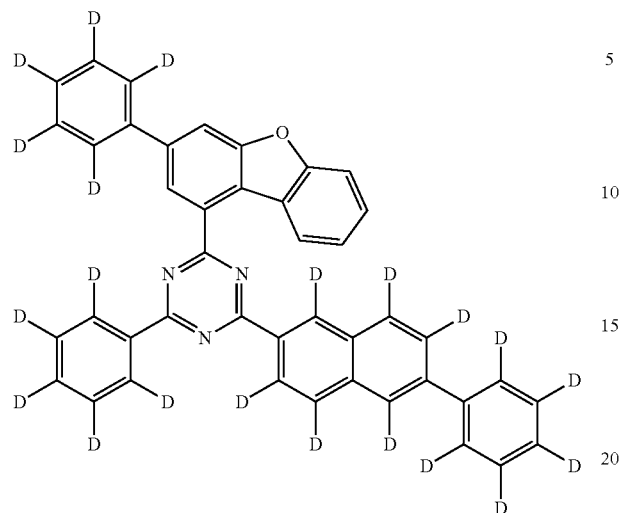
P-11
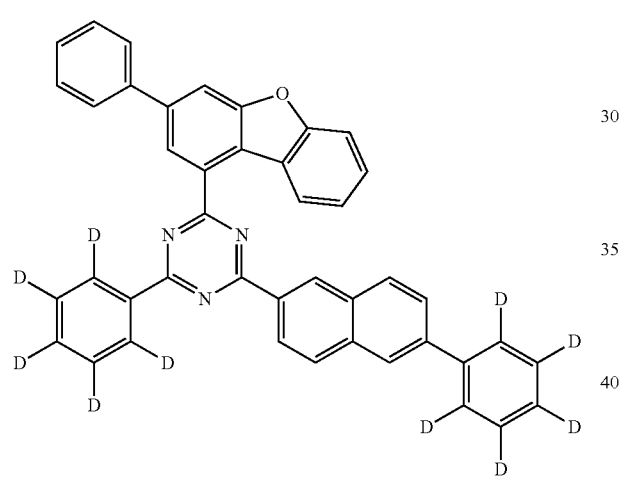
P-12
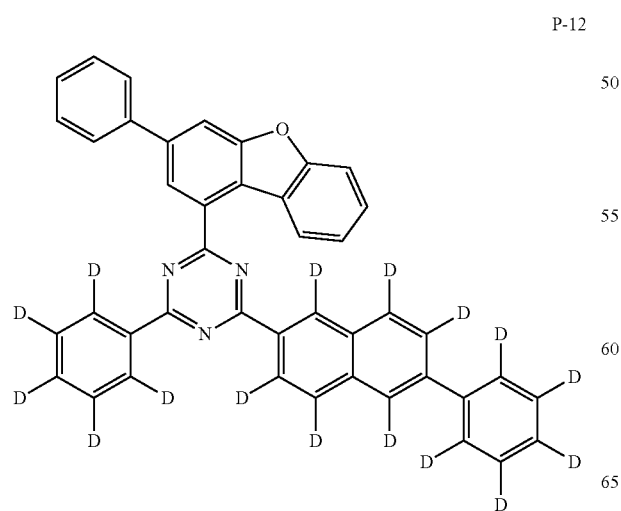
264
-continued
P-13
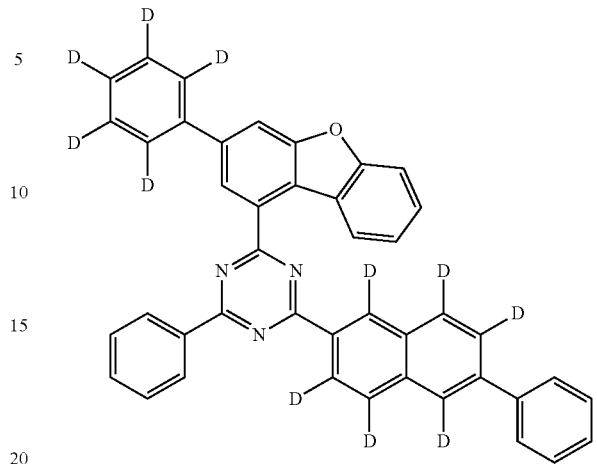
P-14
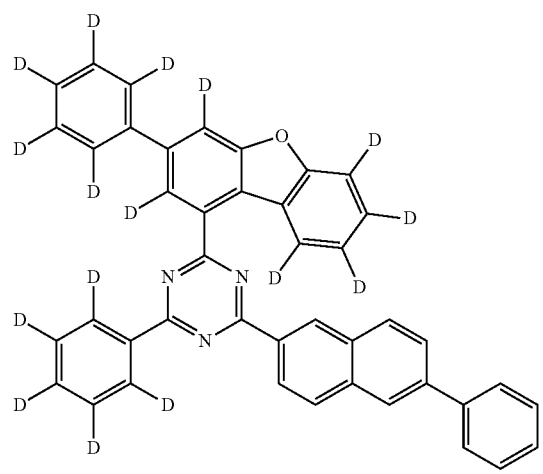
P-15
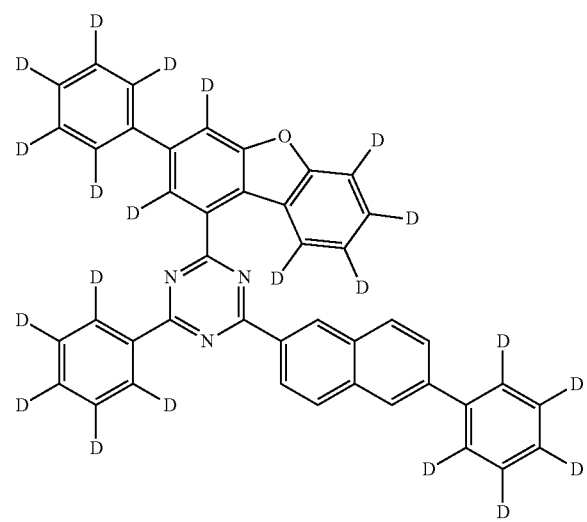

-continued
P-16
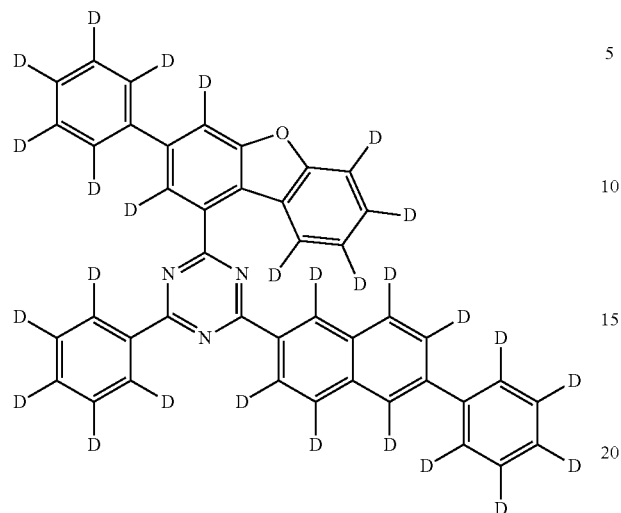
P-22
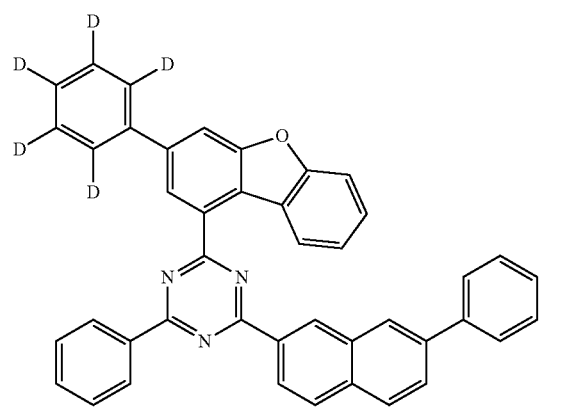
P-23
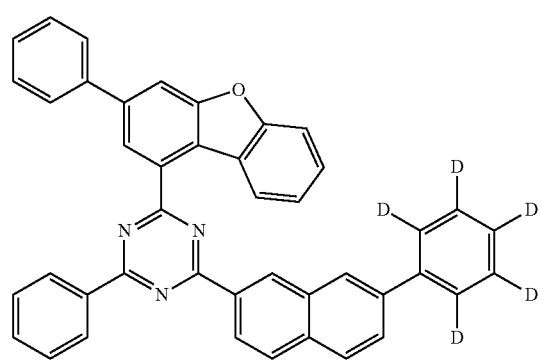
-continued
P-24
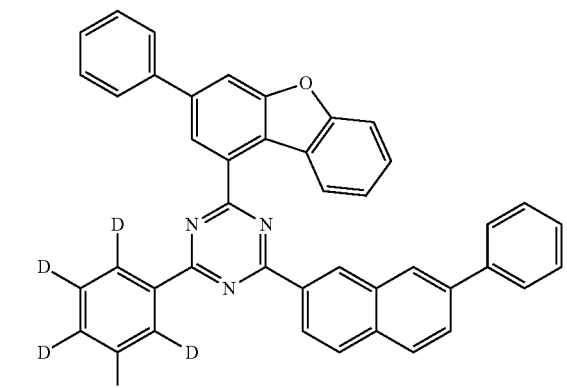
P-25
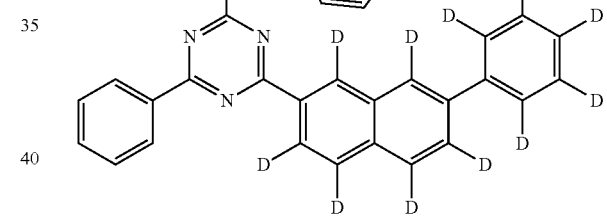
P-26
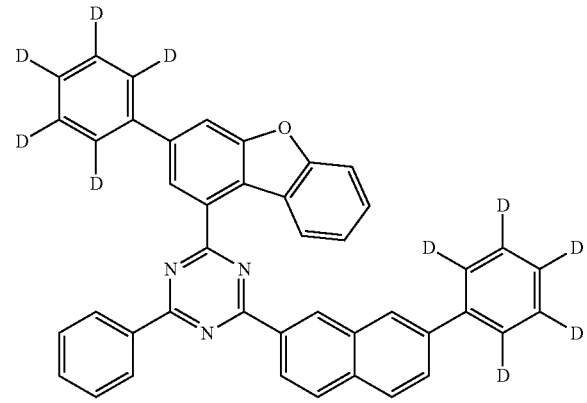

P-27
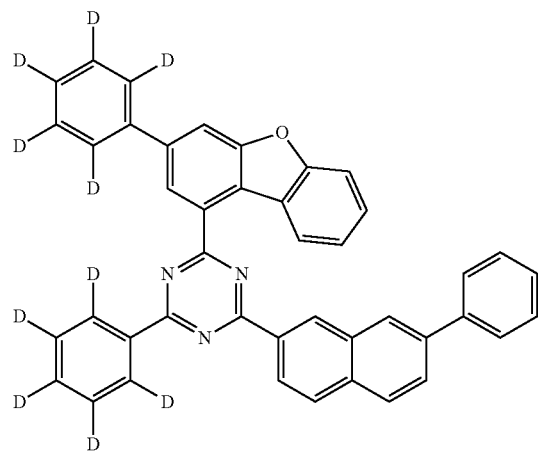
P-28
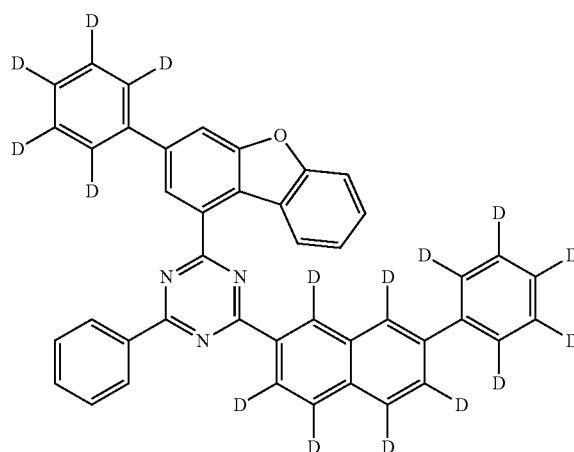
P-29
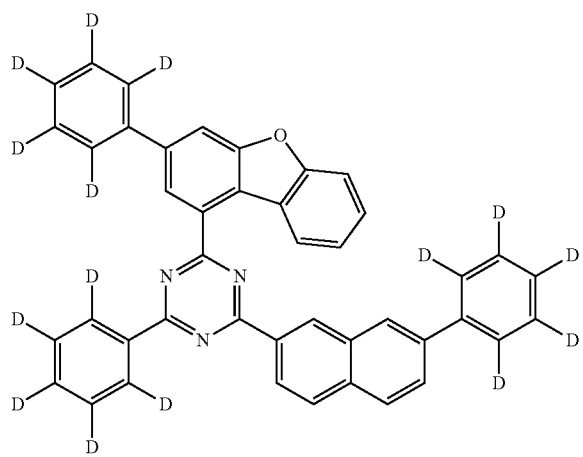
P-30
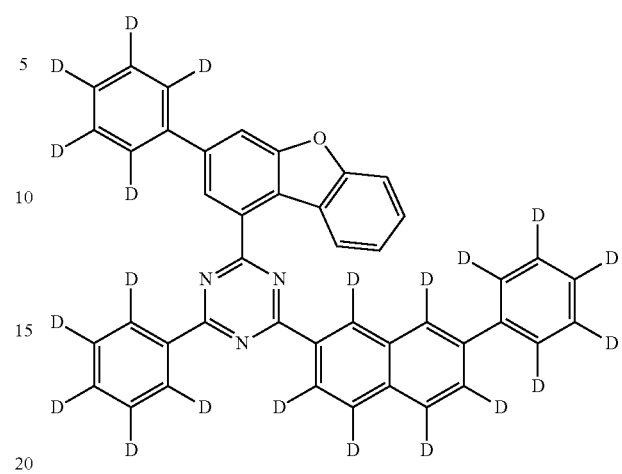
P-31
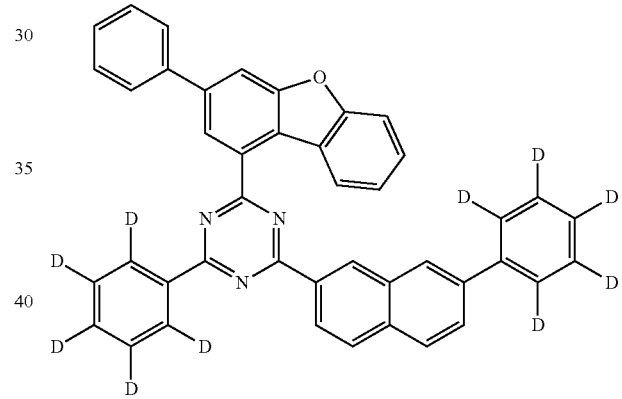
P-32
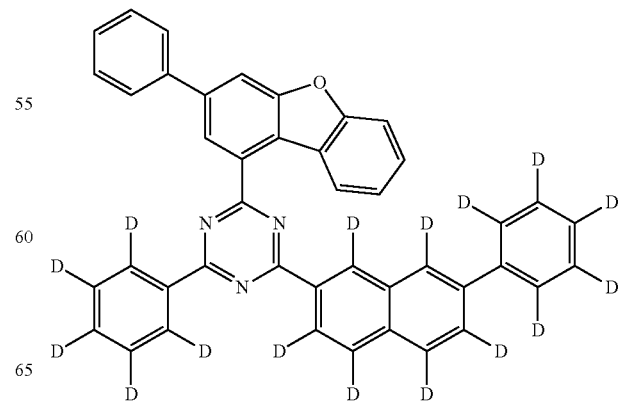

P-33

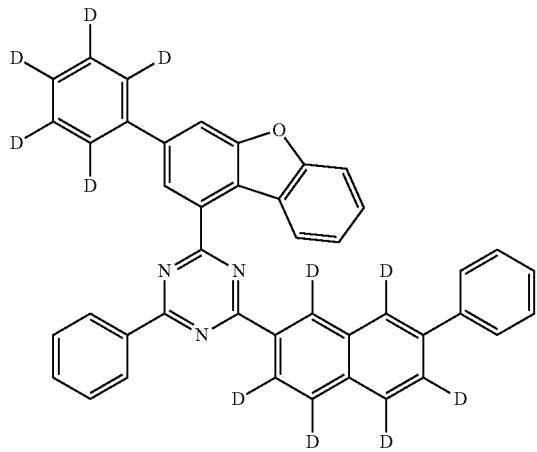

P-34

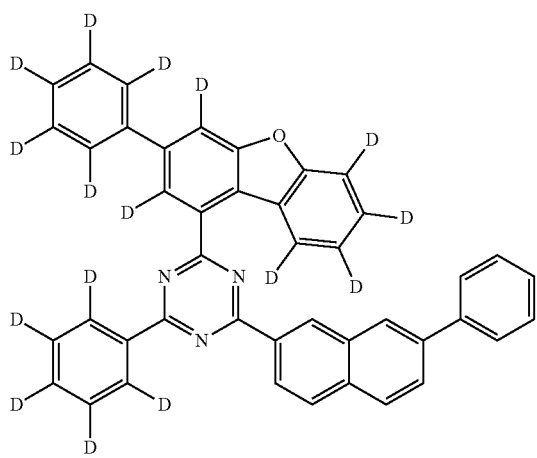

P-35

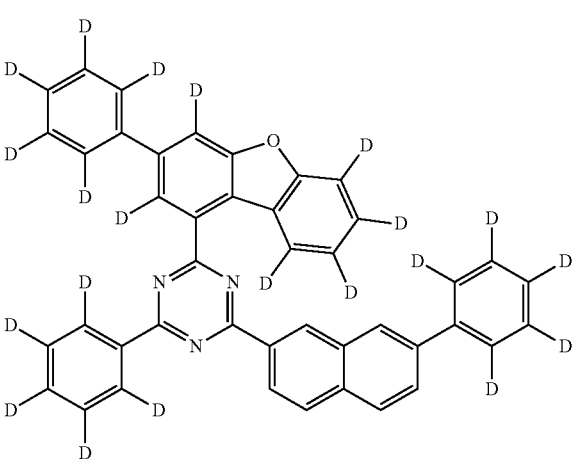

P-36

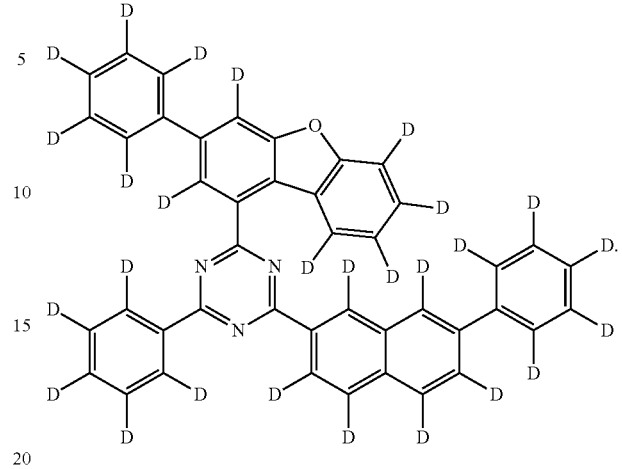

8. An organic electronic element comprising a first electrode; a second electrode; and an organic material layer formed between the first electrode and the second electrode, wherein the organic material layer comprises the composition of claim 1.

9. The organic electronic element according to claim 8, further comprising a light efficiency enhancing layer formed on at least one surface of the first electrode and the second electrode, the surface being opposite to the organic material layer.

10. The organic electronic element according to claim 8, wherein the organic material layer comprises 2 or more stacks comprising a hole transport layer, an emitting layer and an electron transport layer sequentially formed on the first electrode.

11. The organic electronic element according to claim 10, the organic material layer further comprises a charge generation layer formed between the 2 or more stacks.

12. An electronic device comprising a display device comprising the organic electronic element of claim 8; and a control unit for driving the display device.

13. The electronic device according to claim 12, wherein the organic electronic element is at least one of an OLED, an organic solar cell, an organic photo conductor (OPC), organic transistor (organic TFT) and an element for monochromic or white illumination.

14. An organic electronic element comprising a first electrode; a second electrode; and an organic material layer formed between the first electrode and the second electrode, wherein the organic material layer comprises the compound of claim 7.

15. The organic electronic element according to claim 14, wherein the organic material layer comprises 2 or more stacks comprising a hole transport layer, an emitting layer and an electron transport layer sequentially formed on the first electrode.

16. An electronic device comprising a display device comprising the organic electronic element of claim 14; and a control unit for driving the display device.

17. A method for reusing a compound of claim 7 comprising:
   recovering a crude organic light emitting material comprising the compound of claim 10 from a deposition apparatus used in the process for depositing the organic emitting material to prepare an organic light emitting device;

removing impurities from the crude organic light emitting material;

recovering the organic light emitting material after the impurities are removed; and purifying the recovered organic light emitting material to have a purity of 99.9% or higher.

\* \* \* \* \*